(12) United States Patent
Parihar et al.

(10) Patent No.: US 9,925,003 B2
(45) Date of Patent: Mar. 27, 2018

(54) ROBOTICALLY CONTROLLED SURGICAL INSTRUMENT

(71) Applicant: Ethicon Endo-Surgery, LLC, Guaynabo, PR (US)

(72) Inventors: Shailendra K. Parihar, Mason, OH (US); Matthew C. Miller, Cincinnati, OH (US); Barry C. Worrell, Centerville, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 0 days.

(21) Appl. No.: 14/963,905

(22) Filed: Dec. 9, 2015

(65) Prior Publication Data

US 2016/0089209 A1    Mar. 31, 2016

Related U.S. Application Data

(62) Division of application No. 13/760,560, filed on Feb. 6, 2013, now Pat. No. 9,232,979.

(Continued)

(51) Int. Cl.
*A61B 18/18* (2006.01)
*A61B 18/14* (2006.01)
(Continued)

(52) U.S. Cl.
CPC .............. *A61B 18/18* (2013.01); *A61B 34/30* (2016.02); *A61B 90/10* (2016.02);
(Continued)

(58) Field of Classification Search
CPC ......... A61B 18/18; A61B 34/30; A61B 19/20; A61B 90/03; A61B 18/1445;
(Continued)

(56) References Cited

U.S. PATENT DOCUMENTS 969,528 A    9/1910   Disbrow
1,570,025 A  1/1926   Young
(Continued)

FOREIGN PATENT DOCUMENTS

AU    2003241752 A1    9/2003
CA       2535467 A1    4/1993
(Continued)

OTHER PUBLICATIONS

International Search Report for PCT/US2013/024736, dated May 15, 2013 (4 pages).
(Continued)

*Primary Examiner* — Catherine Voorhees

(57) ABSTRACT

A surgical tool is disclosed. The surgical tool has a tool mounting portion having a tool mounting housing, a tool mounting plate, and a coupler to couple a shaft assembly having an articulation section to the tool mounting portion. An articulation mechanism is located within the tool mounting portion and is configured to receive a proximal end of the shaft assembly to articulate the articulation section of the shaft assembly. The articulation mechanism has a cam mechanism operative to articulate the articulation section of the shaft assembly. An interface mechanically and electrically couples the tool mounting portion to a manipulator.

16 Claims, 89 Drawing Sheets

Related U.S. Application Data

(60) Provisional application No. 61/597,603, filed on Feb. 10, 2012.

(51) Int. Cl.
*A61B 34/30* (2016.01)
*A61B 90/10* (2016.01)
*A61B 17/00* (2006.01)
*A61B 18/12* (2006.01)
*A61B 90/00* (2016.01)

(52) U.S. Cl.
CPC ......... *A61B 18/1445* (2013.01); *A61B 90/03* (2016.02); *A61B 2017/00477* (2013.01); *A61B 2017/00734* (2013.01); *A61B 2018/1226* (2013.01)

(58) Field of Classification Search
CPC ........... A61B 2017/00477; A61B 2017/00734; A61B 2018/1226
See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,425,245 A | 8/1947 | Johnson |
| 2,442,966 A | 6/1948 | Wallace |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,526,219 A | 9/1970 | Balamuth |
| 3,554,198 A | 1/1971 | Tatoian et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,776,238 A | 12/1973 | Peyman et al. |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 4,012,647 A | 3/1977 | Balamuth et al. |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,444 A | 5/1980 | Bonnell et al. |
| 4,300,083 A | 11/1981 | Heiges |
| 4,302,728 A | 11/1981 | Nakamura |
| 4,306,570 A | 12/1981 | Matthews |
| 4,445,063 A | 4/1984 | Smith |
| 4,491,132 A | 1/1985 | Aikins |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,541,638 A | 9/1985 | Ogawa et al. |
| 4,545,374 A | 10/1985 | Jacobson |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,708,127 A | 11/1987 | Abdelghani |
| 4,712,722 A | 12/1987 | Hood et al. |
| 4,808,154 A | 2/1989 | Freeman |
| 4,819,635 A | 4/1989 | Shapiro |
| 4,827,911 A | 5/1989 | Broadwin et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,850,354 A | 7/1989 | McGurk-Burleson et al. |
| 4,852,578 A | 8/1989 | Companion et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,881,550 A | 11/1989 | Kothe |
| 4,896,009 A | 1/1990 | Pawlowski |
| 4,903,696 A | 2/1990 | Stasz et al. |
| 4,915,643 A | 4/1990 | Samejima et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,013,956 A | 5/1991 | Kurozumi et al. |
| 5,015,227 A | 5/1991 | Broadwin et al. |
| 5,026,370 A | 6/1991 | Lottick |
| 5,026,387 A | 6/1991 | Thomas |
| 5,035,695 A | 7/1991 | Weber, Jr. et al. |
| 5,042,707 A | 8/1991 | Taheri |
| 5,084,052 A | 1/1992 | Jacobs |
| 5,105,117 A | 4/1992 | Yamaguchi |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,162,044 A | 11/1992 | Gahn et al. |
| 5,163,421 A | 11/1992 | Bernstein et al. |
| 5,163,537 A | 11/1992 | Radev |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grezeszykowski |
| 5,188,102 A | 2/1993 | Idemoto et al. |
| D334,173 S | 3/1993 | Liu et al. |
| 5,209,719 A | 5/1993 | Baruch et al. |
| 5,213,569 A | 5/1993 | Davis |
| 5,214,339 A | 5/1993 | Naito |
| 5,218,529 A | 6/1993 | Meyer et al. |
| 5,221,282 A | 6/1993 | Wuchinich |
| 5,222,937 A | 6/1993 | Kagawa |

(56) References Cited

U.S. PATENT DOCUMENTS

| | | |
|---|---|---|
| 5,226,909 A | 7/1993 | Evans et al. |
| 5,226,910 A | 7/1993 | Kajiyama et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,261,922 A | 11/1993 | Hood |
| 5,263,957 A | 11/1993 | Davison |
| 5,264,925 A | 11/1993 | Shipp et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,312,023 A | 5/1994 | Green et al. |
| 5,312,425 A | 5/1994 | Evans et al. |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,387,215 A | 2/1995 | Fisher |
| 5,389,098 A | 2/1995 | Tsuruta et al. |
| 5,394,187 A | 2/1995 | Shipp |
| 5,396,266 A | 3/1995 | Brimhall |
| 5,403,312 A | 4/1995 | Yates et al. |
| 5,403,334 A | 4/1995 | Evans et al. |
| 5,408,268 A | 4/1995 | Shipp |
| D358,887 S | 5/1995 | Feinberg |
| 5,411,481 A | 5/1995 | Allen et al. |
| 5,419,761 A | 5/1995 | Narayanan et al. |
| 5,421,829 A | 6/1995 | Olichney et al. |
| 5,423,844 A | 6/1995 | Miller |
| 5,438,997 A | 8/1995 | Sieben et al. |
| 5,445,639 A | 8/1995 | Kuslich et al. |
| 5,449,370 A | 9/1995 | Vaitekunas |
| 5,451,220 A | 9/1995 | Ciervo |
| 5,456,684 A | 10/1995 | Schmidt et al. |
| 5,471,988 A | 12/1995 | Fujio et al. |
| 5,472,443 A | 12/1995 | Cordis et al. |
| 5,478,003 A | 12/1995 | Green et al. |
| 5,483,501 A | 1/1996 | Park et al. |
| 5,486,162 A | 1/1996 | Brumbach |
| 5,490,860 A | 2/1996 | Middle et al. |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,540,693 A | 7/1996 | Fisher |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,573,424 A | 11/1996 | Poppe |
| 5,577,654 A | 11/1996 | Bishop |
| 5,591,187 A | 1/1997 | Dekel |
| 5,593,414 A | 1/1997 | Shipp et al. |
| 5,601,601 A | 2/1997 | Tal et al. |
| 5,603,773 A | 2/1997 | Campbell |
| 5,607,436 A | 3/1997 | Pratt et al. |
| 5,609,573 A | 3/1997 | Sandock |
| 5,618,304 A | 4/1997 | Hart et al. |
| 5,618,492 A | 4/1997 | Auten et al. |
| 5,620,447 A | 4/1997 | Smith et al. |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,717 A | 5/1997 | Yoon |
| 5,640,741 A | 6/1997 | Yano |
| D381,077 S | 7/1997 | Hunt |
| 5,649,937 A | 7/1997 | Bito |
| 5,651,780 A | 7/1997 | Jackson et al. |
| 5,653,713 A | 8/1997 | Michelson |
| 5,662,662 A | 9/1997 | Bishop et al. |
| 5,669,922 A | 9/1997 | Hood |
| 5,674,235 A | 10/1997 | Parisi |
| 5,678,568 A | 10/1997 | Uchikubo et al. |
| 5,690,269 A | 11/1997 | Bolanos et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,717,306 A | 2/1998 | Shipp |
| 5,728,130 A | 3/1998 | Ishikawa et al. |
| 5,730,752 A | 3/1998 | Alden et al. |
| 5,733,074 A | 3/1998 | Stöck et al. |
| 5,741,226 A | 4/1998 | Strukel et al. |
| 5,766,164 A | 6/1998 | Mueller et al. |
| 5,772,659 A | 6/1998 | Becker et al. |
| 5,792,135 A | 8/1998 | Madhani et al. |
| 5,792,138 A | 8/1998 | Shipp |
| 5,792,165 A | 8/1998 | Klieman et al. |
| 5,797,959 A | 8/1998 | Castro et al. |
| 5,805,140 A | 9/1998 | Rosenberg et al. |
| 5,808,396 A | 9/1998 | Boukhny |
| 5,810,859 A | 9/1998 | DiMatteo et al. |
| 5,817,084 A | 10/1998 | Jensen |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,957 A | 11/1998 | Schulz et al. |
| 5,843,109 A | 12/1998 | Mehta et al. |
| 5,851,212 A | 12/1998 | Zirps et al. |
| 5,858,018 A | 1/1999 | Shipp et al. |
| 5,865,361 A * | 2/1999 | Milliman ......... A61B 17/07207 227/176.1 |
| 5,873,873 A | 2/1999 | Smith et al. |
| 5,873,882 A | 2/1999 | Straub et al. |
| 5,878,193 A | 3/1999 | Wang et al. |
| 5,879,364 A | 3/1999 | Bromfield et al. |
| 5,883,615 A | 3/1999 | Fago et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,627 A | 5/1999 | Spaulding |
| 5,906,628 A | 5/1999 | Miyawaki et al. |
| 5,911,699 A | 6/1999 | Anis et al. |
| 5,916,229 A | 6/1999 | Evans |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |

(56) References Cited

U.S. PATENT DOCUMENTS

| | | |
|---|---|---|
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,024,741 A | 2/2000 | Williamson, IV et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,048,224 A | 4/2000 | Kay |
| 6,050,943 A | 4/2000 | Slayton et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,096,033 A | 8/2000 | Tu et al. |
| 6,099,542 A | 8/2000 | Cohn et al. |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,147,560 A | 11/2000 | Erhage et al. |
| 6,152,902 A | 11/2000 | Christian et al. |
| 6,154,198 A | 11/2000 | Rosenberg |
| 6,159,160 A | 12/2000 | Hsei et al. |
| 6,159,175 A | 12/2000 | Strukel et al. |
| 6,162,194 A | 12/2000 | Shipp |
| 6,165,150 A | 12/2000 | Banko |
| 6,174,310 B1 | 1/2001 | Kirwan, Jr. |
| 6,179,853 B1 | 1/2001 | Sachse et al. |
| 6,183,426 B1 | 2/2001 | Akisada et al. |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,245,065 B1 | 6/2001 | Panescu et al. |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,299,591 B1 | 10/2001 | Banko |
| 6,306,131 B1 | 10/2001 | Hareyama |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,109 B1 | 5/2002 | Davison et al. |
| 6,388,657 B1 | 5/2002 | Natoli |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,500,312 B2 | 12/2002 | Wedekamp |
| 6,506,208 B2 | 1/2003 | Hunt et al. |
| 6,511,478 B1 | 1/2003 | Burnside et al. |
| 6,511,493 B1 | 1/2003 | Moutafis et al. |
| 6,514,267 B2 | 2/2003 | Jewett |
| 6,524,251 B2 | 2/2003 | Rabiner et al. |
| 6,524,316 B1 | 2/2003 | Nicholson et al. |
| 6,527,736 B1 | 3/2003 | Attinger et al. |

(56) References Cited

U.S. PATENT DOCUMENTS

| | | |
|---|---|---|
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,558,376 B2 | 5/2003 | Bishop |
| 6,561,983 B2 | 5/2003 | Cronin et al. |
| 6,562,035 B1 | 5/2003 | Levin |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| D477,408 S | 7/2003 | Bromley |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,607,540 B1 | 8/2003 | Shipp |
| 6,610,059 B1 | 8/2003 | West, Jr. |
| 6,616,450 B2 | 9/2003 | Mossle et al. |
| 6,619,529 B2 | 9/2003 | Green et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,899 B2 | 1/2004 | Wiener et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,702,821 B2 | 3/2004 | Bonutti |
| 6,716,215 B1 | 4/2004 | David et al. |
| 6,719,692 B2 | 4/2004 | Kleffner et al. |
| 6,719,776 B2 | 4/2004 | Baxter |
| 6,723,091 B2 | 4/2004 | Goble et al. |
| D490,059 S | 5/2004 | Conway et al. |
| 6,731,047 B2 | 5/2004 | Kauf et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,770,072 B1 | 8/2004 | Truckai et al. |
| 6,773,409 B2 | 8/2004 | Truckai et al. |
| 6,773,443 B2 | 8/2004 | Truwit et al. |
| 6,773,444 B2 | 8/2004 | Messerly |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,790,173 B2 | 9/2004 | Saadat et al. |
| 6,790,216 B1 | 9/2004 | Ishikawa |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,827,712 B2 | 12/2004 | Tovey et al. |
| 6,828,712 B2 | 12/2004 | Battaglin et al. |
| 6,835,082 B2 | 12/2004 | Gonnering |
| 6,849,073 B2 | 2/2005 | Hoey et al. |
| 6,860,878 B2 | 3/2005 | Brock |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,899,685 B2 | 5/2005 | Kermode et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,929,602 B2 | 8/2005 | Hirakui et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,994,708 B2 | 2/2006 | Manzo |
| 7,001,335 B2 | 2/2006 | Adachi et al. |
| 7,011,657 B2 | 3/2006 | Truckai et al. |
| 7,014,638 B2 | 3/2006 | Michelson |
| 7,033,357 B2 | 4/2006 | Baxter et al. |
| 7,037,306 B2 | 5/2006 | Podany |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,066,893 B2 | 6/2006 | Hibner et al. |
| 7,066,895 B2 | 6/2006 | Podany |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,618 B2 | 8/2006 | Couture |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,371 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |

(56) References Cited

U.S. PATENT DOCUMENTS

| | | |
|---|---|---|
| D531,311 S | 10/2006 | Guerra et al. |
| 7,117,034 B2 | 10/2006 | Kronberg |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| D541,418 S | 4/2007 | Schechter et al. |
| 7,198,635 B2 | 4/2007 | Danek et al. |
| 7,204,820 B2 | 4/2007 | Akahoshi |
| 7,207,997 B2 | 4/2007 | Shipp et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,235,071 B2 | 6/2007 | Gonnering |
| 7,244,262 B2 | 7/2007 | Wiener et al. |
| 7,258,688 B1 | 8/2007 | Shah et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupré |
| 7,300,431 B2 | 11/2007 | Dubrovsky |
| 7,300,435 B2 | 11/2007 | Wham et al. |
| 7,300,446 B2 | 11/2007 | Beaupre |
| 7,303,531 B2 | 12/2007 | Lee et al. |
| 7,303,557 B2 | 12/2007 | Wham et al. |
| 7,306,597 B2 | 12/2007 | Manzo |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,364,577 B2 | 4/2008 | Wham et al. |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,462,181 B2 | 12/2008 | Kraft et al. |
| 7,464,846 B2 | 12/2008 | Sheltion, IV et al. |
| 7,472,815 B2 | 1/2009 | Shelton, IV et al. |
| 7,473,263 B2 | 1/2009 | Johnston et al. |
| 7,479,148 B2 | 1/2009 | Beaupré |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,494,468 B2 | 2/2009 | Rabiner et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,544,200 B2 | 6/2009 | Houser |
| 7,549,564 B2 | 6/2009 | Boudreaux |
| 7,559,450 B2 | 7/2009 | Wales et al. |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,095 B2 | 9/2009 | Shipp et al. |
| 7,585,181 B2 | 9/2009 | Olsen |
| 7,588,176 B2 | 9/2009 | Timm et al. |
| 7,601,119 B2 | 10/2009 | Shahinian |
| 7,607,557 B2 | 10/2009 | Shelton, IV et al. |
| 7,621,930 B2 | 11/2009 | Houser |
| 7,641,653 B2 | 1/2010 | Dalla Betta et al. |
| 7,645,278 B2 | 1/2010 | Ichihashi et al. |
| 7,654,431 B2 | 2/2010 | Hueil et al. |
| 7,659,833 B2 | 2/2010 | Warner et al. |
| 7,665,647 B2 | 2/2010 | Shelton, IV et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,098 B2 | 4/2010 | Wallace et al. |
| 7,699,846 B2 | 4/2010 | Ryan |
| 7,713,202 B2 | 5/2010 | Boukhny et al. |
| 7,714,481 B2 | 5/2010 | Sakai |
| 7,717,312 B2 | 5/2010 | Beetel |
| 7,717,915 B2 | 5/2010 | Miyazawa |
| 7,721,935 B2 | 5/2010 | Racenet et al. |
| D618,797 S | 6/2010 | Price et al. |
| 7,726,537 B2 | 6/2010 | Olson et al. |
| 7,727,177 B2 | 6/2010 | Bayat |
| 7,738,969 B2 | 6/2010 | Bleich |
| 7,740,594 B2 | 6/2010 | Hibner |
| 7,751,115 B2 | 7/2010 | Song |
| D621,503 S | 8/2010 | Otten et al. |
| 7,766,210 B2 | 8/2010 | Shelton, IV et al. |
| 7,766,693 B2 | 8/2010 | Sartor et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |

(56) References Cited

U.S. PATENT DOCUMENTS

| | | |
|---|---|---|
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,784,662 B2 | 8/2010 | Wales et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,819,819 B2 | 10/2010 | Quick et al. |
| 7,821,143 B2 | 10/2010 | Wiener |
| D627,066 S | 11/2010 | Romero |
| 7,824,401 B2 | 11/2010 | Manzo et al. |
| 7,832,611 B2 | 11/2010 | Boyden et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,892,606 B2 | 2/2011 | Thies et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,824 B2 | 3/2011 | Masuda et al. |
| 7,922,061 B2 | 4/2011 | Shelton, IV et al. |
| 7,922,651 B2 | 4/2011 | Yamada et al. |
| D637,288 S | 5/2011 | Houghton |
| D638,540 S | 5/2011 | Ijiri et al. |
| 7,936,203 B2 | 5/2011 | Zimlich |
| 7,951,095 B2 | 5/2011 | Makin et al. |
| 7,951,165 B2 | 5/2011 | Golden et al. |
| 7,959,050 B2 | 6/2011 | Smith et al. |
| 7,959,626 B2 | 6/2011 | Hong et al. |
| 7,972,329 B2 | 7/2011 | Refior et al. |
| 7,976,544 B2 | 7/2011 | McClurken et al. |
| 7,981,050 B2 | 7/2011 | Ritchart et al. |
| 7,998,157 B2 | 8/2011 | Culp et al. |
| 8,038,693 B2 | 10/2011 | Allen |
| 8,057,498 B2 | 11/2011 | Robertson |
| 8,058,771 B2 | 11/2011 | Giordano et al. |
| 8,061,014 B2 | 11/2011 | Smith et al. |
| 8,070,711 B2 | 12/2011 | Bassinger et al. |
| 8,070,762 B2 | 12/2011 | Escudero et al. |
| 8,075,558 B2 | 12/2011 | Truckai et al. |
| 8,089,197 B2 | 1/2012 | Rinner et al. |
| 8,097,012 B2 | 1/2012 | Kagarise |
| 8,105,323 B2 | 1/2012 | Buysse et al. |
| 8,142,461 B2 | 3/2012 | Houser et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,877 B2 | 5/2012 | Klimovitch et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,502 B2 | 6/2012 | Smith et al. |
| 8,207,651 B2 | 6/2012 | Gilbert |
| 8,210,411 B2 | 7/2012 | Yates et al. |
| 8,226,675 B2 | 7/2012 | Houser et al. |
| 8,235,917 B2 | 8/2012 | Joseph et al. |
| 8,236,019 B2 | 8/2012 | Houser |
| 8,236,020 B2 | 8/2012 | Smith et al. |
| 8,241,271 B2 | 8/2012 | Millman et al. |
| 8,246,575 B2 | 8/2012 | Viola |
| 8,246,615 B2 | 8/2012 | Behnke |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,273,087 B2 | 9/2012 | Kimura et al. |
| D669,992 S | 10/2012 | Schafer et al. |
| D669,993 S | 10/2012 | Merchant et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,888 B2 | 10/2012 | Whitman |
| 8,298,223 B2 | 10/2012 | Wham et al. |
| 8,298,225 B2 | 10/2012 | Gilbert |
| 8,303,576 B2 | 11/2012 | Brock |
| 8,303,580 B2 | 11/2012 | Wham et al. |
| 8,303,583 B2 | 11/2012 | Hosier et al. |
| 8,319,400 B2 | 11/2012 | Houser et al. |
| 8,323,302 B2 | 12/2012 | Robertson et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,348,967 B2 | 1/2013 | Stulen |
| 8,357,103 B2 | 1/2013 | Mark et al. |
| 8,366,727 B2 | 2/2013 | Witt et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,545 B2 | 4/2013 | Smith et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,664 B2 | 5/2013 | Balanev et al. |
| 8,460,288 B2 | 6/2013 | Tamai et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,359 B2 | 8/2013 | Whitman et al. |
| 8,512,365 B2 | 8/2013 | Wiener et al. |

(56) References Cited

U.S. PATENT DOCUMENTS

| | | |
|---|---|---|
| 8,523,889 B2 | 9/2013 | Stulen et al. |
| 8,531,064 B2 | 9/2013 | Robertson et al. |
| 8,535,340 B2 | 9/2013 | Allen |
| 8,535,341 B2 | 9/2013 | Allen |
| 8,546,996 B2 | 10/2013 | Messerly et al. |
| 8,546,999 B2 | 10/2013 | Houser et al. |
| 8,551,086 B2 | 10/2013 | Kimura et al. |
| 8,568,400 B2 | 10/2013 | Gilbert |
| 8,573,461 B2 | 11/2013 | Shelton, IV et al. |
| 8,573,465 B2 | 11/2013 | Shelton, IV |
| 8,579,928 B2 | 11/2013 | Robertson et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,616,431 B2 | 12/2013 | Timm et al. |
| 8,623,027 B2 | 1/2014 | Price et al. |
| 8,650,728 B2 | 2/2014 | Wan et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,690,582 B2 | 4/2014 | Rohrbach et al. |
| 8,696,366 B2 | 4/2014 | Chen et al. |
| 8,704,425 B2 | 4/2014 | Giordano et al. |
| 8,709,031 B2 | 4/2014 | Stulen |
| 8,747,351 B2 | 6/2014 | Schultz |
| 8,749,116 B2 | 6/2014 | Messerly et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,352 B2 | 6/2014 | Cooper et al. |
| 8,764,735 B2 | 7/2014 | Coe et al. |
| 8,771,270 B2 | 7/2014 | Burbank |
| 8,773,001 B2 | 7/2014 | Wiener et al. |
| 8,779,648 B2 | 7/2014 | Giordano et al. |
| 8,784,418 B2 | 7/2014 | Romero |
| 8,808,319 B2 | 8/2014 | Houser et al. |
| 8,827,992 B2 | 9/2014 | Koss et al. |
| 8,845,537 B2 | 9/2014 | Tanaka et al. |
| 8,882,791 B2 | 11/2014 | Stulen |
| 8,888,776 B2 | 11/2014 | Dietz et al. |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,911,460 B2 | 12/2014 | Neurohr et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,547 B2 | 2/2015 | Dietz et al. |
| 8,968,283 B2 | 3/2015 | Kharin |
| 8,968,355 B2 | 3/2015 | Malkowski et al. |
| 8,974,477 B2 | 3/2015 | Yamada |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,903 B2 | 3/2015 | Weir et al. |
| 9,017,326 B2 | 4/2015 | DiNardo et al. |
| 9,039,695 B2 | 5/2015 | Giordano et al. |
| 9,043,018 B2 | 5/2015 | Mohr |
| 9,044,261 B2 | 6/2015 | Houser |
| 9,050,093 B2 | 6/2015 | Aldridge et al. |
| 9,050,124 B2 | 6/2015 | Houser |
| 9,060,775 B2 | 6/2015 | Wiener et al. |
| 9,060,776 B2 | 6/2015 | Yates et al. |
| 9,066,747 B2 | 6/2015 | Robertson |
| 9,072,539 B2 | 7/2015 | Messerly et al. |
| 9,089,360 B2 | 7/2015 | Messerly et al. |
| 9,095,367 B2 | 8/2015 | Olson et al. |
| 9,107,689 B2 | 8/2015 | Robertson et al. |
| 9,113,940 B2 | 8/2015 | Twomey |
| 9,168,054 B2 | 10/2015 | Turner et al. |
| 9,198,714 B2 | 12/2015 | Worrell et al. |
| 9,220,527 B2 | 12/2015 | Houser et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,921 B2 | 1/2016 | Messerly et al. |
| 9,241,728 B2 | 1/2016 | Price et al. |
| 9,241,731 B2 | 1/2016 | Boudreaux et al. |
| 9,259,234 B2 | 2/2016 | Robertson et al. |
| 9,283,045 B2 | 3/2016 | Rhee et al. |
| 9,326,788 B2 | 5/2016 | Batross et al. |
| 9,339,289 B2 | 5/2016 | Robertson |
| 9,351,754 B2 | 5/2016 | Vakharia et al. |
| 9,393,037 B2 | 7/2016 | Olson et al. |
| 9,408,622 B2 | 8/2016 | Stulen et al. |
| 9,414,853 B2 | 8/2016 | Stulen et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,445,832 B2 | 9/2016 | Wiener et al. |
| 2001/0025173 A1 | 9/2001 | Ritchie et al. |
| 2001/0025183 A1 | 9/2001 | Shahidi et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0156466 A1 | 10/2002 | Sakurai et al. |
| 2002/0156493 A1 | 10/2002 | Houser et al. |
| 2003/0014087 A1 | 1/2003 | Fang et al. |
| 2003/0036705 A1 | 2/2003 | Hare et al. |
| 2003/0050572 A1 | 3/2003 | Brautigam et al. |
| 2003/0055443 A1 | 3/2003 | Spotnitz |
| 2003/0114851 A1 | 6/2003 | Truckai et al. |
| 2003/0144680 A1 | 7/2003 | Kellogg et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0132383 A1 | 7/2004 | Langford et al. |
| 2004/0147934 A1 | 7/2004 | Kiester |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0199193 A1 | 10/2004 | Hayashi et al. |
| 2004/0204728 A1 | 10/2004 | Haefner |
| 2004/0215132 A1 | 10/2004 | Yoon |
| 2004/0243147 A1 | 12/2004 | Lipow |
| 2004/0260300 A1 | 12/2004 | Gorensek et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0096683 A1 | 5/2005 | Ellins et al. |
| 2005/0099824 A1 | 5/2005 | Dowling et al. |
| 2005/0103819 A1 | 5/2005 | Racenet et al. |

(56) References Cited

U.S. PATENT DOCUMENTS

| | | |
|---|---|---|
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0209620 A1 | 9/2005 | Du et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261581 A1 | 11/2005 | Hughes et al. |
| 2005/0261588 A1 | 11/2005 | Makin et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0084963 A1 | 4/2006 | Messerly |
| 2006/0095046 A1 | 5/2006 | Trieu et al. |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217697 A1* | 9/2006 | Lau ................ A61B 17/29 606/29 |
| 2006/0217729 A1 | 9/2006 | Eskridge et al. |
| 2006/0224160 A1 | 10/2006 | Trieu et al. |
| 2006/0235306 A1 | 10/2006 | Cotter et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0271030 A1 | 11/2006 | Francis et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0074584 A1 | 4/2007 | Talarico et al. |
| 2007/0078458 A1 | 4/2007 | Dumbauld et al. |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0156163 A1 | 7/2007 | Davison et al. |
| 2007/0162050 A1 | 7/2007 | Sartor |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175949 A1 | 8/2007 | Shelton, IV et al. |
| 2007/0185380 A1 | 8/2007 | Kucklick |
| 2007/0191712 A1 | 8/2007 | Messerly et al. |
| 2007/0219481 A1 | 9/2007 | Babaev |
| 2007/0239028 A1 | 10/2007 | Houser et al. |
| 2007/0239101 A1 | 10/2007 | Kellogg |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2007/0288055 A1 | 12/2007 | Lee |
| 2008/0009848 A1 | 1/2008 | Paraschiv et al. |
| 2008/0013809 A1 | 1/2008 | Zhu et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114364 A1 | 5/2008 | Goldin et al. |
| 2008/0125768 A1 | 5/2008 | Tahara et al. |
| 2008/0140158 A1 | 6/2008 | Hamel et al. |
| 2008/0147092 A1 | 6/2008 | Rogge et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243106 A1 | 10/2008 | Coe et al. |
| 2008/0243162 A1 | 10/2008 | Shibata et al. |
| 2008/0245371 A1 | 10/2008 | Gruber |
| 2008/0249553 A1 | 10/2008 | Gruber et al. |
| 2008/0255423 A1 | 10/2008 | Kondo et al. |
| 2008/0262490 A1 | 10/2008 | Williams |
| 2008/0281200 A1 | 11/2008 | Voic et al. |
| 2008/0281315 A1 | 11/2008 | Gines |
| 2008/0281322 A1 | 11/2008 | Sherman et al. |
| 2008/0287948 A1 | 11/2008 | Newton et al. |
| 2009/0023985 A1 | 1/2009 | Ewers |
| 2009/0024141 A1 | 1/2009 | Stahler et al. |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0088738 A1 | 4/2009 | Guerra et al. |
| 2009/0088785 A1 | 4/2009 | Masuda |
| 2009/0112229 A1 | 4/2009 | Omori et al. |
| 2009/0118751 A1 | 5/2009 | Wiener et al. |
| 2009/0118802 A1 | 5/2009 | Mioduski et al. |
| 2009/0138006 A1 | 5/2009 | Bales et al. |
| 2009/0143799 A1 | 6/2009 | Smith et al. |
| 2009/0143800 A1 | 6/2009 | Deville et al. |
| 2009/0143806 A1 | 6/2009 | Witt et al. |
| 2009/0149801 A1 | 6/2009 | Crandall et al. |
| 2009/0163807 A1 | 6/2009 | Sliwa |
| 2009/0207923 A1 | 8/2009 | Dress |
| 2009/0216157 A1 | 8/2009 | Yamada |
| 2009/0223033 A1 | 9/2009 | Houser |
| 2009/0254077 A1 | 10/2009 | Craig |
| 2009/0254080 A1 | 10/2009 | Honda |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270899 A1 | 10/2009 | Carusillo et al. |
| 2009/0275940 A1 | 11/2009 | Malackowski et al. |
| 2009/0299141 A1 | 12/2009 | Downey |
| 2009/0318945 A1 | 12/2009 | Yoshimine et al. |
| 2009/0327715 A1 | 12/2009 | Smith et al. |
| 2010/0004508 A1 | 1/2010 | Naito et al. |
| 2010/0016785 A1 | 1/2010 | Takuma |
| 2010/0016852 A1* | 1/2010 | Manzo ................ A61B 34/71 606/46 |
| 2010/0022825 A1 | 1/2010 | Yoshie |
| 2010/0030233 A1 | 2/2010 | Whitman et al. |
| 2010/0030248 A1 | 2/2010 | Palmer et al. |
| 2010/0036370 A1 | 2/2010 | Mirel et al. |
| 2010/0042077 A1 | 2/2010 | Okada |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupré |
| 2010/0069940 A1 | 3/2010 | Miller et al. |
| 2010/0158307 A1 | 6/2010 | Kubota et al. |
| 2010/0168741 A1 | 7/2010 | Sanai et al. |
| 2010/0187283 A1 | 7/2010 | Crainich et al. |
| 2010/0222714 A1 | 9/2010 | Muir et al. |

(56) References Cited

U.S. PATENT DOCUMENTS

| | | |
|---|---|---|
| 2010/0228264 A1 | 9/2010 | Robinson et al. |
| 2010/0228284 A1* | 9/2010 | Cooper ............ A61B 17/00234 606/206 |
| 2010/0234906 A1 | 9/2010 | Koh |
| 2010/0262134 A1 | 10/2010 | Jensen et al. |
| 2010/0274160 A1 | 10/2010 | Yachi et al. |
| 2010/0280407 A1 | 11/2010 | Polster |
| 2010/0292691 A1 | 11/2010 | Brogna |
| 2010/0298743 A1 | 11/2010 | Nield et al. |
| 2010/0298851 A1 | 11/2010 | Nield |
| 2010/0331742 A1 | 12/2010 | Masuda |
| 2011/0004233 A1 | 1/2011 | Muir et al. |
| 2011/0009850 A1 | 1/2011 | Main et al. |
| 2011/0077648 A1 | 3/2011 | Lee et al. |
| 2011/0087218 A1 | 4/2011 | Boudreaux et al. |
| 2011/0112526 A1 | 5/2011 | Fritz et al. |
| 2011/0125151 A1 | 5/2011 | Strauss et al. |
| 2011/0125174 A1 | 5/2011 | Babaev |
| 2011/0144806 A1 | 6/2011 | Sandhu et al. |
| 2011/0224689 A1 | 9/2011 | Larkin et al. |
| 2011/0238065 A1 | 9/2011 | Hunt et al. |
| 2011/0257650 A1 | 10/2011 | Deville et al. |
| 2011/0270126 A1 | 11/2011 | Gunday et al. |
| 2011/0290853 A1* | 12/2011 | Shelton, IV ..... A61B 17/07207 227/177.1 |
| 2011/0290856 A1 | 12/2011 | Shelton, IV et al. |
| 2011/0295242 A1* | 12/2011 | Spivey ............. A61B 17/07207 606/1 |
| 2012/0004655 A1 | 1/2012 | Kim et al. |
| 2012/0022525 A1 | 1/2012 | Dietz et al. |
| 2012/0022530 A1 | 1/2012 | Woodruff et al. |
| 2012/0022583 A1 | 1/2012 | Sugalski et al. |
| 2012/0059289 A1 | 3/2012 | Nield et al. |
| 2012/0065628 A1 | 3/2012 | Naito |
| 2012/0071863 A1 | 3/2012 | Lee et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078278 A1 | 3/2012 | Bales, Jr. et al. |
| 2012/0080332 A1 | 4/2012 | Shelton, IV et al. |
| 2012/0101495 A1 | 4/2012 | Young et al. |
| 2012/0101501 A1 | 4/2012 | Nishimura et al. |
| 2012/0109159 A1 | 5/2012 | Jordan et al. |
| 2012/0116379 A1 | 5/2012 | Yates et al. |
| 2012/0116391 A1 | 5/2012 | Houser et al. |
| 2012/0116394 A1 | 5/2012 | Timm et al. |
| 2012/0116395 A1 | 5/2012 | Madan et al. |
| 2012/0130256 A1 | 5/2012 | Buysse et al. |
| 2012/0130365 A1 | 5/2012 | McLawhorn |
| 2012/0136354 A1 | 5/2012 | Rupp |
| 2012/0138660 A1 | 6/2012 | Shelton, IV |
| 2012/0143211 A1 | 6/2012 | Kishi |
| 2012/0150170 A1 | 6/2012 | Buysse et al. |
| 2012/0165816 A1 | 6/2012 | Kersten et al. |
| 2012/0172873 A1 | 7/2012 | Artale et al. |
| 2012/0172904 A1 | 7/2012 | Muir et al. |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199632 A1 | 8/2012 | Spivey et al. |
| 2012/0203143 A1 | 8/2012 | Sanai et al. |
| 2012/0203247 A1 | 8/2012 | Shelton, IV et al. |
| 2012/0209289 A1 | 8/2012 | Duque et al. |
| 2012/0209303 A1 | 8/2012 | Frankhouser et al. |
| 2012/0210223 A1 | 8/2012 | Eppolito |
| 2012/0215220 A1 | 8/2012 | Manzo et al. |
| 2012/0245582 A1 | 9/2012 | Kimball et al. |
| 2012/0253370 A1 | 10/2012 | Ross et al. |
| 2012/0269676 A1 | 10/2012 | Houser et al. |
| 2012/0330307 A1 | 12/2012 | Ladtkow et al. |
| 2013/0012957 A1 | 1/2013 | Shelton, IV et al. |
| 2013/0030433 A1 | 1/2013 | Heard |
| 2013/0035680 A1 | 2/2013 | Ben-Haim et al. |
| 2013/0053840 A1 | 2/2013 | Krapohl et al. |
| 2013/0072856 A1 | 3/2013 | Frankhouser et al. |
| 2013/0072857 A1 | 3/2013 | Frankhouser et al. |
| 2013/0079762 A1 | 3/2013 | Twomey et al. |
| 2013/0103023 A1 | 4/2013 | Monson et al. |
| 2013/0103024 A1 | 4/2013 | Monson et al. |
| 2013/0110145 A1 | 5/2013 | Weitzman |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0123822 A1 | 5/2013 | Wellman et al. |
| 2013/0131660 A1 | 5/2013 | Monson et al. |
| 2013/0165929 A1 | 6/2013 | Muir et al. |
| 2013/0217967 A1 | 8/2013 | Mohr et al. |
| 2013/0253498 A1 | 9/2013 | Germain et al. |
| 2013/0274734 A1 | 10/2013 | Maass et al. |
| 2013/0282021 A1* | 10/2013 | Parihar ................ A61B 17/105 606/130 |
| 2013/0282038 A1 | 10/2013 | Dannaher et al. |
| 2013/0296908 A1 | 11/2013 | Schulte et al. |
| 2013/0338661 A1 | 12/2013 | Behnke, II |
| 2013/0345689 A1 | 12/2013 | Ruddenklau et al. |
| 2014/0005640 A1 | 1/2014 | Shelton, IV et al. |
| 2014/0005653 A1 | 1/2014 | Shelton, IV et al. |
| 2014/0005656 A1 | 1/2014 | Mucilli et al. |
| 2014/0005661 A1 | 1/2014 | Shelton, IV et al. |
| 2014/0005662 A1 | 1/2014 | Shelton, IV et al. |
| 2014/0005676 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005702 A1 | 1/2014 | Timm et al. |
| 2014/0005705 A1 | 1/2014 | Weir et al. |
| 2014/0005708 A1 | 1/2014 | Shelton, IV et al. |
| 2014/0005718 A1 | 1/2014 | Shelton, IV et al. |
| 2014/0012299 A1 | 1/2014 | Stoddard et al. |
| 2014/0066962 A1 | 3/2014 | Robertson et al. |
| 2014/0087569 A1 | 3/2014 | Lee |
| 2014/0107538 A1 | 4/2014 | Wiener et al. |
| 2014/0114327 A1 | 4/2014 | Boudreaux et al. |
| 2014/0135804 A1 | 5/2014 | Weisenburgh, II et al. |
| 2014/0155921 A1 | 6/2014 | Price et al. |
| 2014/0180280 A1 | 6/2014 | Sigmon, Jr. |
| 2014/0243864 A1 | 8/2014 | Voegele et al. |
| 2014/0276970 A1 | 9/2014 | Messerly et al. |
| 2015/0045819 A1 | 2/2015 | Houser et al. |
| 2015/0066067 A1 | 3/2015 | Stulen |
| 2015/0073460 A1 | 3/2015 | Stulen |
| 2015/0112335 A1 | 4/2015 | Boudreaux et al. |
| 2015/0119914 A1 | 4/2015 | Neurohr et al. |
| 2015/0119915 A1 | 4/2015 | Neurohr et al. |
| 2015/0119916 A1 | 4/2015 | Dietz et al. |
| 2015/0123348 A1 | 5/2015 | Robertson et al. |
| 2015/0157355 A1 | 6/2015 | Price et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182251 A1 | 7/2015 | Messerly et al. |
| 2015/0182276 A1 | 7/2015 | Wiener et al. |
| 2015/0182277 A1 | 7/2015 | Wiener et al. |
| 2015/0196318 A1 | 7/2015 | Messerly et al. |
| 2015/0250495 A1 | 9/2015 | Robertson et al. |
| 2015/0257780 A1 | 9/2015 | Houser |
| 2015/0257781 A1 | 9/2015 | Houser et al. |
| 2015/0265308 A1 | 9/2015 | Houser et al. |
| 2015/0327883 A1 | 11/2015 | Messerly et al. |
| 2015/0328484 A1 | 11/2015 | Messerly et al. |
| 2015/0340586 A1 | 11/2015 | Wiener et al. |
| 2015/0351789 A1 | 12/2015 | Robertson et al. |
| 2015/0351792 A1* | 12/2015 | Houser .................. A61B 17/12 606/171 |
| 2016/0030076 A1 | 2/2016 | Faller et al. |
| 2016/0089533 A1 | 3/2016 | Turner et al. |
| 2016/0095617 A1 | 4/2016 | Price et al. |
| 2016/0106509 A1 | 4/2016 | Worrell et al. |
| 2016/0120563 A1 | 5/2016 | Messerly et al. |
| 2016/0144204 A1 | 5/2016 | Akagane |

(56) References Cited

U.S. PATENT DOCUMENTS

| | | | |
|---|---|---|---|
| 2016/0192999 A1 | 7/2016 | Stulen et al. |
| 2016/0206342 A1 | 7/2016 | Robertson et al. |
| 2016/0262786 A1 | 9/2016 | Madan et al. |
| 2016/0296249 A1 | 10/2016 | Robertson |
| 2016/0296250 A1 | 10/2016 | Olson et al. |
| 2016/0296251 A1 | 10/2016 | Olson et al. |
| 2016/0296252 A1 | 10/2016 | Olson et al. |
| 2016/0317217 A1 | 11/2016 | Batross et al. |

FOREIGN PATENT DOCUMENTS

| | | | |
|---|---|---|---|
| CN | 1233944 | A | 11/1999 |
| CN | 1253485 | A | 5/2000 |
| CN | 1634601 | A | 7/2005 |
| CN | 1640365 | A | 7/2005 |
| CN | 1694649 | A | 11/2005 |
| CN | 1922563 | A | 2/2007 |
| CN | 1951333 | A | 4/2007 |
| CN | 101040799 | A | 9/2007 |
| CN | 101467917 | A | 1/2009 |
| DE | 3904558 | A1 | 8/1990 |
| DE | 4323585 | A1 | 1/1995 |
| DE | 19608716 | C1 | 4/1997 |
| DE | 20021619 | U1 | 3/2001 |
| DE | 10042606 | A1 | 8/2001 |
| EP | 0136855 | B1 | 9/1984 |
| EP | 0171967 | A2 | 2/1986 |
| EP | 1839599 | A1 | 10/1987 |
| EP | 0336742 | A2 | 4/1989 |
| EP | 0342448 | A1 | 11/1989 |
| EP | 0424685 | B1 | 5/1991 |
| EP | 0443256 | A1 | 8/1991 |
| EP | 0456470 | A1 | 11/1991 |
| EP | 0238667 | B1 | 2/1993 |
| EP | 0598976 | A2 | 1/1994 |
| EP | 0677275 | A2 | 3/1995 |
| EP | 0482195 | B1 | 1/1996 |
| EP | 0695535 | A1 | 2/1996 |
| EP | 0741996 | A2 | 11/1996 |
| EP | 0612570 | B1 | 6/1997 |
| EP | 1108394 | A2 | 6/2001 |
| EP | 1138264 | A1 | 10/2001 |
| EP | 0908148 | B1 | 1/2002 |
| EP | 1229515 | A2 | 8/2002 |
| EP | 1285634 | A1 | 2/2003 |
| EP | 0908155 | B1 | 6/2003 |
| EP | 0705570 | B1 | 4/2004 |
| EP | 0765637 | B1 | 7/2004 |
| EP | 0870473 | B1 | 9/2005 |
| EP | 0624346 | B1 | 11/2005 |
| EP | 1594209 | A1 | 11/2005 |
| EP | 1199044 | B1 | 12/2005 |
| EP | 1609428 | A1 | 12/2005 |
| EP | 1199043 | B1 | 3/2006 |
| EP | 1433425 | B1 | 6/2006 |
| EP | 1256323 | B1 | 9/2006 |
| EP | 1698289 | A2 | 9/2006 |
| EP | 1704824 | A1 | 9/2006 |
| EP | 1749479 | A1 | 2/2007 |
| EP | 1815950 | A1 | 8/2007 |
| EP | 1844720 | A1 | 10/2007 |
| EP | 1862133 | A1 | 12/2007 |
| EP | 1875875 | A1 | 1/2008 |
| EP | 1199045 | B1 | 6/2008 |
| EP | 1964530 | A1 | 9/2008 |
| EP | 1972264 | A1 | 9/2008 |
| EP | 1974771 | A1 | 10/2008 |
| EP | 1435852 | B1 | 12/2008 |
| EP | 1498082 | B1 | 12/2008 |
| EP | 1707131 | B1 | 12/2008 |
| EP | 1997438 | A2 | 12/2008 |
| EP | 1477104 | B1 | 1/2009 |
| EP | 2014218 | A2 | 1/2009 |
| EP | 2042112 | A2 | 4/2009 |
| EP | 1832259 | B1 | 6/2009 |
| EP | 2074959 | A1 | 7/2009 |
| EP | 2106758 | A1 | 10/2009 |
| EP | 2111813 | A1 | 10/2009 |
| EP | 2200145 | A1 | 6/2010 |
| EP | 1214913 | B1 | 7/2010 |
| EP | 2238938 | A1 | 10/2010 |
| EP | 2298154 | A2 | 3/2011 |
| EP | 1510178 | B1 | 6/2011 |
| EP | 1946708 | B1 | 6/2011 |
| EP | 2305144 | A1 | 6/2011 |
| EP | 2335630 | A1 | 6/2011 |
| EP | 1502551 | B1 | 7/2011 |
| EP | 2361562 | A1 | 8/2011 |
| EP | 2365608 | A2 | 9/2011 |
| EP | 2420197 | A2 | 2/2012 |
| EP | 2422721 | A2 | 2/2012 |
| EP | 1927321 | B1 | 4/2012 |
| EP | 2510891 | A1 | 10/2012 |
| EP | 2316359 | B1 | 3/2013 |
| EP | 1586275 | B1 | 5/2013 |
| EP | 1616529 | B1 | 9/2013 |
| EP | 2583633 | B1 | 10/2014 |
| EP | 2113210 | B1 | 3/2016 |
| GB | 1482943 | A | 8/1977 |
| GB | 2032221 | | 4/1980 |
| GB | 2317566 | A | 4/1998 |
| GB | 2379878 | B | 11/2004 |
| GB | 2447767 | B | 8/2011 |
| JP | S 50-100891 | A | 8/1975 |
| JP | S 59-68513 | U | 5/1984 |
| JP | S 59141938 | A | 8/1984 |
| JP | 62-221343 | A | 9/1987 |
| JP | S 62-227343 | A | 10/1987 |
| JP | S 62-292154 | A | 12/1987 |
| JP | 63-109386 | A | 5/1988 |
| JP | 63-315049 | A | 12/1988 |
| JP | H 01-151452 | A | 6/1989 |
| JP | H 01-198540 | A | 8/1989 |
| JP | 02-71510 | U | 5/1990 |
| JP | 2-286149 | A | 11/1990 |
| JP | H 02-292193 | A | 12/1990 |
| JP | H 03-37061 | A | 2/1991 |
| JP | 04-25707 | U | 2/1992 |
| JP | H 04-64351 | A | 2/1992 |
| JP | 4-30508 | U | 3/1992 |
| JP | H 04-150847 | A | 5/1992 |
| JP | H 04-152942 | A | 5/1992 |
| JP | 05-095955 | A | 4/1993 |
| JP | H 05-115490 | A | 5/1993 |
| JP | H 06-070938 | A | 3/1994 |
| JP | 6-104503 | A | 4/1994 |
| JP | 6-507081 | A | 8/1994 |
| JP | H 06-217988 | A | 8/1994 |
| JP | H 7-508910 | A | 10/1995 |
| JP | 7-308323 | A | 11/1995 |
| JP | 8-24266 | A | 1/1996 |
| JP | 8-275951 | A | 10/1996 |
| JP | H 08-299351 | A | 11/1996 |
| JP | H 08-336545 | A | 12/1996 |
| JP | H 09-503146 | A | 3/1997 |
| JP | H 09-135553 | A | 5/1997 |
| JP | H 09-140722 | A | 6/1997 |
| JP | H 10-005237 | A | 1/1998 |
| JP | 10-295700 | A | 11/1998 |
| JP | H 11-501543 | A | 2/1999 |
| JP | H 11-128238 | A | 5/1999 |
| JP | H 11-192235 | A | 7/1999 |
| JP | 11-253451 | A | 9/1999 |
| JP | H 11-318918 | A | 11/1999 |
| JP | 2000-041991 | A | 2/2000 |
| JP | 2000-070279 | A | 3/2000 |
| JP | 2000-210299 | A | 8/2000 |
| JP | 2000-271145 | A | 10/2000 |
| JP | 2000-287987 | A | 10/2000 |
| JP | 2001-029353 | A | 2/2001 |
| JP | 2001-502216 | A | 2/2001 |
| JP | 2003612 | A | 6/2001 |
| JP | 2001-309925 | A | 11/2001 |
| JP | 2002-186901 | A | 7/2002 |

(56) References Cited

FOREIGN PATENT DOCUMENTS

| | | |
|---|---|---|
| JP | 2002-204808 A | 7/2002 |
| JP | 2002-238919 A | 8/2002 |
| JP | 2002-263579 A | 9/2002 |
| JP | 2002-301086 A | 10/2002 |
| JP | 2002-306504 A | 10/2002 |
| JP | 2002-330977 A | 11/2002 |
| JP | 2002-542690 A | 12/2002 |
| JP | 2003-000612 A | 1/2003 |
| JP | 2003-010201 | 1/2003 |
| JP | 2003-510158 A | 3/2003 |
| JP | 2003-116870 A | 4/2003 |
| JP | 2003-126104 A | 5/2003 |
| JP | 2003-126110 A | 5/2003 |
| JP | 2003-310627 A | 5/2003 |
| JP | 2003-530921 A | 10/2003 |
| JP | 2003-339730 A | 12/2003 |
| JP | 2004-129871 A | 4/2004 |
| JP | 2004-147701 A | 5/2004 |
| JP | 2005027026 A | 1/2005 |
| JP | 2005-040222 A | 2/2005 |
| JP | 2005-066316 A | 3/2005 |
| JP | 2005-074088 A | 3/2005 |
| JP | 2005-507679 A | 3/2005 |
| JP | 2005-534451 A | 11/2005 |
| JP | 2006-6410 A | 1/2006 |
| JP | 2006-512149 A | 4/2006 |
| JP | 2006-116194 A | 5/2006 |
| JP | 2006-158525 A | 6/2006 |
| JP | 2006-218296 A | 8/2006 |
| JP | 2006217716 A | 8/2006 |
| JP | 2006-288431 A | 10/2006 |
| JP | 2007-050181 A | 3/2007 |
| JP | 2007-229454 A | 9/2007 |
| JP | 2007-527747 A | 10/2007 |
| JP | 2008-036390 A | 2/2008 |
| JP | 2008-508065 A | 3/2008 |
| JP | 2008-119250 A | 5/2008 |
| JP | 2008-521503 A | 6/2008 |
| JP | D1339835 S | 8/2008 |
| JP | 2008-212679 A | 9/2008 |
| JP | 2008-536562 A | 9/2008 |
| JP | 2008-284374 A | 11/2008 |
| JP | 2009-511206 A | 3/2009 |
| JP | 2009-517181 A | 4/2009 |
| JP | 4262923 B2 | 5/2009 |
| JP | 2009-523567 A | 6/2009 |
| JP | 2009-148557 A | 7/2009 |
| JP | 2009-236177 A | 10/2009 |
| JP | 2009-254819 A | 11/2009 |
| JP | 2010-000336 A | 1/2010 |
| JP | 2010-009686 A | 1/2010 |
| JP | 2010-514923 A | 5/2010 |
| JP | 2010-121865 A | 6/2010 |
| JP | 2010-534522 A | 11/2010 |
| JP | 2010-540186 A | 12/2010 |
| JP | 2011-505198 A | 2/2011 |
| JP | 2012-235658 A | 11/2012 |
| JP | 5208761 B2 | 6/2013 |
| JP | 5714508 B2 | 5/2015 |
| JP | 5836543 B1 | 12/2015 |
| RU | 2154437 C1 | 8/2000 |
| RU | 22035 U1 | 3/2002 |
| WO | WO 92/22259 A2 | 12/1992 |
| WO | WO 93/08757 A1 | 5/1993 |
| WO | WO 93/14708 A1 | 8/1993 |
| WO | WO 93/16646 A1 | 9/1993 |
| WO | WO 93/20877 A1 | 10/1993 |
| WO | WO 94/21183 A1 | 9/1994 |
| WO | WO 94/24949 A1 | 11/1994 |
| WO | WO 95/09572 A1 | 4/1995 |
| WO | WO 95/34259 A1 | 12/1995 |
| WO | WO 96/30885 A1 | 10/1996 |
| WO | WO 96/39086 A1 | 12/1996 |
| WO | WO 98/16156 A1 | 4/1998 |
| WO | WO 98/26739 A1 | 6/1998 |
| WO | WO 98/35621 A1 | 8/1998 |
| WO | WO 98/37815 A1 | 9/1998 |
| WO | WO 98/47436 A1 | 10/1998 |
| WO | WO 99/20213 A1 | 4/1999 |
| WO | WO 99/52489 A1 | 10/1999 |
| WO | WO 00/64358 A2 | 11/2000 |
| WO | WO 00/74585 A2 | 12/2000 |
| WO | WO 01/24713 A1 | 4/2001 |
| WO | WO 01/54590 A1 | 8/2001 |
| WO | WO 01/67970 A1 | 9/2001 |
| WO | WO 01/95810 A2 | 12/2001 |
| WO | WO 02/24080 A2 | 3/2002 |
| WO | WO 02/38057 A1 | 5/2002 |
| WO | WO 02/062241 A1 | 8/2002 |
| WO | WO 03/082133 A1 | 10/2003 |
| WO | WO 2004/012615 A1 | 2/2004 |
| WO | WO 2004/026104 A2 | 4/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/037095 A2 | 5/2004 |
| WO | WO 2004/060141 A2 | 7/2004 |
| WO | WO 2004/098426 A1 | 11/2004 |
| WO | WO 2004/112618 A2 | 12/2004 |
| WO | WO 2005/117735 A1 | 12/2005 |
| WO | WO 2005/122917 A1 | 12/2005 |
| WO | WO 2006/012797 A1 | 2/2006 |
| WO | WO 2006/042210 A2 | 4/2006 |
| WO | WO 2006/058223 A2 | 6/2006 |
| WO | WO 2006/063199 A2 | 6/2006 |
| WO | WO 2006/083988 A1 | 8/2006 |
| WO | WO 2006/101661 A2 | 9/2006 |
| WO | WO 2006/119139 A2 | 11/2006 |
| WO | WO 2006/119376 A2 | 11/2006 |
| WO | WO 2006/129465 A1 | 12/2006 |
| WO | WO 2007/008703 A2 | 1/2007 |
| WO | WO 2007/008710 A2 | 1/2007 |
| WO | WO 2007/038538 A1 | 4/2007 |
| WO | WO 2007/040818 A1 | 4/2007 |
| WO | WO 2007/047380 A2 | 4/2007 |
| WO | WO 2007/047531 A2 | 4/2007 |
| WO | WO 2007/056590 A1 | 5/2007 |
| WO | WO 2007/087272 A2 | 8/2007 |
| WO | WO 2007/143665 A2 | 12/2007 |
| WO | WO 2008/016886 A2 | 2/2008 |
| WO | WO 2008/042021 A1 | 4/2008 |
| WO | WO 2008/049084 A2 | 4/2008 |
| WO | WO 2008/051764 A2 | 5/2008 |
| WO | WO 2008/089174 A2 | 7/2008 |
| WO | WO 2008/118709 A1 | 10/2008 |
| WO | WO 2008/130793 A1 | 10/2008 |
| WO | WO 2009/010565 A1 | 1/2009 |
| WO | WO 2009/018067 A1 | 2/2009 |
| WO | WO 2009/018406 A2 | 2/2009 |
| WO | WO 2009/027065 A1 | 3/2009 |
| WO | WO 2009/046234 A2 | 4/2009 |
| WO | WO 2009/073402 A2 | 6/2009 |
| WO | WO 2009/120992 A2 | 10/2009 |
| WO | WO 2010/017149 A1 | 2/2010 |
| WO | WO 2010/068783 A1 | 6/2010 |
| WO | WO 2011/008672 A2 | 1/2011 |
| WO | WO 2011/052939 A2 | 5/2011 |
| WO | WO 2011/060031 A1 | 5/2011 |
| WO | WO 2011/100321 A2 | 8/2011 |
| WO | WO 2011/144911 A1 | 11/2011 |
| WO | WO 2012/061722 A2 | 5/2012 |
| WO | WO 2012/128362 A1 | 9/2012 |
| WO | WO 2012/135705 A1 | 10/2012 |
| WO | WO 2012/135721 A1 | 10/2012 |
| WO | WO 2013/018934 A1 | 2/2013 |
| WO | WO 2013/062978 A2 | 5/2013 |
| WO | WO 2014/092108 A1 | 6/2014 |
| WO | WO 2016/009921 A1 | 12/2016 |

OTHER PUBLICATIONS

Written Opinion for PCT/US2013/024736, dated May 15, 2013 (5 pages).

(56) References Cited

OTHER PUBLICATIONS

*Technology Overview*, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., "Fundamentals of Heat and Mass Transfer", Wiley, New York (1990). (Book—not attached).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in *Medical Infrared Imaging*, N. A. Diakides and J. D. Bronzino, Eds. (2008).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Covidien 501(k) Summary Sonicision, dated Feb. 24, 2011 (7 pages).
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
U.S. Appl. No. 13/751,680, filed Jan. 28, 2013.
International Preliminary Report on Patentability for PCT/US2013/024736, dated Aug. 12, 2014 (6 pages).

\* cited by examiner

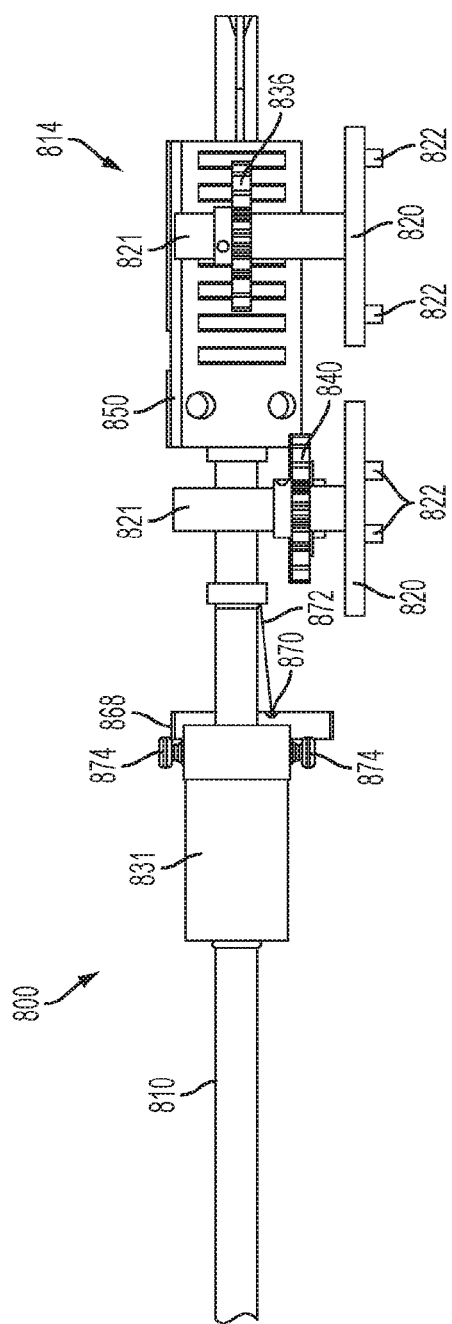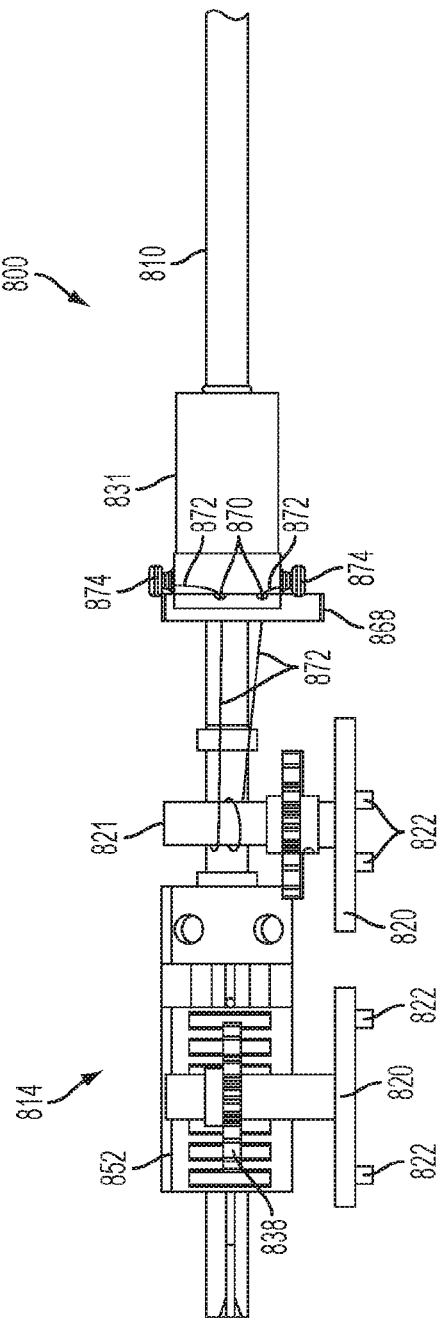
FIG. 61
FIG. 62

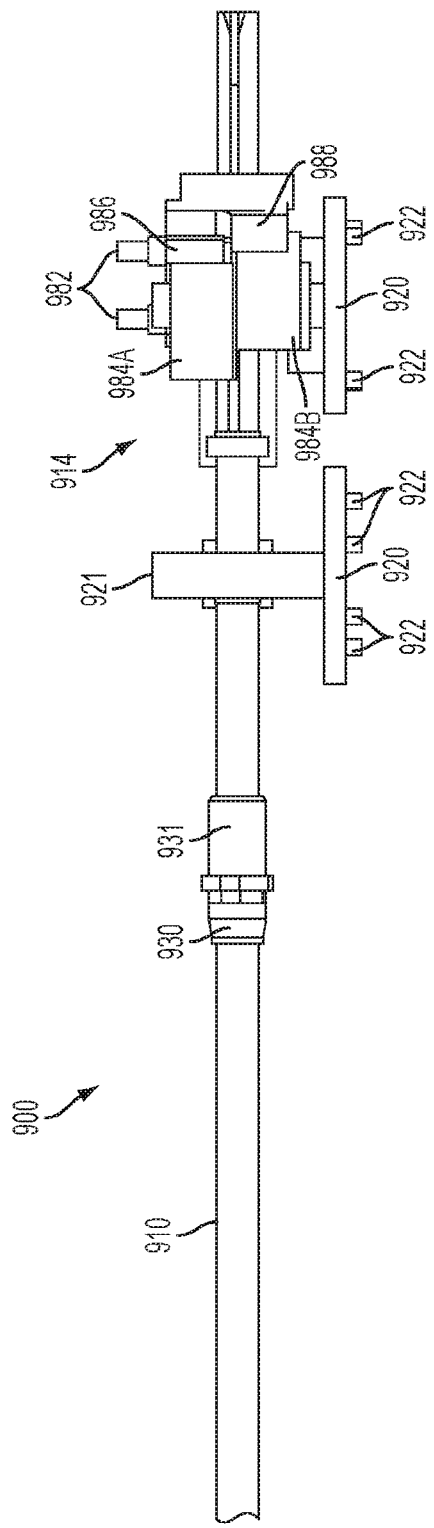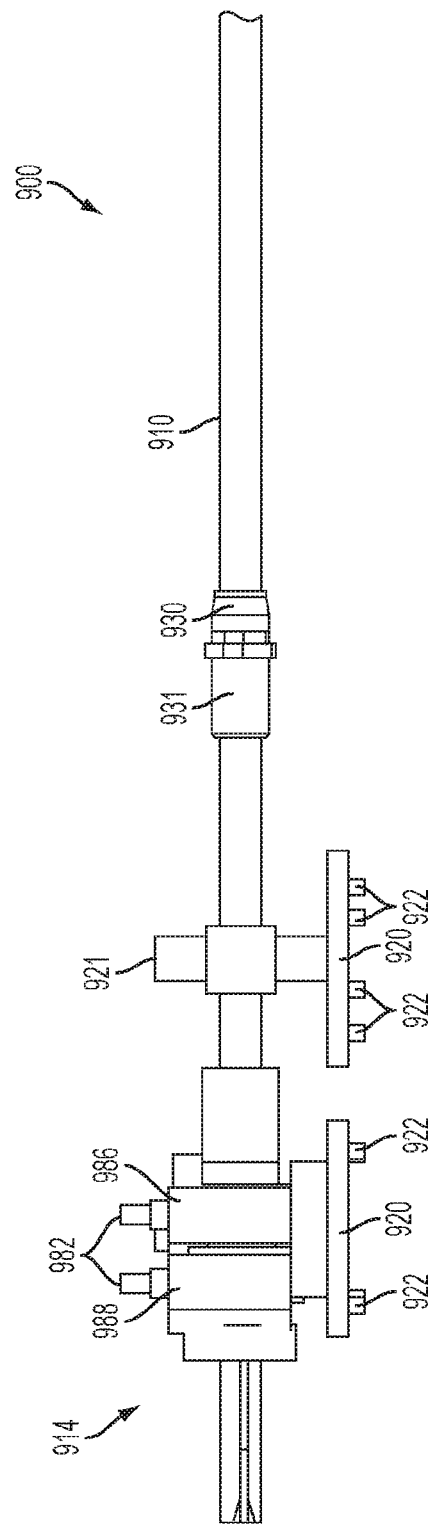

ROBOTICALLY CONTROLLED SURGICAL INSTRUMENT

CROSS-REFERENCE TO RELATED APPLICATION

This application is a divisional application claiming priority under 35 U.S.C. § 121 to U.S. patent application Ser. No. 13/760,560, entitled ROBOTICALLY CONTROLLED SURGICAL INSTRUMENT, filed Feb. 6, 2013, which claims the benefit under 35 U.S.C. § 119(e) of U.S. Provisional Patent Application Ser. No. 61/597,603, entitled ROBOTICALLY CONTROLLED SURGICAL INSTRUMENT, filed Feb. 10, 2012, the entire disclosures of which are hereby incorporated by reference herein.

BACKGROUND

The present disclosure relates generally to the field of robotic surgery. In particular, the present disclosure relates to, although not exclusively, robotically controlled surgical instruments. More particularly, the present disclosure relates to, although not exclusively, robotically controlled electrosurgical instruments having robotically controlled articulation features for robotically articulating the surgical instrument.

Many surgical procedures require cutting or ligating blood vessels or other internal tissue. Many surgical procedures are performed using minimally invasive techniques where a hand-held instrument is used by the surgeon to perform the cutting or ligating.

Electrosurgical medical instruments generally include an end effector having an electrical contact, a radio frequency (RF) generation circuit for generating an RF drive signal and to provide the RF drive signal to the at least one electrical contact where the RF generation circuit also includes a resonant circuit. The RF circuit includes circuitry to generate a cyclically varying signal, such as a square wave signal, from a direct current (DC) energy source and the resonant circuit is configured to receive the cyclically varying signal from the switching circuitry. The DC energy source is generally provided by one or more batteries that can be mounted in a housing portion of the instrument, for example.

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; and U.S. patent application Ser. No. 13/151,181, entitled "Motor Driven Electrosurgical Device with Mechanical and Electrical Feedback," filed Jun. 2, 2011, the disclosure of which is incorporated by reference herein.

In addition, a variety of surgical instruments include a shaft having an articulation section, providing enhanced positioning capabilities for an end effector that is located distal to the articulation section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

SUMMARY

In one embodiment, a robotically controlled surgical tool is provided. The surgical tool comprises a tool mounting portion comprising a tool mounting housing, a tool mounting plate, and a coupler to couple a shaft assembly comprising an articulation section to the tool mounting portion. An articulation mechanism is configured to receive a proximal end of the shaft assembly to articulate the articulation section of the shaft assembly. The articulation mechanism comprises a cam mechanism operative to articulate the articulation section of the shaft assembly. An interface mechanically and electrically couples the tool mounting portion to a manipulator.

FIGURES

FIG. 61 illustrates a side view of one embodiment of the surgical tool shown in FIG. 44 with the tool mounting housing and the tool mounting plate removed.

FIG. 62 illustrates a side view of one embodiment of the surgical tool shown in FIG. 44 with the tool mounting housing and the tool mounting plate removed.

FIG. 80 illustrates a side view of one embodiment of the surgical tool shown in FIG. 63 with the tool mounting housing and the tool mounting plate removed.

FIG. 81 illustrates a side view of one embodiment of the surgical tool shown in FIG. 63 with the tool mounting housing and the tool mounting plate removed.

DESCRIPTION

Figure 1:
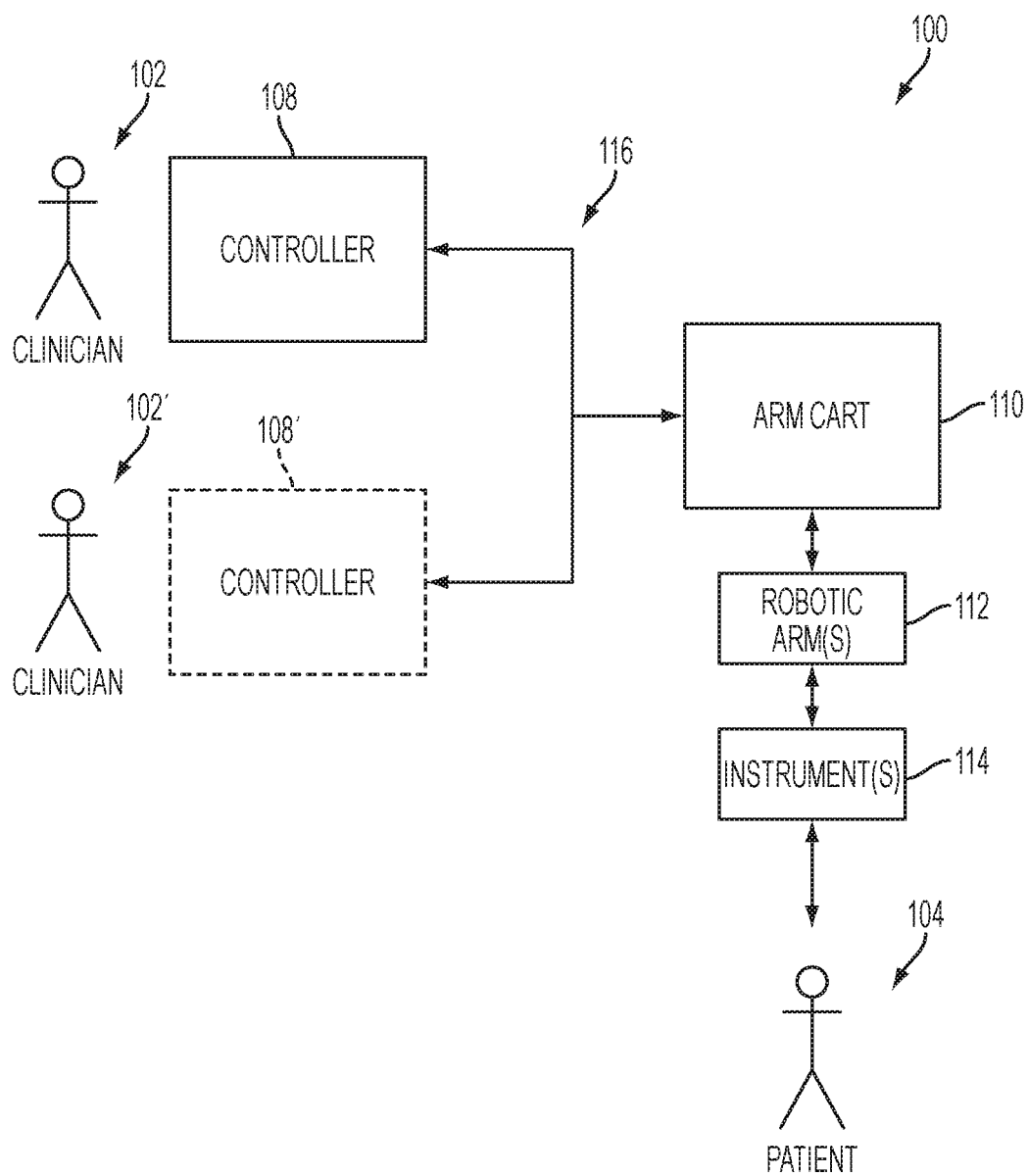
FIG. 1 illustrates one embodiment of a robotic surgical system in block diagram form.

Before explaining various embodiments of robotically controlled surgical instruments in detail, it should be noted that the illustrative embodiments are not limited in application or use to the details of construction and arrangement of parts illustrated in the accompanying drawings and description. It will be appreciated that the illustrative embodiments may be implemented or incorporated in other embodiments, variations and modifications, and may be practiced or carried out in various ways. Further, unless otherwise indicated, the terms and expressions employed herein have been chosen for the purpose of describing the illustrative embodiments for the convenience of the reader and are not for the purpose of limitation thereof.

Further, it is understood that any one or more of the following-described embodiments, expressions of embodiments, and/or examples, can be combined with any one or more of the other following-described embodiments, expressions of embodiments, and/or examples.

The present disclosure provides various embodiments of robotic surgery apparatuses, systems, and methods. In particular, the present disclosure provides various embodiments of robotically controlled surgical instruments. More particularly, the present disclosure provides various embodiments of robotically controlled electrosurgical and/or ultrasonic instruments comprising robotically controlled articulation features for robotically articulating the surgical instrument.

For clarity of disclosure, the terms "proximal" and "distal" are defined herein relative to a robotic surgical tool comprising a proximal housing having an interface which mechanically and electrically couples the surgical tool to a robotic manipulator and a distal surgical end effector. The term "proximal" refers the position of an element closer to the housing and the term "distal" refers to the position of an element closer to the surgical end effector and further away from the housing.

Many robotic surgical procedures require cutting or ligating blood vessels or other vascular tissue. With minimally invasive robotic surgery, surgical operations are performed through a small incision in the patient's body. As a result of the limited space, often difficulties arise in controlling bleeding when clamping and/or tying-off transected blood vessels. By utilizing electrosurgical forceps, a robotic surgical tool can cauterize, coagulate/desiccate, and/or simply reduce or slow bleeding by robotically controlling the electrosurgical energy applied through jaw members of the robotically controlled electrosurgical forceps, otherwise referred to as clamp arms.

Over the years a variety of minimally invasive robotic (or "telesurgical") systems have been developed to increase surgical dexterity as well as to permit a surgeon to operate on a patient in an intuitive manner. Robotic surgical systems can be used with many different types of surgical instruments including, for example, ultrasonic instruments and/or electrosurgical instruments, as described herein. Example robotic systems include those manufactured by Intuitive Surgical, Inc., of Sunnyvale, Calif., U.S.A. Such systems, as well as robotic systems from other manufacturers, are disclosed in the following U.S. patents which are each herein incorporated by reference in their respective entirety: U.S. Pat. No. 5,792,135, entitled "Articulated Surgical Instrument For Performing Minimally Invasive Surgery With Enhanced Dexterity and Sensitivity", U.S. Pat. No. 6,231,565, entitled "Robotic Arm DLUS For Performing Surgical Tasks", U.S. Pat. No. 6,783,524, entitled "Robotic Surgical Tool With Ultrasound Cauterizing and Cutting Instrument", U.S. Pat. No. 6,364,888, entitled "Alignment of Master and Slave In a Minimally Invasive Surgical Apparatus", U.S. Pat. No. 7,524,320, entitled "Mechanical Actuator Interface System For Robotic Surgical Tools", U.S. Pat. No. 7,691,098, entitled Platform Link Wrist Mechanism", U.S. Pat. No. 7,806,891, entitled "Repositioning and Reorientation of Master/Slave Relationship in Minimally Invasive Telesurgery", and U.S. Pat. No. 7,824,401, entitled "Surgical Tool With Wristed Monopolar Electrosurgical End Effectors". Many of such systems, however, have in the past been unable to generate the magnitude of forces required to effectively cut and fasten tissue.

FIG. 1 illustrates one embodiment of a robotic surgical system in block diagram form. FIGS. 1-5 illustrate the structure and operation of several example robotic surgical systems and components thereof. FIG. 1 is a block diagram of an example robotic surgical system 100. The system 100 comprises at least one controller 108 and at least one arm cart 110. The arm cart 110 may be mechanically and/or electrically coupled to one or more robotic manipulators or arms 112. Each of the robotic arms 112 may comprise one or more surgical instruments 114 for performing various surgical tasks on a patient 104. Operation of the arm cart 110, including the arms 112 and instruments 114 may be directed by a clinician 102 from a controller 108. In some embodiments, a second controller 108', operated by a second clinician 102' may also direct operation of the arm cart 110 in conjunction with the first clinician 102. For example, each of the clinicians 102, 102' may control different arms 112 of the cart or, in some cases, complete control of the arm cart 110 may be passed between the clinicians 102, 102'. In some embodiments, additional arm carts (not shown) may be utilized on the patient 104. These additional arm carts may be controlled by one or more of the controllers 108, 108'. The arm cart(s) 110 and the controllers 108, 108' may be in communication with one another via a communications link 116, which may be any suitable type of wired or wireless communications link carrying any suitable type of signal (e.g., electrical, optical, infrared, etc.) according to any suitable communications protocol. The communications link 116 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Example implementations of robotic surgical systems, such as the system 100, are disclosed in U.S. Pat. No. 7,524,320, the disclosure of which is herein incorporated by reference. Thus, various particularities of such devices will not be described in detail herein beyond that which may be necessary to understand various embodiments and forms of the various embodiments of robotic surgery apparatuses, systems, and methods disclosed herein.

Figure 2:
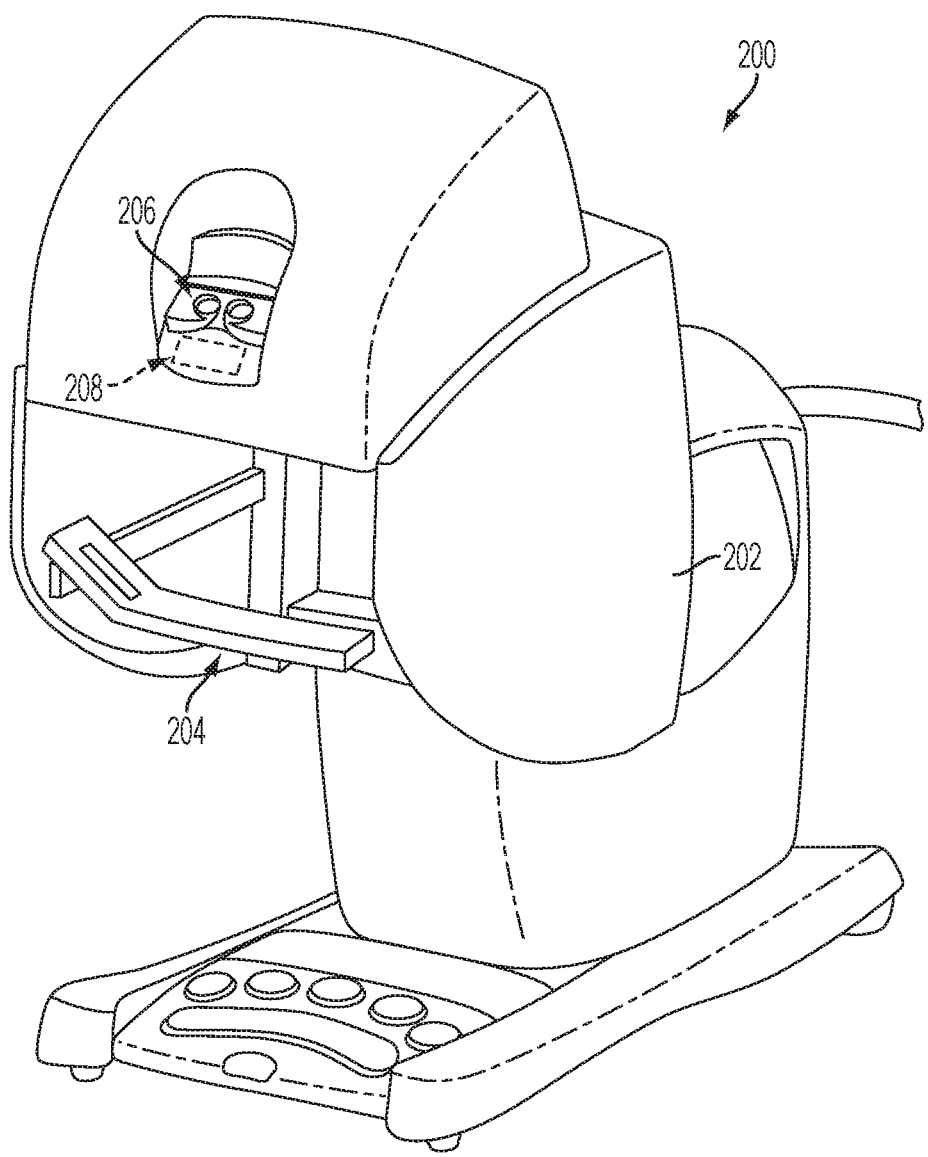
FIG. 2 illustrates one embodiment of a master controller that may be used in connection with a robotic arm slave cart of the type depicted in FIG. 3.
Figure 3:
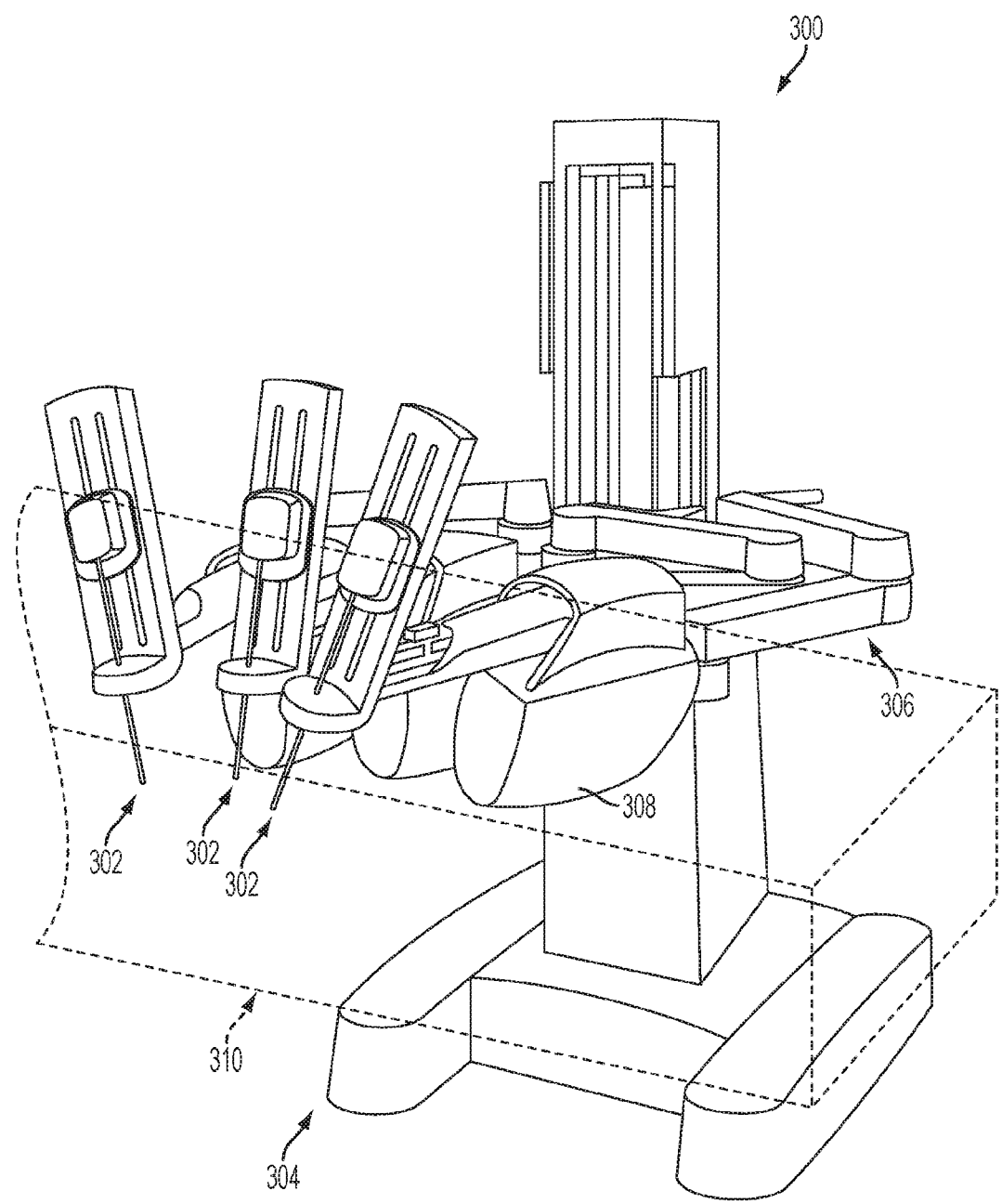
FIG. 3 illustrates one embodiment of robotic arm cart 300 configured to actuate a plurality of surgical tools.

FIG. 2 illustrates one embodiment of a master controller that may be used in connection with a robotic arm slave cart of the type depicted in FIG. 3. In one embodiment, a master controller 202 and a robotic arm slave cart 300, as well as their respective components and control systems are collectively referred to herein as a robotic system 200. Examples of such systems and devices are disclosed in U.S. Pat. No. 7,524,320, which is herein incorporated by reference. Thus, various details of such devices will not be described in detail herein beyond that which may be necessary to understand various embodiments and forms of the present invention. As is known, the master controller 202 generally includes master controllers (generally represented as 204 in FIG. 2), which are grasped by the surgeon and manipulated in space while the surgeon views the procedure via a stereo display 206. The master controllers 202 generally comprise manual input devices which preferably move with multiple degrees of freedom, and which often further have an actuatable handle for actuating tools (for example, for closing grasping saws, applying an electrical potential to an electrode, or the like). Other arrangements may provide the surgeon with a feed back meter 208 that may be viewed through the display 206 and provide the surgeon with a visual indication of the amount of force being applied to the cutting instrument or dynamic clamping member. Other sensor arrangements may be employed to provide the master controller 202 with an indication as to whether a staple cartridge has been loaded into the end effector, whether the anvil has been moved to a closed position prior to firing, for example.

FIG. 3 illustrates one embodiment of robotic arm cart configured to actuate a plurality of surgical tools. As shown in FIG. 3, in one form, the robotic arm cart 300 is configured to actuate a plurality of surgical tools, generally designated as 302. Various robotic surgery systems and methods employing master controller and robotic arm cart arrangements are disclosed in U.S. Pat. No. 6,132,368, entitled "Multi-Component Telepresence System and Method," the full disclosure of which is incorporated herein by reference. In various forms, the robotic arm cart 300 includes a base 304 from which, in the illustrated embodiment, three surgical tools 302 are supported. In various forms, the surgical tools 302 are each supported by a series of manually articulatable linkages, generally referred to as set-up joints 306, and a robotic manipulator 308. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 300. The cart 300 will generally have dimensions suitable for transporting the cart 300 between operating rooms. The cart 300 may be configured to typically fit through standard operating room doors and onto standard hospital elevators. In various forms, the cart 300 would preferably have a weight and include a wheel (or other transportation) system that allows the cart 300 to be positioned adjacent an operating table by a single attendant. In various embodiments, an automated reloading system including a base portion may be strategically located within a work envelope 310 of the robotic arm cart 300 of the robotic system 200.

Figure 4:
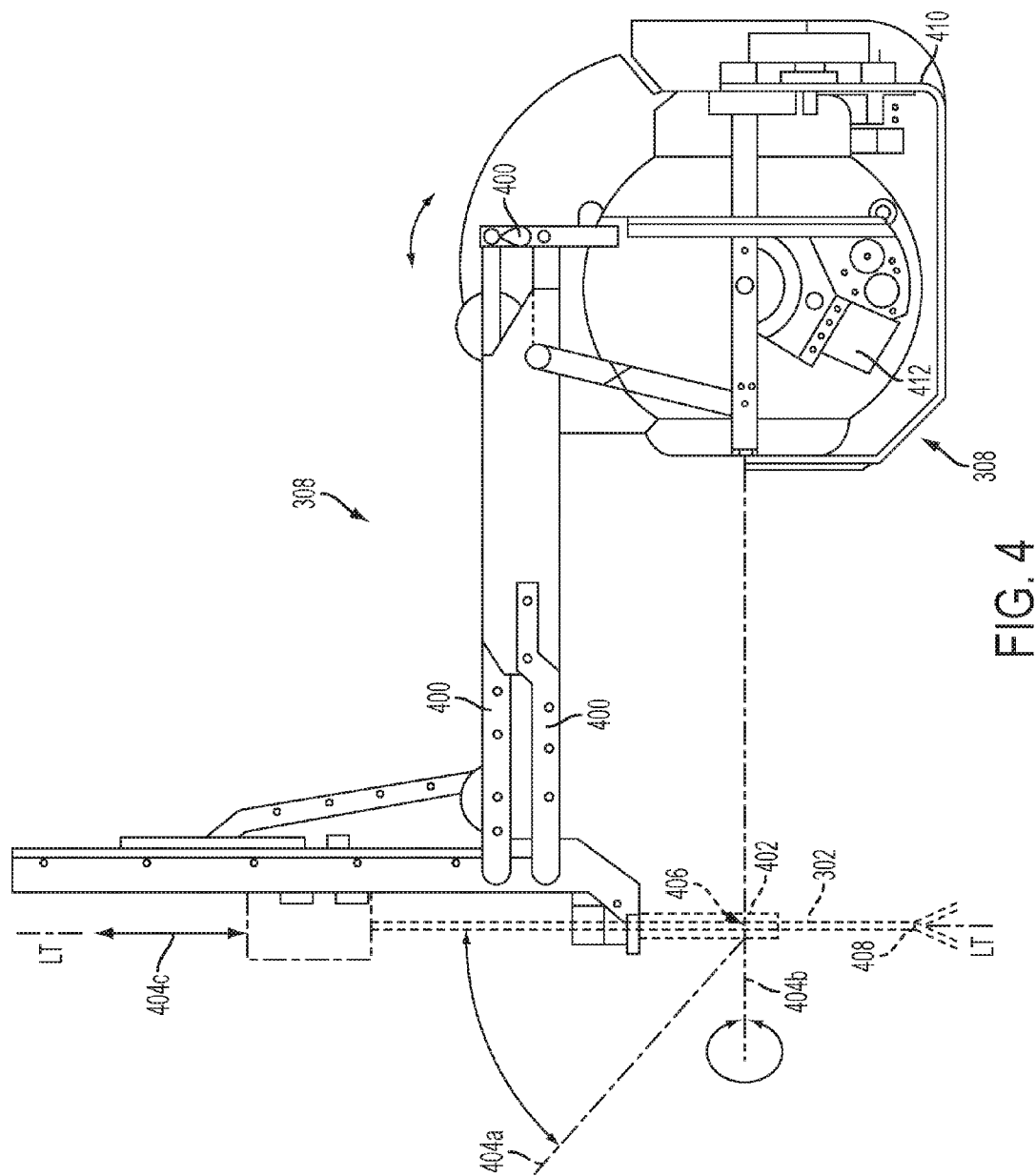
FIG. 4 illustrates one embodiment of a robotic manipulator that may include a linkage to constrain movement of a surgical tool.

FIG. 4 illustrates one embodiment of a robotic manipulator that may include a linkage to constrain movement of a surgical tool. Referring now to FIG. 4, in at least one embodiment, the robotic manipulators 308 may include a linkage 400 that constrains movement of the surgical tool 302. In various embodiments, the linkage 400 includes rigid links coupled together by rotational joints in a parallelogram arrangement so that the surgical tool 302 rotates around a point in space 402, as more fully described in issued U.S. Pat. No. 5,817,084, the entire disclosure is herein incorporated by reference. The parallelogram arrangement constrains rotation to pivoting about an axis 404a, sometimes called the pitch axis. The links supporting the parallelogram linkage are pivotally mounted to set-up joints 306 (FIG. 3) so that the surgical tool 302 further rotates about an axis 404b, sometimes called the yaw axis. The pitch and yaw axes 404a, 404b intersect at the remote center 406, which is aligned along a shaft 408 of the surgical tool 302. The surgical tool 302 may have further degrees of driven freedom as supported by manipulator 308, including sliding motion of the surgical tool 302 along the longitudinal tool axis "LT-LT". As the surgical tool 302 slides along the tool axis LT-LT relative to the manipulator 308 (arrow 404c), the remote center 406 remains fixed relative to a base 410 of the manipulator 308. Hence, the entire manipulator 308 is generally moved to re-position the remote center 406. The linkage 400 of the manipulator 308 is driven by a series of motors 412. These motors 412 actively move the linkage 400 in response to commands from a processor of a control system. The motors 412 are also may be employed to manipulate the surgical tool 302.

Figure 5:
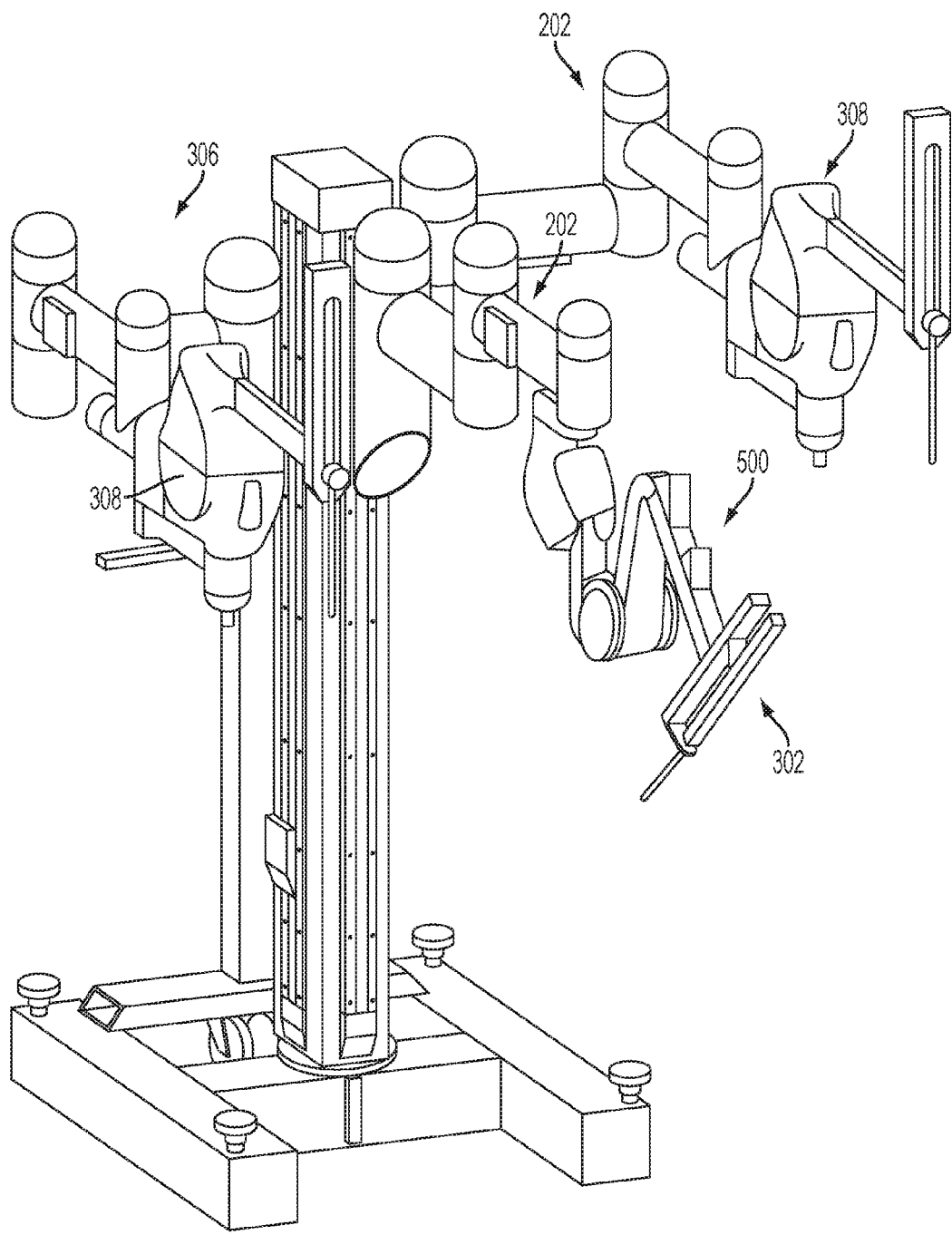
FIG. 5 illustrates one embodiment of an alternative set-up joint structure.

FIG. 5 illustrates one embodiment of an alternative set-up joint structure. In this embodiment, a surgical tool 302 is supported by an alternative manipulator structure 500 between two tissue manipulation tools. Those of ordinary skill in the art will appreciate that various embodiments of the present invention may incorporate a wide variety of alternative robotic structures, including those described in U.S. Pat. No. 5,878,193, entitled "Automated Endoscope System For Optimal Positioning," the full disclosure of which is incorporated herein by reference. Additionally, while the data communication between a robotic component and the processor of the robotic surgical system is primarily described herein with reference to communication between the surgical tool 302 and the master controller 202 (FIG. 2), it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Additional surgical instruments that may be used in the robotic system 200 are described in the following commonly assigned U.S. patent applications: (1) U.S. Patent Application US2013/0012957 filed Feb. 9, 2012, published Jan. 10, 2013, entitled "AUTOMATED END EFFECTOR COMPONENT RELOADING SYSTEM FOR USE WITH A ROBOTIC SYSTEM"; (2) U.S. Patent Application US2012/0199630 filed Feb. 9, 2012, published Aug. 9, 2012, entitled "ROBOTICALLY-CONTROLLED SURGICAL INSTRUMENT WITH FORCE-FEEDBACK CAPABILITIES"; (3) U.S. Patent Application US2012/0132450 filed Feb. 9, 2012, published May 31, 2012, entitled "SHIFTABLE DRIVE INTERFACE FOR ROBOTICALLY-CONTROLLED SURGICAL TOOL"; (4) U.S. Patent Application US2012/0199633 filed Feb. 9, 2012, published Aug. 9, 2012, entitled "SURGICAL STAPLING INSTRUMENTS WITH CAM-DRIVEN STAPLE DEPLOYMENT ARRANGEMENTS"; (5) U.S. Patent Application US2012/0199631, filed Feb. 9, 2012, published Aug. 9, 2012, entitled "ROBOTICALLY-CONTROLLED MOTORIZED SURGICAL END EFFECTOR SYSTEM WITH ROTARY ACTUATED CLOSURE SYSTEMS HAVING VARIABLE ACTUATION SPEEDS"; (6) U.S. Patent Application US2012/0199632, filed Feb. 9, 2012, published Aug. 9, 2012, entitled "ROBOTICALLY-CONTROLLED SURGICAL INSTRUMENT WITH SELECTIVELY ARTICULATABLE END EFFECTOR"; (7) U.S. Patent Application US2012/0203247, filed Feb. 9, 2012, published Aug. 9, 2012, entitled "ROBOTICALLY-CONTROLLED SURGICAL END EFFECTOR SYSTEM"; (8) U.S. Patent Application US2012/0211546, filed Feb. 9, 2012, published Aug. 23, 2012, entitled "DRIVE INTERFACE FOR OPERATIVELY COUPLING A MANIPULATABLE SURGICAL TOOL TO A ROBOT"; (9) U.S. Patent Application US2012/0138660, filed Feb. 9, 2012, published Jun. 7, 2012, entitled "ROBOTICALLY-CONTROLLED CABLE-BASED SURGICAL END EFFECTORS"; and (10) U.S. Patent Application US2012/0205421, filed Feb. 9, 2012, published Aug. 16, 2012, entitled "ROBOTICALLY-CONTROLLED SURGICAL END EFFECTOR SYSTEM WITH ROTARY ACTUATED CLOSURE SYSTEMS"; the disclosure of each of these applications is herein incorporated by reference in its entirety.

Figure 6:
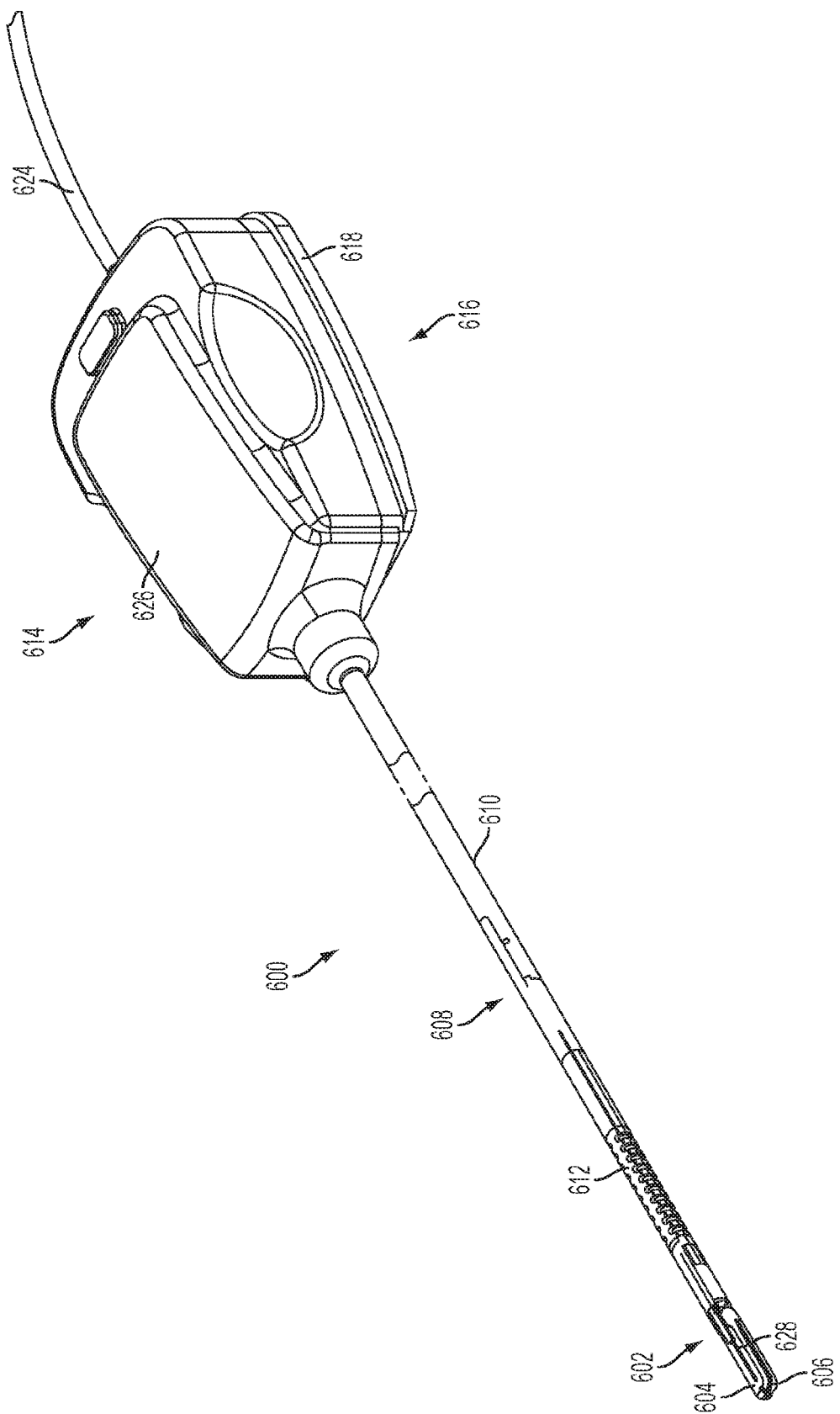
FIG. 6 illustrates a perspective view of one embodiment of a surgical tool that is well-adapted for use with a robotic system.
Figure 7:
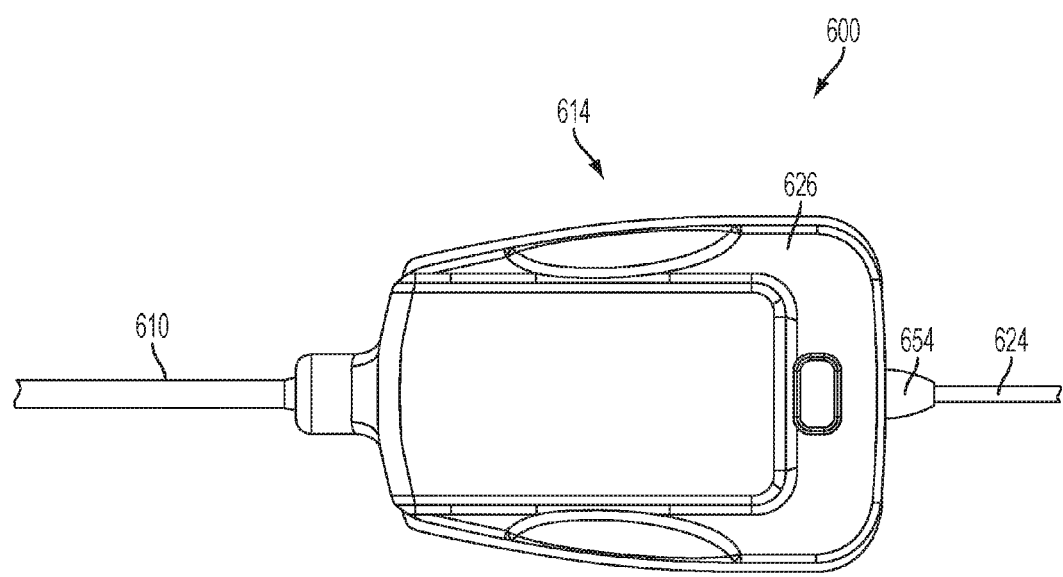
FIG. 7 illustrates a top view of one embodiment of the surgical tool shown in FIG. 6.

FIGS. 6-12 illustrate one embodiment of a surgical tool 600 that is well-adapted for use with the robotic system 200 (FIG. 2) that has a tool drive assembly that is operatively coupled to a master controller 202 (FIG. 2) that is operable by inputs from an operator (i.e., a surgeon). As shown in FIG. 6, in one embodiment the surgical tool 600 comprises a surgical end effector 602 (e.g., clamp jaw 602) that comprises medical forceps having a movable jaw member and a cutting blade coupled to an inner sheath located within an elongate shaft assembly 608 that are controlled by the robotic system 200. The movable jaw member comprises a top jaw 604 and a bottom jaw 606. A center slot 628 is provided for slidably receiving a cutting element (e.g., blade, knife) therein. In one embodiment, the cutting element is shaped like an "I-beam" as disclosed in U.S. Patent Application US2012/0078247 ("'247 application") filed Sep. 19, 2011, published Mar. 29, 2012, entitled "Articulation Joint Features For Articulating Surgical Device," the disclosure of which is herein incorporated by reference in its entirety. Various examples of end effectors including firing beams and operation thereof also are described in the '247 application, which is herein incorporated by reference. In one embodiment, the surgical tool 600 comprises an elongated shaft assembly 608 that has an elongate tube portion 610 and a distal articulation section 612. The surgical tool 600 is operatively coupled to the manipulator 308 (FIGS. 3-5) by a tool mounting portion 614. The surgical tool 600 further comprises an interface 616, which mechanically and electrically couples the tool mounting portion 614 to the manipulator 308.

Figure 8:
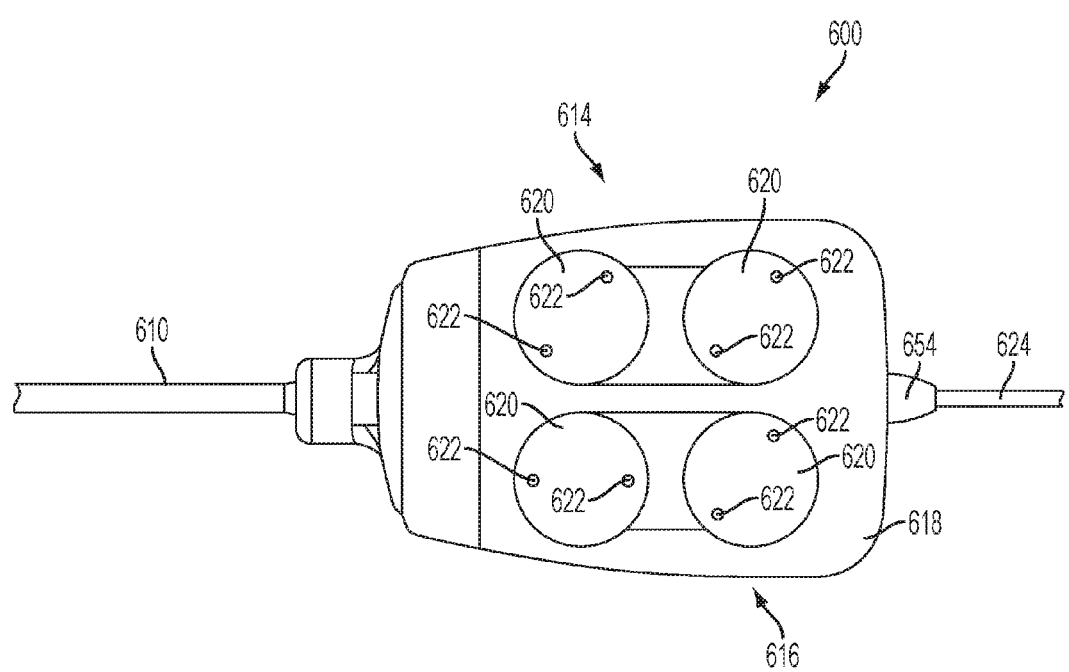
FIG. 8 illustrates a bottom view of one embodiment of the surgical tool shown in FIG. 6.
Figure 9:
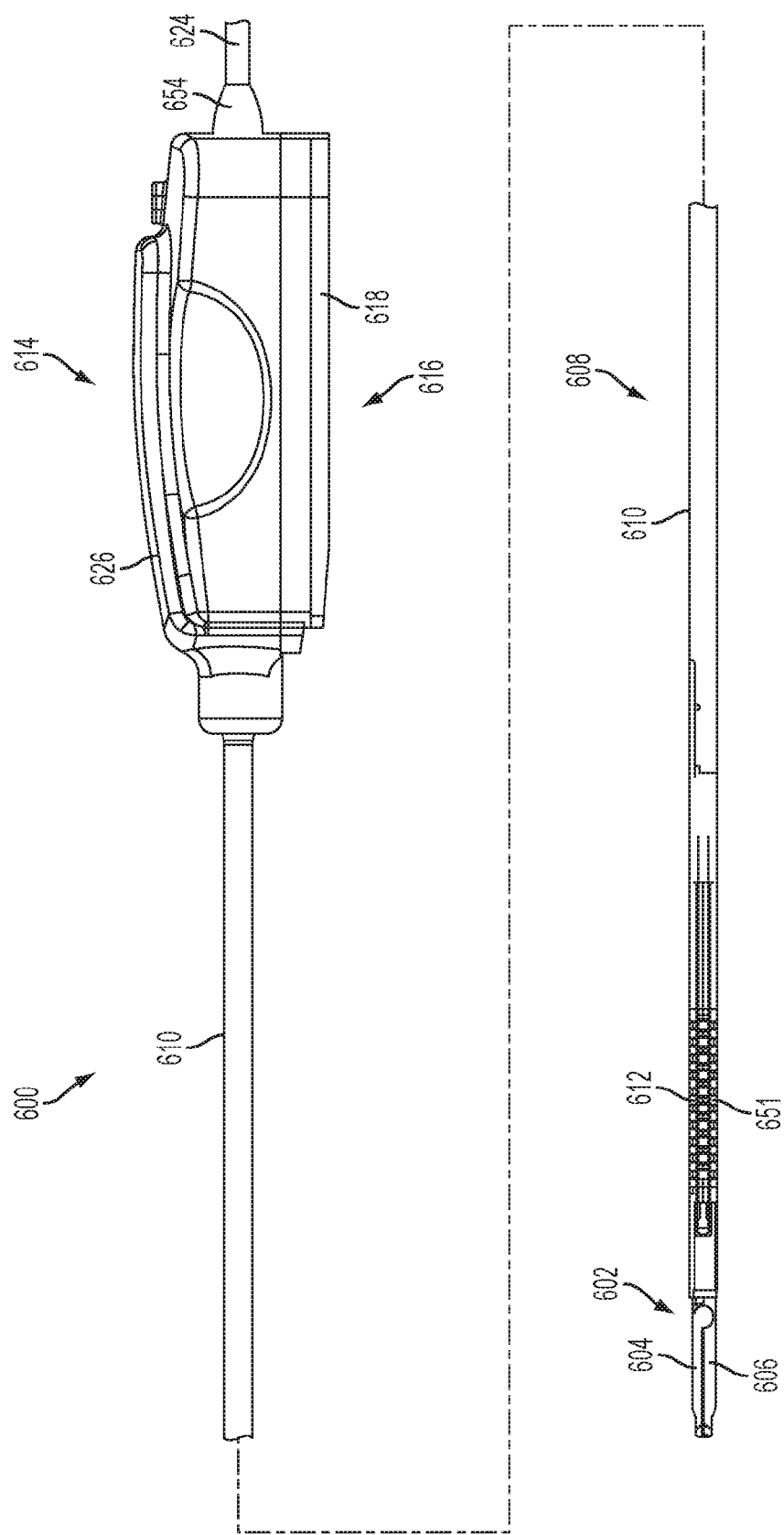
FIG. 9 illustrates a side view of one embodiment of the surgical tool shown in FIG. 6.
Figure 10:
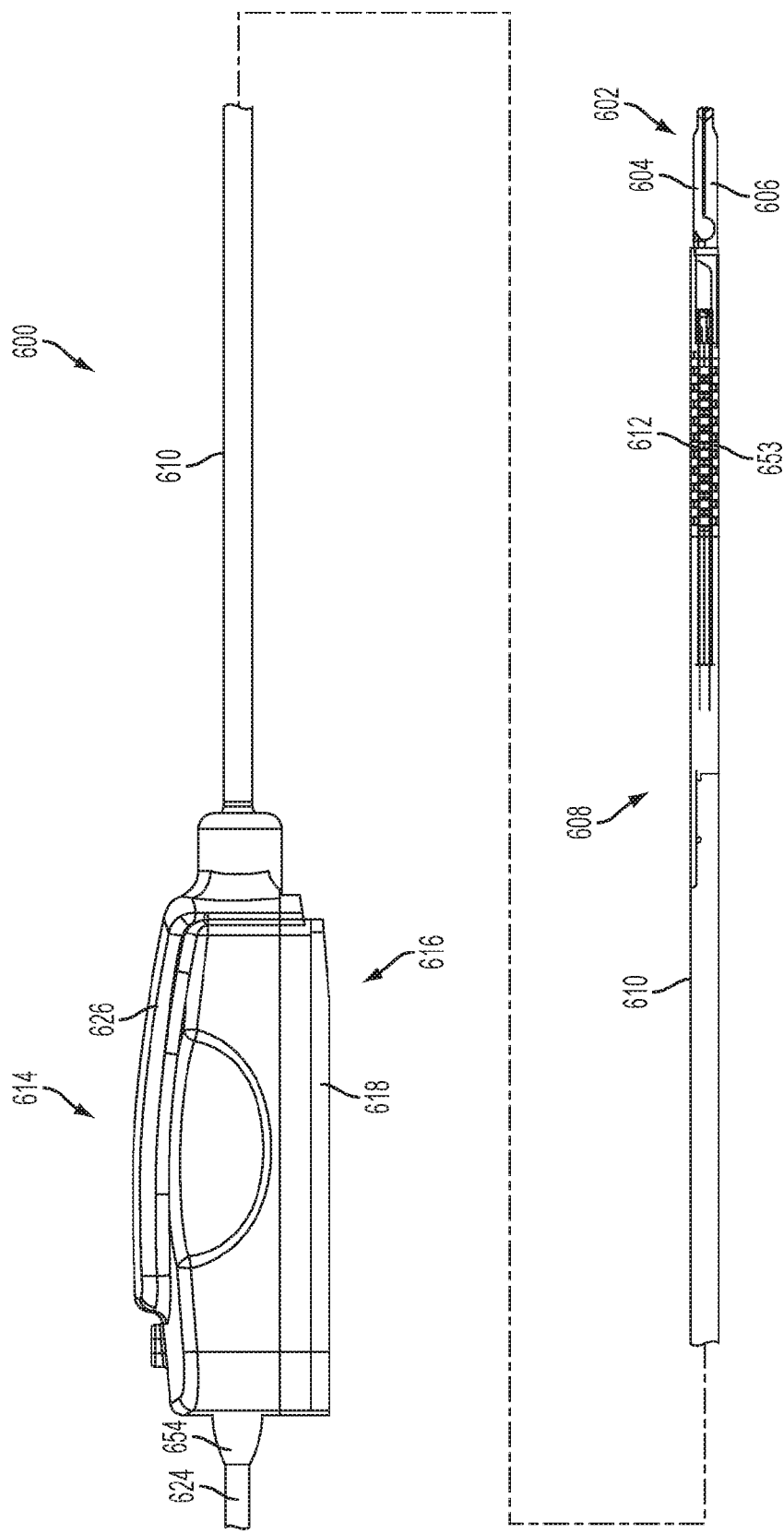
FIG. 10 illustrates a side view of one embodiment of the surgical tool shown in FIG. 6.
Figure 11:
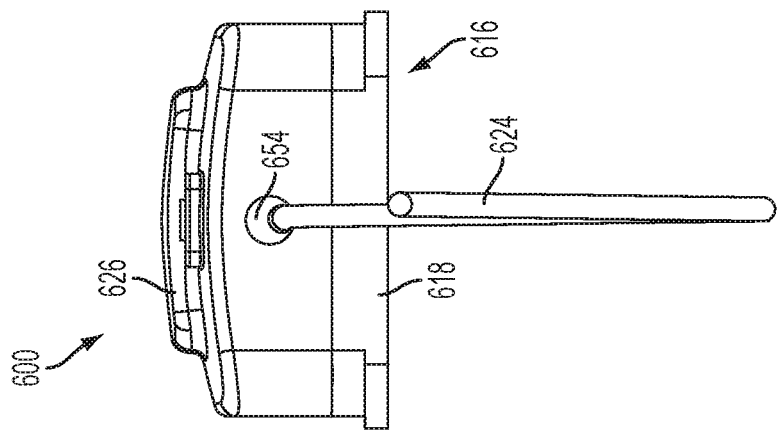
FIG. 11 illustrates a front view of one embodiment of the surgical tool shown in FIG. 6.
Figure 12:
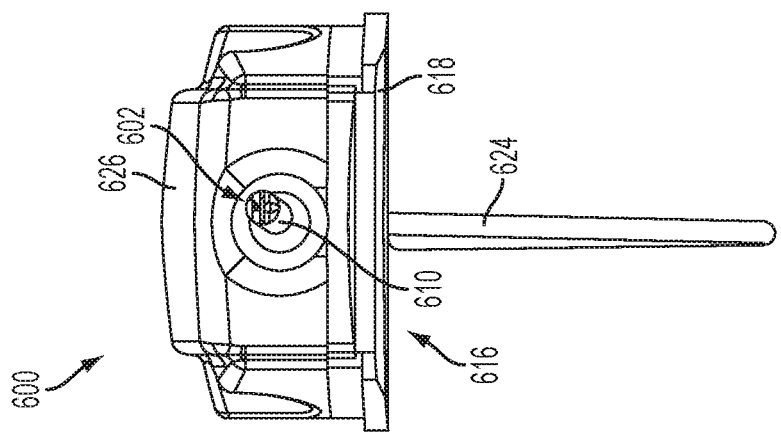
FIG. 12 illustrates a rear view of one embodiment of the surgical tool shown in FIG. 6.

In various embodiments, the tool mounting portion 614 comprises a tool mounting housing 626 and a tool mounting plate 618 that operatively supports a plurality of rotatable body portions, driven discs or elements 620 (four are shown in FIG. 8), that each include a pair of pins 622 that extend from a surface of the driven element 620. One pin 622 is closer to an axis of rotation of each driven element 620 than the other pin 622 on the same driven element 620, which helps to ensure positive angular alignment of the driven element 620. The interface 616 comprises an adaptor portion that is configured to mountingly engage the mounting plate 618 as will be further discussed below. In one embodiment, an adaptor portion may include an array of electrical connecting pins, which may be coupled to a memory structure by a circuit board within the tool mounting portion 614. While the interface 616 is described herein with reference to mechanical, electrical, and magnetic coupling elements, it should be understood that a wide variety of telemetry modalities might be used, including infrared, inductive coupling, or the like. An electrical cable 624 and strain relief 654 are provided to electrically couple the surgical tool 600 to a generator, which may be an ultrasonic energy source, a radio frequency RF energy source, or a combination thereof. In some embodiments, the generators and energy sources as disclosed in commonly assigned U.S. Provisional Patent Application No. 61/550,768, filed on Oct. 24, 2011 and entitled "MEDICAL INSTRUMENT," ("'768 application"), the disclosure of which is herein incorporated by reference in its entirety, may be electrically coupled to the surgical tool 600.

Figure 89:
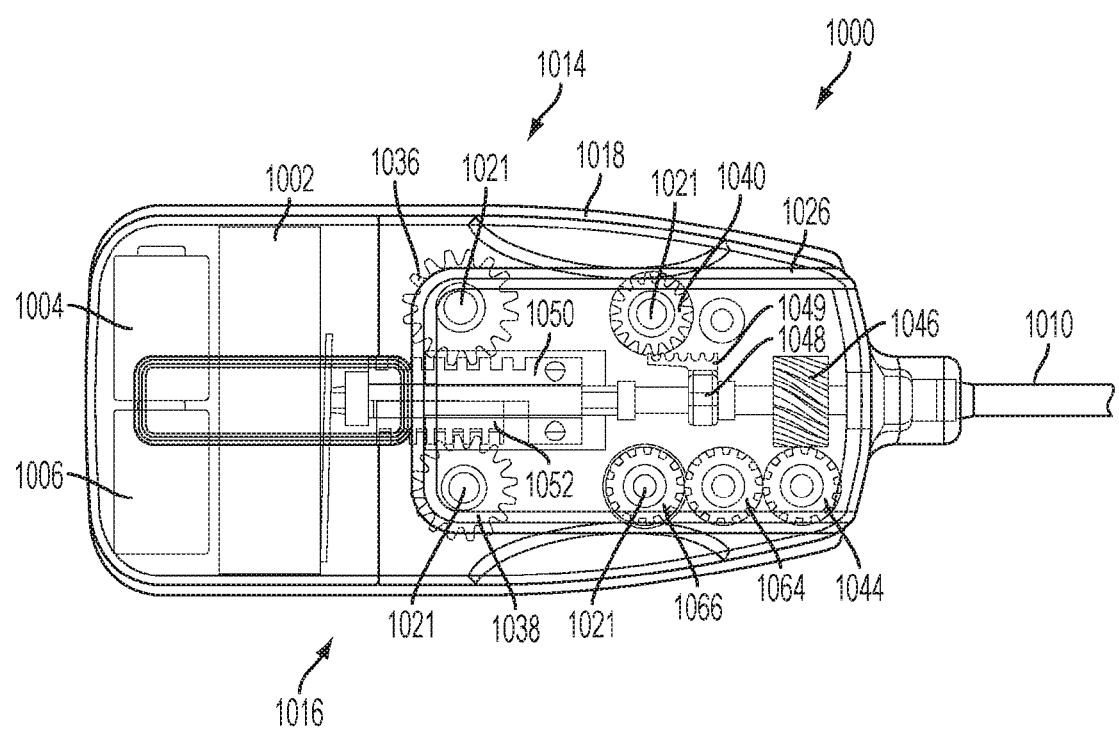
FIG. 89 illustrates one embodiment of a surgical tool comprising an internal battery located within a tool mounting portion with a tool mounting housing.
Figure 90:
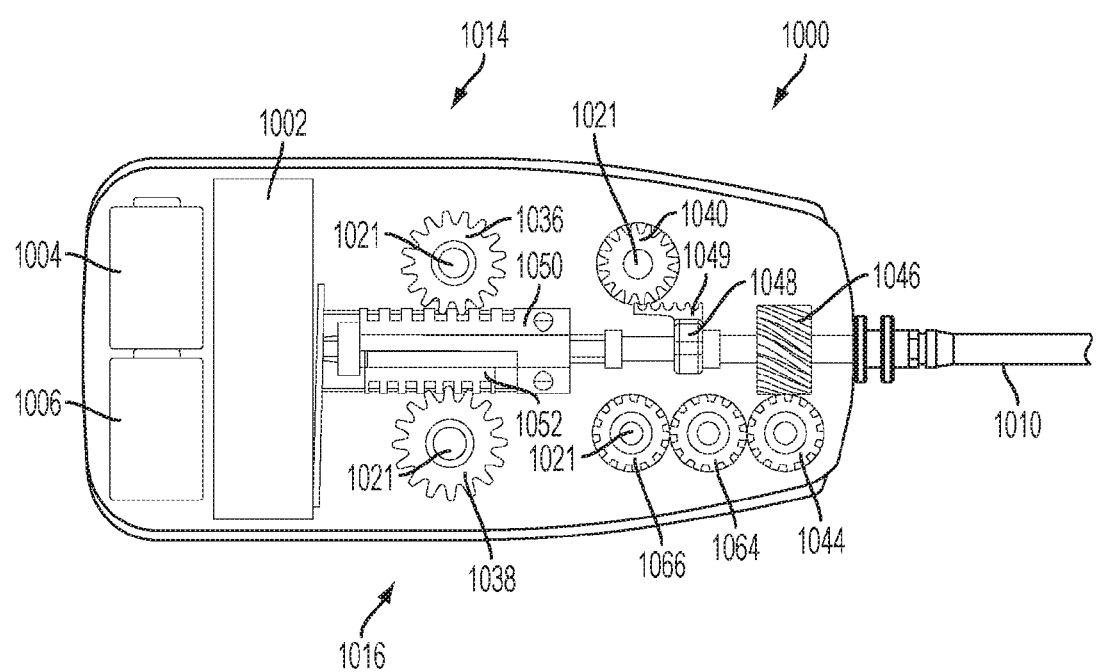
FIG. 90 illustrates one embodiment of the surgical tool shown in FIG. 89 comprising an internal battery located within a tool mounting portion with the tool mounting housing removed.

In one embodiment, the surgical tool 600 provides bipolar RF energy, articulation of the elongate shaft for better access to vessels and tissue, vessel sealing, low thermal spreading, and uniform compression for improved hemostais, among other features. As described in more detail with reference to FIGS. 13-24, the surgical tool 600 provides gearing mechanisms to obtain independent movements of the articulation section 612 of the shaft assembly 608, the top jaw 604 portion of the end effector 602, the cutting element, and rotation of the shaft assembly 608, among other movements. In one embodiment, the tool mounting housing 626 also may comprise an electronic circuit board with electronic elements to identify the surgical tool 600. In one embodiment, the tool mounting housing 626 also may comprise an internal battery, as shown in FIGS. 89 and 90, for example, to generate sufficient energy to cauterize, coagulate/desiccate, and/or simply reduce or slow bleeding of tissue such as a vessel. Such battery energized circuits are described in the '768 application, which is herein incorporated by reference.

Figure 13:
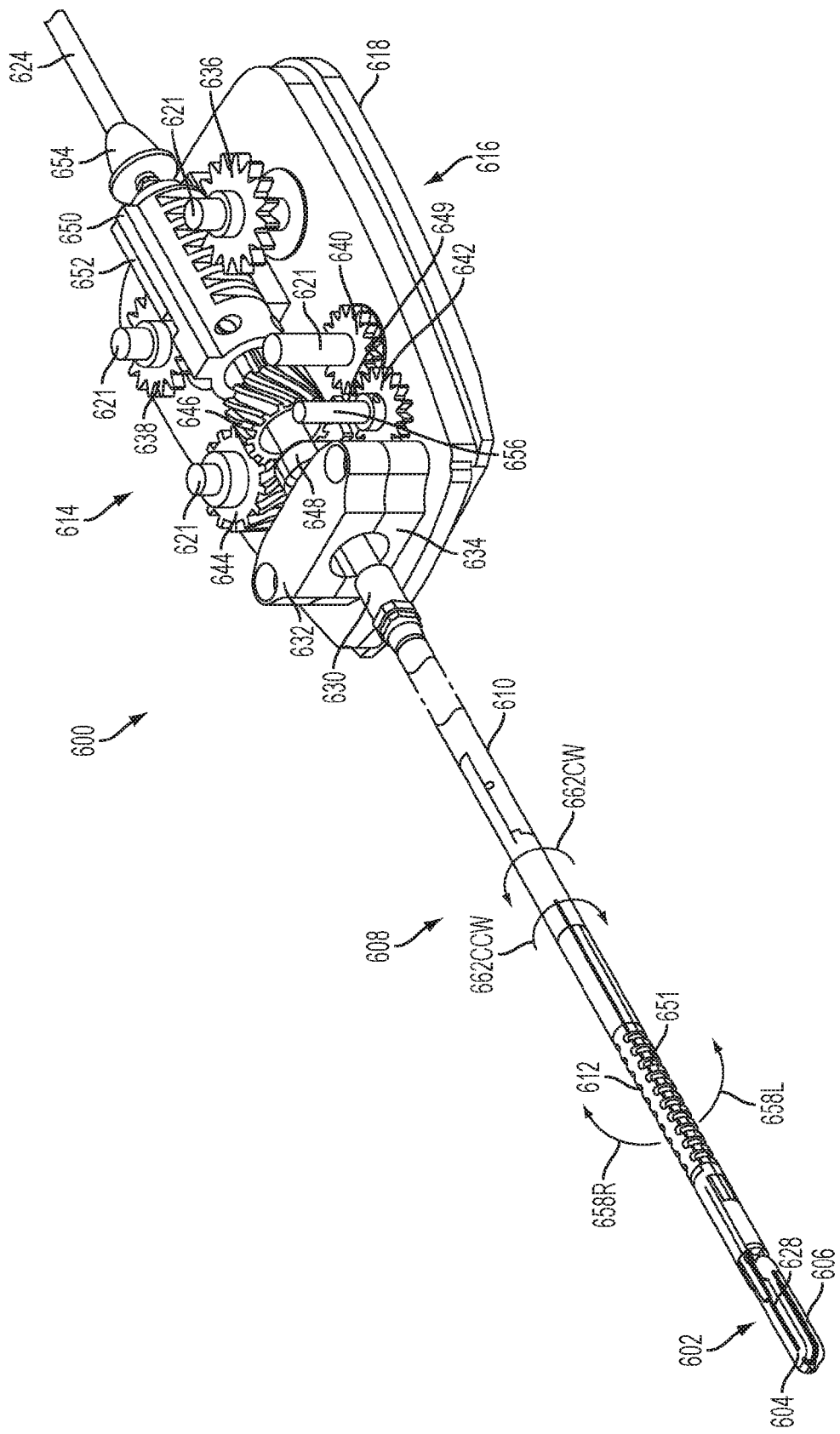
FIG. 13 illustrates a perspective view of one embodiment of the surgical tool shown in FIG. 6 with the tool mounting housing removed.
Figure 14:
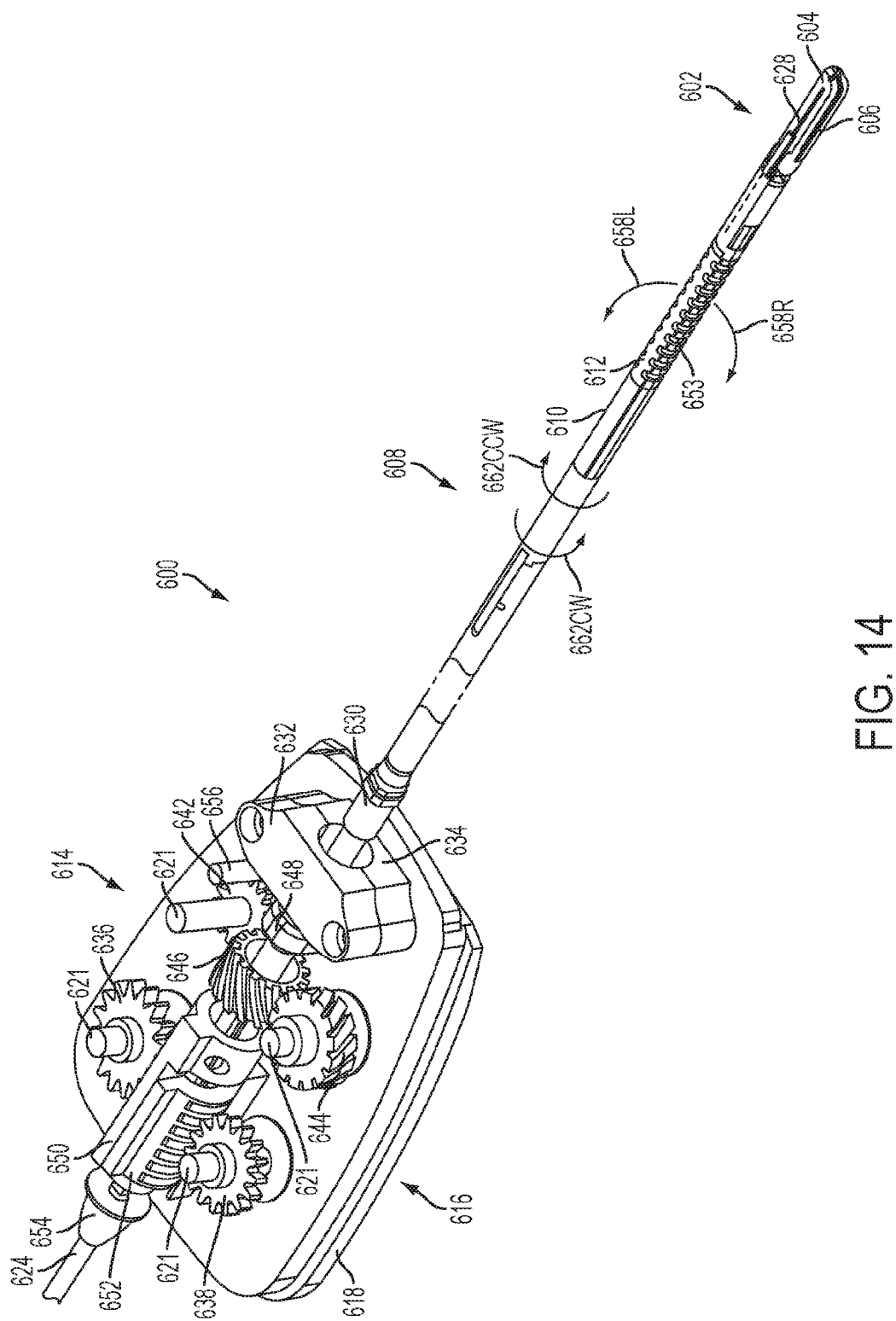
FIG. 14 illustrates a perspective view of one embodiment of the surgical tool shown in FIG. 6 with the tool mounting housing removed.
Figure 16:
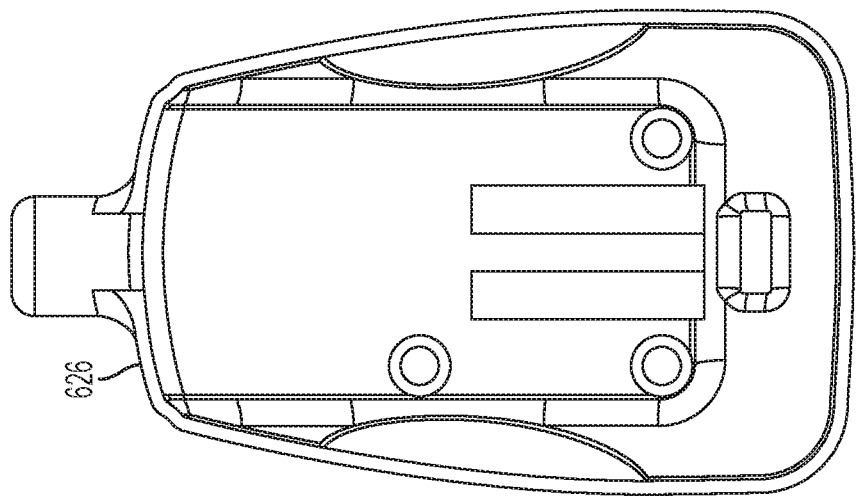
FIG. 16 illustrates a bottom view of one embodiment of the tool mounting housing of the surgical tool shown in FIG. 6.
Figure 15:
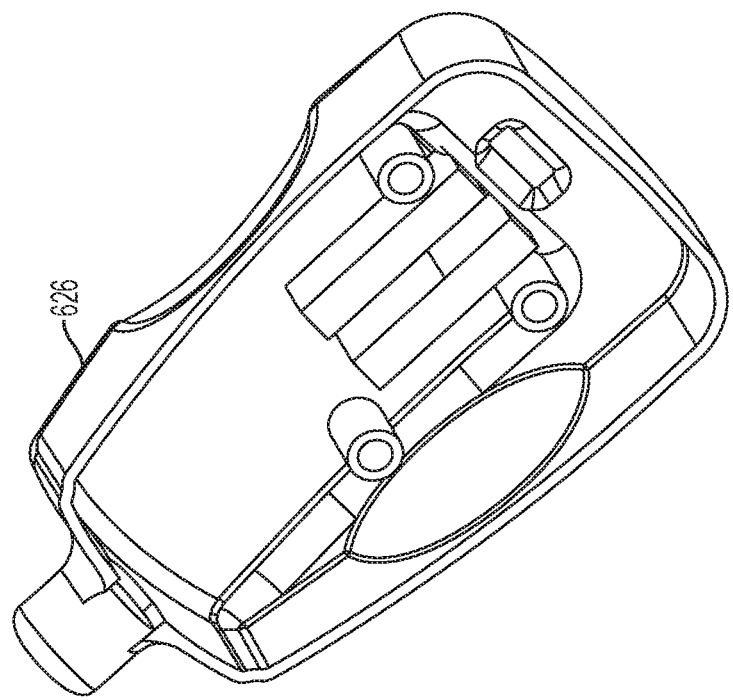
FIG. 15 illustrates a perspective view of one embodiment of the tool mounting housing of the surgical tool shown in FIG. 6.
Figure 17:
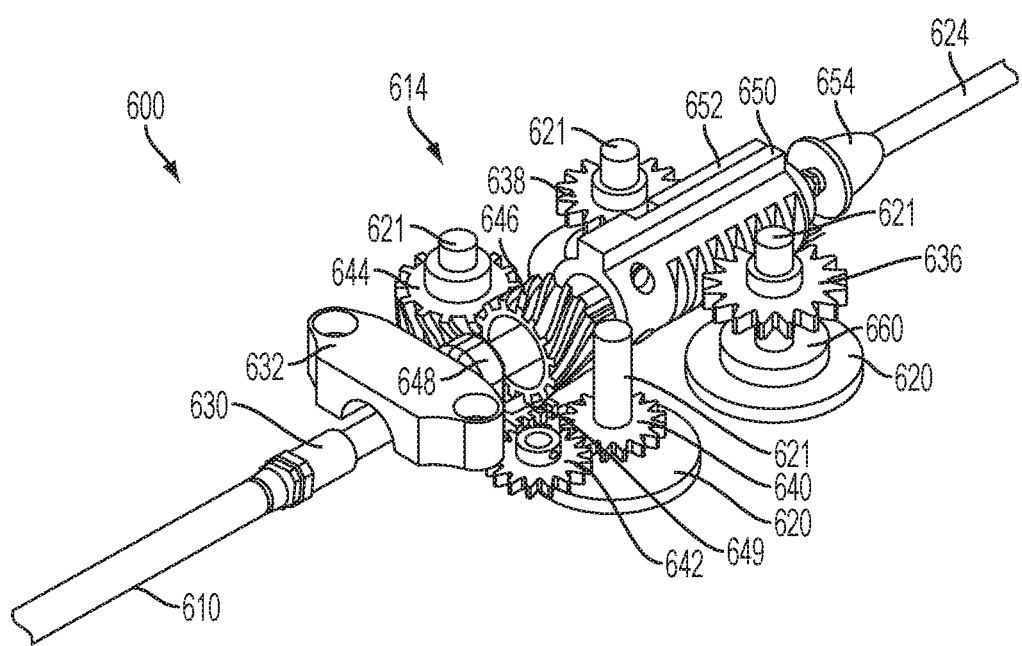
FIG. 17 illustrates a perspective view of one embodiment of the surgical tool shown in FIG. 6 with the tool mounting housing and tool mounting plate removed.
Figure 18:
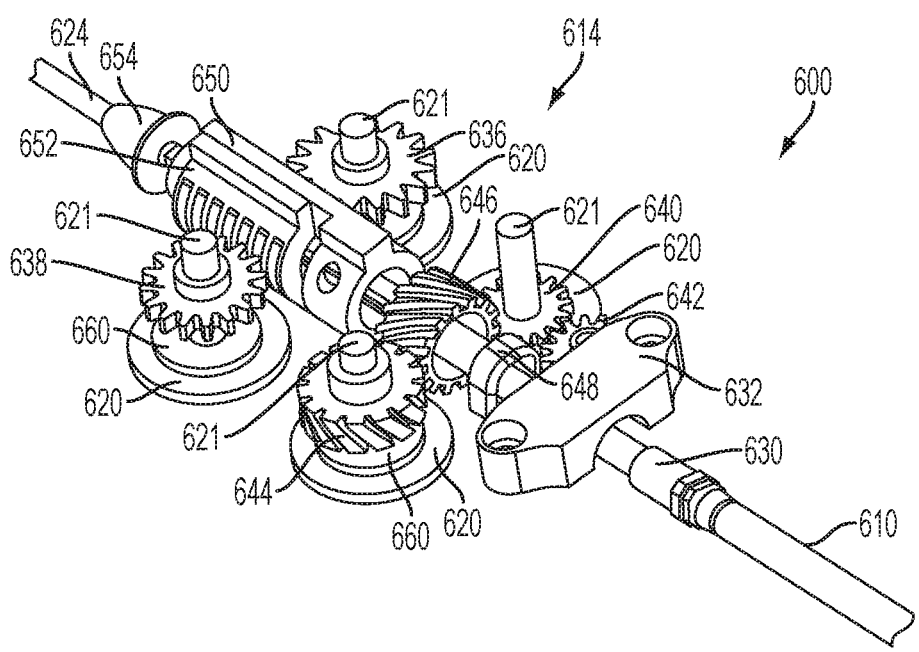
FIG. 18 illustrates a perspective view of one embodiment of the surgical tool shown in FIG. 6 with the tool mounting housing and a tool mounting plate removed.
Figure 20:
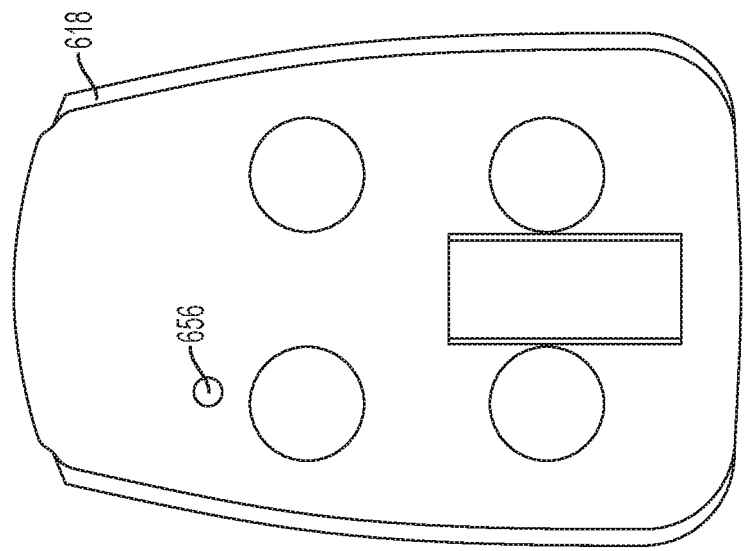
FIG. 20 illustrates a bottom view of one embodiment of the tool mounting plate of the surgical tool shown in FIG. 6.
Figure 19:
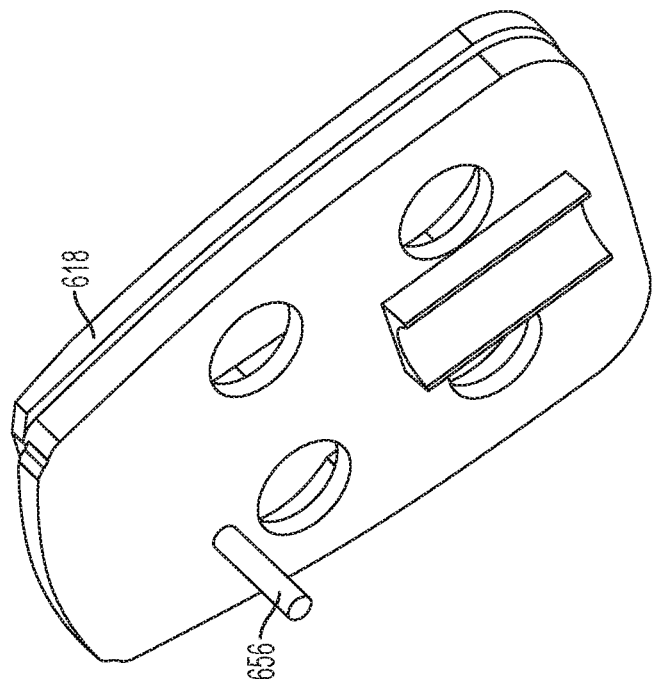
FIG. 19 illustrates a perspective view of one embodiment of the tool mounting plate of the surgical tool shown in FIG. 6.
Figure 21:
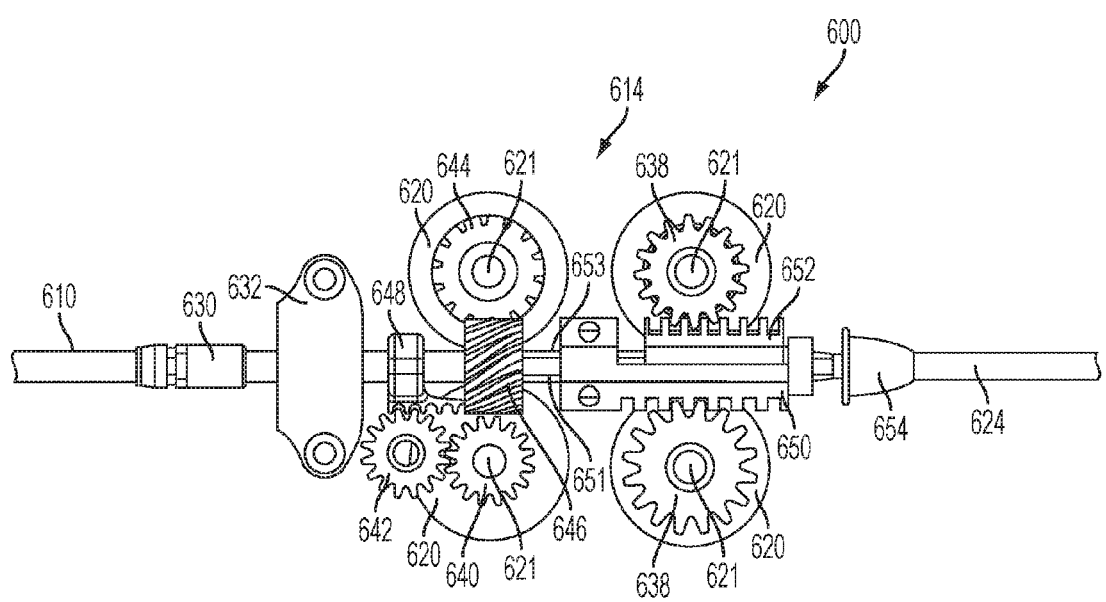
FIG. 21 illustrates a top view of one embodiment of the surgical tool shown in FIG. 6 with the tool mounting housing and the tool mounting plate removed.
Figure 22:
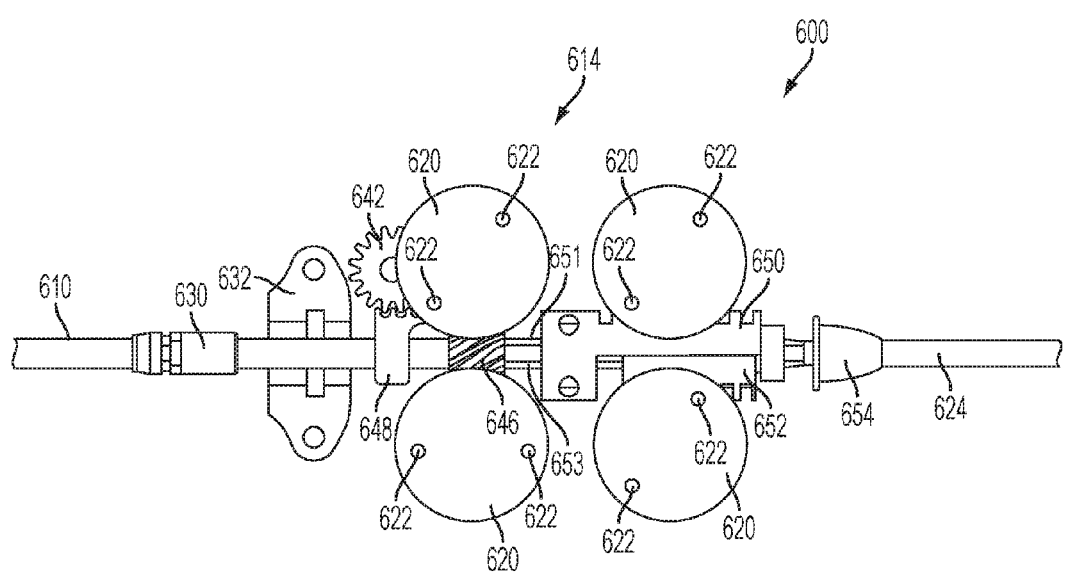
FIG. 22 illustrates a bottom view of one embodiment of the surgical tool shown in FIG. 6 with the tool mounting housing and the tool mounting plate removed.
Figure 23:
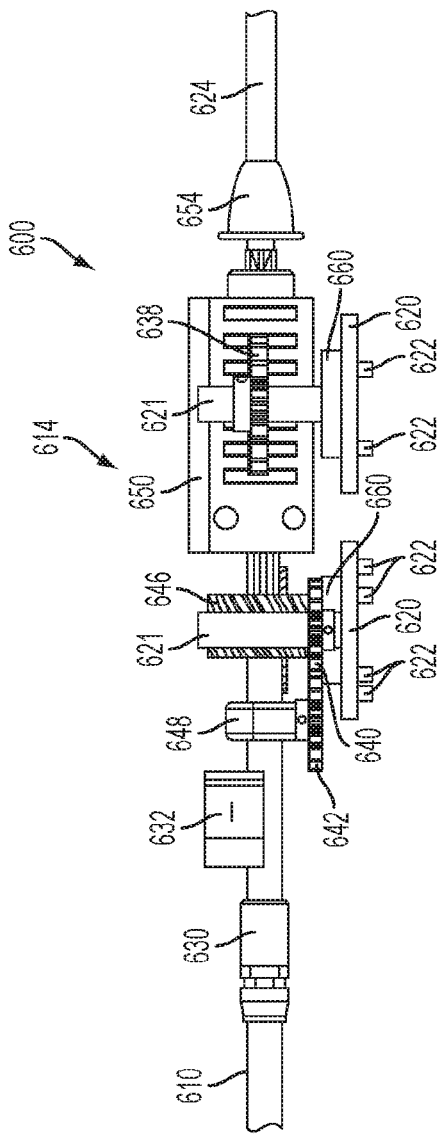
FIG. 23 illustrates a side view of one embodiment of the surgical tool shown in FIG. 6 with the tool mounting housing and the tool mounting plate removed.
Figure 24:
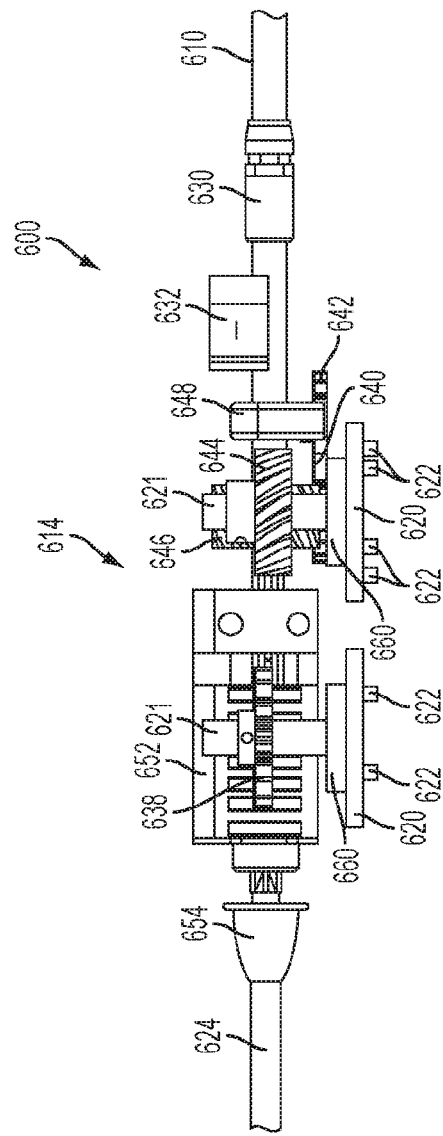
FIG. 24 illustrates a side view of one embodiment of the surgical tool shown in FIG. 6 with the tool mounting housing and the tool mounting plate removed.

For clarity of disclosure, in FIGS. 13 and 14 the surgical tool 600 is illustrated with the tool mounting housing 626 removed. For further clarity of disclosure, in FIGS. 17, 18, and 21-24 the surgical tool 600 is illustrated with the tool mounting housing 626 and the tool mounting plate 618 removed. A detailed view of the tool mounting housing 626 and the tool mounting plate 618 are shown in FIGS. 15, 16 and 19, 20, respectively.

The surgical tool 600 will now be described with reference to FIGS. 6-24. Accordingly, in one embodiment, the surgical tool 600 comprises a coupler 630 to couple the shaft assembly 608 to the tool mounting portion 614. A top shaft holder 632 and a bottom shaft holder 634 rotatably couple the shaft assembly 608 to the tool mounting housing 626.

In one embodiment, the tool mounting portion 614 of the surgical tool 600 comprises a shaft assembly 608 articulation mechanism, a shaft assembly 608 rotation mechanism, a clamp jaw 602 open/close mechanism, and a knife actuation mechanism. In one embodiment, the rotatable bodies 621 (e.g., rotatable spools) are coupled to the driven elements 620. The rotatable bodies 621 may be formed integrally with the driven elements 620. In some embodiments, the rotatable bodies 621 may be formed separately from the driven elements 620 provided that the rotatable bodies 621 and the driven elements 620 are fixedly coupled such that driving the driven elements 620 causes rotation of the rotatable bodies 621. Each of the rotatable bodies 621 is coupled to a gear train or gear mechanism to provide shaft articulation and rotation and clamp jaw open/close and knife actuation.

Figure 99:
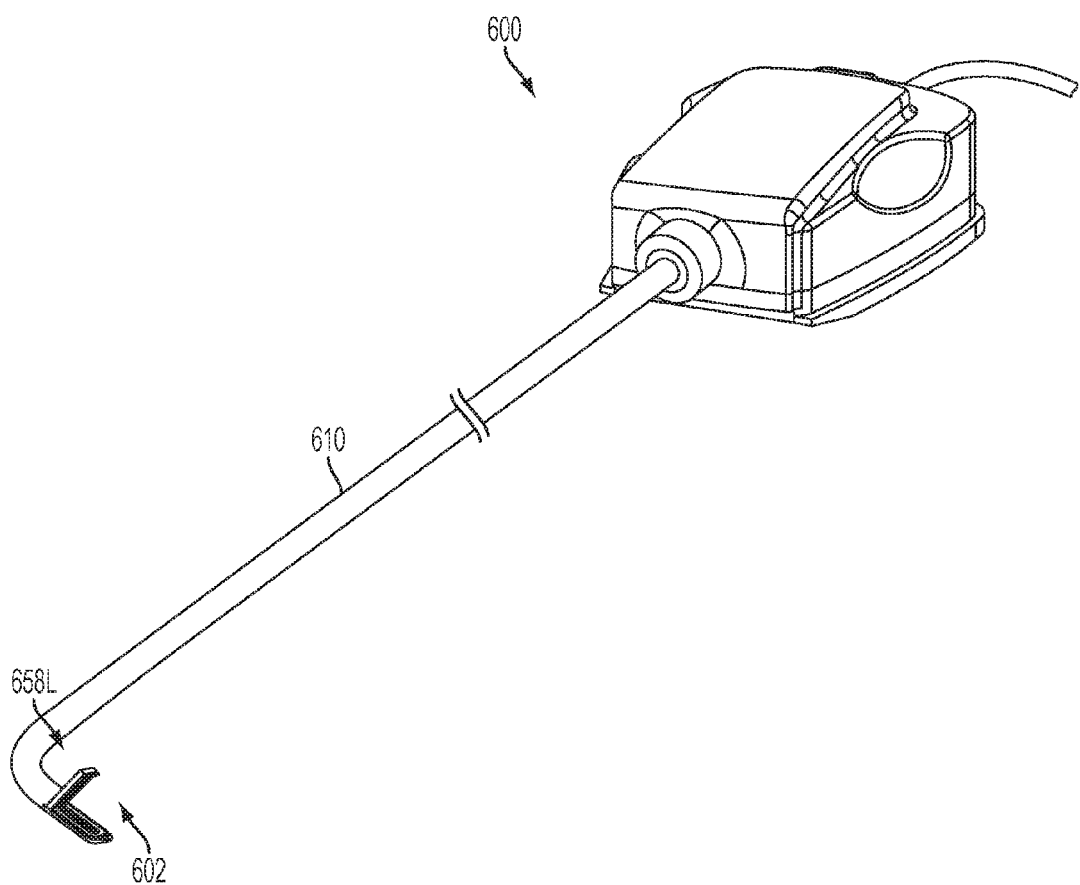
FIG. 99 illustrates one embodiment of the surgical instrument shown in FIG. 6 with an articulation section articulated to the left.
Figure 100:
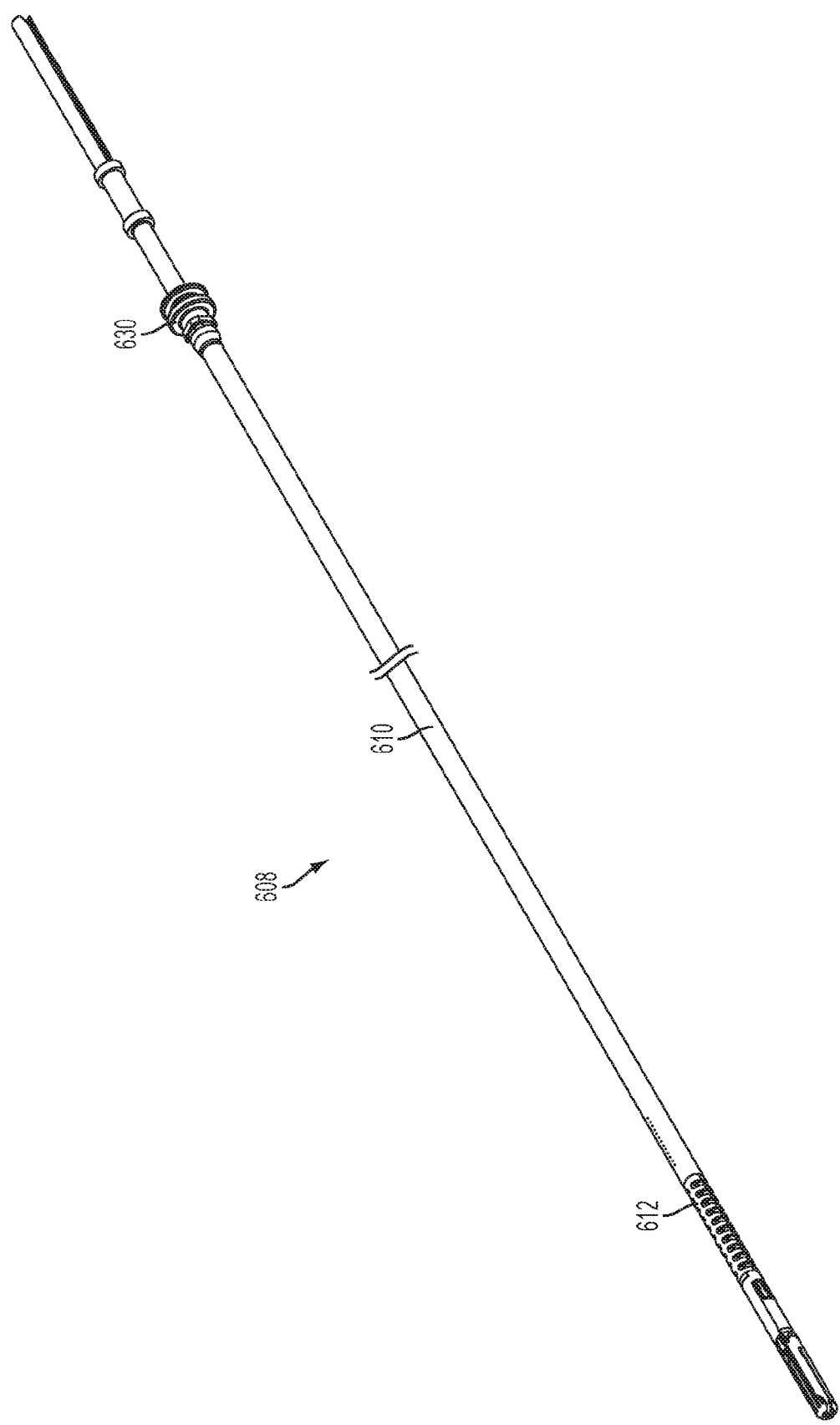
FIG. 100 illustrates a perspective view of one embodiment of a shaft assembly comprising an articulation section.
Figure 101:
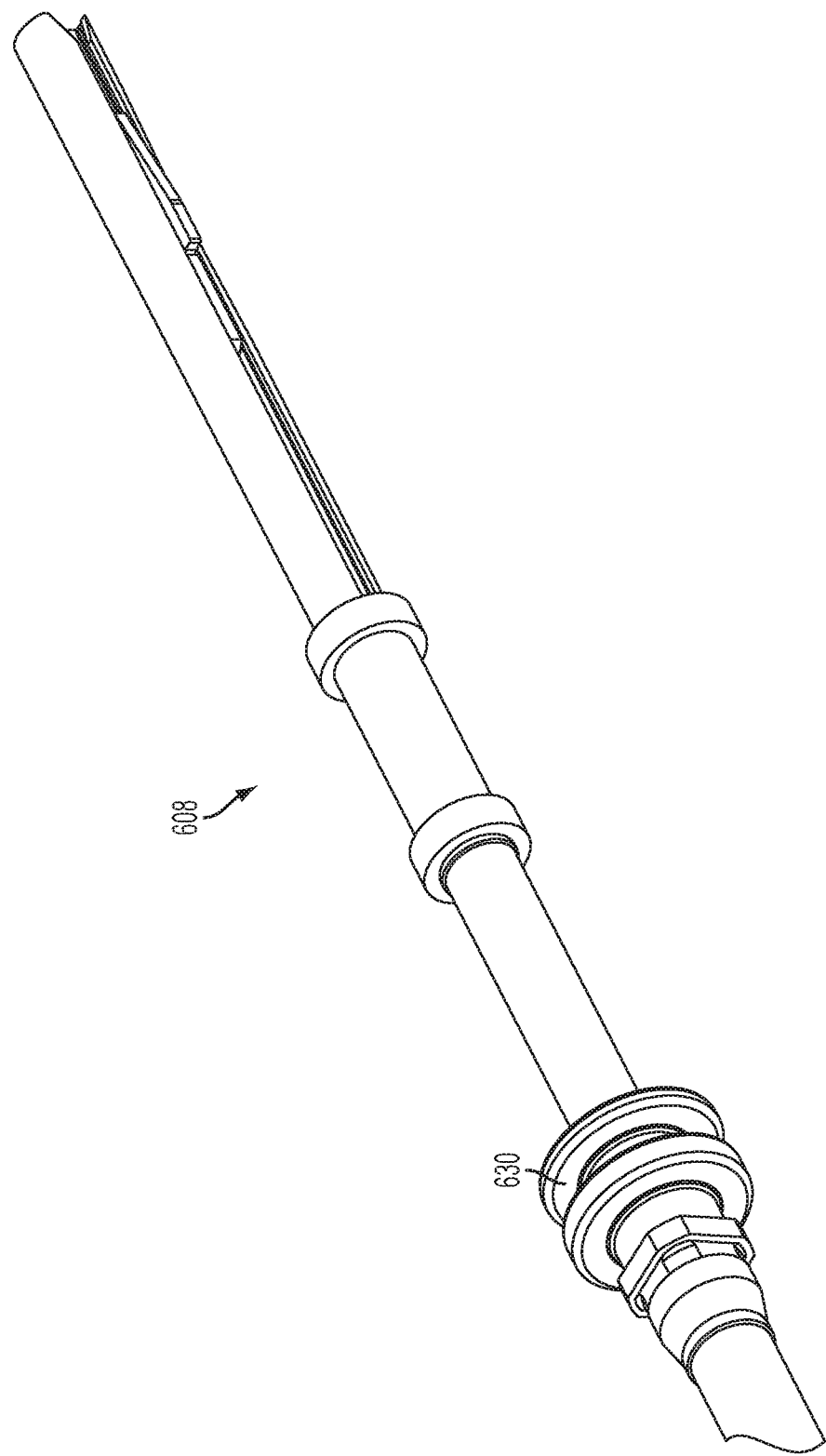
FIG. 101 illustrates a perspective view of a proximal end of the shaft assembly shown in FIG. 100.
Figure 102:
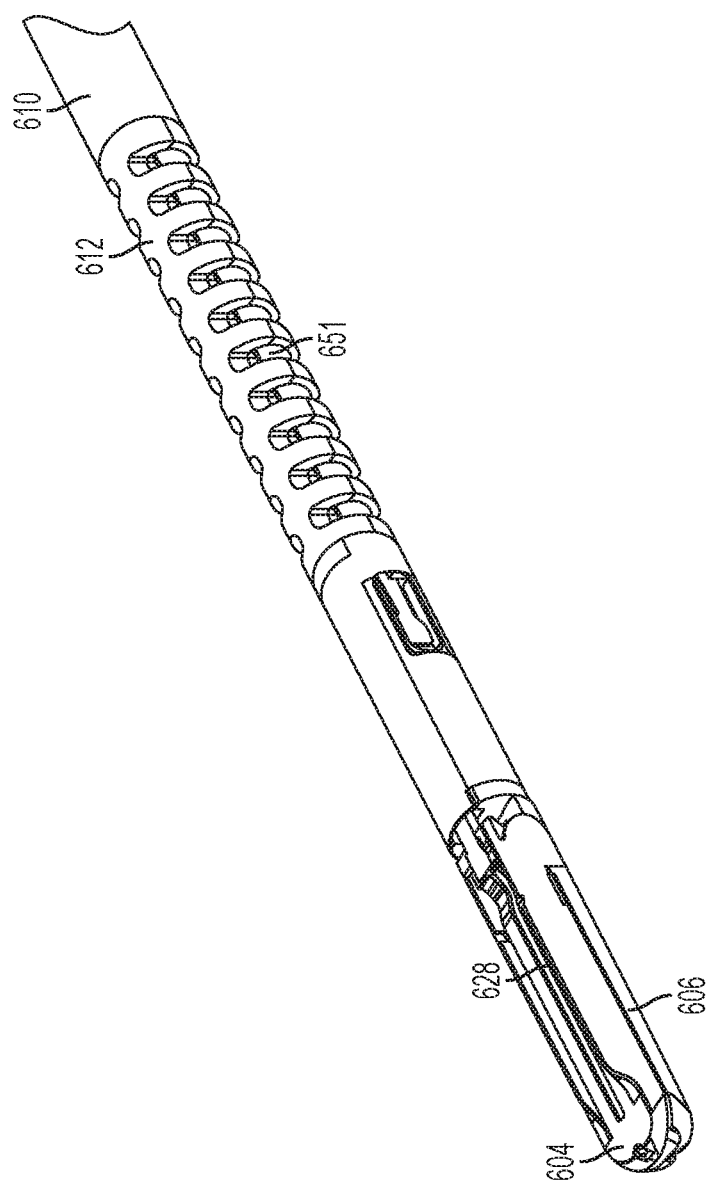
FIG. 102 illustrates a perspective view of a distal end of the shaft assembly shown in FIG. 100.
Figure 103:
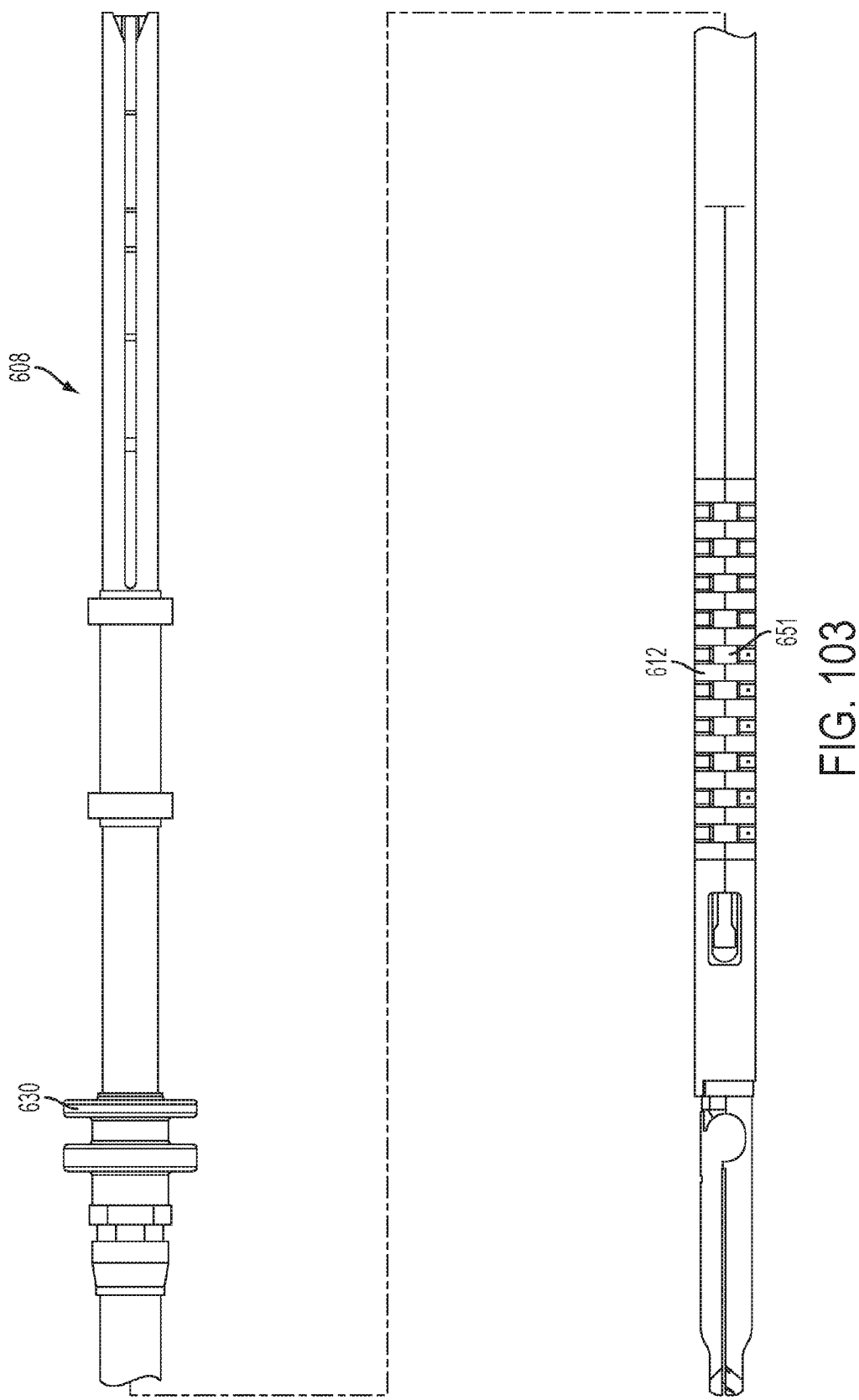
FIG. 103 is a detail view of distal and proximal ends of the shaft assembly shown in FIG. 100.
Figure 104:
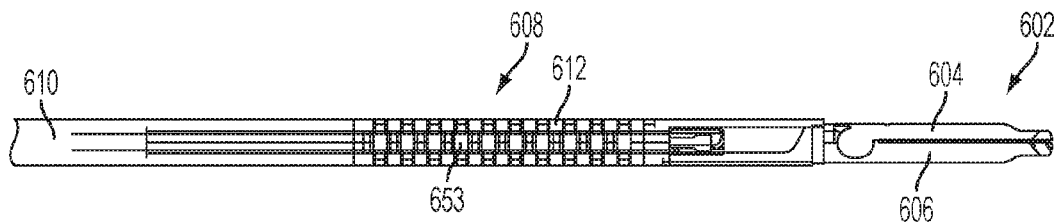
FIG. 104 is a side view of the shaft assembly shown in FIG. 100.
Figure 105:
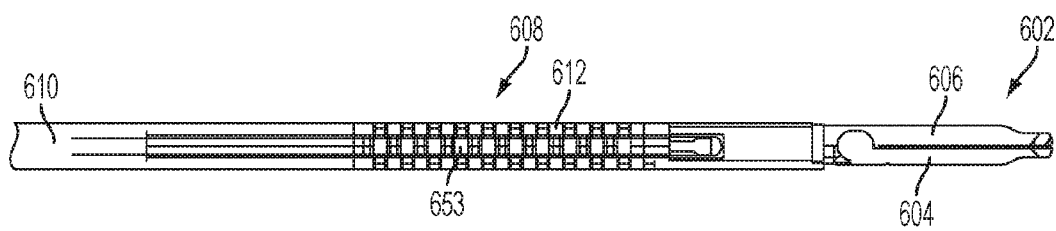
FIG. 105 is a side view of the shaft assembly shown in FIG. 100.
Figure 106:
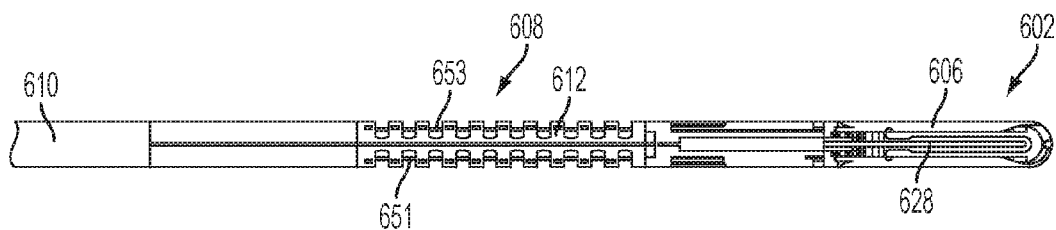
FIG. 106 is a bottom view of the shaft assembly shown in FIG. 100.
Figure 107:
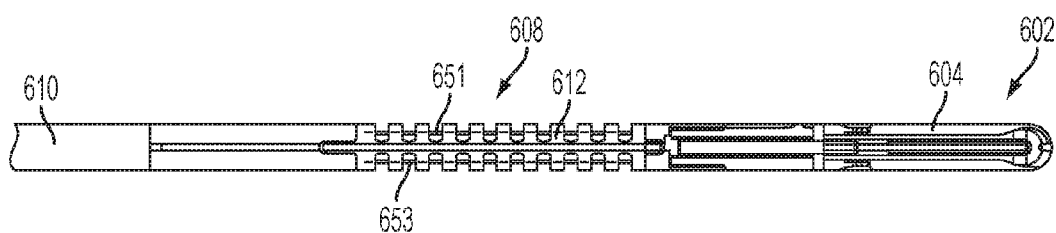
FIG. 107 is a top view of the shaft assembly shown in FIG. 100.
Figure 108:
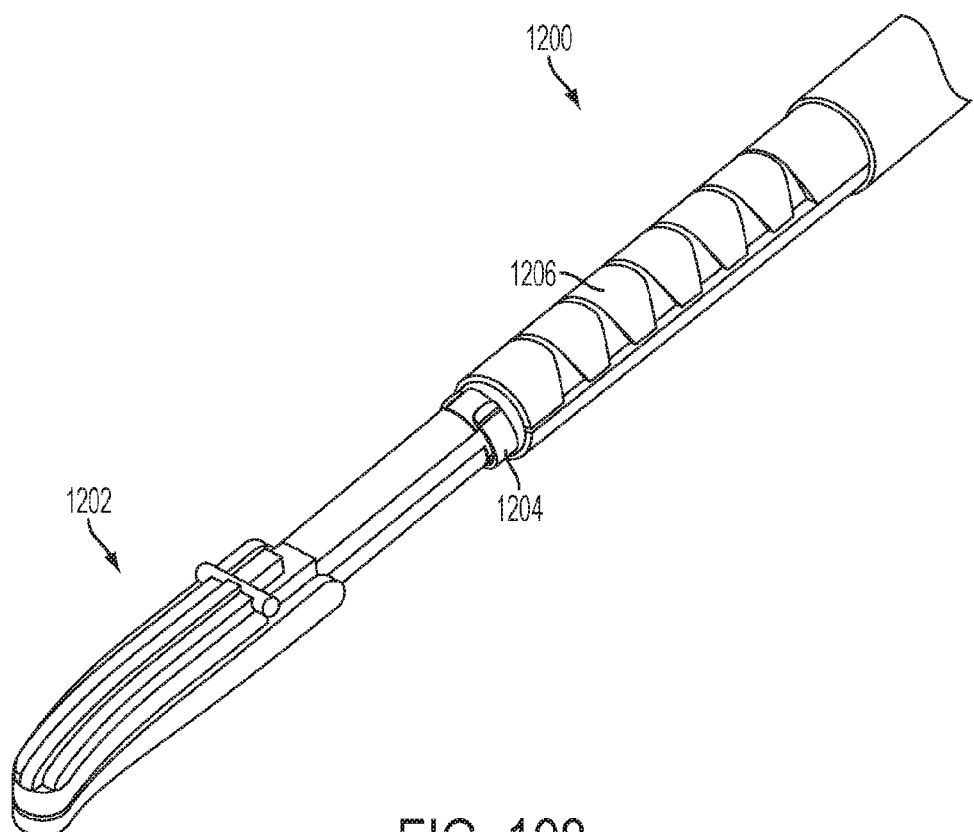
FIG. 108 illustrates one embodiment of a shaft assembly comprising an articulation section.
Figure 109:
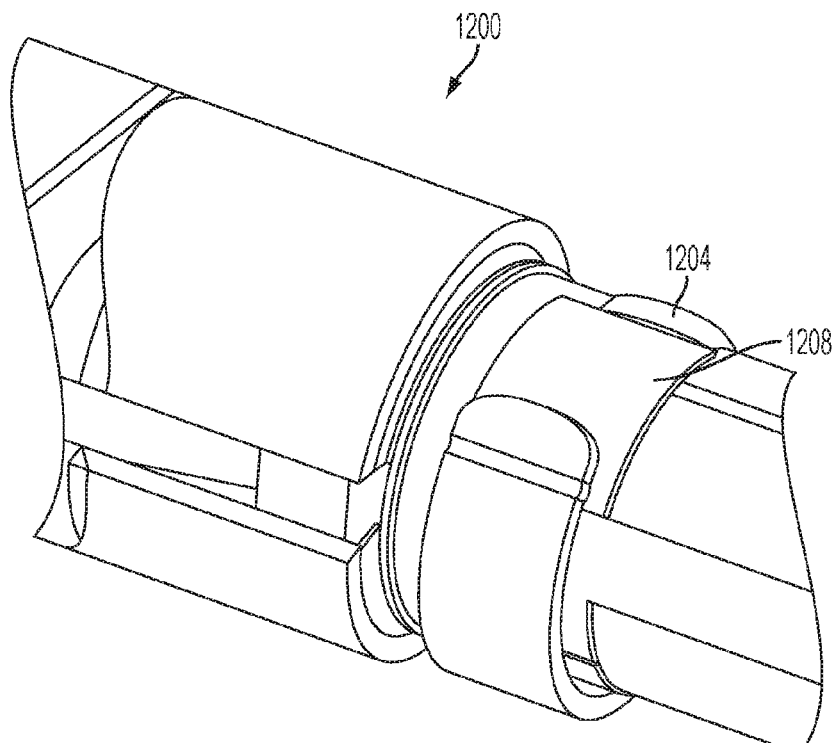
FIG. 109 illustrates a distal end of one embodiment of the shaft assembly shown in FIG. 108.
Figure 110:
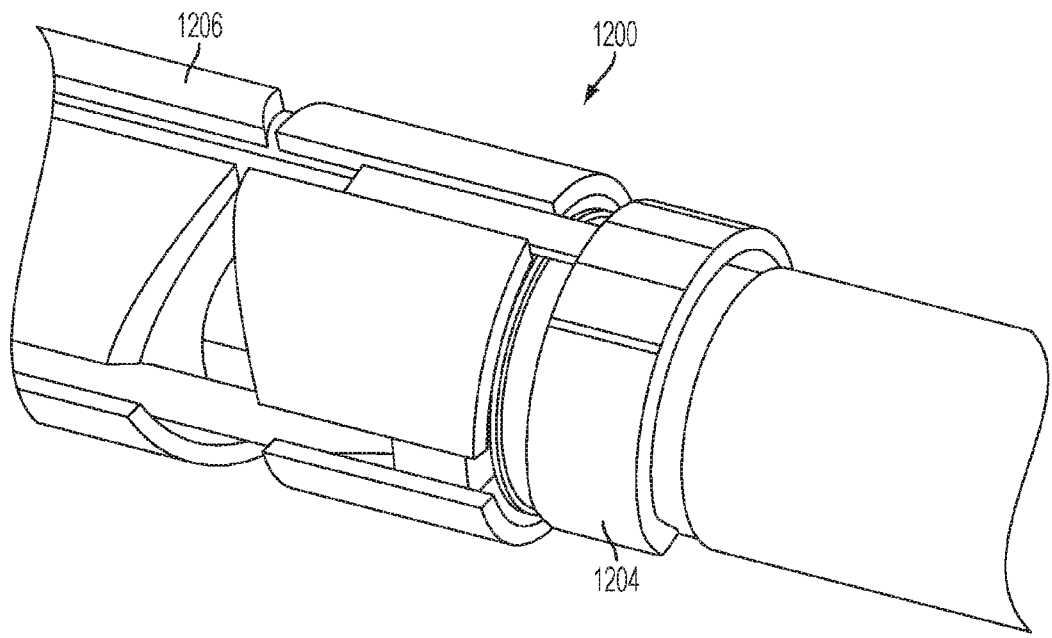
FIG. 110 illustrates a distal end of one embodiment of the shaft assembly shown in FIG. 108.
Figure 111:
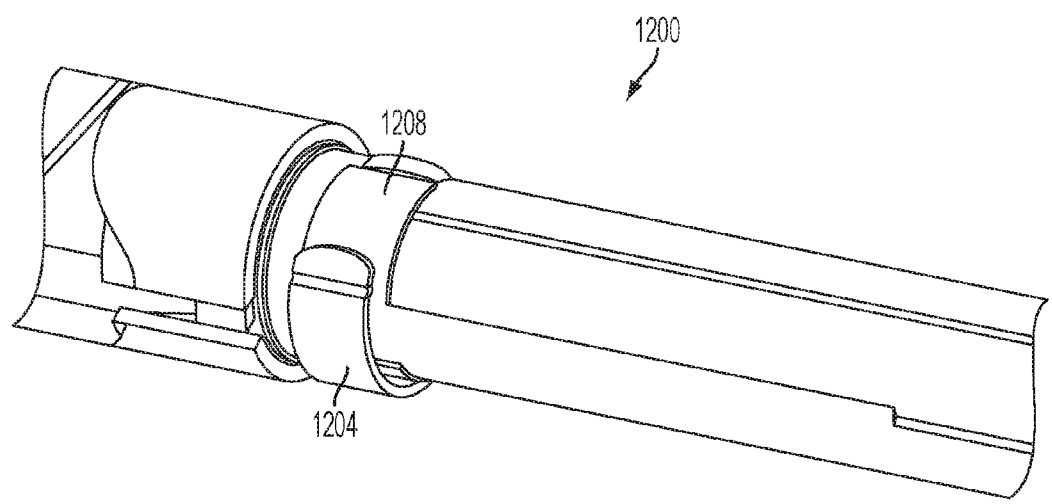
FIG. 111 illustrates a distal end of one embodiment of the shaft assembly shown in FIG. 108.

In one embodiment, the tool mounting portion 614 of the surgical tool 600 comprises a shaft assembly 608 articulation mechanism. In the illustrated embodiment, for example, the surgical tool 600 comprises a rack and pinion gearing mechanism to provide shaft articulation functionality. In one embodiment, the rack and pinion gearing mechanism comprises a first pinion gear 636 coupled to a rotatable body 621 such that rotation of the corresponding driven element 620 causes the first pinion gear 636 to rotate. A bearing 660 (FIG. 17) is coupled to the rotatable body 621 and is provided between the driven element 620 and the first pinion gear 636. The first pinion gear 636 is meshed to a first rack gear 650 to convert the rotational motion of the first pinion gear 636 into linear motion of the first rack gear 650 to control the articulation of the articulation section 612 of the shaft assembly 608 in a left direction 658L (see also FIG. 99). The first rack gear 650 is attached to a first articulation band 651 (FIGS. 9, 13, 21, 22, and 102, 103, 106, 107) such that linear motion of the first rack gear 650 in a distal direction causes the articulation section 612 of the shaft assembly 608 to articulate in the left direction 658L. A second pinion gear 638 is coupled to another rotatable body 621 such that rotation of the corresponding driven element 620 causes the second pinion gear 638 to rotate. A bearing 660 is coupled to the rotatable body 621 and is provided between the driven element 620 and the second pinion gear 638. The second pinion gear 638 is meshed to a second rack gear 652 to convert the rotational motion of the second pinion gear 638 into linear motion of the second rack gear 652 to control the articulation of the articulation section 612 in a right direction 658R. The second rack gear 652 is attached to a second articulation band 653 (FIGS. 10, 14, 21, 22, 106, 107) such that linear motion of the second rack gear 652 in a distal direction causes the articulation section 612 of the shaft assembly 608 to articulate in the right direction 658R. Additional bearings may be provided between the rotatable bodies and the corresponding gears. Any suitable bearings may be provided to support and stabilize the mounting and reduce rotary friction of shaft and gears, for example.

In one embodiment, the tool mounting portion 614 of the surgical tool 600 comprises a shaft assembly 608 rotation mechanism. In the illustrated embodiment, for example, the surgical tool 600 comprises a first spiral worm gear 644 coupled to a rotatable body 621 and a second spiral worm gear 646 coupled to the shaft assembly 608. A bearing 660 (FIG. 17) is coupled to a rotatable body 621 and is provided between a driven element 620 and the first spiral worm gear 644. The first spiral worm gear 644 is meshed to the second spiral worm gear 646, which is coupled to the shaft assembly 608, to control the rotation of the shaft assembly 608 in a clockwise (CW) and counter-clockwise (CCW) direction based on the rotational direction of the first and second spiral worm gears 644, 646. Accordingly, rotation of the first spiral worm gear 644 about a first axis is converted to rotation of the second spiral worm gear 646 about a second axis, which is orthogonal to the first axis. As shown in FIGS. 13 and 14, for example, a CW rotation of the second spiral worm gear 646 results in a CW rotation of the shaft assembly 608 in the direction indicated by 662CW. A CCW rotation of the second spiral worm gear 646 results in a CCW rotation of the shaft assembly 608 in the direction indicated by 662CCW. Additional bearings may be provided between the rotatable bodies and the corresponding gears. Any suitable bearings may be provided to support and stabilize the mounting and reduce rotary friction of shaft and gears, for example.

In one embodiment, the tool mounting portion 614 of the surgical tool 600 comprises a clamp jaw 602 open/close mechanism and a knife actuation mechanism. In the illustrated embodiment, for example, the surgical tool 600 comprises a rack and pinion gearing mechanism to provide the clamp jaw 602 open/close and knife actuation functionality. In the illustrated embodiment, a first gear 640 is coupled to a rotatable body 621 such that rotation of the corresponding driven element 620 causes the first gear 640 to rotate in a first direction. A second gear 642 is free to rotate about a post 656 formed in the tool mounting plate 618. The first gear 640 is meshed to the second gear 642 such that the second gear 642 rotates in a direction that is opposite of the first gear 640. In one embodiment, the gear mechanism comprising the first and second gears 640, 642 is configured to control the opening and closing the top jaw 804 of the clamp jaw 602 and movement of an "I-beam" shaped cutting element through the slot 628 formed in the clamp jaw 602. In one embodiment, the second gear 642 is a pinion gear meshed to a rack gear 649, which moves in a liner direction. The rack gear 649 is coupled to a close/open block 648, which is coupled to a distal portion of the shaft assembly 608. As the rack gear 649 moves in a distal direction, the "I-beam" shaped cutting element advances and closes the top jaw 604 portion of the clamp jaw 602. As the rack gear 649 moves in a proximal direction, the "I-beam" shaped cutting element retracts to enable the top jaw 604 portion of the clamp jaw 602 to open. A description of one embodiment of an "I-beam" shaped cutting element is provided in the '247 application, which is herein incorporated by reference.

Figure 25:
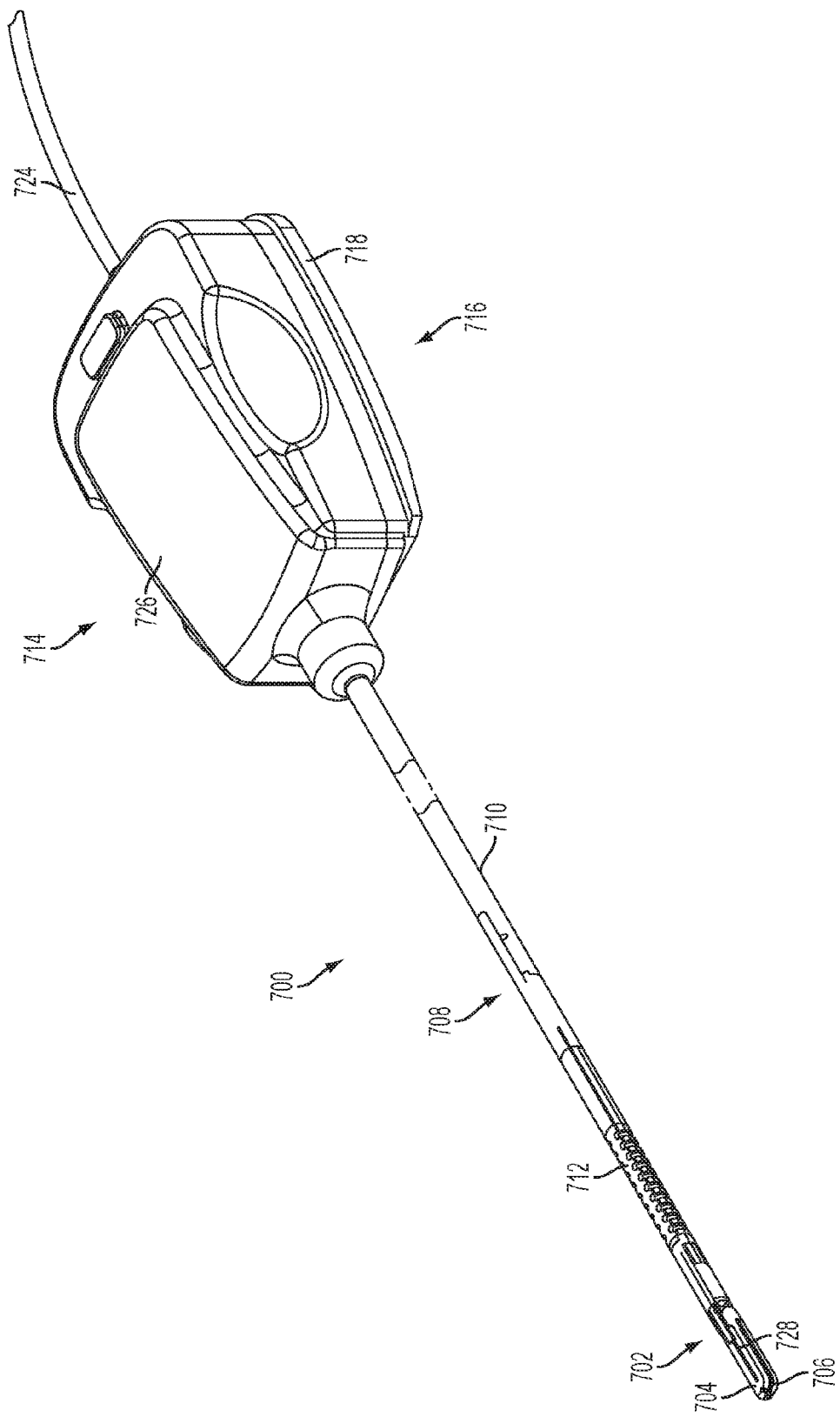
FIG. 25 illustrates a perspective view of one embodiment of a surgical tool that is well-adapted for use with a robotic system.
Figure 26:
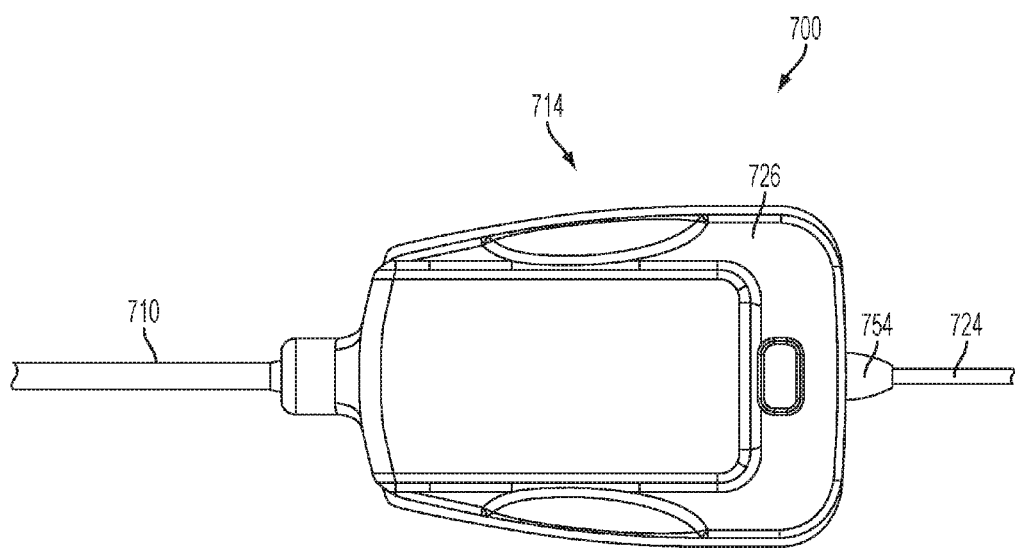
FIG. 26 illustrates a top view of one embodiment of the surgical tool shown in FIG. 25.

FIGS. 25-31 illustrate one embodiment of a surgical tool 700 that is well-adapted for use with the robotic system 200 (FIG. 2) that has a tool drive assembly that is operatively coupled to a master controller 202 (FIG. 2) that is operable by inputs from an operator (i.e., a surgeon). As shown in FIG. 25, the surgical tool 700 comprises a surgical end effector 702 (e.g., clamp jaw 702) that comprises medical forceps having a movable jaw member and a cutting blade coupled to an inner sheath located within an elongate shaft assembly 708 that are controlled by the robotic system 200. The movable jaw member comprises a top jaw 704 and a bottom jaw 706. A center slot 728 is provided for slidably receiving a cutting element (e.g., blade, knife) therein. In one embodiment, the cutting element is shaped like an "I-beam" as disclosed in the '247 application. In one embodiment, the surgical tool 700 comprises an elongated shaft assembly 708 that has an elongate tube portion 710 and a distal articulation section 712. The surgical tool 700 is operatively coupled to the manipulator 308 (FIGS. 3-5) by a tool mounting portion 714. The surgical tool 700 further comprises an interface 716, which mechanically and electrically couples the tool mounting portion 714 to the manipulator 308.

Figure 27:
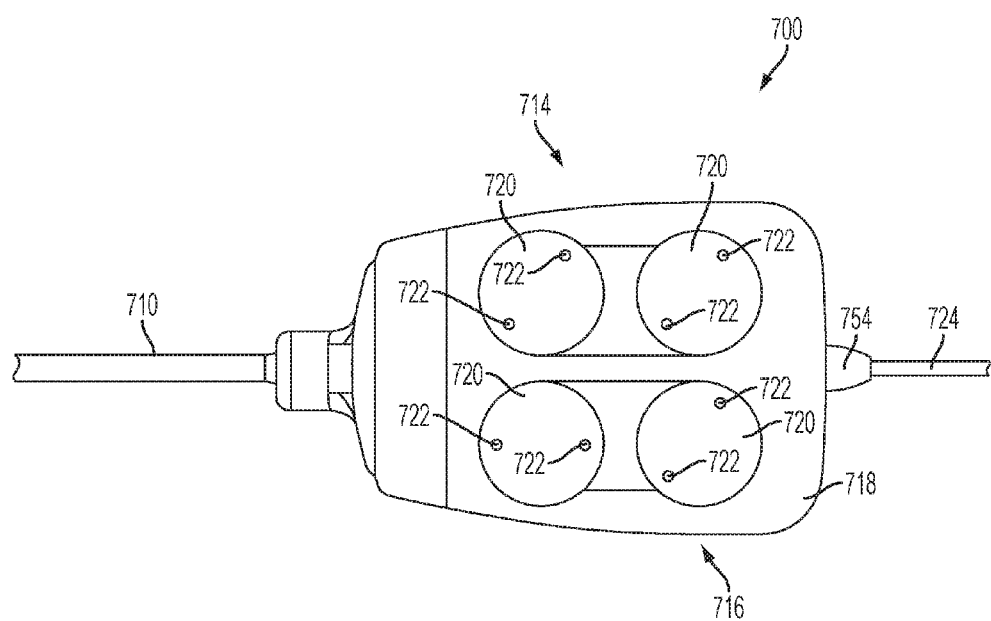
FIG. 27 illustrates a bottom view of one embodiment of the surgical tool shown in FIG. 25.
Figure 28:
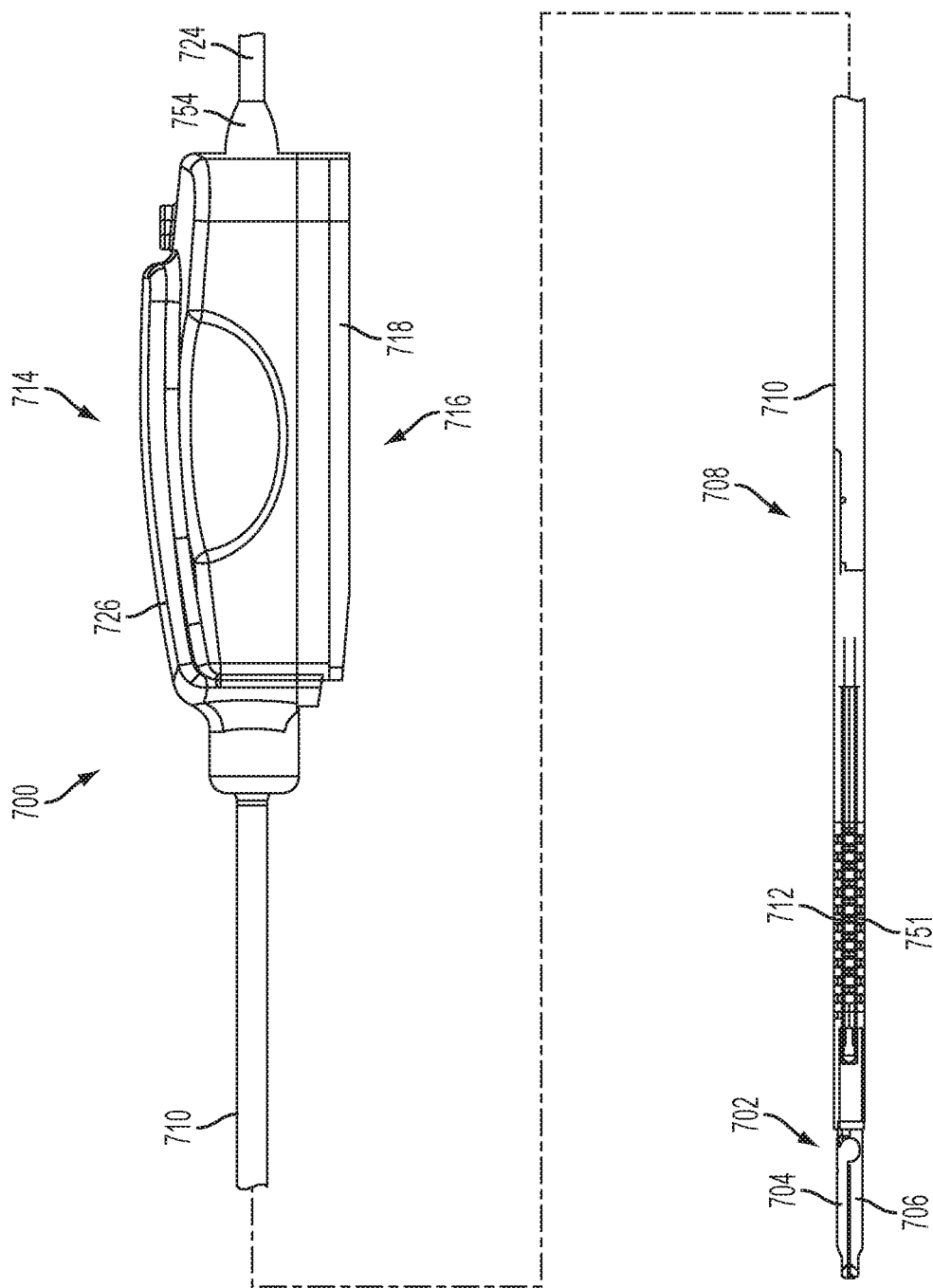
FIG. 28 illustrates a side view of one embodiment of the surgical tool shown in FIG. 25.
Figure 29:
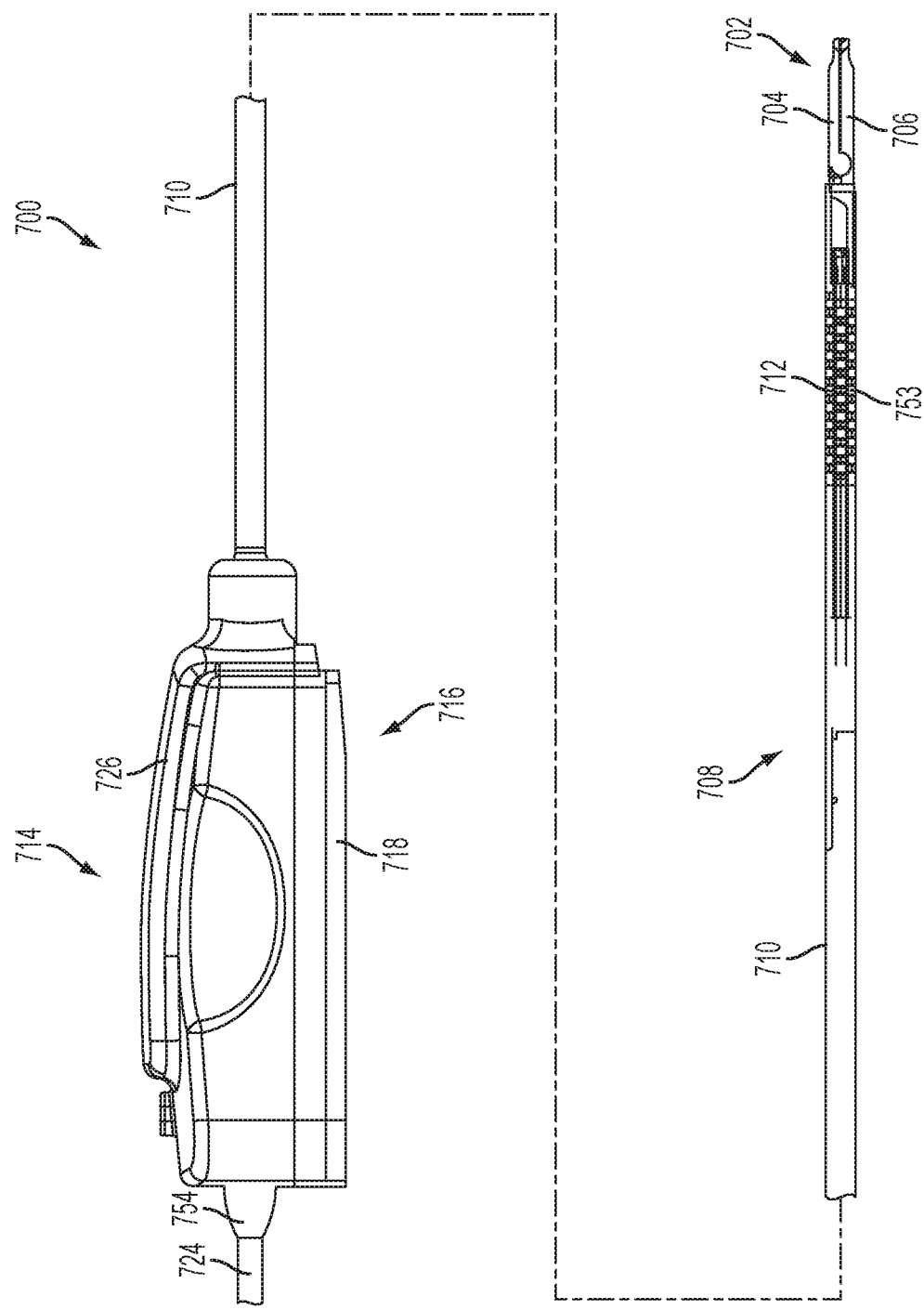
FIG. 29 illustrates a side view of one embodiment of the surgical tool shown in FIG. 25.
Figure 30:
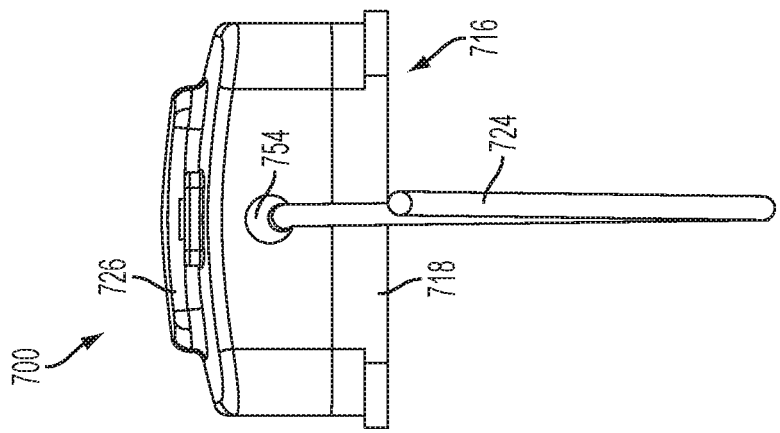
FIG. 30 illustrates a front view of one embodiment of the surgical tool shown in FIG. 25.
Figure 31:
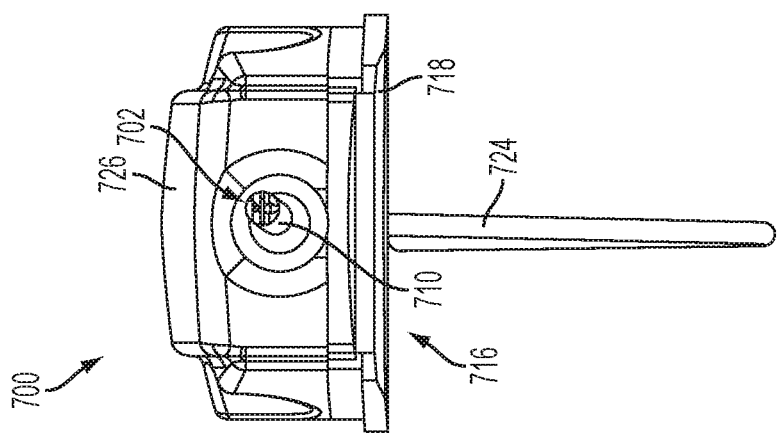
FIG. 31 illustrates a rear view of one embodiment of the surgical tool shown in FIG. 25.

In various embodiments, the tool mounting portion 714 comprises a tool mounting housing 726 and a tool mounting plate 718 that operatively supports a plurality of rotatable body portions, driven discs or elements 720 (four are shown in FIG. 27), that each include a pair of pins 722 (FIG. 27) that extend from a surface of the driven element 720. One pin 722 is closer to an axis of rotation of each driven element 720 than the other pin 722 on the same driven element 720, which helps to ensure positive angular alignment of the driven element 720. The interface 716 comprises an adaptor portion that is configured to mountingly engage the mounting plate 718 as will be further discussed below. In one embodiment, an adaptor portion may include an array of electrical connecting pins, which may be coupled to a memory structure by a circuit board within the tool mounting portion 714. While the interface 716 is described herein with reference to mechanical, electrical, and magnetic coupling elements, it should be understood that a wide variety of telemetry modalities might be used, including infrared, inductive coupling, or the like. An electrical cable 724 and strain relief 754 are provided to electrically couple the surgical tool 700 to a generator, which may be an ultrasonic energy source, an RF energy source, or a combination thereof. In some embodiments, the generators and energy sources as disclosed in the '768 application may be electrically coupled to the surgical tool 700.

In one embodiment, the surgical tool 700 provides bipolar RF energy, articulation of the elongate shaft for better access to vessels and tissue, vessel sealing, low thermal spreading, and uniform compression for improved hemostasis, among other features. As described in more detail with reference to FIGS. 32-43, the surgical tool 700 provides gearing mechanisms to obtain independent movements of the articulation section 712 of the shaft assembly 708, the top jaw 704 portion of the end effector 702, the cutting element, and rotation of the shaft assembly 708, among other movements. In one embodiment, the tool mounting housing 726 also may comprise an electronic circuit board with electronic elements to identify the surgical tool 700. In one embodiment, the tool mounting housing 726 also may comprise an internal battery, as shown in FIGS. 89 and 90, for example, to generate sufficient energy to cauterize, coagulate/desiccate, and/or simply reduce or slow bleeding of tissue such as a vessel. Such battery energized circuits are described in the '768 application.

Figure 32:
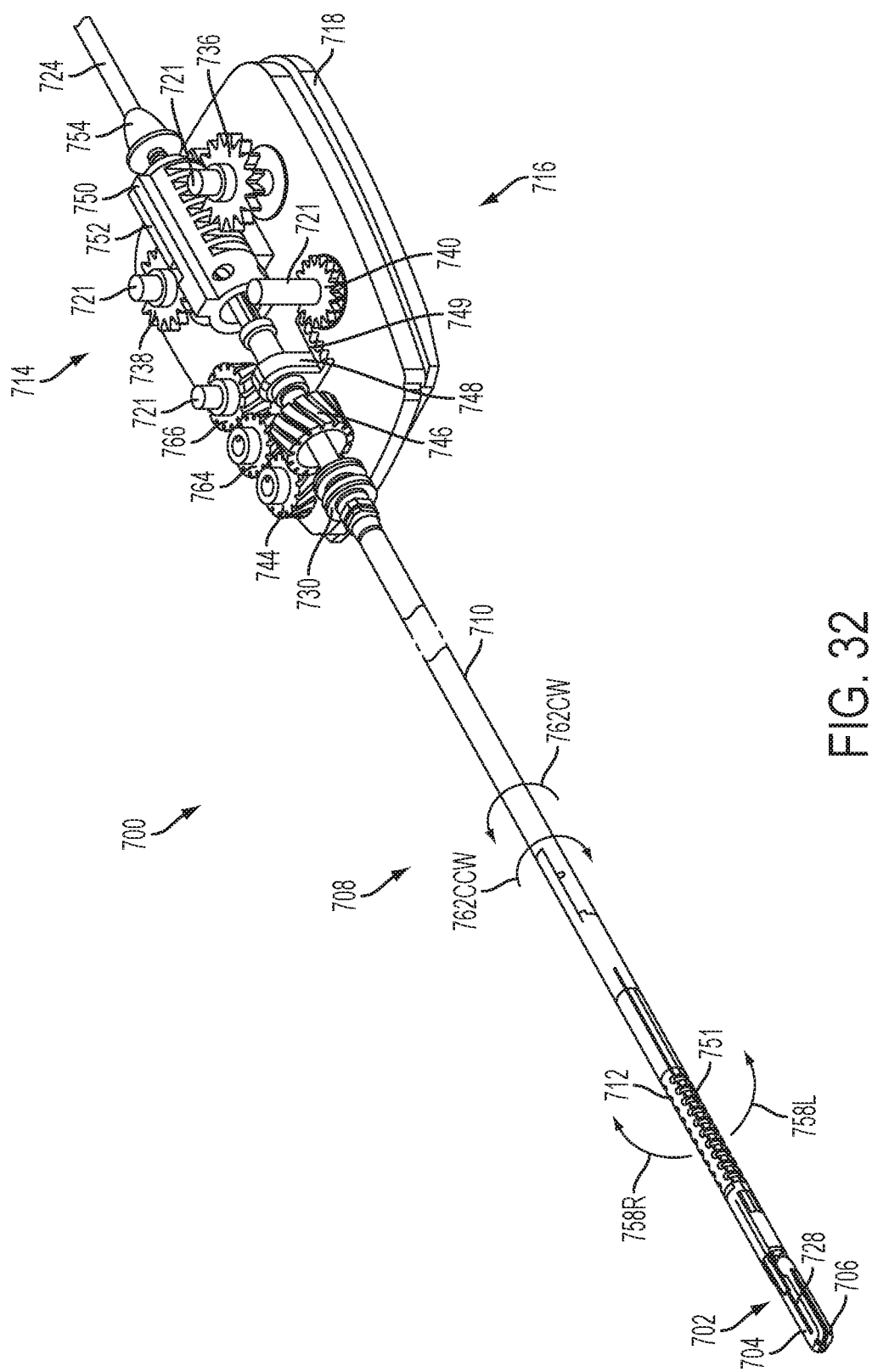
FIG. 32 illustrates a perspective view of one embodiment of the surgical tool shown in FIG. 25 with the tool mounting housing removed.
Figure 33:
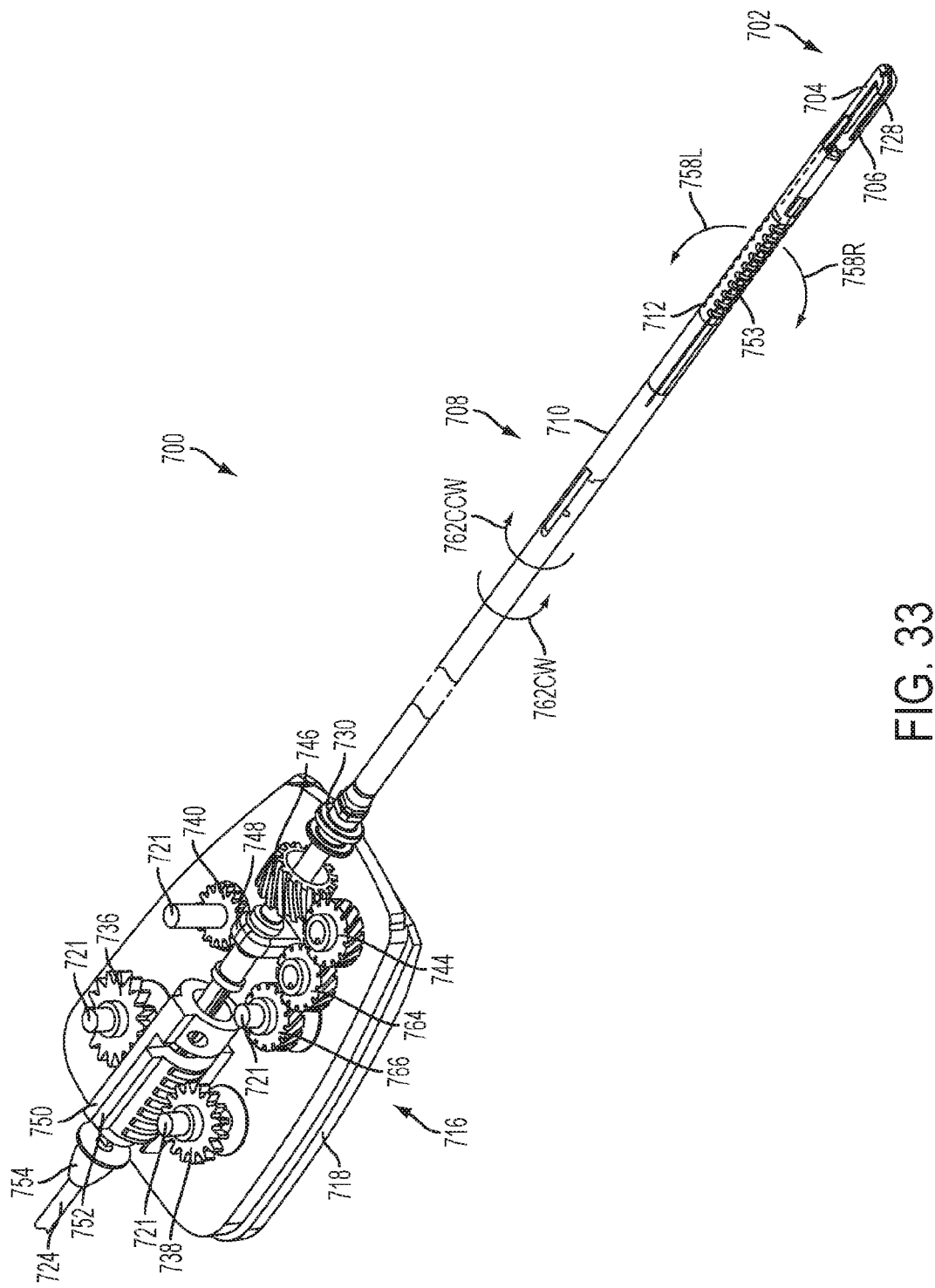
FIG. 33 illustrates a perspective view of one embodiment of the surgical tool shown in FIG. 25 with the tool mounting housing removed.
Figure 35:
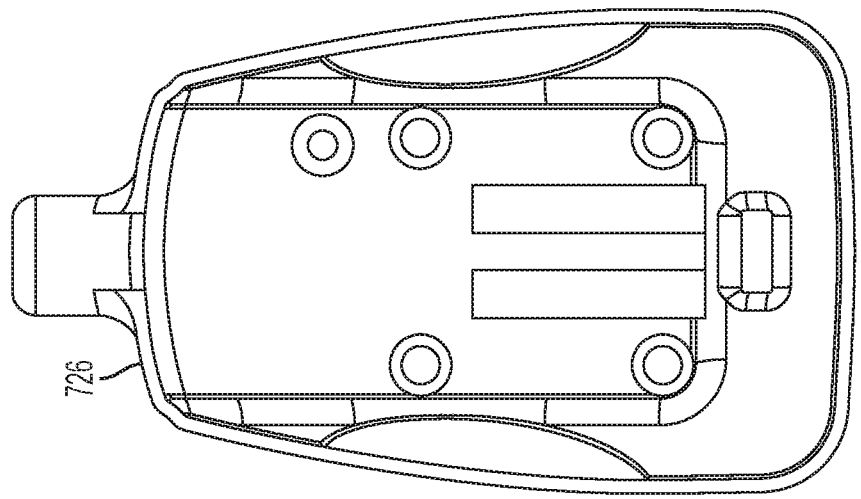
FIG. 35 illustrates a bottom view of one embodiment of the tool mounting housing of the surgical tool shown in FIG. 25.
Figure 34:
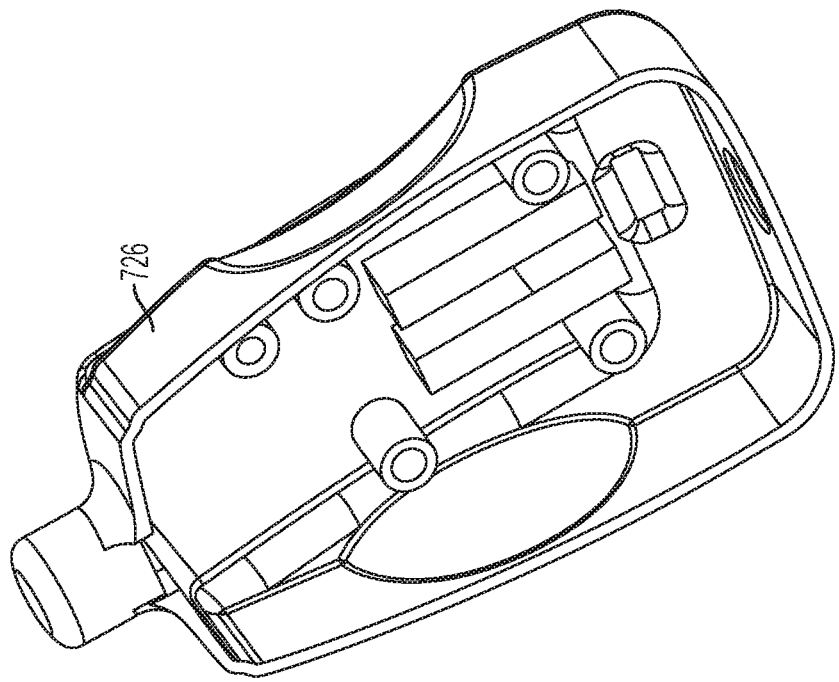
FIG. 34 illustrates a perspective view of one embodiment of the tool mounting housing of the surgical tool shown in FIG. 25.
Figure 36:
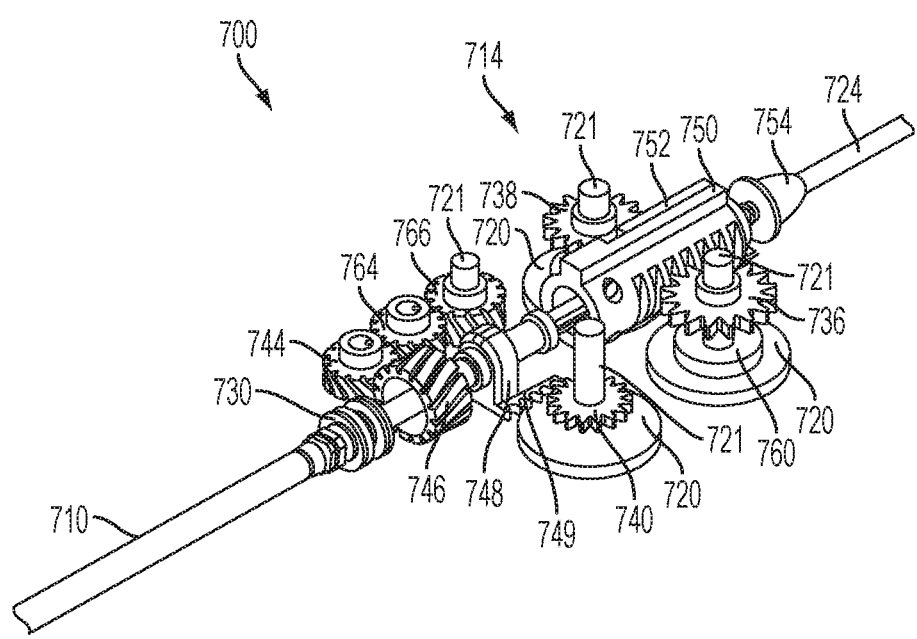
FIG. 36 illustrates a perspective view of one embodiment of the surgical tool shown in FIG. 25 with the tool mounting housing and tool mounting plate removed.
Figure 37:
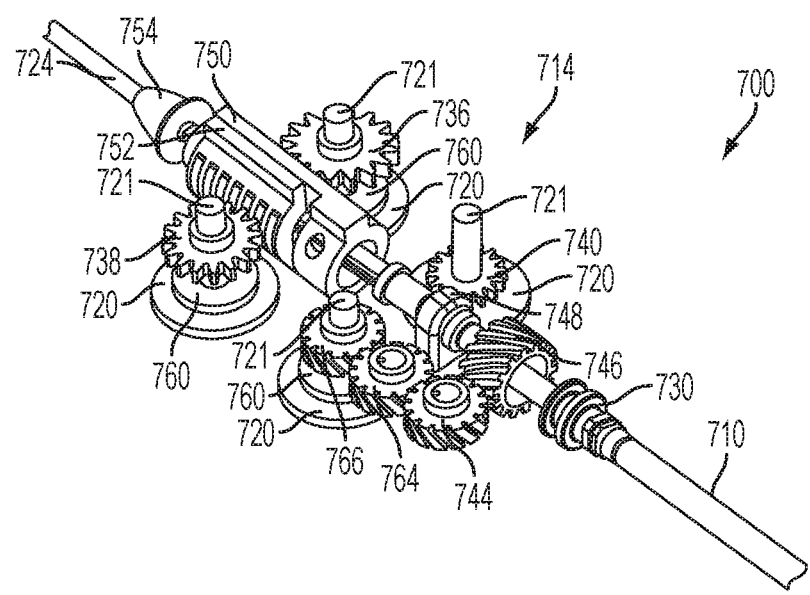
FIG. 37 illustrates a perspective view of one embodiment of the surgical tool shown in FIG. 25 with the tool mounting housing and a tool mounting plate removed.
Figure 39:
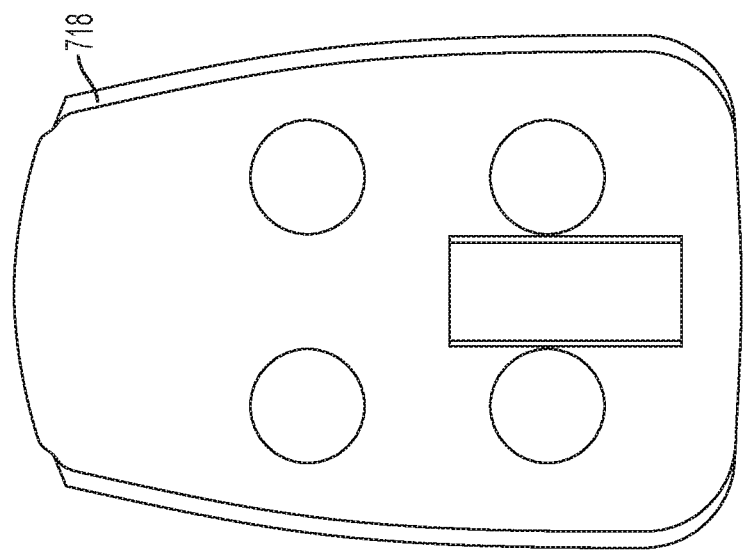
FIG. 39 illustrates a bottom view of one embodiment of the tool mounting plate of the surgical tool shown in FIG. 25.
Figure 38:
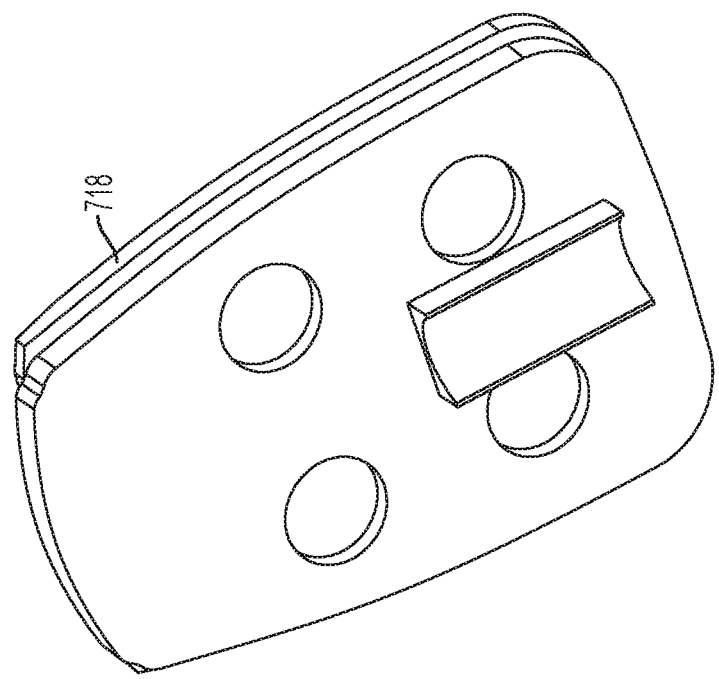
FIG. 38 illustrates a perspective view of one embodiment of the tool mounting plate of the surgical tool shown in FIG. 25.
Figure 40:
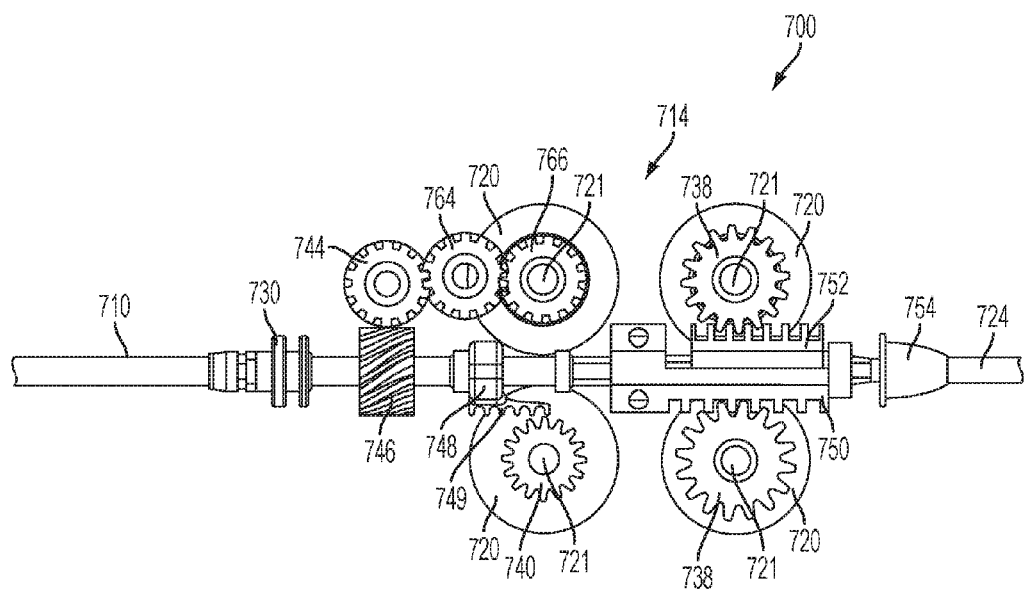
FIG. 40 illustrates a top view of one embodiment of the surgical tool shown in FIG. 25 with the tool mounting housing and the tool mounting plate removed.
Figure 41:
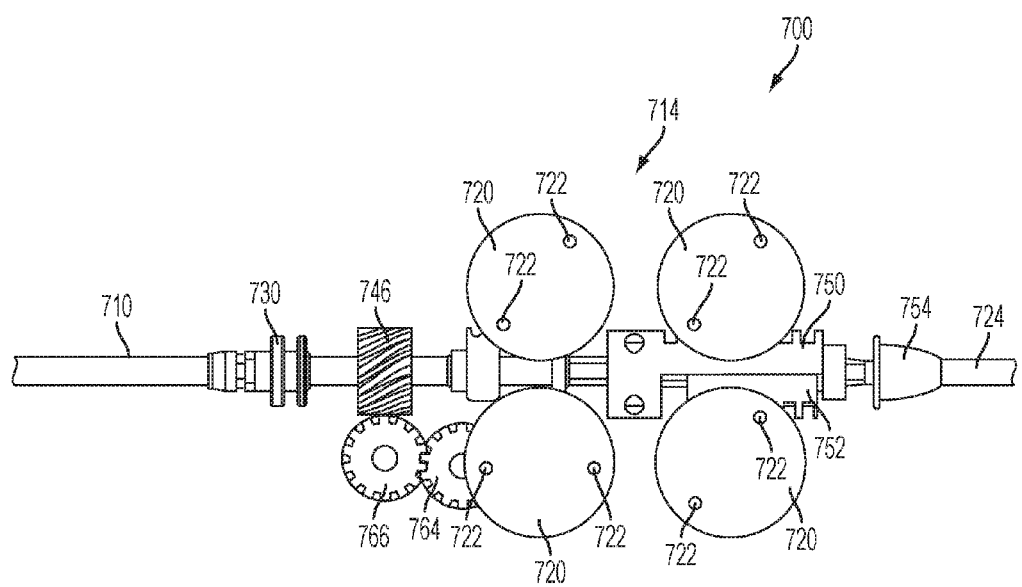
FIG. 41 illustrates a bottom view of one embodiment of the surgical tool shown in FIG. 25 with the tool mounting housing and the tool mounting plate removed.
Figure 42:
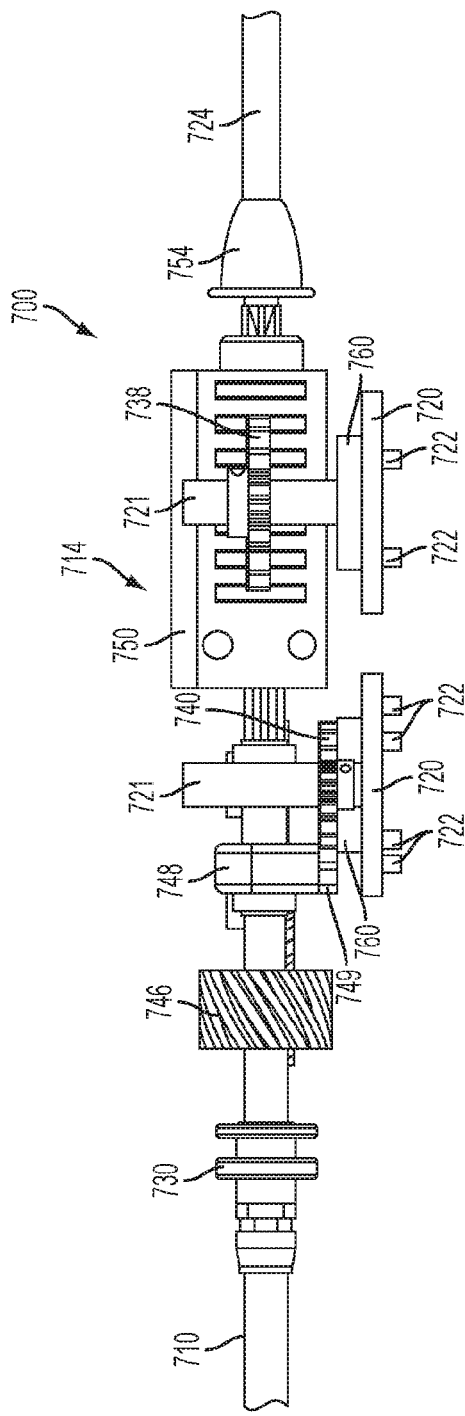
FIG. 42 illustrates a side view of one embodiment of the surgical tool shown in FIG. 25 with the tool mounting housing and the tool mounting plate removed.
Figure 43:
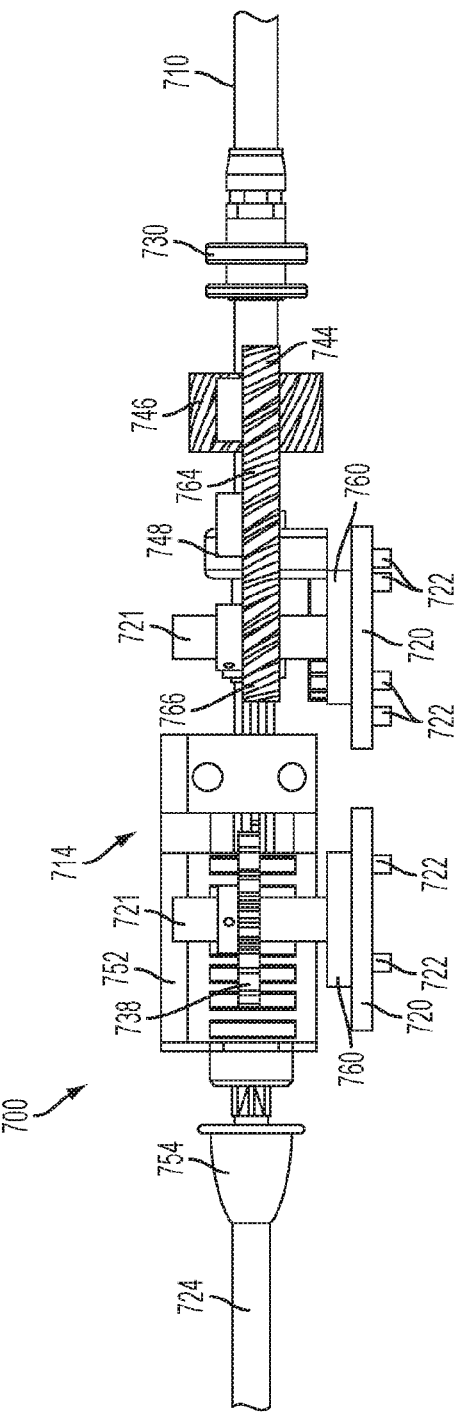
FIG. 43 illustrates a side view of one embodiment of the surgical tool shown in FIG. 25 with the tool mounting housing and the tool mounting plate removed.

For clarity of disclosure, in FIGS. 32 and 33 the surgical tool 700 is illustrated with the tool mounting housing 726 removed. For further clarity of disclosure, in FIGS. 36, 37, and 40-43 the surgical tool 700 is illustrated with both the tool mounting housing 726 and the tool mounting plate 718 removed. Detailed views of the tool mounting housing 726 and the tool mounting plate 718 are shown in FIGS. 34, 35 and 38, 39, respectively.

The surgical tool 700 will now be described with reference to FIGS. 25-43. Accordingly, in one embodiment, the surgical tool 700 comprises a coupler 730 to couple the shaft assembly 708 to the tool mounting portion 714. A top shaft holder similar to the top shaft holder 632 (FIGS. 13, 14) and a bottom shaft holder similar to the bottom shaft holder 634 (FIGS. 13, 14) rotatably couple the shaft assembly 708 to the tool mounting housing 726.

In one embodiment, the tool mounting portion 714 of the surgical tool 700 comprises a shaft assembly 708 articulation mechanism, a shaft assembly 708 rotation mechanism, a clamp jaw 702 open/close mechanism, and a knife actuation mechanism. In one embodiment, the rotatable bodies 721 (e.g., rotatable spools) are coupled to the driven elements 720. The rotatable bodies 721 may be formed integrally with the driven elements 720. In some embodiments, the rotatable bodies 721 may be formed separately from the driven elements 720 provided that the rotatable bodies 721 and the driven elements 720 are fixedly coupled such that driving the driven elements 720 causes rotation of the rotatable bodies 721. Each of the rotatable bodies 721 is coupled to a gear train or gear mechanism to provide shaft articulation and rotation and clamp jaw open/close and knife actuation.

In one embodiment, the tool mounting portion 714 of the surgical tool 700 comprises a shaft assembly 708 articulation mechanism. In the illustrated embodiment, for example, the surgical tool 700 comprises a rack and pinion mechanism to provide shaft articulation functionality. In one embodiment, the rack and pinion gearing mechanism comprises a first pinion gear 736 coupled to a rotatable body 721 such that rotation of the corresponding driven element 720 causes the first pinion gear 736 to rotate. A bearing 760 (FIG. 36) is coupled to the rotatable body 721 and is provided between the driven element 720 and the first pinion gear 736. The first pinion gear 736 is meshed to a first rack gear 750 to convert the rotational motion of the first pinion gear 736 into linear motion of the first rack gear 750 to control the articulation of the articulation section 712 of the shaft assembly 708 in a left direction 758L. The first rack gear 750 is attached to a first articulation band 751 such that linear motion of the first rack gear 750 in a distal direction causes the articulation section 712 of the shaft assembly 708 to articulate in the left direction 758L. A second pinion gear 738 is coupled to another rotatable body 721 such that rotation of the corresponding driven element 720 causes the second pinion gear 738 to rotate. A bearing 760 is coupled to the rotatable body 721 and is provided between the driven element 720 and the second pinion gear 738. The second pinion gear 738 is meshed to a second rack gear 752 to convert the rotational motion of the second pinion gear 738 into linear motion of the second rack gear 752 to control the articulation of the articulation section 712 of the shaft assembly 708 in a right direction 758R. The second rack gear 752 is attached to a second articulation band 753 such that linear motion of the second rack gear 752 in a distal direction causes the articulation section 712 of the shaft assembly 708 to articulate in the right direction 758R. Additional bearings may be provided between the rotatable bodies and the corresponding gears. Any suitable bearings may be provided to support and stabilize the mounting and reduce rotary friction of shaft and gears, for example.

In one embodiment, the tool mounting portion 714 of the surgical tool 700 comprises a shaft assembly 708 rotation mechanism. In the illustrated embodiment, for example, the surgical tool 700 comprises a first spiral worm gear 766 coupled to a second spiral worm gear 764, which is coupled to a third spiral worm gear 744. Such an arrangement is provided for various reasons including maintaining compatibility with existing robotic systems 200 and/or where space may be limited. The first spiral worm gear 766 is coupled to a rotatable body 721. The third spiral worm gear 744 is meshed with a fourth spiral worm gear 746 coupled to the shaft assembly 708. A bearing 760 (FIG. 37) is coupled to a rotatable body 721 and is provided between a driven element 720 and the first spiral worm gear 738. Another bearing 760 is coupled to a rotatable body 721 and is provided between a driven element 720 and the third spiral worm gear 766. The third spiral worm gear 766 is meshed to the fourth spiral worm gear 746, which is coupled to the shaft assembly 708, to control the rotation of the shaft assembly 708 in a CW and a CCW direction based on the rotational direction of the spiral worm gears 744, 746. Accordingly, rotation of the third spiral worm gear 744 about a first axis is converted to rotation of the fourth spiral worm gear 746 about a second axis, which is orthogonal to the first axis. As shown in FIGS. 32, 33, for example, a CW rotation of the fourth spiral worm gear 746 results in a CW rotation of the shaft assembly 708 in the direction indicated by 762CW. A CCW rotation of the fourth spiral worm gear 746 results in a CCW rotation of the shaft assembly 708 in the direction indicated by 762CCW. Additional bearings may be provided between the rotatable bodies and the corresponding gears. Any suitable bearings may be provided to support and stabilize the mounting and reduce rotary friction of shaft and gears, for example.

In one embodiment, the tool mounting portion 714 of the surgical tool 700 comprises a clamp jaw 702 open/close mechanism and a knife actuation mechanism. In the illustrated embodiment, for example, the surgical tool 700 comprises a rack and pinion gearing mechanism to provide the clamp jaw 702 open/close and knife actuation functionality. In one embodiment, a third pinion gear 740 is coupled to a rotatable body 721 such that rotation of the corresponding driven element 720 causes the third pinion gear 740 to rotate in a first direction. The third pinion gear 740 is meshed to a rack gear 749, which moves in a linear direction. The rack gear 749 is coupled to a close/open block 748, which is coupled to a distal portion of the shaft assembly 708. In one embodiment, the gear mechanism comprising the pinion gear 740 is configured to control the opening and closing of the clamp jaw 702 and movement of an "I-beam" shaped cutting element through the slot 728 formed in the clamp jaw 702. As the rack gear 749 moves in a distal direction, the "I-beam" shaped cutting element advances and closes the top jaw 704 portion of the clamp jaw 702. As the rack gear 749 moves in a proximal direction, the "I-beam" shaped cutting element retracts and enables the top jaw 704 portion of the clamp jaw 702 to open. A description of one embodiment of an "I-beam" shaped cutting element is provided in the '247 application.

Figure 44:
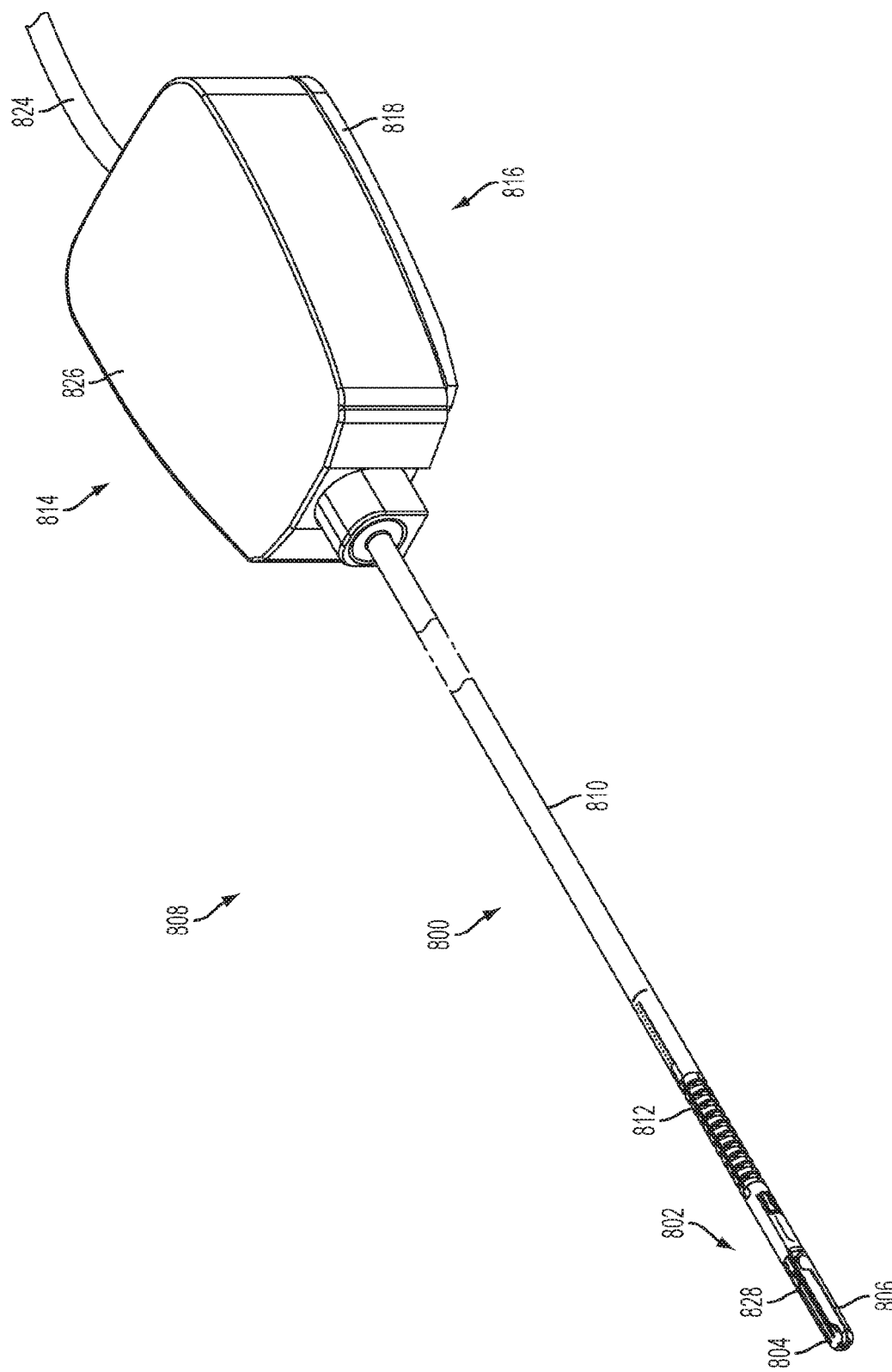
FIG. 44 illustrates a perspective view of one embodiment of a surgical tool that is well-adapted for use with a robotic system.
Figure 45:
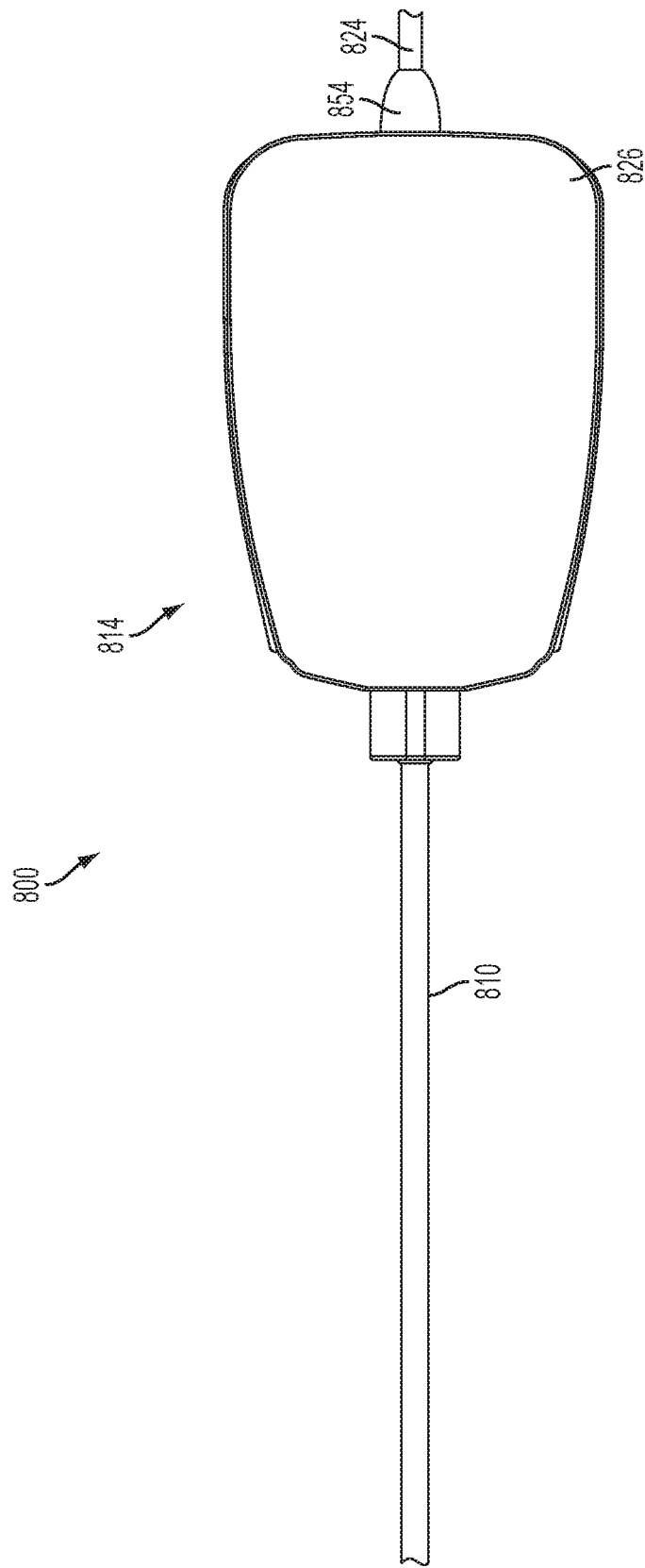
FIG. 45 illustrates a top view of one embodiment of the surgical tool shown in FIG. 44.

FIGS. 44-50 illustrate one embodiment of a surgical tool 800 that is well-adapted for use with the robotic system 200 (FIG. 2) that has a tool drive assembly that is operatively coupled to a master controller 202 (FIG. 2) that is operable by inputs from an operator (i.e., a surgeon). As shown in FIG. 44, the surgical tool 800 comprises a surgical end effector 802 (e.g., clamp jaw 802) that comprises medical forceps having a movable jaw member and a cutting blade coupled to an inner sheath located within an elongate shaft assembly 808 that are controlled by the robotic system 200. The movable jaw member comprises a top jaw 804 and a bottom jaw 806. A center slot 828 is provided for slidably receiving a cutting element (e.g., blade, knife) therein. In one embodiment, the cutting element is shaped like an "I-beam" as disclosed in the '247 application. In one embodiment, the surgical tool 800 comprises an elongated shaft assembly 808 that has an elongate tube portion 810 and a distal articulation section 812. The surgical tool 800 is operatively coupled to the manipulator 308 (FIGS. 3-5) by a tool mounting portion 814. The surgical tool 800 further comprises an interface 816, which mechanically and electrically couples the tool mounting portion 814 to the manipulator 308.

Figure 46:
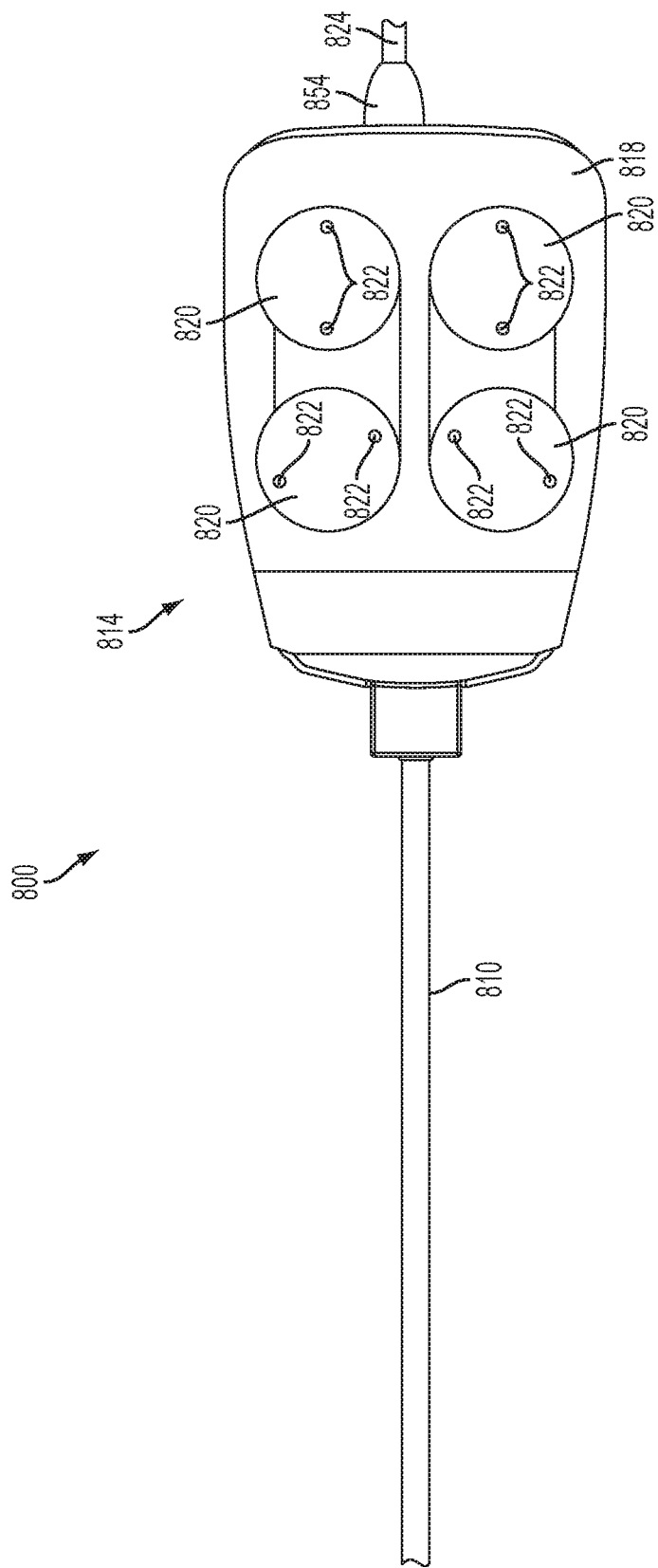
FIG. 46 illustrates a bottom view of one embodiment of the surgical tool shown in FIG. 44.
Figure 47:
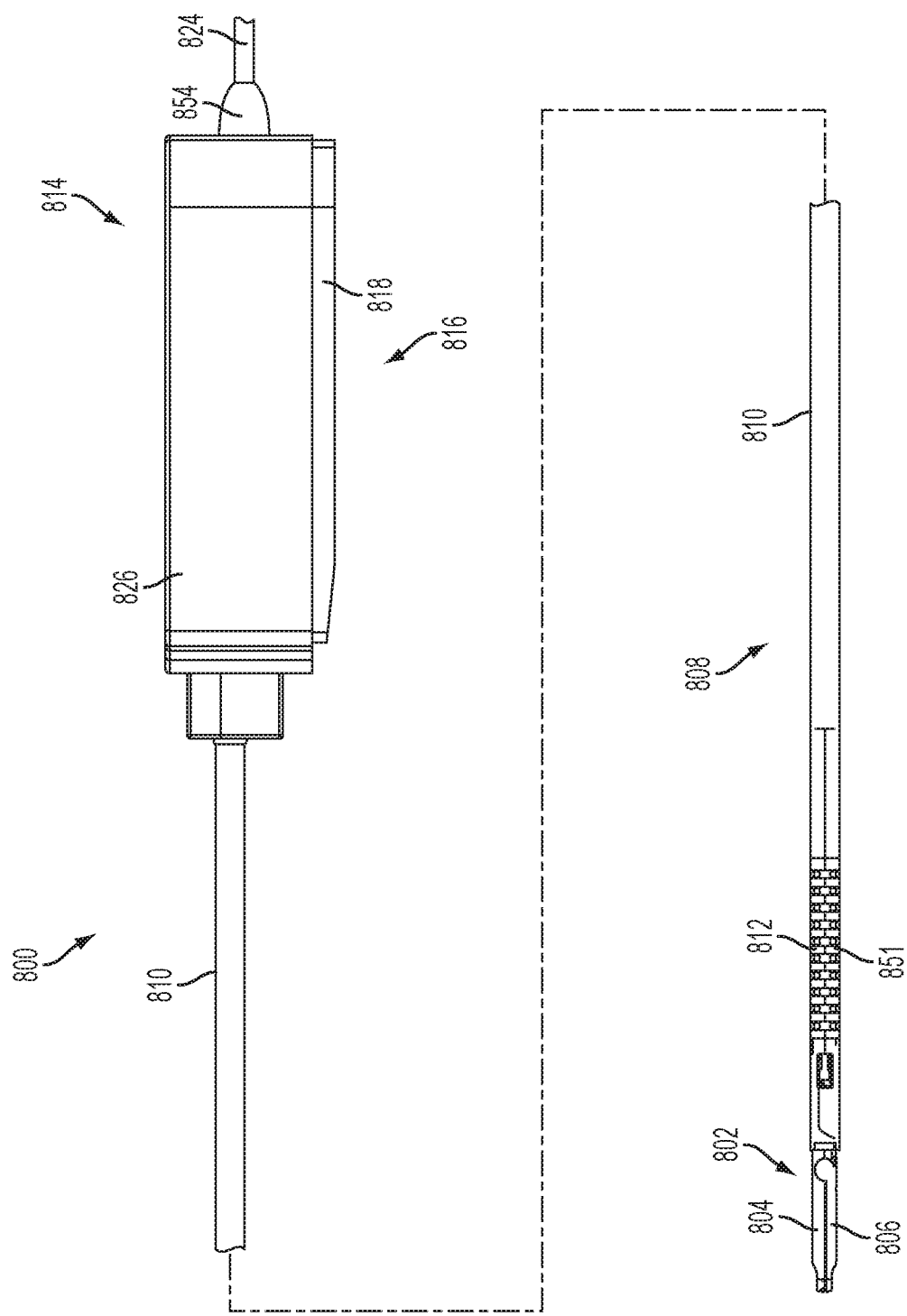
FIG. 47 illustrates a side view of one embodiment of the surgical tool shown in FIG. 44.
Figure 48:
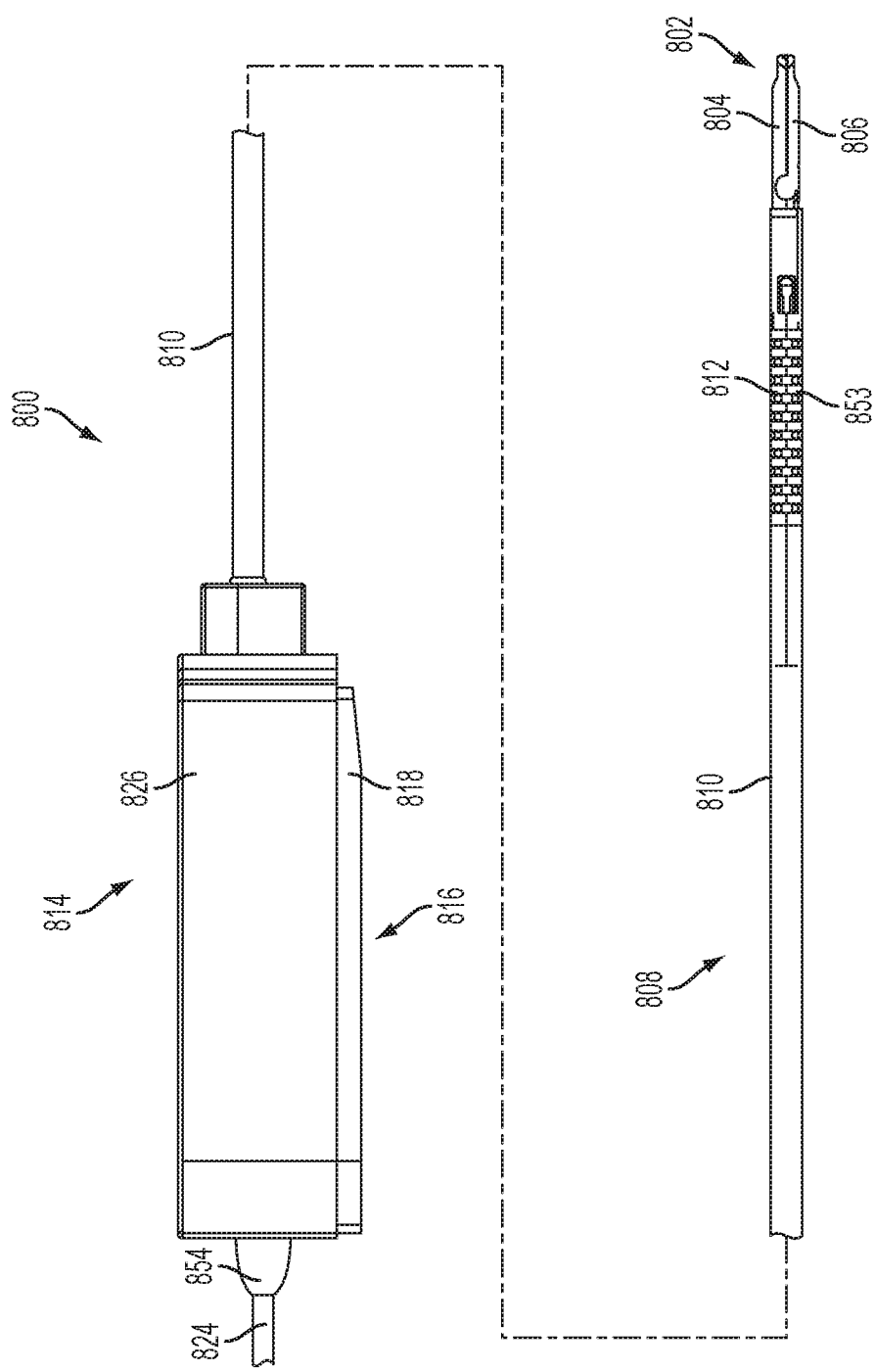
FIG. 48 illustrates a side view of one embodiment of the surgical tool shown in FIG. 44.
Figure 50:
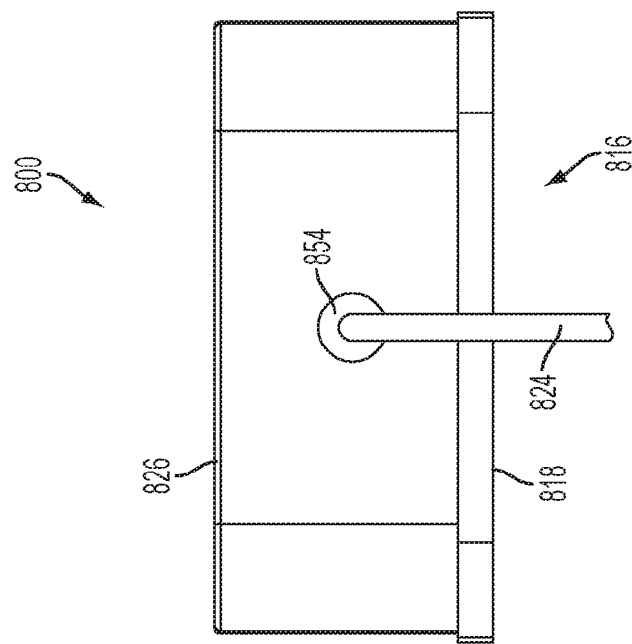
FIG. 50 illustrates a rear view of one embodiment of the surgical tool shown in FIG. 44.
Figure 49:
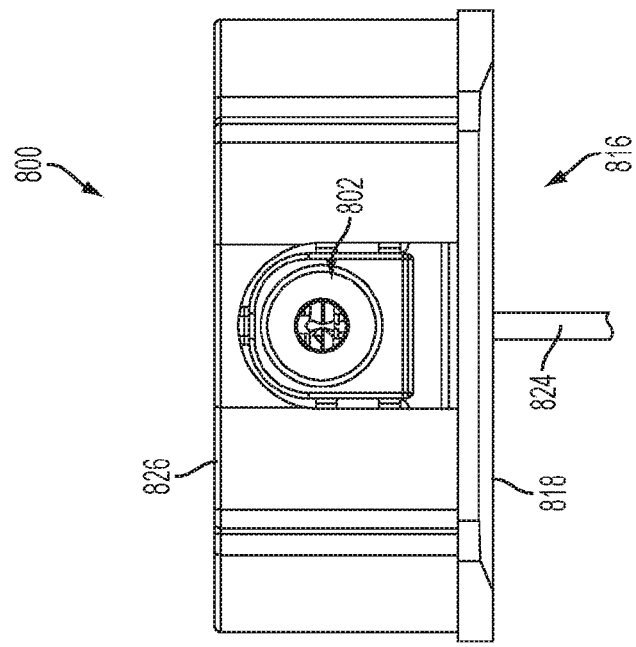
FIG. 49 illustrates a front view of one embodiment of the surgical tool shown in FIG. 44.

In various embodiments, the tool mounting portion 814 comprises a tool mounting housing 826 and a tool mounting plate 818 that operatively supports a plurality of rotatable body portions, driven discs or elements 820 (four are shown in FIG. 46), that each include a pair of pins 822 (FIG. 46) that extend from a surface of the driven element 820. One pin 822 is closer to an axis of rotation of each driven element 820 than the other pin 822 on the same driven element 820, which helps to ensure positive angular alignment of the driven element 820. The interface 816 comprises an adaptor portion that is configured to mountingly engage the mounting plate 818 as will be further discussed below. In one embodiment, an adaptor portion may include an array of electrical connecting pins, which may be coupled to a memory structure by a circuit board within the tool mounting portion 814. While the interface 816 is described herein with reference to mechanical, electrical, and magnetic coupling elements, it should be understood that a wide variety of telemetry modalities might be used, including infrared, inductive coupling, or the like. An electrical cable 824 and strain relief 854 are provided to electrically couple the surgical tool 800 to a generator, which may be an ultrasonic energy source, an RF energy source, or a combination thereof. In some embodiments, the generators and energy sources as disclosed in the '768 application may be electrically coupled to the surgical tool 800.

In one embodiment, the surgical tool 800 provides bipolar RF energy, articulation of the elongate shaft for better access to vessels and tissue, vessel sealing, low thermal spreading, and uniform compression for improved hemostasis, among other features. As described in more detail with reference to FIGS. 51-62, the surgical tool 800 provides gearing mechanisms to obtain independent movements of the articulation section 812 of the shaft assembly 808, the top jaw 804 portion of the end effector 802, the cutting element, and rotation of the shaft assembly 808, among other movements. In one embodiment, the tool mounting housing 826 also may comprise an electronic circuit board with electronic elements to identify the surgical tool 800. In one embodiment, the tool mounting housing 826 also may comprise an internal battery, as shown in FIGS. 89 and 90, for example, to generate sufficient energy to cauterize, coagulate/desiccate, and/or simply reduce or slow bleeding of tissue such as a vessel. Such battery energized circuits are described in the '768 application.

Figure 51:
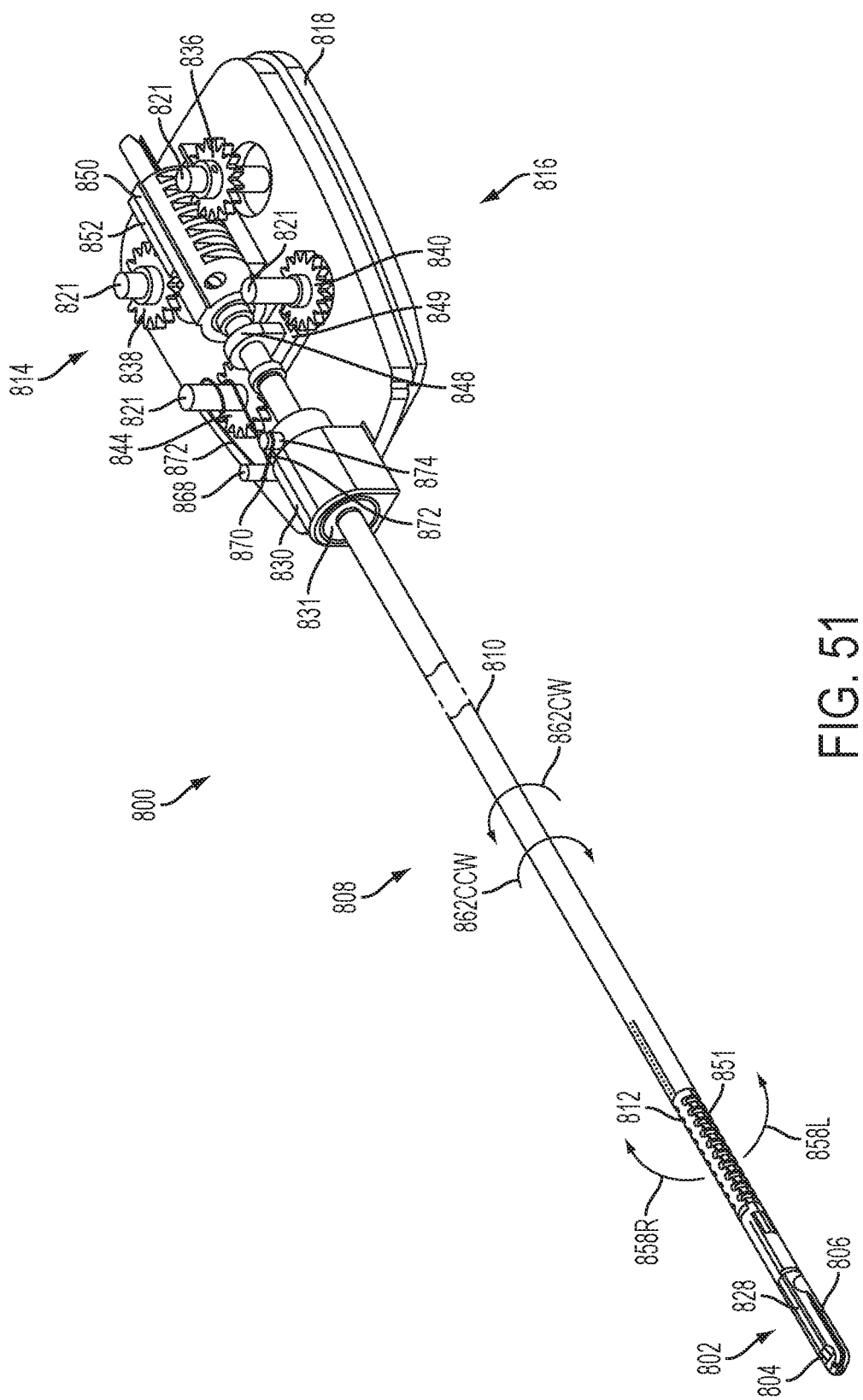
FIG. 51 illustrates a perspective view of one embodiment of the surgical tool shown in FIG. 44 with the tool mounting housing removed.
Figure 52:
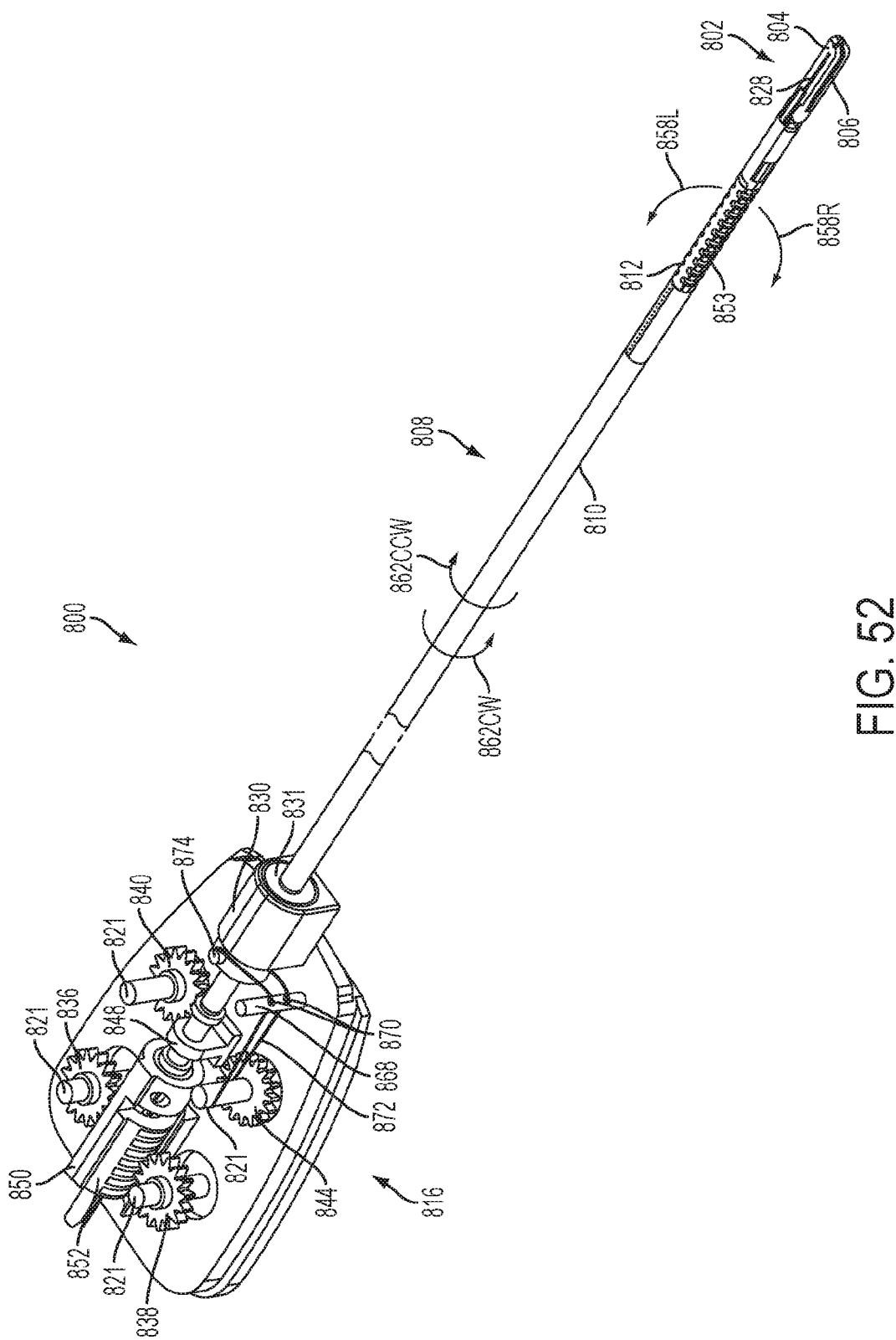
FIG. 52 illustrates a perspective view of one embodiment of the surgical tool shown in FIG. 44 with the tool mounting housing removed.
Figure 54:
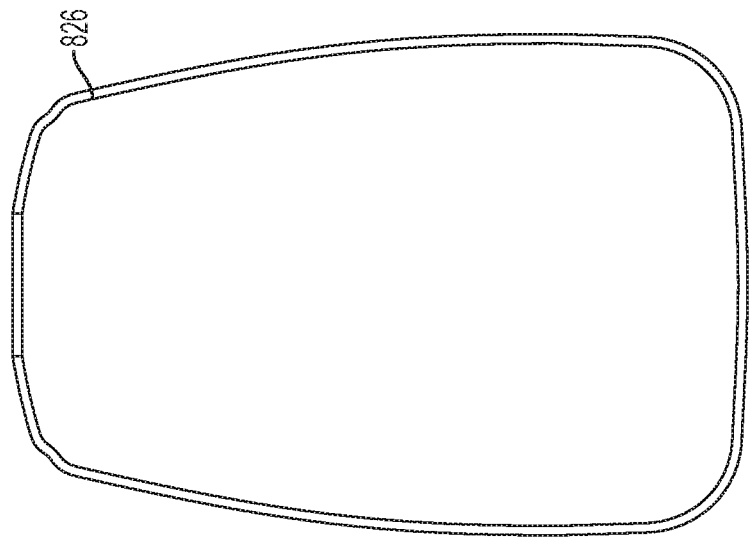
FIG. 54 illustrates a bottom view of one embodiment of the tool mounting housing of the surgical tool shown in FIG. 44.
Figure 53:
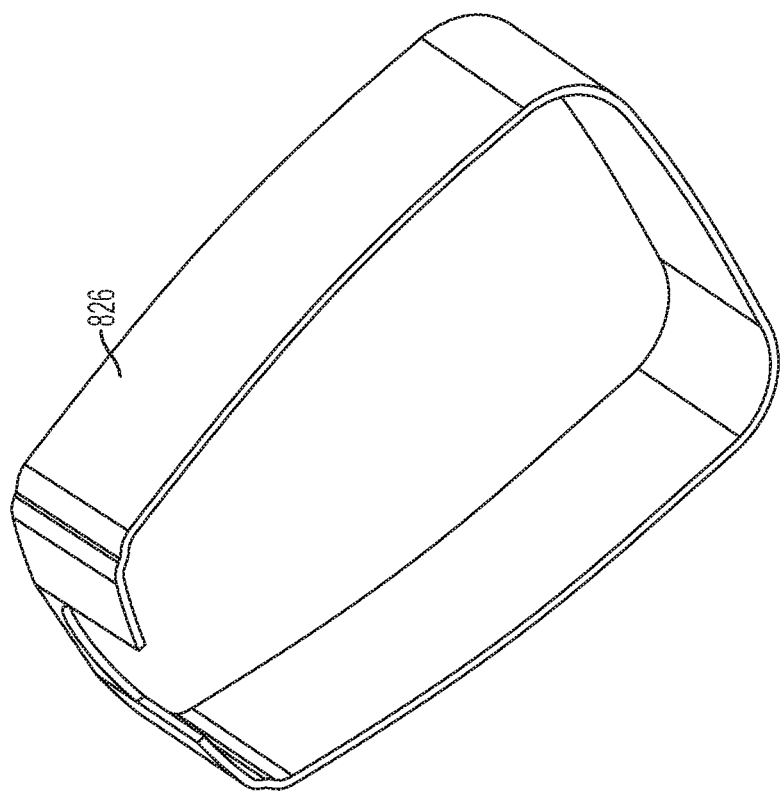
FIG. 53 illustrates a perspective view of one embodiment of the tool mounting housing of the surgical tool shown in FIG. 44.
Figure 55:
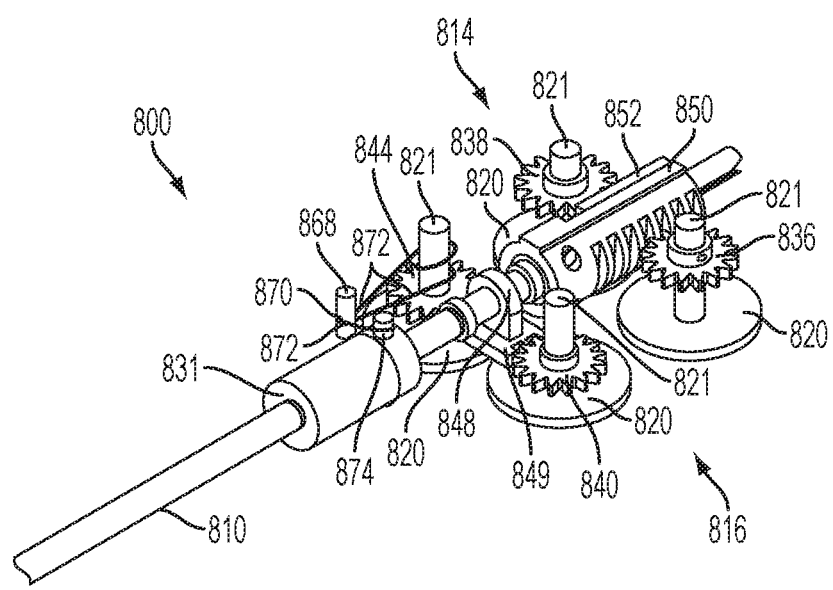
FIG. 55 illustrates a perspective view of one embodiment of the surgical tool shown in FIG. 44 with the tool mounting housing and tool mounting plate removed.
Figure 56:
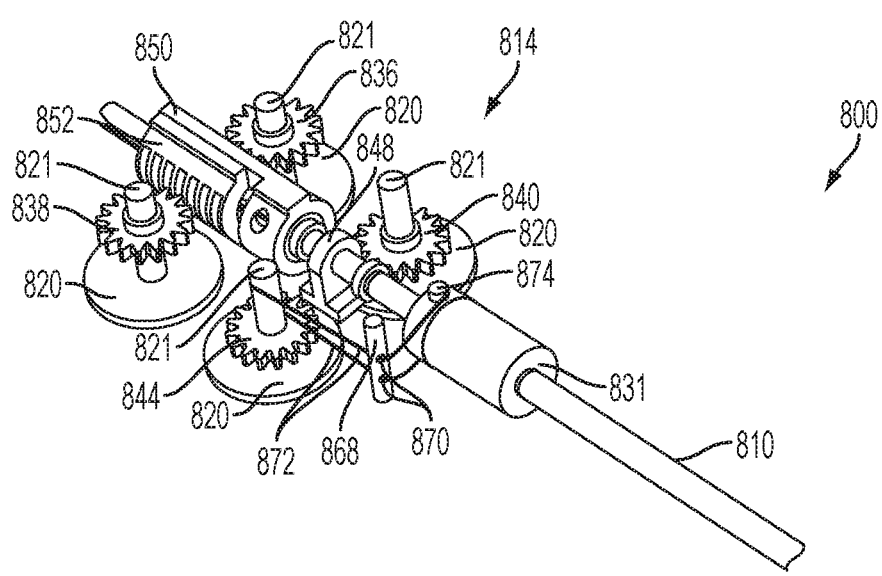
FIG. 56 illustrates a perspective view of one embodiment of the surgical tool shown in FIG. 44 with the tool mounting housing and a tool mounting plate removed.
Figure 58:
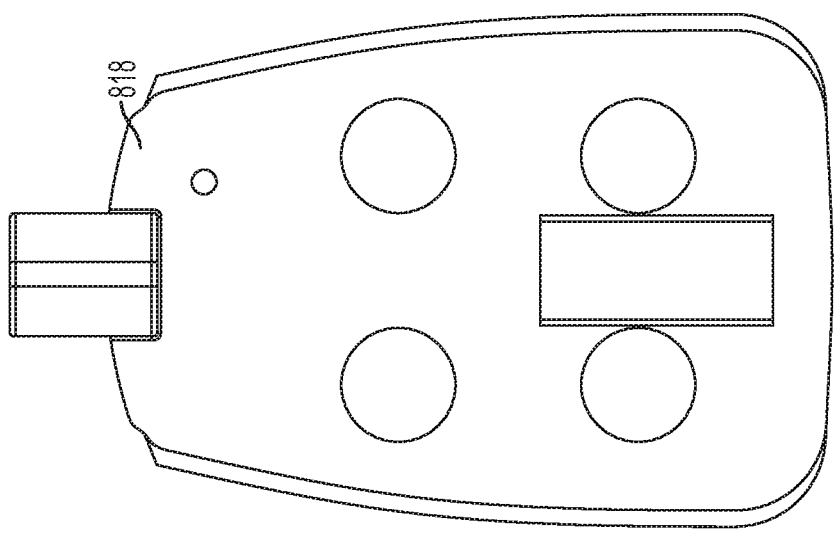
FIG. 58 illustrates a bottom view of one embodiment of the tool mounting plate of the surgical tool shown in FIG. 44.
Figure 57:
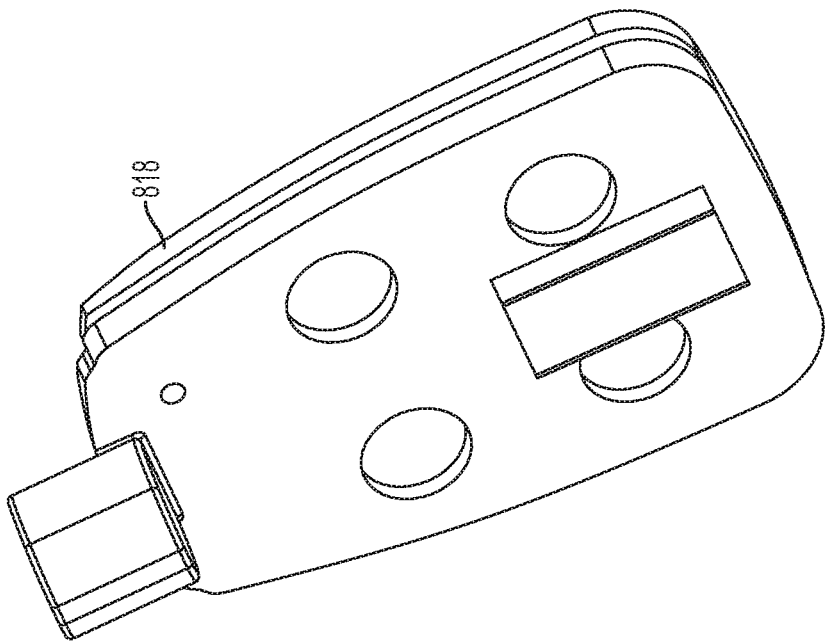
FIG. 57 illustrates a perspective view of one embodiment of the tool mounting plate of the surgical tool shown in FIG. 44.
Figure 59:
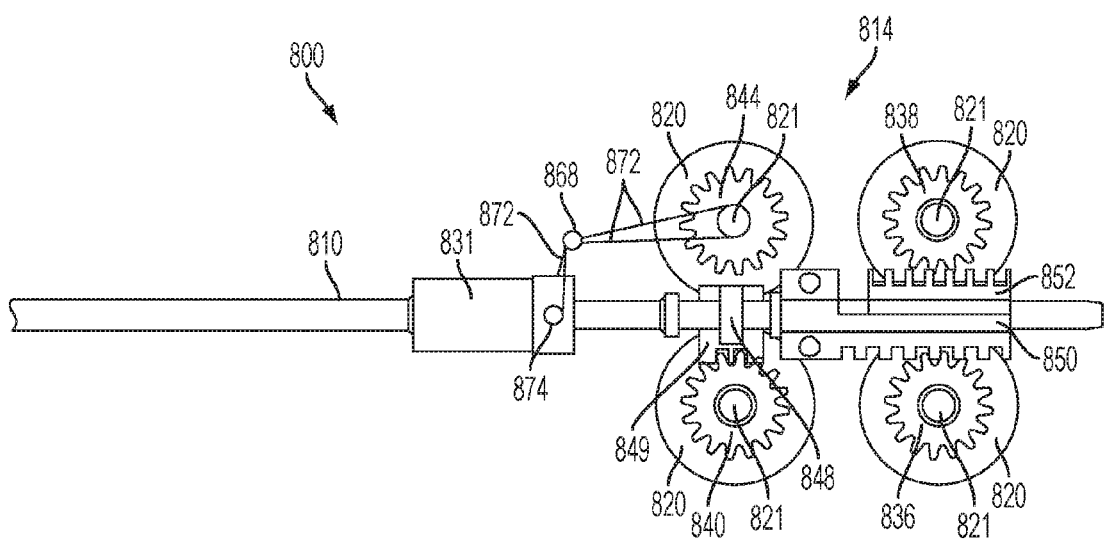
FIG. 59 illustrates a top view of one embodiment of the surgical tool shown in FIG. 44 with the tool mounting housing and the tool mounting plate removed.
Figure 60:
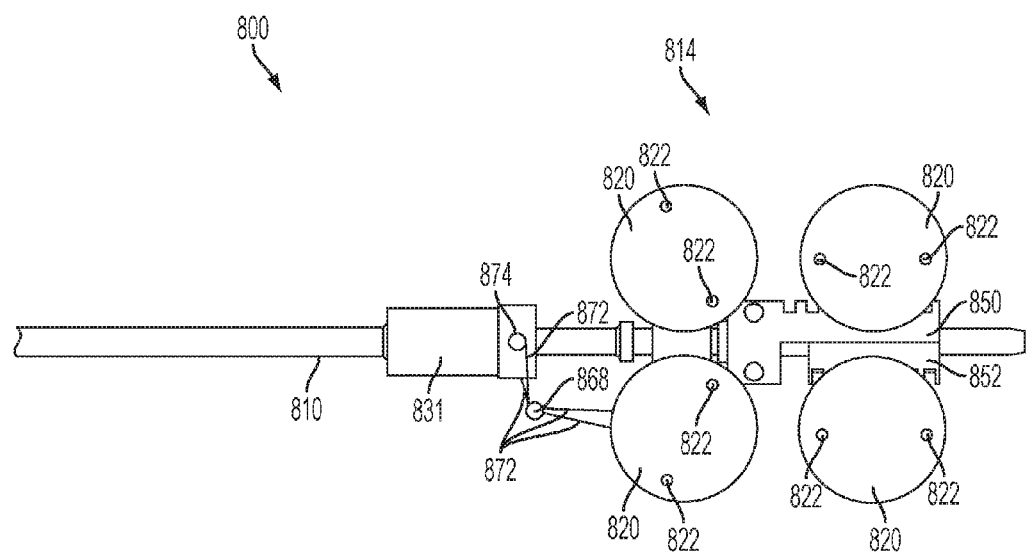
FIG. 60 illustrates a bottom view of one embodiment of the surgical tool shown in FIG. 44 with the tool mounting housing and the tool mounting plate removed.

For clarity of disclosure, in FIGS. 51 and 52 the surgical tool 800 is illustrated with the tool mounting housing 826 removed. For further clarity of disclosure, in FIGS. 55, 56, and 59-62 the surgical tool 800 is illustrated with both the tool mounting housing 826 and the tool mounting plate 818 removed. Detailed views of the tool mounting housing 826 and the tool mounting plate 818 are shown in FIGS. 53, 54 and 57, 58, respectively.

The surgical tool 800 will now be described with reference to FIGS. 44-62. Accordingly, in one embodiment, the surgical tool 800 comprises a coupler 830 to couple the shaft assembly 808 to the tool mounting portion 814. A coupler 830 and a bushing 831 rotatably couple the shaft assembly 808 to the tool mounting housing 826.

In one embodiment, the tool mounting portion 814 of the surgical tool 800 comprises a shaft assembly 808 articulation mechanism, a shaft assembly 808 rotation mechanism, a clamp jaw 802 open/close mechanism, and a knife actuation mechanism. In one embodiment, the rotatable bodies 821 (e.g., rotatable spools) are coupled to the driven elements 820. The rotatable bodies 821 may be formed integrally with the driven elements 820. In some embodiments, the rotatable bodies 821 may be formed separately from the driven elements 820 provided that the rotatable bodies 821 and the driven elements 820 are fixedly coupled such that driving the driven elements 820 causes rotation of the rotatable bodies 821. Each of the rotatable bodies 821 is coupled to a gear train or gear mechanism to provide shaft articulation and rotation and clamp jaw open/close and knife actuation.

In one embodiment, the tool mounting portion 814 of the surgical tool 800 comprises a shaft assembly 808 articulation mechanism. In the illustrated embodiment, for example, the surgical tool 800 comprises a rack and pinion gearing mechanism to provide shaft articulation functionality. In one embodiment, the rack and pinion gearing mechanism comprises a first pinion gear 836 coupled to a rotatable body 821 such that rotation of the corresponding driven element 820 causes the first pinion gear 836 to rotate. The first pinion gear 836 is meshed to a first rack gear 850 to convert the rotational motion of the first pinion gear 836 into linear motion of the first rack gear 850 to control the articulation of the articulation section 812 of the shaft assembly 808 in a left direction 858L. The first rack gear 850 is attached to a first articulation band 851 such that linear motion of the first rack gear 850 in a distal direction causes the articulation section 812 of the shaft assembly 808 to articulate in the left direction 858L. A second pinion gear 838 is coupled to another rotatable body 821 such that rotation of the corresponding driven element 820 causes the second pinion gear 838 to rotate. The second pinion gear 838 is meshed to a second rack gear 852 to convert the rotational motion of the second pinion gear 838 into linear motion of the second rack gear 852 to control the articulation of the articulation section 812 of the shaft assembly 808 in a right direction 858R. The second rack gear 852 is attached to a second articulation band 853 such that linear motion of the second rack gear 852 in a distal direction causes the articulation section 812 of the shaft assembly 808 to articulate in the right direction 858R.

In one embodiment, the tool mounting portion 814 of the surgical tool 800 comprises a shaft assembly 808 rotation mechanism. In the illustrated embodiment, for example, the surgical tool 800 comprises a first gear 844 coupled to a rotatable body 821, a fixed post 868 comprising first and second openings 870, first and second rotatable pins 874 coupled to the shaft assembly, and a cable 872 (or rope). The cable is wrapped around the rotatable body 821. One end of the cable 872 is located through a top opening 870 of the fixed post 868 and fixedly coupled to a top rotatable pin 874. Another end of the cable 872 is located through a bottom opening 870 of the fixed post 868 and fixedly coupled to a bottom rotating pin 874. Such an arrangement is provided for various reasons including maintaining compatibility with existing robotic systems 200 and/or where space may be limited. Accordingly, rotation of the rotatable body 821 causes the rotation of the shaft assembly 808, to control the rotation of the shaft assembly 808 in a CW and a CCW direction based on the rotational direction of the rotatable body 821. Accordingly, rotation of the rotatable body 821 about a first axis is converted to rotation of the shaft assembly 808 about a second axis, which is orthogonal to the first axis. As shown in FIGS. 51, 52, for example, a CW rotation of the rotatable body 821 results in a CW rotation of the shaft assembly 808 in the direction indicated by 862CW. A CCW rotation of the rotatable body 821 results in a CCW rotation of the shaft assembly 808 in the direction indicated by 862CCW. Additional bearings may be provided between the rotatable bodies and the corresponding gears. Any suitable bearings may be provided to support and stabilize the mounting and reduce rotary friction of shaft and gears, for example.

In one embodiment, the tool mounting portion 814 of the surgical tool 800 comprises a clamp jaw 802 open/close mechanism and a knife actuation mechanism. In the illustrated embodiment, for example, the surgical tool 800 comprises a rack and pinion mechanism to provide the clamp jaw 802 open/close and knife actuation functionality. In one embodiment, a third pinion gear 840. The third pinion gear 840 is coupled to a rotatable body 821 such that rotation of the corresponding driven element 820 causes the third pinion gear 840 to rotate in a first direction. The third pinion gear 840 is meshed to a rack gear 849, which moves in a linear direction. The rack gear 849 is coupled to a close/open block 848, which is coupled to a distal portion of the shaft assembly 808. In one embodiment, the gear mechanism comprising the pinion gear 840 is configured to control the opening and closing of the top jaw 804 portion of the clamp jaw 802 and movement of an "I-beam" shaped cutting element through the slot 828 formed in the clamp jaw 802. As the rack gear 849 moves in a distal direction, the "I-beam" shaped cutting element advances and closes the top jaw 804 portion of the clamp jaw 802. As the rack gear 849 moves in a proximal direction, the "I-beam" shaped cutting element retracts and enables the top jaw 804 portion of the clamp jaw 802 to open. A description of one embodiment of an "I-beam" shaped cutting element is provided in the '247 application.

Figure 63:
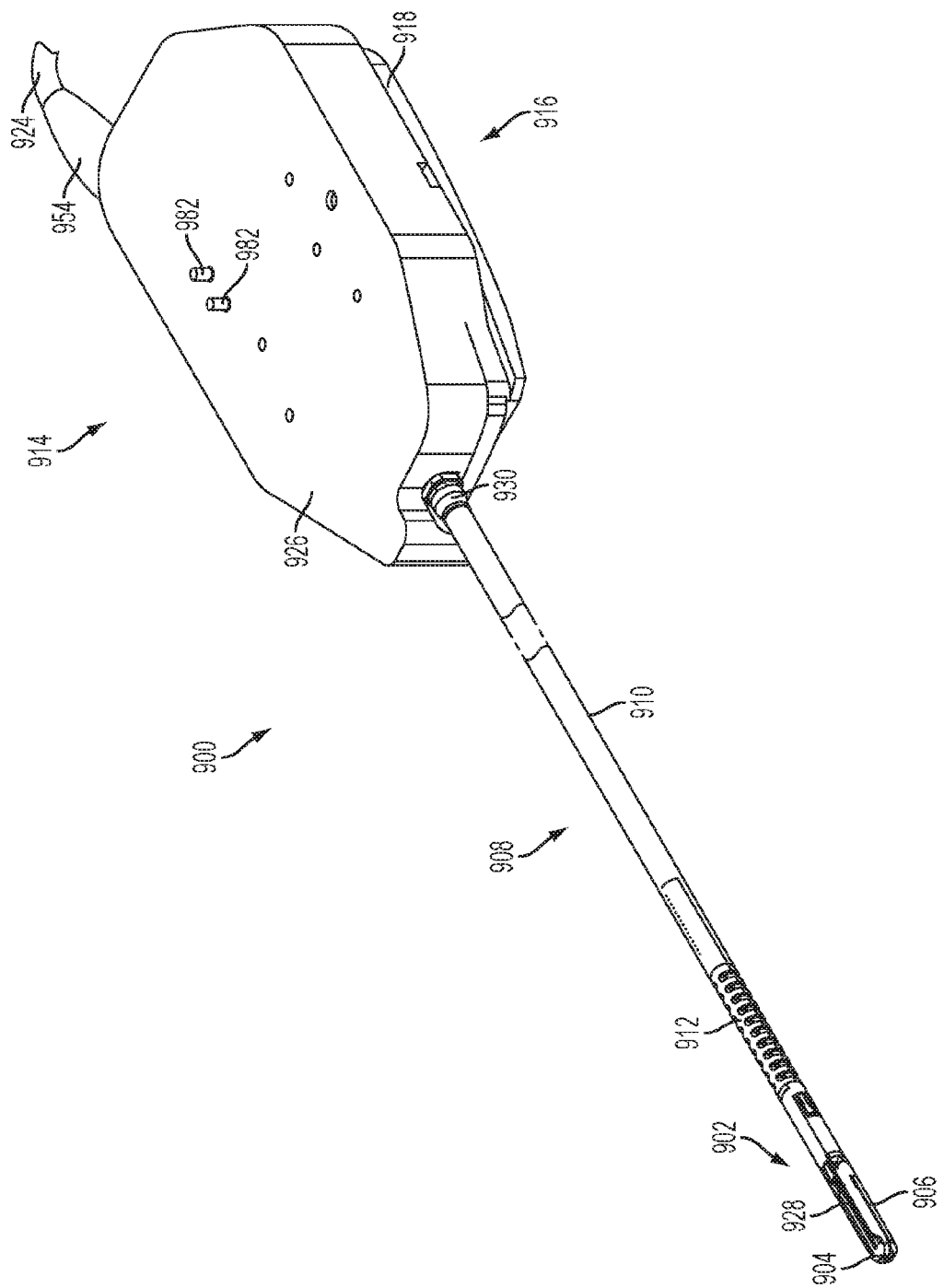
FIG. 63 illustrates a perspective view of one embodiment of a surgical tool that is well-adapted for use with a robotic system.
Figure 64:
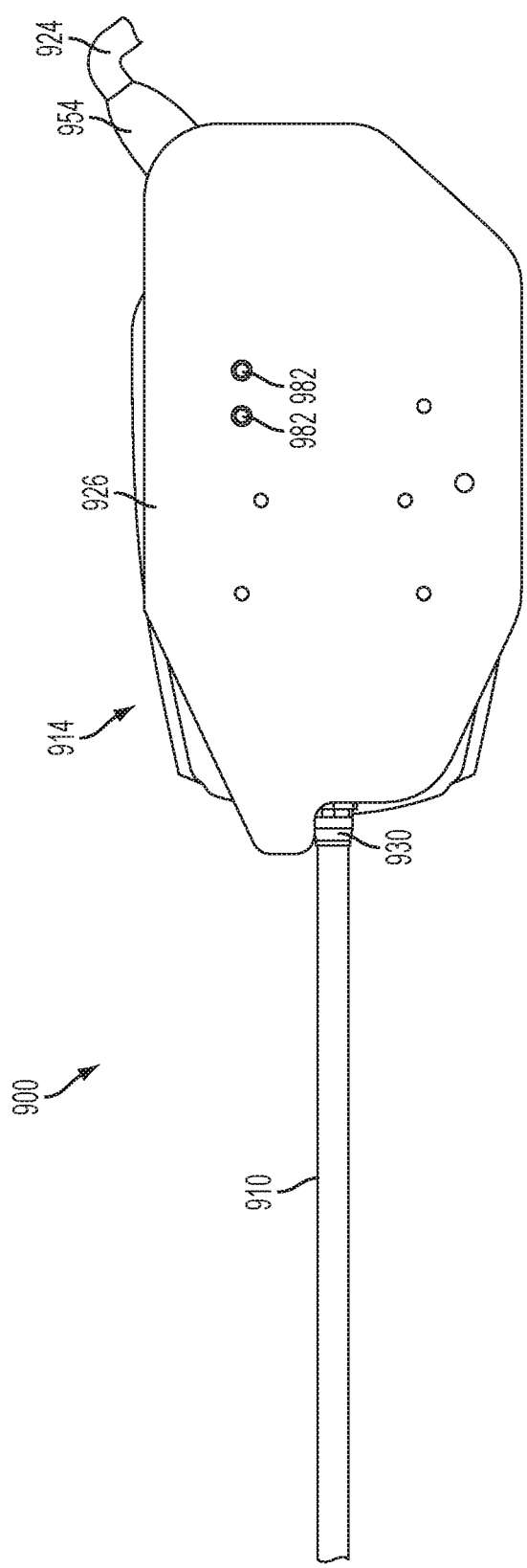
FIG. 64 illustrates a top view of one embodiment of the surgical tool shown in FIG. 63.

FIGS. 63-68 illustrate one embodiment of a surgical tool 900 that is well-adapted for use with the robotic system 200 (FIG. 2) that has a tool drive assembly that is operatively coupled to a master controller 202 (FIG. 2) that is operable by inputs from an operator (i.e., a surgeon). As shown in FIG. 63, the surgical tool 900 comprises a surgical end effector 902 (e.g., clamp jaw 902) that comprises medical forceps having a movable jaw member and a cutting blade coupled to an inner sheath located within an elongate shaft assembly 908 that are controlled by the robotic system 200. The movable jaw member comprises a top jaw 904 and a bottom jaw 906. A center slot 928 is provided for slidably receiving a cutting element (e.g., blade, knife) therein. In one embodiment, the cutting element is shaped like an "I-beam" as disclosed in the '247 application. In one embodiment, the surgical tool 900 comprises an elongated shaft assembly 908 that has an elongate tube portion 910 and a distal articulation section 912. The surgical tool 900 is operatively coupled to the manipulator 308 (FIGS. 3-5) by a tool mounting portion 914. The surgical tool 900 further comprises an interface 916, which mechanically and electrically couples the tool mounting portion 914 to the manipulator 308.

Figure 65:
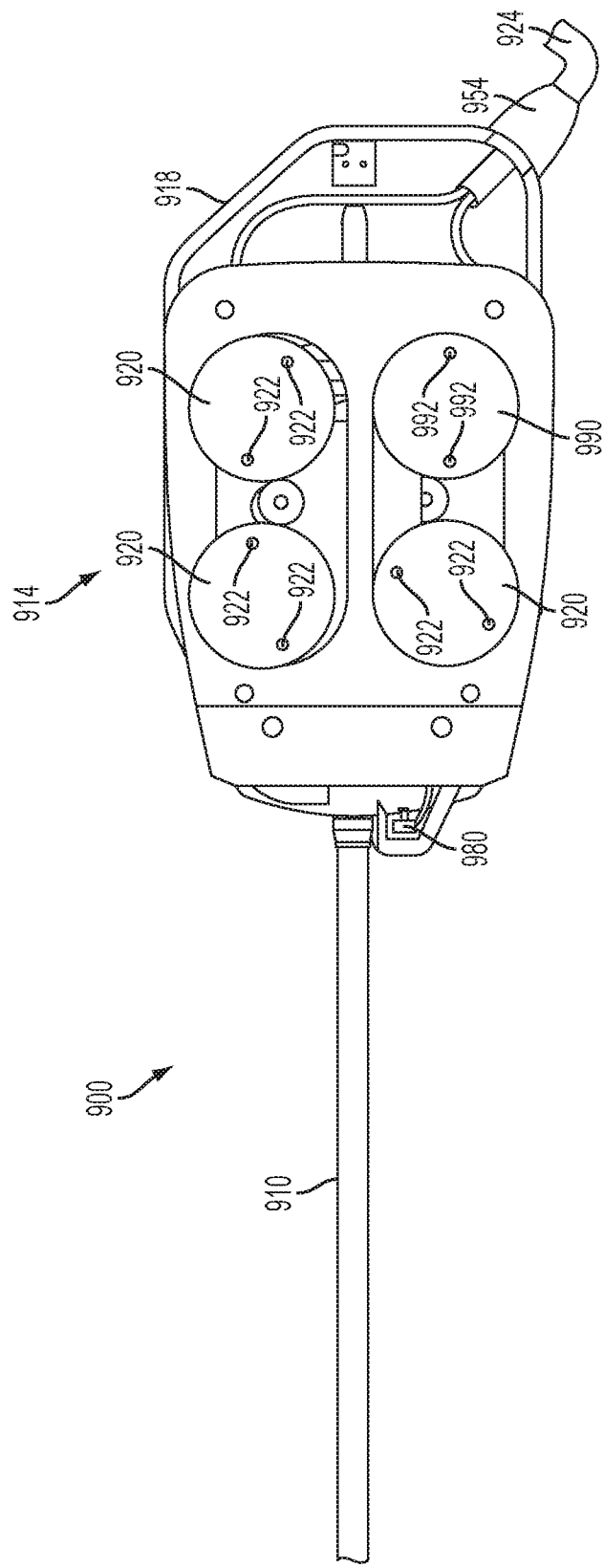
FIG. 65 illustrates a bottom view of one embodiment of the surgical tool shown in FIG. 63.
Figure 66:
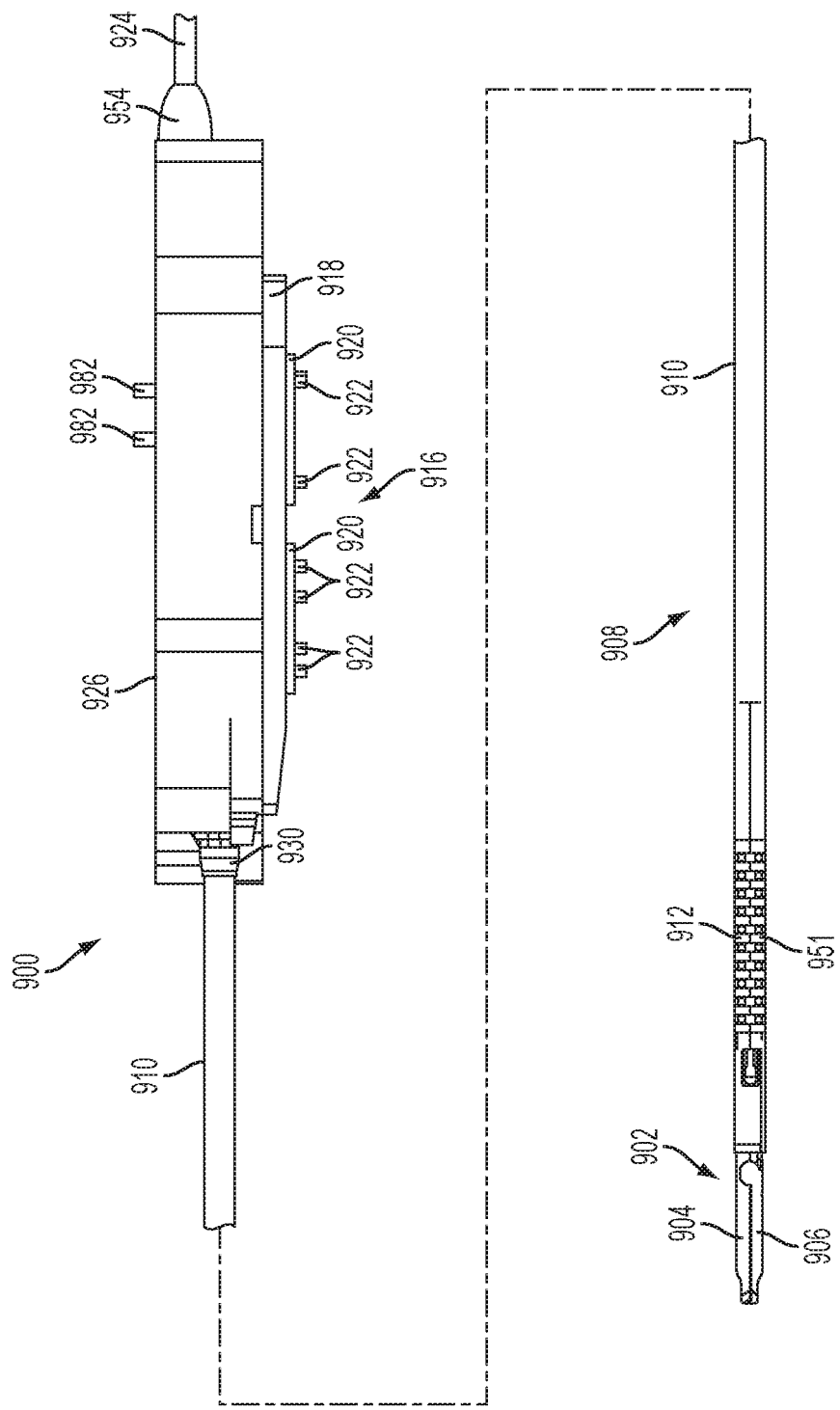
FIG. 66 illustrates a side view of one embodiment of the surgical tool shown in FIG. 63.
Figure 67:
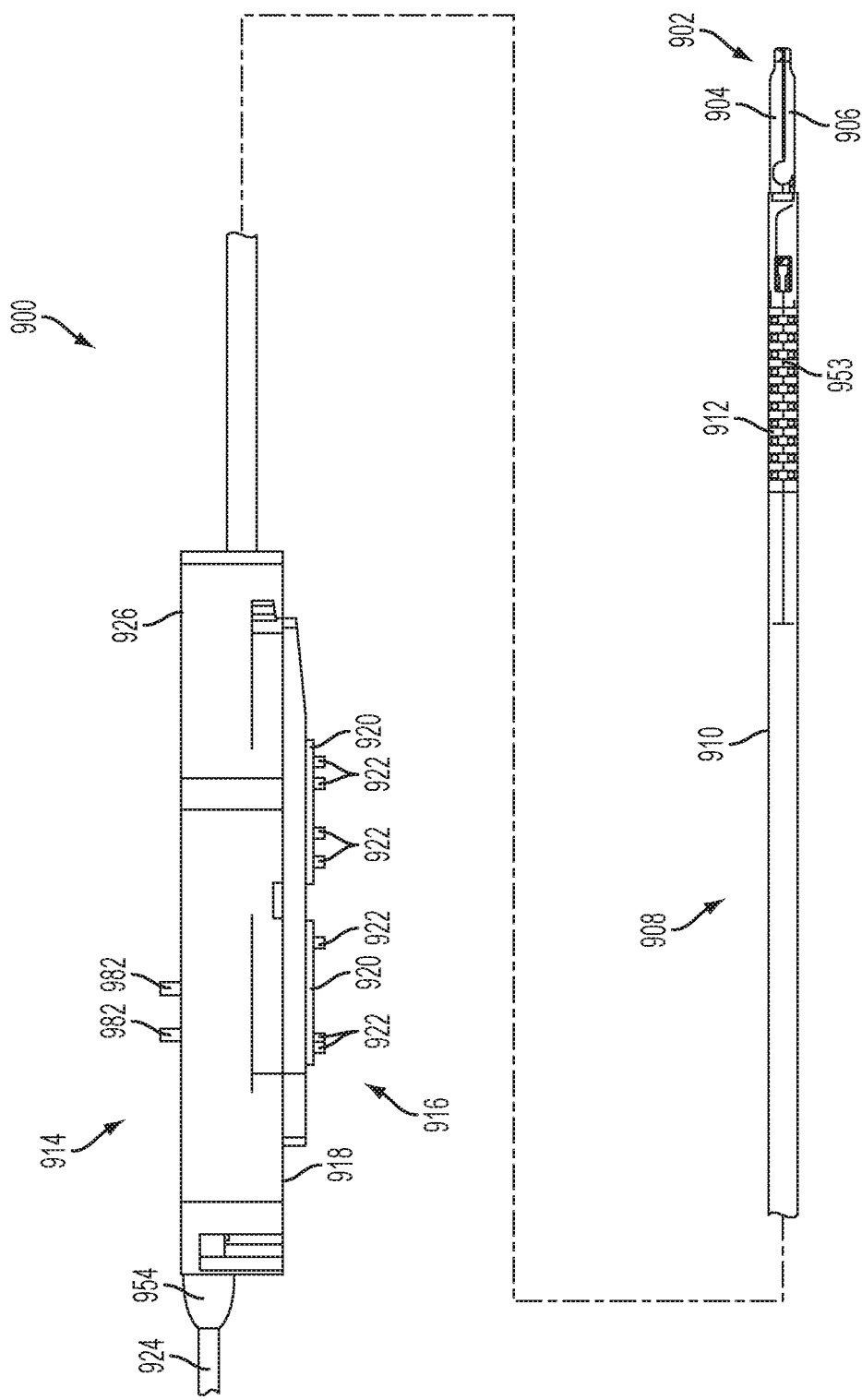
FIG. 67 illustrates a side view of one embodiment of the surgical tool shown in FIG. 63.
Figure 69:
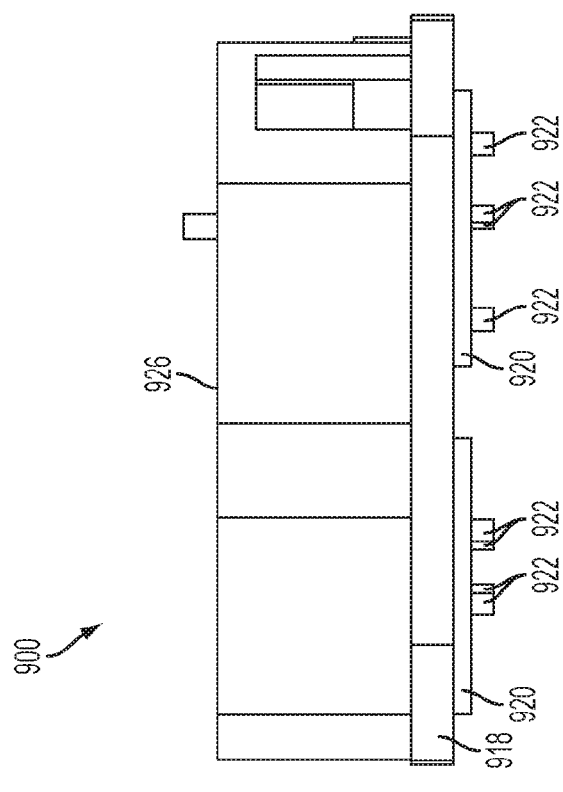
FIG. 69 illustrates a rear view of one embodiment of the surgical tool shown in FIG. 63.
Figure 68:
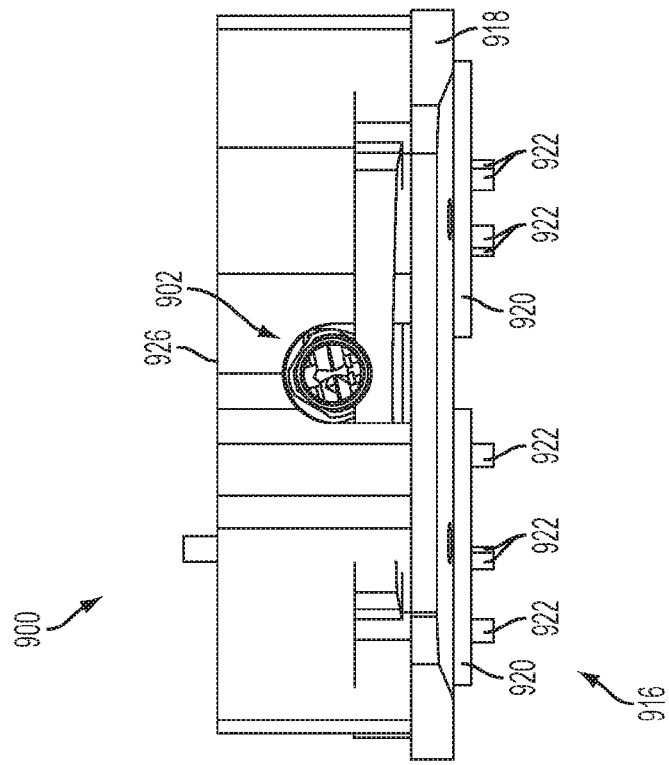
FIG. 68 illustrates a front view of one embodiment of the surgical tool shown in FIG. 63.
Figure 91:
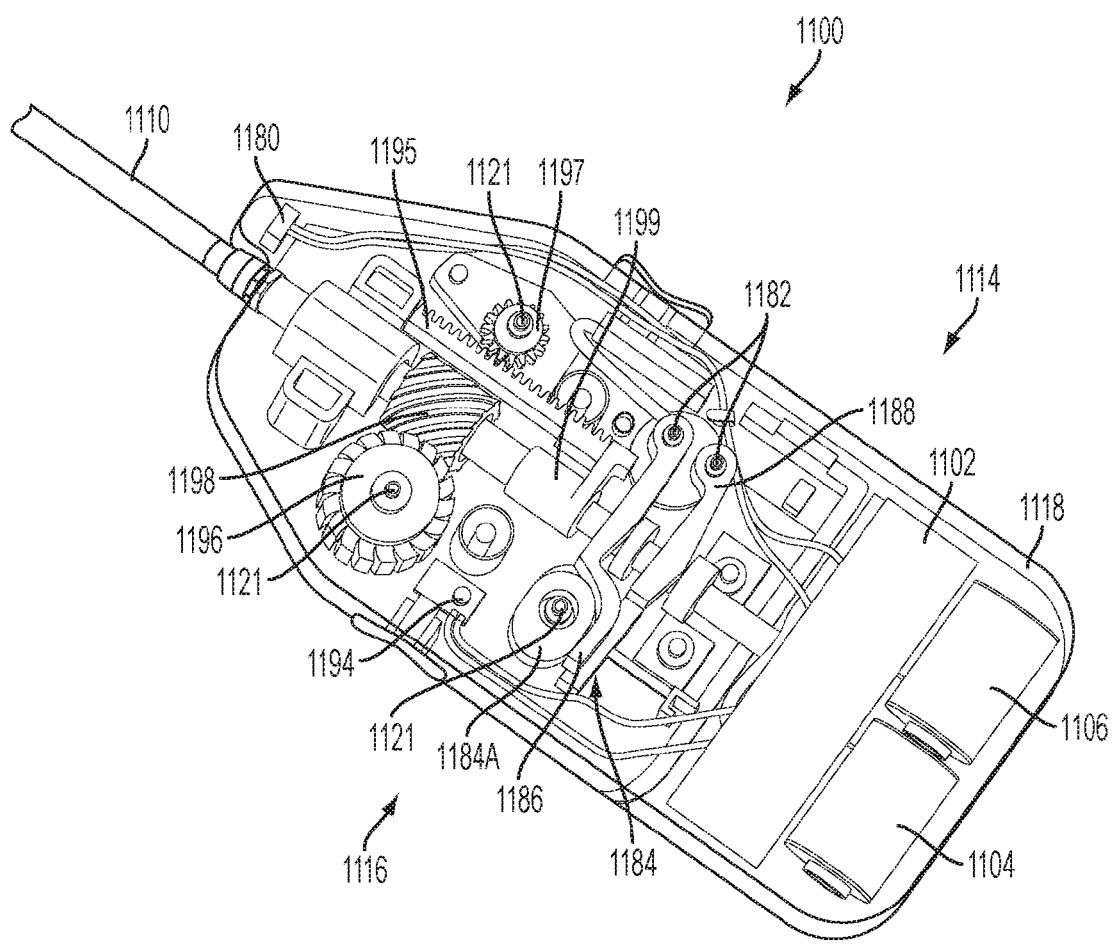
FIG. 91 illustrates one embodiment of a surgical tool comprising an internal battery located within a tool mounting portion with a tool mounting housing.

In various embodiments, the tool mounting portion 914 comprises a tool mounting housing 926 and a tool mounting plate 918 that operatively supports a plurality of rotatable body portions, driven discs or elements 920, and a fixed disc or element 990 (three driven and one fixed are shown in FIG. 65). The driven elements 920 each include a pair of pins 922 (FIG. 65) extending from a surface of the driven element 920. One pin 922 is closer to an axis of rotation of each driven element 920 than the other pin 922 on the same driven element 920, which helps to ensure positive angular alignment of the driven element 920. A fixed element 990 includes two pins 992. The interface 916 comprises an adaptor portion that is configured to mountingly engage the mounting plate 918 as will be further discussed below. In one embodiment, an adaptor portion may include an array of electrical connecting pins, which may be coupled to a memory structure by a circuit board within the tool mounting portion 914. While the interface 916 is described herein with reference to mechanical, electrical, and magnetic coupling elements, it should be understood that a wide variety of telemetry modalities might be used, including infrared, inductive coupling, or the like. An electrical cable 924 and strain relief 954 are provided to electrically couple the surgical tool 800 to a generator, which may be an ultrasonic energy source, an RF energy source, or a combination thereof. In some embodiments, the generators and energy sources as disclosed in the '768 application may be electrically coupled to the surgical tool 900. The power cable 924 exiting the back of the tool mounting housing 926 can be connected to a power (control module) during operations. As shown in FIG. 91, an electronic circuit board 1102 can be mounted within the tool mounting portion 914 or the interface 916 to provide feedback controls.

In one embodiment, the surgical tool 900 provides bipolar RF energy, articulation of the elongate shaft for better access to vessels and tissue, vessel sealing, low thermal spreading, and uniform compression for improved hemostasis, among other features. As described in more detail with reference to FIGS. 70-88, the surgical tool 900 provides gearing mechanisms to obtain independent movements of the articulation section 912 of the shaft assembly 908, the top jaw 904 portion of the end effector 902, the cutting element, and rotation of the shaft assembly 908, among other movements. In one embodiment, the tool mounting housing 926 also may comprise an electronic circuit board with electronic elements to identify the surgical tool 900. In one embodiment, the tool mounting housing 926 also may comprise an internal battery, as shown in FIG. 91, for example, to generate sufficient energy to cauterize, coagulate/desiccate, and/or simply reduce or slow bleeding of tissue such as a vessel. Such battery energized circuits are described in the '768 application.

Figure 70:
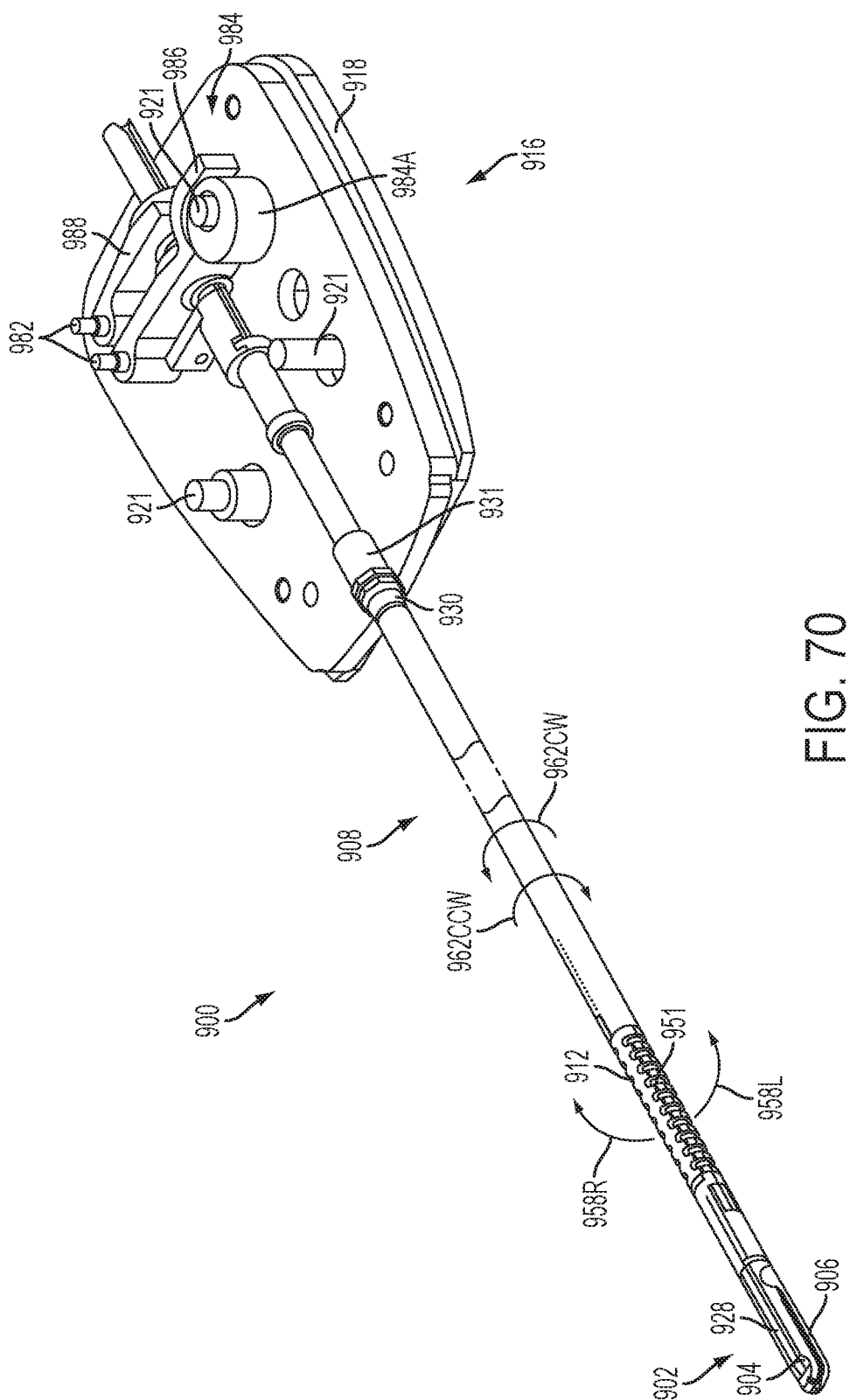
FIG. 70 illustrates a perspective view of one embodiment of the surgical tool shown in FIG. 63 with the tool mounting housing removed.
Figure 71:
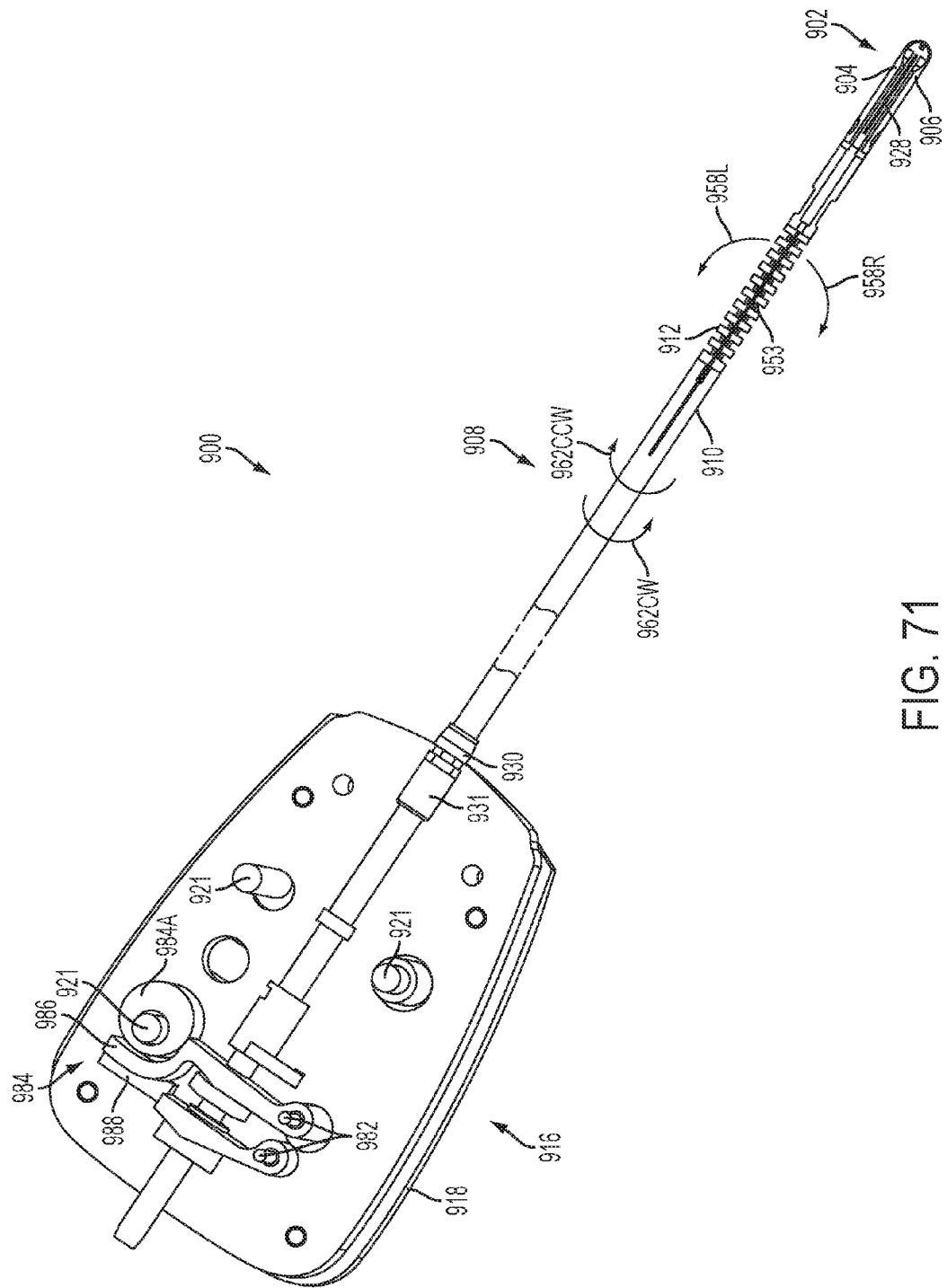
FIG. 71 illustrates a perspective view of one embodiment of the surgical tool shown in FIG. 63 with the tool mounting housing removed.
Figure 73:
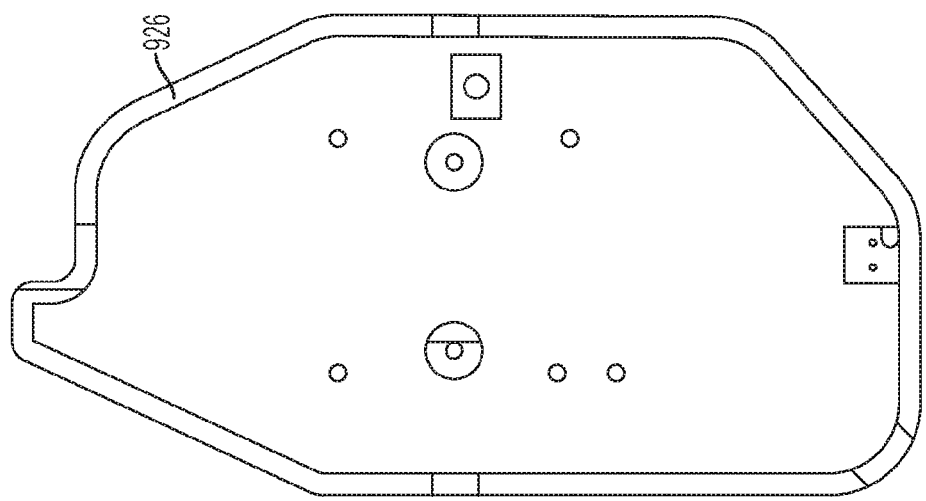
FIG. 73 illustrates a bottom view of one embodiment of the tool mounting housing of the surgical tool shown in FIG. 63.
Figure 72:
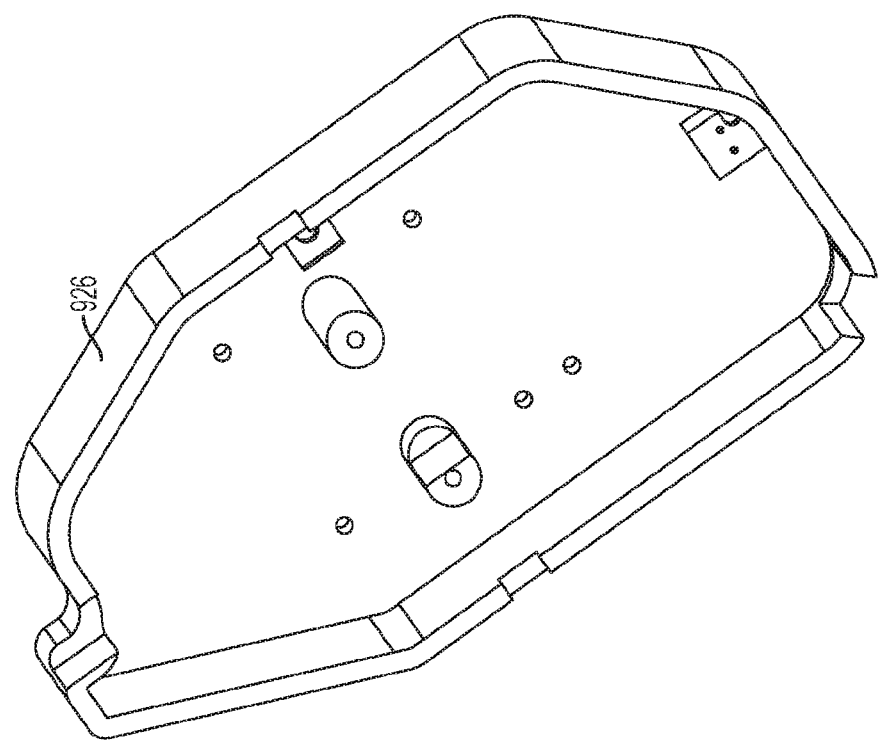
FIG. 72 illustrates a perspective view of one embodiment of the tool mounting housing of the surgical tool shown in FIG. 63.
Figure 74:
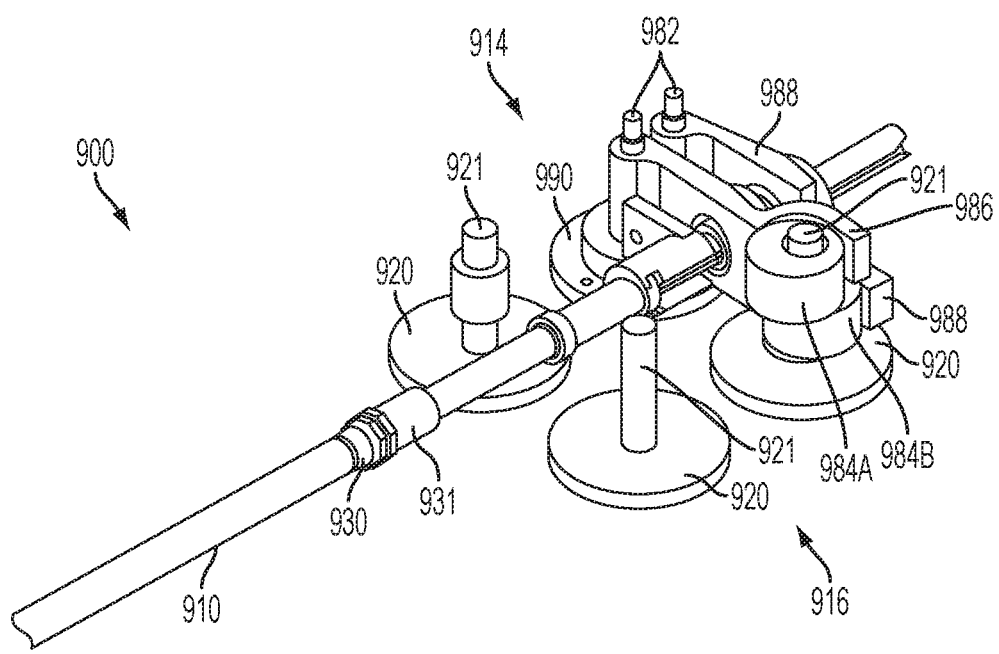
FIG. 74 illustrates a perspective view of one embodiment of the surgical tool shown in FIG. 63 with the tool mounting housing and tool mounting plate removed.
Figure 75:
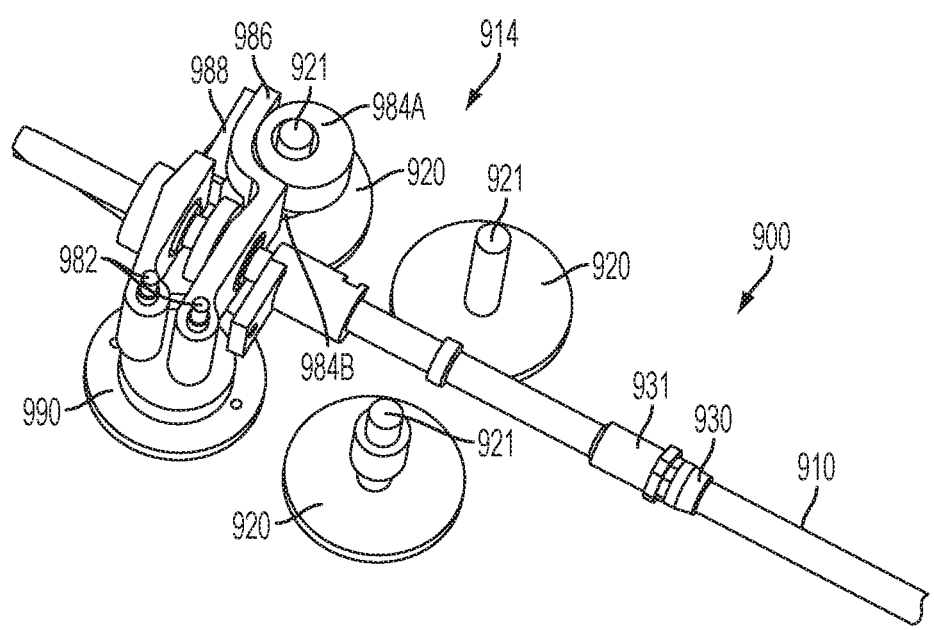
FIG. 75 illustrates a perspective view of one embodiment of the surgical tool shown in FIG. 63 with the tool mounting housing and a tool mounting plate removed.
Figure 77:
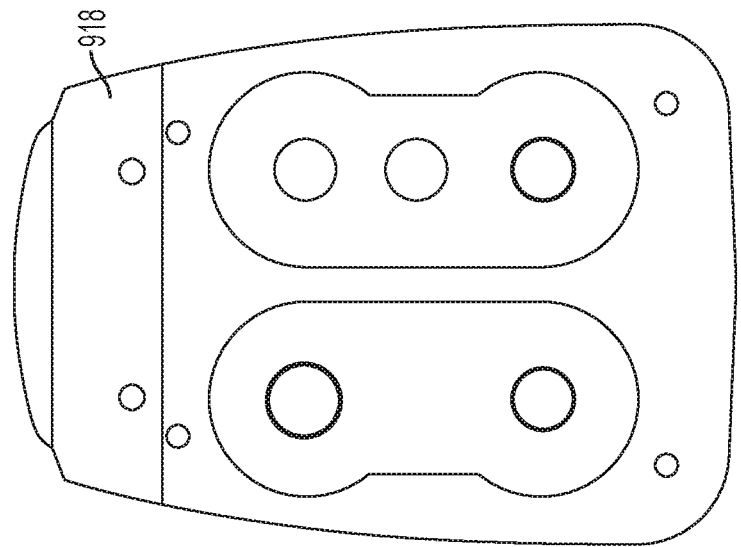
FIG. 77 illustrates a bottom view of one embodiment of the tool mounting plate of the surgical tool shown in FIG. 63.
Figure 76:
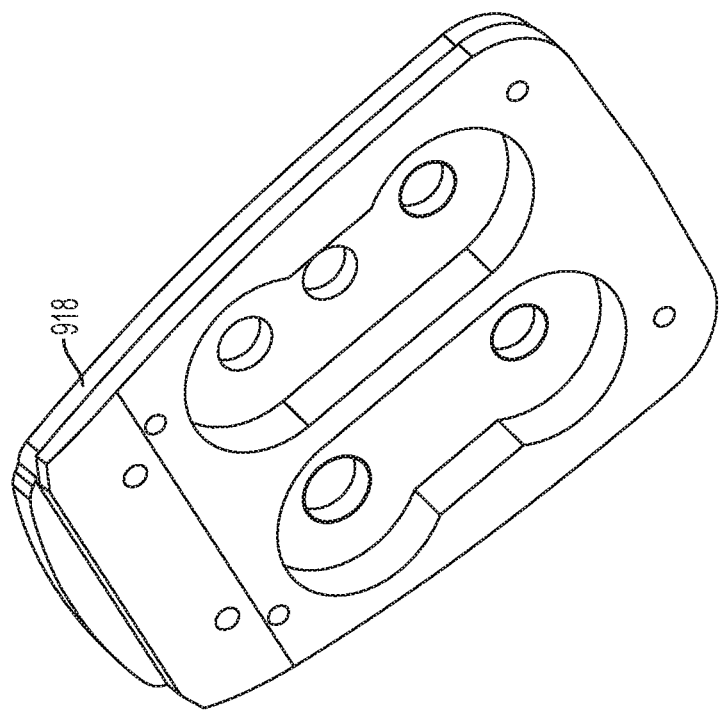
FIG. 76 illustrates a perspective view of one embodiment of the tool mounting plate of the surgical tool shown in FIG. 63.

For clarity of disclosure, in FIGS. 70 and 71 the surgical tool 900 is illustrated with the tool mounting housing 926 removed. For further clarity of disclosure, in FIGS. 74, 75, and 78-81 the surgical tool 900 is illustrated with both the tool mounting housing 926 and the tool mounting plate 918 removed. Detailed views of the tool mounting housing 926 and the tool mounting plate 918 are shown in FIGS. 72, 73 and 76, 77 respectively.

The surgical tool 900 will now be described with reference to FIGS. 63-88. Accordingly, in one embodiment, the surgical tool 900 comprises a coupler 930 to couple the shaft assembly 908 to the tool mounting portion 914. A coupler 930 and a bushing 931 rotatably couple the shaft assembly 908 to the tool mounting housing 926.

In one embodiment, the tool mounting portion 914 of the surgical tool 900 comprises a shaft assembly 908 articulation mechanism, a shaft assembly 908 rotation mechanism, a clamp jaw 902 open/close mechanism, and a knife actuation mechanism. In one embodiment, the rotatable bodies 921 (e.g., rotatable spools) are coupled to the driven elements 920. The rotatable bodies 921 may be formed integrally with the driven elements 920. In some embodiments, the rotatable bodies 921 may be formed separately from the driven elements 920 provided that the rotatable bodies 921 and the driven elements 920 are fixedly coupled such that driving the driven elements 920 causes rotation of the rotatable bodies 921. In one embodiment, some of the rotatable bodies 921 are coupled to a double cam mechanism to provide shaft articulation and other rotatable bodies may be coupled to a gear train or gear mechanism to provided shaft rotation and clamp jaw open/close and knife actuation.

Figure 78A:
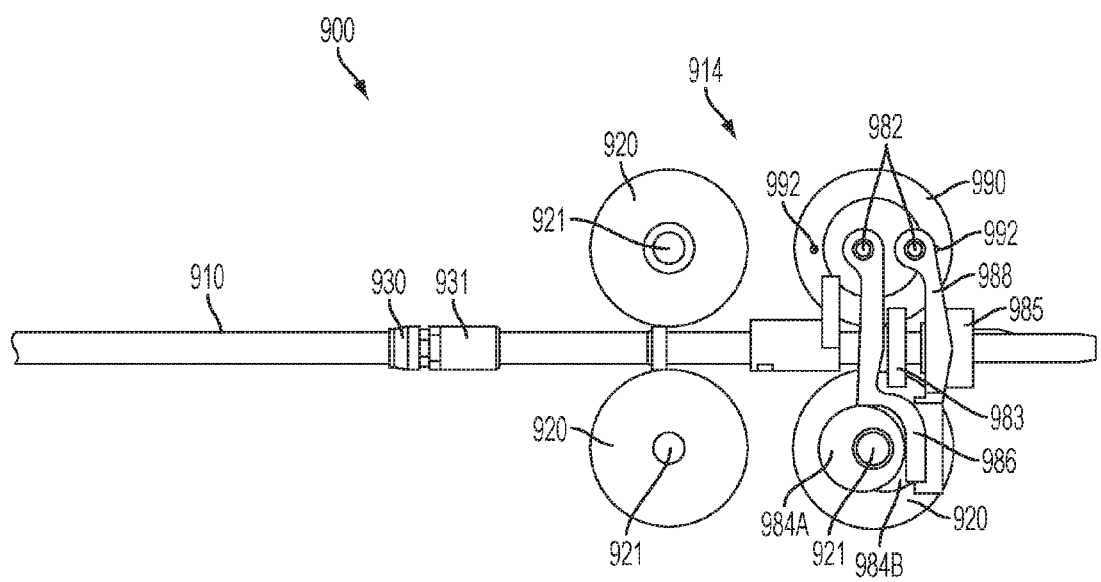
FIG. 78A illustrates a top view of one embodiment of the surgical tool shown in FIG. 63 with the tool mounting housing and the tool mounting plate removed.
Figure 78B:
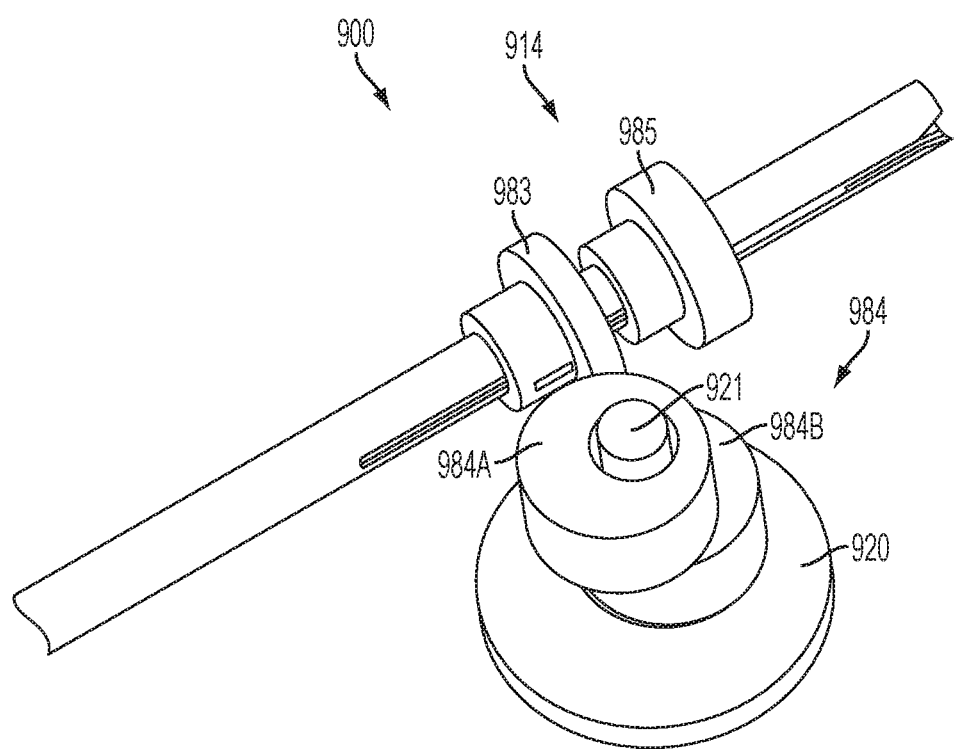
FIG. 78B illustrates a perspective view of one embodiment of the surgical tool shown in FIG. 63 with the tool mounting housing, the tool mounting plate removed, and first and second follower arms removed.
Figure 79:
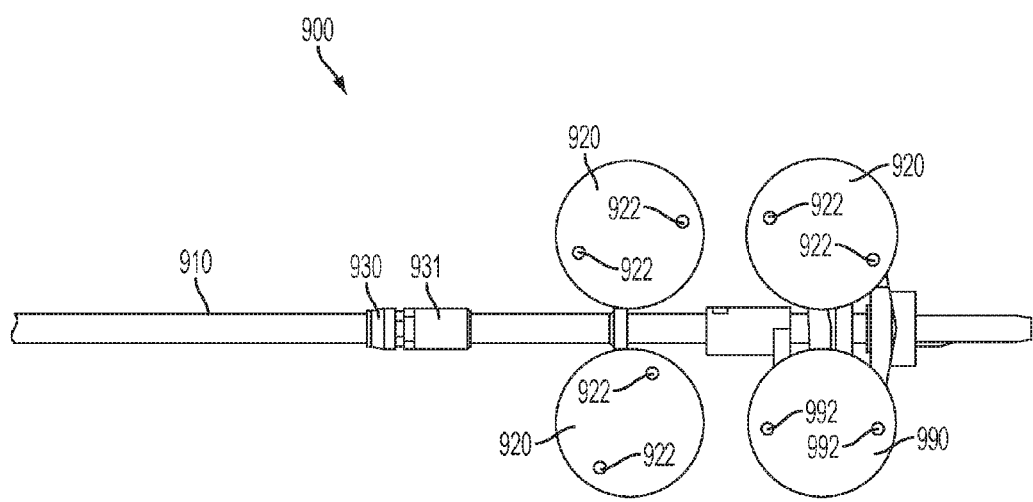
FIG. 79 illustrates a bottom view of one embodiment of the surgical tool shown in FIG. 63 with the tool mounting housing and the tool mounting plate removed.

In one embodiment, the tool mounting portion 914 of the surgical tool 900 comprises a shaft assembly 908 articulation mechanism. In the illustrated embodiment, for example, the surgical tool 900 comprises a double cam mechanism 984 to provide the shaft articulation functionality. In one embodiment, the double cam mechanism 984 comprises first and second cam portions 984A, 984B. First and second follower arms 986, 988 are pivotally coupled to corresponding pivot spools 982. As the rotatable body 921 coupled to the double cam mechanism 984 rotates, the first cam portion 984A acts on the first follower arm 986 and the second cam portion 984B acts on the second follower arm 988. As the cam mechanism 984 rotates the follower arms 986, 988 pivot about the pivot spools 982. The first follower arm 986 is attached to the first articulation band 951 and the second follower arm 988 is attached to the second articulation band 953. As the top cam portion 984A acts of the first follower arm 986, the shaft assembly 908 articulates in a left direction 958L. As the bottom cam portion 984B acts of the second follower arm 988, the shaft assembly 908 articulates in a right direction 958R. The first and second follower arms 986, 988 (or levers) are mounted on the shaft within the tool mounting portion 914 and are connected to the articulating bands (wires) coming from the distal end of the shaft assembly 908. Two separate bushings 983, 985 are mounted beneath the respective first and second follower arms 986, 988 to allow the rotation of the shaft without affecting the articulating positions of the first and second follower arms 986, 988. For articulation motion, these bushings reciprocate with the first and second follower arms 986, 988 without affecting the rotary position of the jaw 902. FIG. 78B shows the bushings 983, 985 and the dual cam assembly 984, including the first and second cam portions 984B, 984B, with the first and second follower arms 986, 988 removed to provide a more detailed and clearer view.

Figure 82:
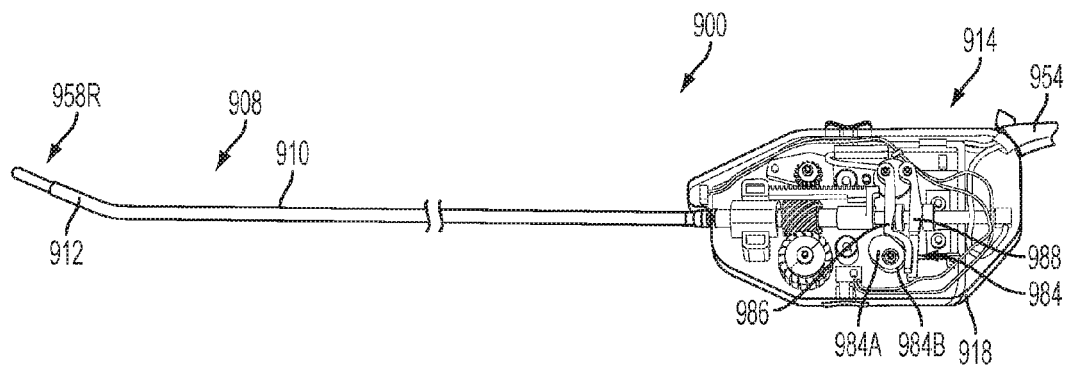
FIG. 82 illustrates one embodiment of the surgical tool shown in FIG. 63 with the articulation section articulated to the right.
Figure 83:
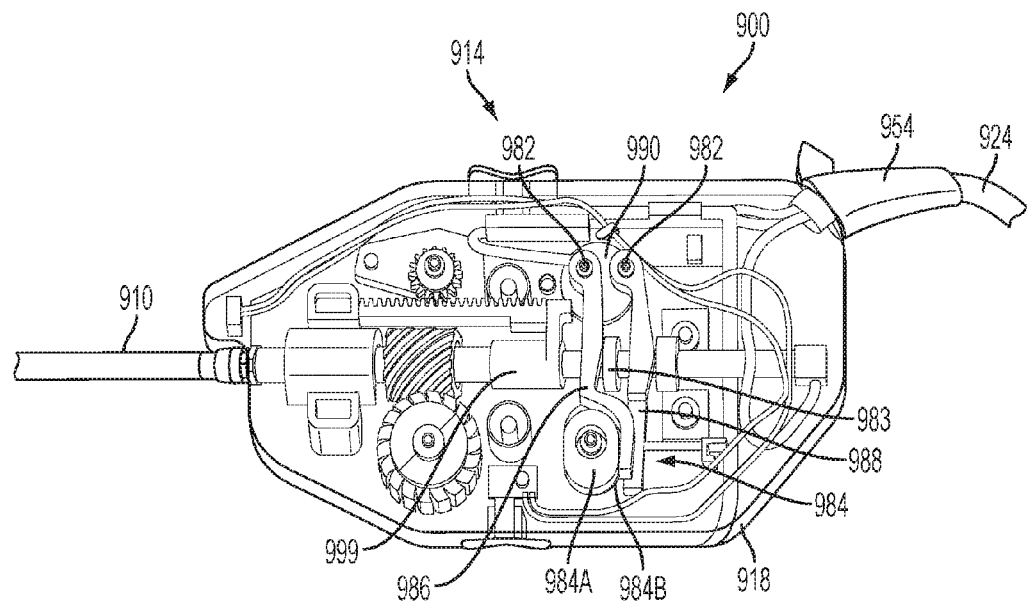
FIG. 83 illustrates one embodiment of the surgical tool shown in FIG. 63.
Figure 84:
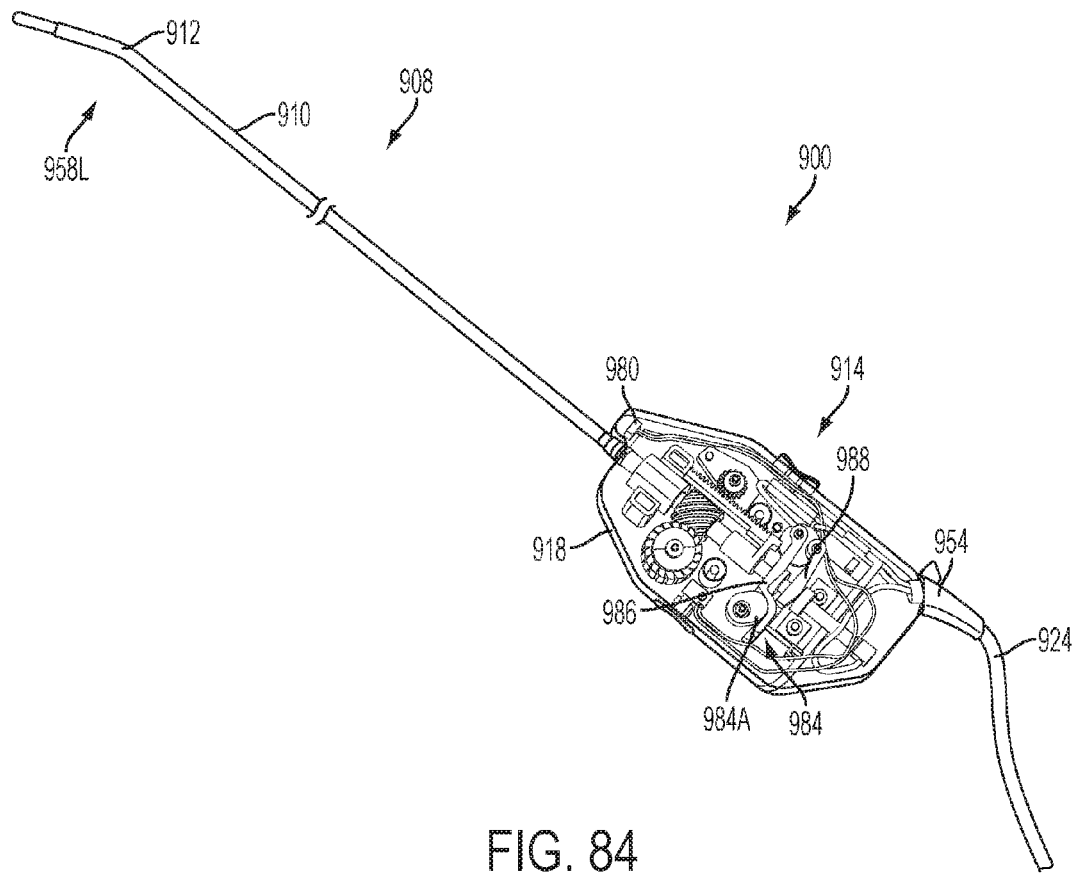
FIG. 84 illustrates one embodiment of the surgical tool shown in FIG. 63 with the articulation section articulated to the left.
Figure 85:
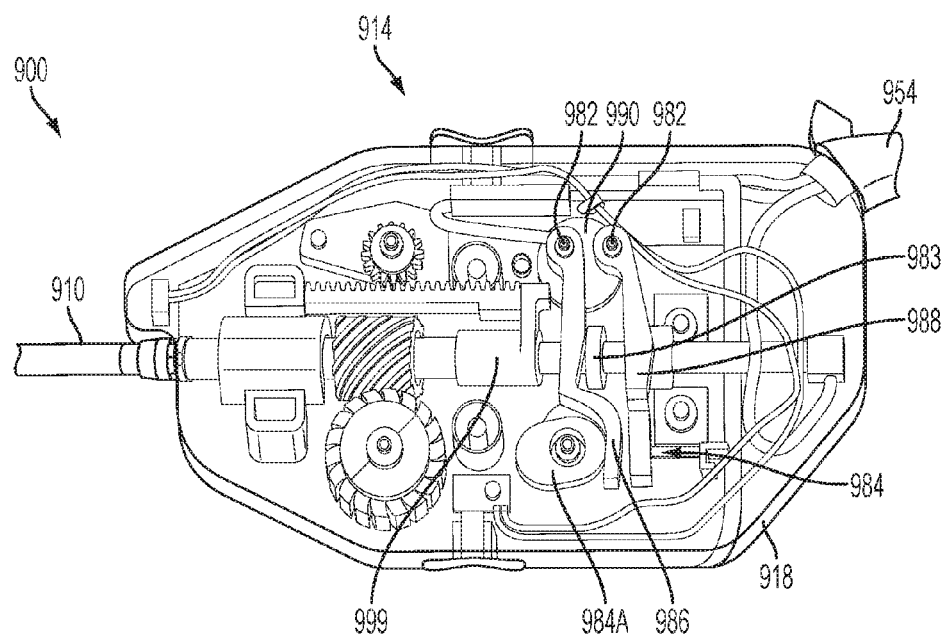
FIG. 85 illustrates one embodiment of the surgical tool shown in FIG. 63.

The operation of the left and right articulation of the shaft assembly 908 using the double cam mechanism 984 is further illustrated in FIGS. 82-85. In FIGS. 82 and 83, the double cam mechanism 984 is positioned to articulate the shaft assembly 908 in the right direction 958R. By rotating the cam mechanism 984 in a CCW direction from its neutral position, the articulation section 912 of the shaft assembly 908 distal end of the shaft assembly 908 moves in the right direction 958R. In FIGS. 84 and 85, the double cam mechanism 954 is positioned to articulate the shaft assembly 908 in the left direction 958L. By rotating the cam mechanism 984 in a CW direction from its neutral position, the articulation section 912 of the shaft assembly 908 distal end of the shaft assembly 908 moves in the left direction 958L.

Figure 86:
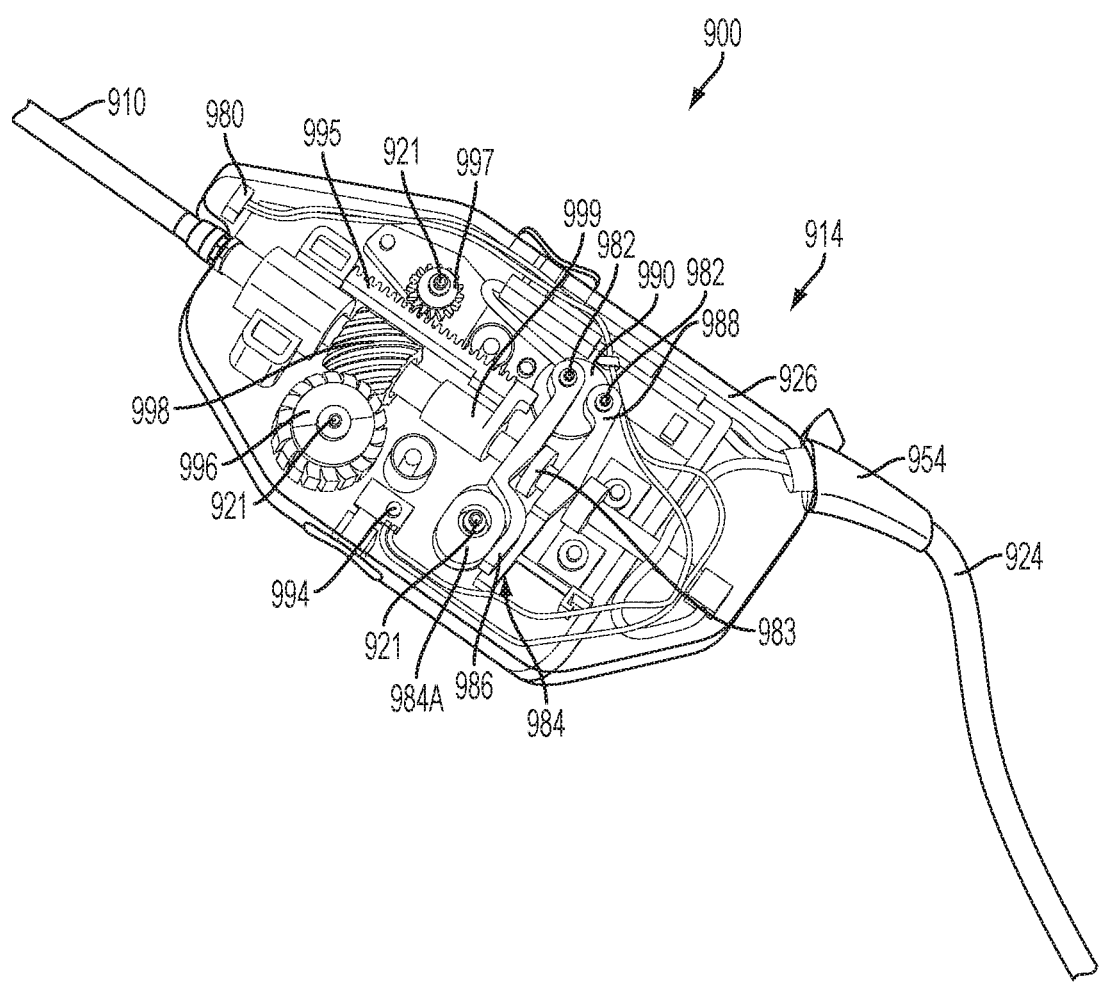
FIG. 86 illustrates one embodiment of the surgical tool shown in FIG. 63 with shaft rotation, clamp jaw open/close mechanism, and knife actuation mechanism.

As shown in more detail in FIG. 86, in one embodiment, the tool mounting portion 914 of the surgical tool 900 comprises a shaft assembly 908 rotation mechanism. In the illustrated embodiment, for example, the surgical tool 900 comprises a first spiral worm gear 996 coupled to a rotatable body 921 and meshed to a second spiral worm gear 998 coupled to the shaft assembly 908. Accordingly, rotation of the first spiral worm gear 996 cause rotation of the second spiral worm gear 998 and thus rotation of the shaft assembly 908 in a CW and CCW direction (designated as 962CW and 962CCW) based on the rotational direction of the rotatable body 921 coupled to the first spiral worm gear 996. Accordingly, rotation of the rotatable body 921 about a first axis is converted to rotation of the shaft assembly 908 about a second axis, which is orthogonal to the first axis. Additional bearings may be provided between the rotatable bodies and the corresponding gears. Any suitable bearings may be provided to support and stabilize the mounting and reduce rotary friction of shaft and gears, for example.

In one embodiment, the tool mounting portion 914 of the surgical tool 900 comprises a clamp jaw 902 open/close mechanism and a knife actuation mechanism. In the illustrated embodiment, for example, the surgical tool 900 comprises a rack and pinion gearing mechanism to provide the clamp jaw 902 open/close and knife actuation functionality. In embodiment, the rack and pinion gearing mechanism comprises a rotatable body 921 coupled to a pinion gear 997 that is meshed to a rack gear 995. The pinion gear 997 is coupled to a rotatable body 921 such that rotation of the corresponding driven element 920 causes the pinion gear 997 to rotate in a first direction. The pinion gear 997 is meshed to the rack gear 995, which moves in a linear direction. The rack gear 995 is coupled to a close/open block 999, which is coupled to a distal portion of the shaft assembly 908. In one embodiment, the rack and pinion gear mechanism comprising the pinion gear 997 is configured to control the opening and closing of the top jaw 904 portion of the clamp jaw 902 and movement of an "I-beam" shaped cutting element through the slot 928 formed in the clamp jaw 902. As the rack gear 995 moves in a distal direction, the "I-beam" shaped cutting element advances and closes the top jaw 904 portion of the clamp jaw 902. As the rack gear 995 moves in a proximal direction, the "I-beam" shaped cutting element retracts and enables the top jaw 904 portion of the clamp jaw 902 to open. A description of one embodiment of an "I-beam" shaped cutting element is provided in the '247 application.

Figure 87:
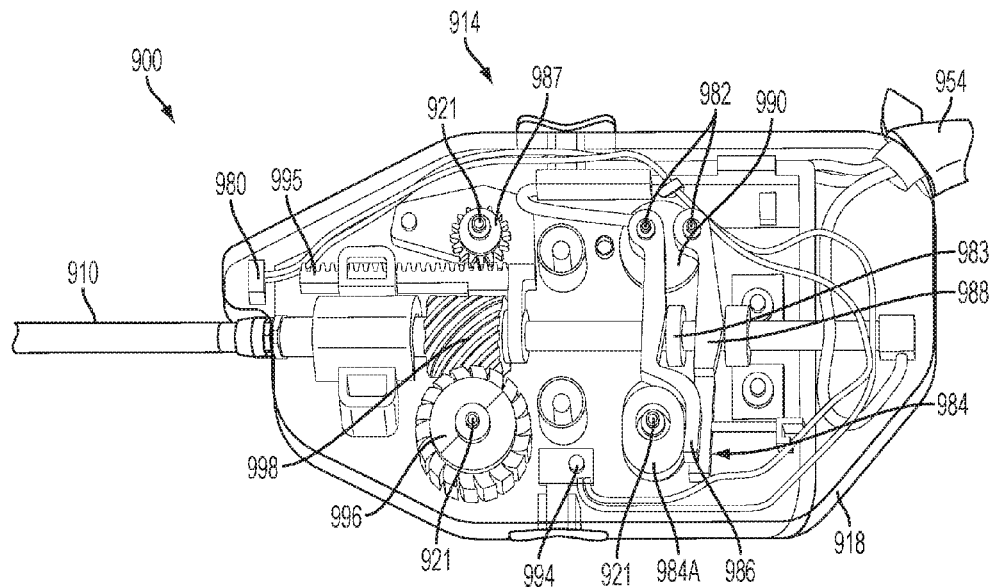
FIG. 87 illustrates one embodiment of the surgical tool shown in FIG. 63 with a limit switch in compressed mode.
Figure 88:
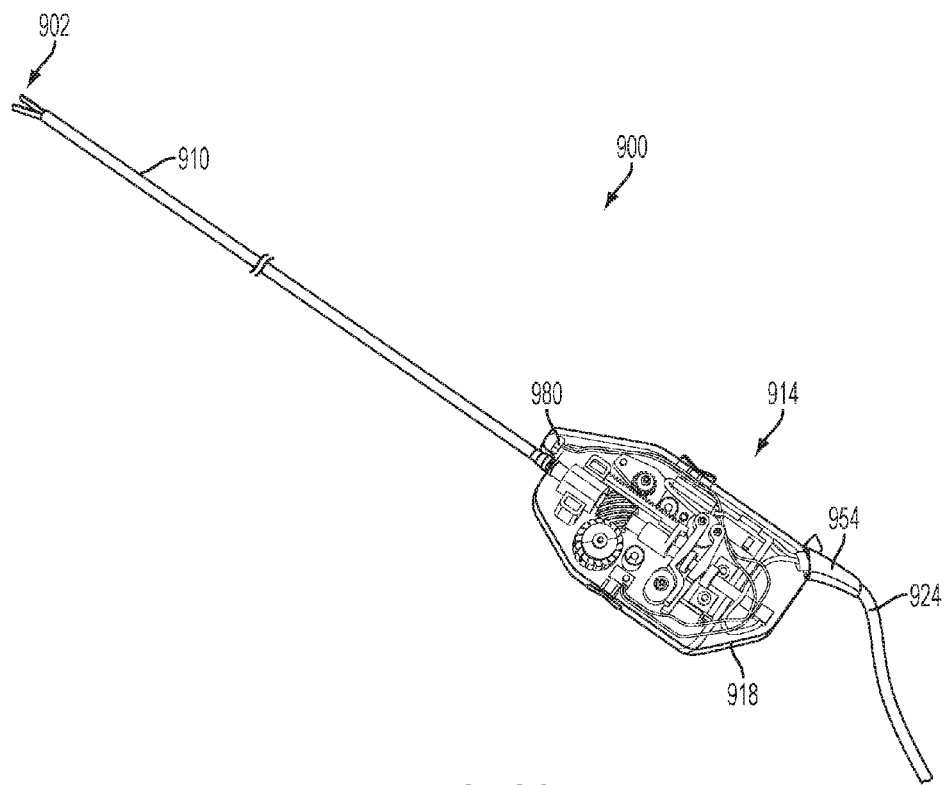
FIG. 88 illustrates one embodiment of the surgical tool shown in FIG. 63 with a limit switch free to provide an indication to a controller that a top jaw of a clamp jaw is open and a cutter element is in a proximal position.

With reference now to FIGS. 86-88, a limit switch 980 is provided to indicate the position of the cutter element in the end effector 902. In one embodiment, an on/off switch 994 can be mounted to the tool mounting housing 926 to provide external controls or to provide the electrical state of the surgical tool 900. As shown in FIG. 87, for example, at the complete closure of the top jaw 904 and cutter element at the distal portion of the surgical tool 900, the rack gear 995 compresses the limit switch 980 to provide a signal for power actuation and/or an indication to a controller that the top jaw 904 of the clamp jaw 902 is closed and the cutter element is "out" in a distal position. As shown in FIG. 88, for example, the limit switch 908 is free and provides an indication to a controller that the top jaw 902 of the clamp jaw 902 is open and the cutter element is in a proximal position.

In various embodiments, the surgical tools 600, 700, 800, 900 may be operated with external power and energy sources. In other embodiments, surgical tools 1000, 1100 as shown in FIGS. 89-91 may comprise internal energy sources for driving electronics and providing the desired cauterization electrical energy at an RF frequency (it has been found that frequencies above about 50 kHz do not affect the human nervous system) is then applied by, in a controlled manner, to the end effector forceps.

Accordingly, FIGS. 89 and 90 illustrate one embodiment of a surgical tool 1000 that is well-adapted for use with the robotic system 200 (FIG. 2) that has a tool drive assembly that is operatively coupled to a master controller 202 (FIG. 2) that is operable by inputs from an operator (i.e., a surgeon). As shown in FIGS. 89, 90, the surgical tool comprises an internal direct current (DC) energy source and an internal drive and control circuit 1002. In the illustrated embodiment, the energy source comprises a first and second battery 1004, 1006. In other respects, the surgical tool 1000 is similar to the surgical tool 700 illustrated in FIGS. 25-43. Accordingly, in one embodiment the surgical tool 1000 comprises a shaft assembly having elongate tube portion 1010 and a distal articulation section (not shown). The surgical tool 1000 further comprises an interface 1016, which mechanically and electrically couples the tool mounting portion 1014 to the manipulator 308. In various embodiments, the tool mounting portion 1014 comprises a tool mounting housing 1026 and a tool mounting plate 1018 that operatively supports a plurality of rotatable body portions, driven discs or elements that each include a pair of pins that extend from a surface of the driven element. One pin is closer to an axis of rotation of each driven element than the other pin on the same driven element, which helps to ensure positive angular alignment of the driven element. The interface 1016 comprises an adaptor portion that is configured to mountingly engage the mounting plate 1018. In one embodiment, an adaptor portion may include an array of electrical connecting pins, which may be coupled to a memory structure by a circuit board 1002 within the tool mounting portion 1014. While the interface 1016 is described herein with reference to mechanical, electrical, and magnetic coupling elements, it should be understood that a wide variety of telemetry modalities might be used, including infrared, inductive coupling, or the like.

In one embodiment, the tool mounting portion 1014 of the surgical tool 1000 comprises a shaft assembly articulation mechanism, a shaft assembly rotation mechanism, a clamp jaw open/close mechanism, and a knife actuation mechanism. In one embodiment, the rotatable bodies 721 (e.g., rotatable spools) are coupled to the driven elements. The rotatable bodies 1021 may be formed integrally with the driven elements. In some embodiments, the rotatable bodies 1021 may be formed separately from the driven elements provided that the rotatable bodies 1021 and the driven elements are fixedly coupled such that driving the driven elements causes rotation of the rotatable bodies 1021. Each of the rotatable bodies 1021 is coupled to a gear train or gear mechanism to provide shaft articulation and rotation and clamp jaw open/close and knife actuation.

In one embodiment, the tool mounting portion 1014 of the surgical tool 1000 comprises a shaft assembly articulation mechanism. In the illustrated embodiment, for example, the surgical tool 1000 comprises a rack and pinion mechanism to provide shaft articulation functionality. In one embodiment, the rack and pinion gearing mechanism comprises a first pinion gear 1036 coupled to a rotatable body 1021 such that rotation of the corresponding driven element causes the first pinion gear 1036 to rotate. The first pinion gear 1036 is meshed to a first rack gear 1050 to convert the rotational motion of the first pinion gear 1036 into linear motion of the first rack gear 1050 to control the articulation of the articulation section of the shaft assembly in a left direction. The first rack gear 1050 is attached to a first articulation band such that linear motion of the first rack gear 1050 in a distal direction causes the articulation section of the shaft assembly to articulate in the left direction. A second pinion gear 1038 is coupled to another rotatable body 1021 such that rotation of the corresponding driven element 1020 causes the second pinion gear 1038 to rotate. The second pinion gear 1038 is meshed to a second rack gear 1052 to convert the rotational motion of the second pinion gear 1038 into linear motion of the second rack gear 1052 to control the articulation of the articulation section of the shaft assembly in a right direction. The second rack gear 1052 is attached to a second articulation band such that linear motion of the second rack gear 1052 in a distal direction causes the articulation section of the shaft assembly to articulate in the right direction.

In one embodiment, the tool mounting portion 1014 of the surgical tool 1000 comprises a shaft assembly rotation mechanism. In the illustrated embodiment, for example, the surgical tool 1000 comprises a first spiral worm gear 1066 coupled to a second spiral worm gear 1064, which is coupled to a third spiral worm gear 1044. Such an arrangement is provided for various reasons including maintaining compatibility with existing robotic systems 200 and/or where space may be limited. The first spiral worm gear 1066 is coupled to a rotatable body 1021. The third spiral worm gear 1044 is meshed with a fourth spiral worm gear 1046 coupled to the shaft assembly. The third spiral worm gear 1066 is meshed to the fourth spiral worm gear 1046, which is coupled to the shaft assembly, to control the rotation of the shaft assembly in a CW and a CCW direction based on the rotational direction of the spiral worm gears 1044, 1046. Accordingly, rotation of the third spiral worm gear 1044 about a first axis is converted to rotation of the fourth spiral worm gear 1046 about a second axis, which is orthogonal to the first axis.

In one embodiment, the tool mounting portion 1014 of the surgical tool 1000 comprises a clamp jaw open/close mechanism and a knife actuation mechanism. In the illustrated embodiment, for example, the surgical tool 1000 comprises a rack and pinion gearing mechanism to provide the clamp jaw open/close and knife actuation functionality. In one embodiment, a third pinion gear 1040 is coupled to a rotatable body 1021 such that rotation of the corresponding driven element causes the third pinion gear 1040 to rotate in a first direction. The third pinion gear 1040 is meshed to a rack gear 1049, which moves in a linear direction. The rack gear 1049 is coupled to a close/open block 1048, which is coupled to a distal portion of the shaft assembly. In one embodiment, the gear mechanism comprising the pinion gear 1040 is configured to control the opening and closing of the clamp jaw and movement of an "I-beam" shaped cutting element through the slot formed in the clamp jaw. As the rack gear 1049 moves in a distal direction, the "I-beam" shaped cutting element advances and closes the top jaw portion of the clamp jaw. As the rack gear 1049 moves in a proximal direction, the "I-beam" shaped cutting element retracts and enables the top jaw portion of the clamp jaw to open. A description of one embodiment of an "I-beam" shaped cutting element is provided in the '247 application.

FIG. 91 illustrates one embodiment of a surgical tool 1100 that is well-adapted for use with the robotic system 200 (FIG. 2) that has a tool drive assembly that is operatively coupled to a master controller 202 (FIG. 2) that is operable by inputs from an operator (i.e., a surgeon). As shown in FIGS. 89, 90, the surgical tool comprises an internal direct current (DC) energy source and an internal drive and control circuit. In the illustrated embodiment, the energy source comprises a first battery 1104 and a second battery 1106. In other respects, the surgical tool 1100 is similar to the surgical tool 900 illustrated in FIGS. 63-88. Accordingly, in one embodiment the surgical tool 1100 comprises a shaft assembly having elongate tube portion 1110 and a distal articulation section (not shown). The surgical tool 1100 further comprises an interface 1116, which mechanically and electrically couples the tool mounting portion 1114 to the manipulator 308. In various embodiments, the tool mounting portion 1114 comprises a tool mounting housing and a tool mounting plate 1118 that operatively supports a plurality of rotatable body portions, driven discs or elements that each include a pair of pins that extend from a surface of the driven element. One pin is closer to an axis of rotation of each driven element than the other pin on the same driven element, which helps to ensure positive angular alignment of the driven element. The interface 1116 comprises an adaptor portion that is configured to mountingly engage the mounting plate 1118. In one embodiment, an adaptor portion may include an array of electrical connecting pins, which may be coupled to a memory structure by a circuit board within the tool mounting portion 1114. While the interface 1116 is described herein with reference to mechanical, electrical, and magnetic coupling elements, it should be understood that a wide variety of telemetry modalities might be used, including infrared, inductive coupling, or the like.

In one embodiment, the tool mounting portion 1014 of the surgical tool 1100 comprises a shaft assembly articulation mechanism. In the illustrated embodiment, for example, the surgical tool 1100 comprises a double cam mechanism 1184 to provide the shaft articulation functionality. In one embodiment, the double cam mechanism 1184 comprises a first cam portion 1184A and a second cam portion (not shown). First and second follower arms 1186, 1188 are pivotally coupled to corresponding pivot spools 1182. As the rotatable body 1121 coupled to the double cam mechanism 1184 rotates, the first cam portion 1184A acts on the first follower arm 1186 and the second cam portion acts on the second follower arm 1188. As the cam mechanism 1184 rotates the follower arms 1186, 1188 pivot about the pivot spools 1182. The first follower arm 1186 is attached to the first articulation band 1151 and the second follower arm 1188 is attached to the second articulation band 1153. As the top cam portion 1184A acts of the first follower arm 1186, the shaft assembly articulates in a left direction 1158L. As the bottom cam portion acts of the second follower arm 1188, the shaft assembly articulates in a right direction 1158R.

As shown in more detail in FIG. 86, in one embodiment, the tool mounting portion 1114 of the surgical tool 1100 comprises a shaft assembly rotation mechanism. In the illustrated embodiment, for example, the surgical tool 1100 comprises a first spiral worm gear 1196 coupled to a rotatable body 1121 and meshed to a second spiral worm gear 1198 coupled to the shaft assembly. Accordingly, rotation of the first spiral worm gear 1196 cause rotation of the second spiral worm gear 1198 and thus rotation of the shaft assembly in a CW and CCW direction based on the rotational direction of the rotatable body 1121 coupled to the first spiral worm gear 1196. Accordingly, rotation of the rotatable body 1121 about a first axis is converted to rotation of the shaft assembly about a second axis, which is orthogonal to the first axis.

In one embodiment, the tool mounting portion 1114 of the surgical tool 1100 comprises a clamp jaw open/close mechanism and a knife actuation mechanism. In the illustrated embodiment, for example, the surgical tool 1100 comprises a rack and pinion gearing mechanism to provide the clamp jaw open/close and knife actuation functionality. In embodiment, the rack and pinion gearing mechanism comprises a rotatable body 1121 coupled to a pinion gear 1197 that is meshed to a rack gear 1195. The pinion gear 1197 is coupled to a rotatable body 1121 such that rotation of the corresponding driven element 1120 causes the pinion gear 1197 to rotate in a first direction. The pinion gear 1197 is meshed to the rack gear 1195, which moves in a linear direction. The rack gear 1195 is coupled to a close/open block 1199, which is coupled to a distal portion of the shaft assembly. In one embodiment, the rack and pinion gear mechanism comprising the pinion gear 1197 is configured to control the opening and closing of the top jaw portion of the clamp jaw and movement of an "I-beam" shaped cutting element through the slot 1128 formed in the clamp jaw. As the rack gear 1195 moves in a distal direction, the "I-beam" shaped cutting element advances and closes the top jaw portion of the clamp jaw. As the rack gear 1195 moves in a proximal direction, the "I-beam" shaped cutting element retracts and enables the top jaw portion of the clamp jaw to open. A description of one embodiment of an "I-beam" shaped cutting element is provided in the '247 application.

A limit switch 1180 is provided to indicate the position of the cutter element in the end effector. An on/off switch 1194 is provided to controls the electrical state of the surgical tool 1100. The limit switch 1180 is compressed and provides an indication to a controller that the top jaw 1104 of the clamp jaw is closed and the cutter element is "out" in a distal position. The limit switch is free and provides an indication to a controller that the top jaw of the clamp jaw is open and the cutter element is in a proximal position.

Although the modified surgical tools 1000, 1100 shown in FIGS. 89-91 were described with reference to the embodiments of the surgical tools 700 and 900, the other embodiments of the surgical tools 600 and 800 also may be modified in a manner similar to hat shown and discussed in connection with FIGS. 89-91, without limitation.

The description now turns FIGS. 92-98 where one embodiment of RF drive and control circuit sections of a battery powered electrosurgical instrument, according to one embodiment, is described. The RF drive and control circuitry sections of the electronics circuits 1002, 1102 as shown in connection with surgical tools 1000, 1100, respectively. The electronics elements of the power supply and RF amplifier sections should be designed to have the highest efficiency possible in order to minimize the heat rejected into the relatively small handheld housing. Efficiency also provides the longest storage and operational battery life possible.

In various embodiments, efficiency of the power supply and RF drive and control circuitry sections also may minimize the size of the batteries 1004, 1006, 1104, 1106 shown in FIGS. 89-91, and otherwise referred to hereinbelow as battery 1300 in connection with FIGS. 92-98, required to fulfill the mission life, or to extend the mission life for a given size battery 1300. In one embodiment, the battery 1300 provides a low source impedance at a terminal voltage of 12.6V (unloaded) and a 1030 mA-Hour capacity. Under load, the battery voltage is a nominal 11.1.V, for example.

Radio frequency drive amplifier topologies may vary according to various embodiments. In one embodiment, for example, a series resonant approach may be employed where the operating frequency is varied to change the output voltage to force the surgical tool to operate according to a pre-programmed load curve. In a series resonant approach, the impedance of a series resonant network is at a minimum at the resonant frequency, because the reactance of the capacitive and inductive elements cancel, leaving a small real resistance. The voltage maximum for a series resonant circuit also occurs at the resonant frequency (and also depends upon the circuit Q). Accordingly, to produce a high voltage on the output, the series resonant circuit should operate closer to the resonant frequency, which increases the current draw from the DC supply (e.g., battery 1300) to feed the RF amplifier section with the required current. Although the series resonant approach may be referred to as a resonant mode boost converter, in reality, the design is rarely operated at the resonant frequency, because that is the point of maximum voltage. The benefit of a resonant mode topology is that if it is operated very close to the resonant frequency, the switching field effect transistors (FETs) can be switched "ON" or "OFF" at either a voltage or current zero crossing, which dissipates the least amount of power in the switching FETs as is possible.

Another feature of the RF drive and control circuitry section according to one embodiment, provides a relatively high turns ratio transformer which steps up the output voltage to about 85 VRMS from the nominal battery 1300 voltage of about 11.1V. This provides a more compact implementation because only one transformer and one other inductor are required. In such a circuit, high currents are necessary on the transformer primary to create the desired output voltage or current. Such device, however, cannot be operated at the resonant frequency because allowances are made to take into account for the battery voltage dropping as it is expended. Accordingly, some headroom is provided to maintain the output voltage at the required level. A more detailed description of a series resonant approach is provided in commonly assigned international PCT Patent Application No. PCT/GB2011/000778, titled "Medical Device," filed May 20, 2011, the disclosure of which is incorporated herein by reference in its entirety.

According to another embodiment, an RF instrument topology comprising a novel and unique architecture is provided for a handheld battery powered RF based generator for the electrosurgical surgical tool. Accordingly, in one embodiment, the present disclosure provides an RF instrument topology with an architecture configured such that each power section of the device operate at maximum efficiency regardless of the load resistance presented by the tissue or what voltage, current, or power level is commanded by the controller. In one embodiment, this may be implemented by employing the most efficient modalities of energy transformation presently known and by minimizing the component size to provide a small and light weight electronics package to fit within the housing, for example.

In one embodiment, the RF power electronics section of the electronics system 400 may be partitioned as a boost mode converter, synchronous buck converter, and a parallel resonant amplifier. According to one embodiment, a resonant mode boost converter section of the surgical tool may be employed to convert the DC battery 1300 voltage to a higher DC voltage for use by the synchronous mode buck converter. One aspect to consider for achieving a predetermined efficiency of the resonant mode boost converter section is ratio between input and output voltages of the boost converter. In one embodiment, although a 10:1 ratio is achievable, the cost is that for any appreciable power on the secondary the input currents to the boost mode transformer become quite heavy, in the range of about 15-25 A, depending on the load. In another embodiment a transformer turns ratio of about 5:1 is provided. It will be appreciated that transformer ratios in the range of about 5:1 to about 10:1 also may be implemented, without limitation. In a 5:1 transformer turns ratio, the design tradeoff is managing the Q of the parallel resonant output against the boost ratio. The resonant output network performs two functions. First, it filters the square, digital pulses from the Class D output amplifier and removes all but the fundamental frequency sine wave from the output. Second, it provides a passive voltage gain due to the Q of the filter network. In other words, current from the amplifier is turned into output voltage, at a gain determined by the circuit's unloaded Q and the load resistance, which affects the Q of the circuit.

Another aspect to consider for achieving a predetermined efficiency in the resonant mode boost converter section is to utilize a full bridge switcher topology, which allows half the turns ratio for the boost transformer for the same input voltage. The tradeoff is that this approach may require additional FET transistors, e.g., an additional two FETs are required over a half bridge approach, for example. Presently available switchmode FETs, however, are relatively small, and while the gate drive power is not negligible, it provides a reasonable design tradeoff.

Yet another aspect to consider for achieving a predetermined efficiency in the resonant mode boost converter section and operating the boost converter at maximum efficiency, is to always run the circuit at the resonant frequency so that the FETs are always switching at either a voltage or current minima, whichever is selected by the designer (ZCS vs. ZVS switching), for example. This can include monitoring the resonant frequency of the converter as the load changes, and making adjustments to the switching frequency of the boost converter to allow ZVS or ZCS (Zero Voltage Switching/Zero Current Switching) to occur for minimum power dissipation.

Yet another aspect to consider for achieving a predetermined efficiency in the resonant mode boost converter section is to utilize a synchronous rectifier circuit instead of a conventional full-wave diode rectifier block. Synchronous rectification employs FETs as diodes because the on-resistance of the FET is so much lower than that of even a Schottky power diode optimized for low forward voltage drop under high current conditions. A synchronous rectifier requires gate drive for the FETs and the logic to control them, but offers significant power savings over a traditional full bridge rectifier.

In accordance with various embodiments, the predetermined efficiency of a resonant mode boost converter is approximately 98-99% input to output, for example. Any suitable predetermined efficiency may be selected based on the particular implementation. Accordingly, the embodiments described herein are limited in this context.

According to one embodiment, a synchronous buck converter section of the surgical tool may be employed to reduce the DC voltage fed to the RF amplifier section to the predetermined level to maintain the commanded output power, voltage or current as dictated by the load curve, with as little loss as is possible. The buck converter is essentially an LC lowpass filter fed by a low impedance switch, along with a regulation circuit to control the switch to maintain the commanded output voltage. The operating voltage is dropped to the predetermined level commanded by the main controller, which is running the control system code to force the system to follow the assigned load curve as a function of sensed tissue resistance. In accordance with various embodiments, the predetermined efficiency of a synchronous buck regulator is approximately 99%, for example. Any suitable predetermined efficiency may be selected based on the particular implementation. Accordingly, the embodiments described herein are limited in this context.

According to one embodiment, a resonant mode RF amplifier section comprising a parallel resonant network on the RF amplifier section output is provided. In one embodiment, a predetermined efficiency may be achieved by a providing a parallel resonant network on the RF amplifier section output. The RF amplifier section may be driven at the resonant frequency of the output network which accomplished three things. First, the high Q network allows some passive voltage gain on the output, reducing the boost required from the boost regulator in order to produce high voltage output levels. Second, the square pulses produced by the RF amplifier section are filtered and only the fundamental frequency is allowed to pass to the output. Third, a full-bridge amplifier is switched at the resonant frequency of the output filter, which is to say at either the voltage zero crossings or the current zero crossings in order to dissipate minimum power. Accordingly, a predetermined efficiency of the RF amplifier section is approximately 98%. Gate drive losses may limit the efficiency to this figure or slightly lower. Any suitable predetermined efficiency may be selected based on the particular implementation. Accordingly, the embodiments described herein are limited in this context.

In view of the RF instrument topology and architecture described above, an overall system efficiency of approximately 0.99*0.99*0.98, which is approximately 96%, may be achieved. Accordingly, to deliver approximately 45 W, approximately 1.8 W would be dissipated by the electronics exclusive of the power required to run the main and housekeeping microprocessors, and the support circuits such as the ADC and analog amplifiers and filters. To deliver approximately 135 W, approximately 5.4 W would be dissipated. This is the amount of power that would be required to implement a large jaw class generator in a hand held electrosurgical medical instrument. Overall system efficiency would likely only be a weak function of load resistance, instead of a relatively strong one as it may be the case in some conventional instruments.

In various other embodiments of the electrosurgical surgical tool, a series resonant topology may be employed to achieve certain predetermined efficiency increase by employing a full bridge amplifier for the primary circuit and isolate the full bridge amplifier from ground to get more voltage on the primary. This provides a larger primary inductance and lower flux density due to the larger number of turns on the primary.

Figure 92:
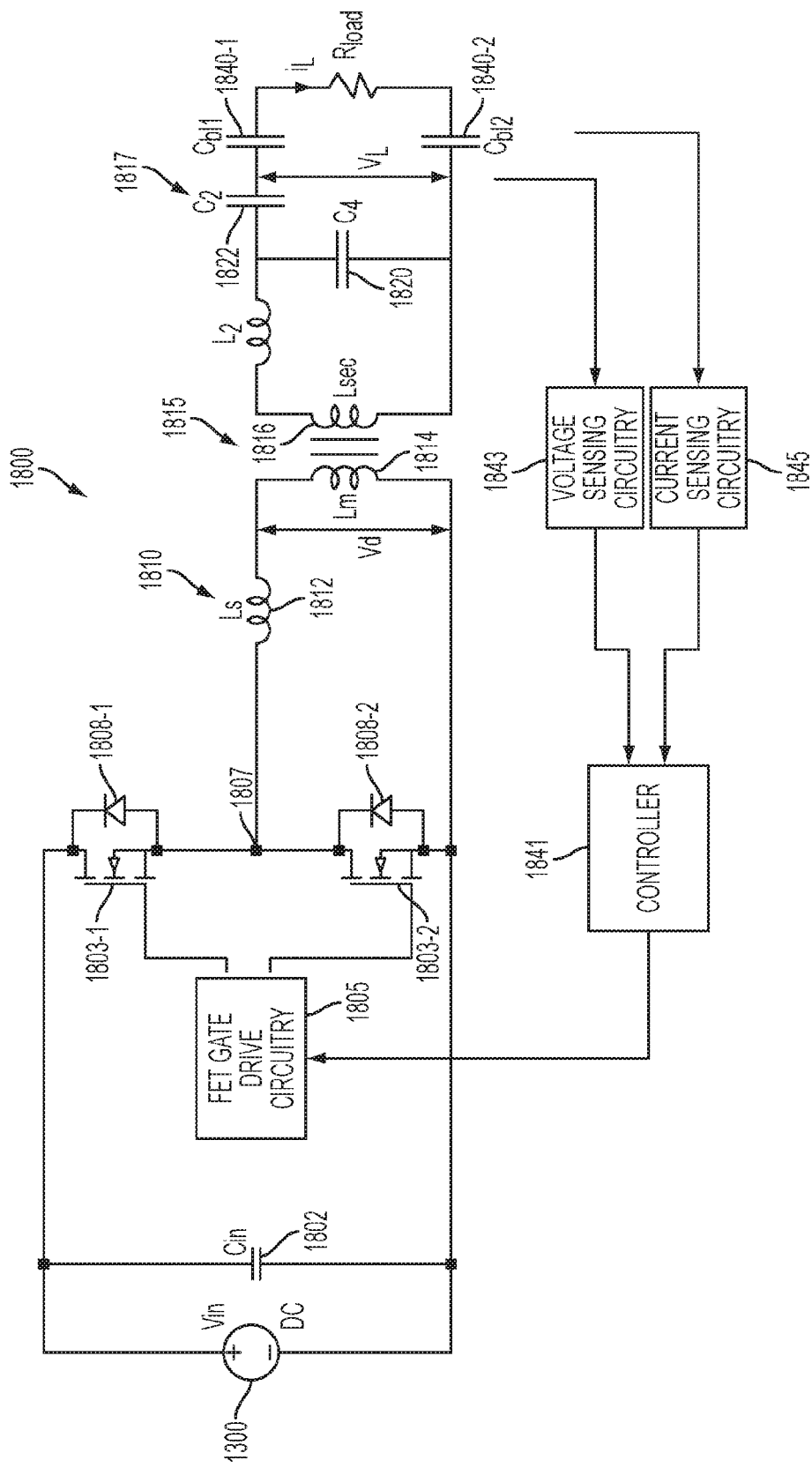
FIG. 92 illustrates a radio frequency (RF) drive and control circuit, according to one embodiment.

FIG. 92 illustrates an RF drive and control circuit 1800, according to one embodiment. FIG. 92 is a part schematic part block diagram illustrating the RF drive and control circuitry 1800 used in this embodiment to generate and control the RF electrical energy supplied to the forceps. As will be explained in more detail below, in this embodiment, the drive circuitry 1800 is a resonant mode RF amplifier comprising a parallel resonant network on the RF amplifier output and the control circuitry operates to control the operating frequency of the drive signal so that it is maintained at the resonant frequency of the drive circuit, which in turn controls the amount of power supplied to the forceps 108. The way that this is achieved will become apparent from the following description.

As shown in FIG. 92, the RF drive and control circuit 1800 comprises the above described battery 1300 are arranged to supply, in this example, about 0V and about 12V rails. An input capacitor ($C_{in}$) 1802 is connected between the 0V and the 12V for providing a low source impedance. A pair of FET switches 1803-1 and 1803-2 (both of which are N-channel in this embodiment to reduce power losses) is connected in series between the 0V rail and the 12V rail. FET gate drive circuitry 1805 is provided that generates two drive signals—one for driving each of the two FETs 1803. The FET gate drive circuitry 1805 generates drive signals that causes the upper FET (1803-1) to be on when the lower FET (1803-2) is off and vice versa. This causes the node 1807 to be alternately connected to the 12V rail (when the FET 1803-1 is switched on) and the 0V rail (when the FET 1803-2 is switched on). FIG. 92 also shows the internal parasitic diodes 1808-1 and 1808-2 of the corresponding FETs 1803, which conduct during any periods that the FETs 1803 are open.

As shown in FIG. 92, the node 1807 is connected to an inductor-inductor resonant circuit 1810 formed by inductor $L_s$ 1812 and inductor $L_m$ 1814. The FET gate driving circuitry 1805 is arranged to generate drive signals at a drive frequency ($f_d$) that opens and crosses the FET switches 1803 at the resonant frequency of the parallel resonant circuit 1810. As a result of the resonant characteristic of the resonant circuit 1810, the square wave voltage at node 1807 will cause a substantially sinusoidal current at the drive frequency ($f_d$) to flow within the resonant circuit 1810. As illustrated in FIG. 92, the inductor $L_m$ 1814 is the primary of a transformer 1815, the secondary of which is formed by inductor $L_{sec}$ 1816. The inductor $L_{sec}$ 1816 of the transformer 1815 secondary is connected to an inductor-capacitor-capacitor parallel resonant circuit 1817 formed by inductor $L_2$ 1818, capacitor $C_4$ 1820, and capacitor $C_2$ 1822. The transformer 1815 up-converts the drive voltage ($V_d$) across the inductor $L_m$ 1814 to the voltage that is applied to the output parallel resonant circuit 1817. The load voltage ($V_L$) is output by the parallel resonant circuit 1817 and is applied to the load (represented by the load resistance $R_{load}$ 1819 in FIG. 92) corresponding to the impedance of the forceps' jaws and any tissue or vessel gripped by the forceps. As shown in FIG. 92, a pair of DC blocking capacitors $C_{b1}$ 1840-1 and 1840-2 is provided to prevent any DC signal being applied to the load 1819.

In one embodiment, the transformer 1815 may be implemented with a Core Diameter (mm), Wire Diameter (mm), and Gap between secondary windings in accordance with the following specifications:

Core Diameter, D (mm)

$$D=19.9\times10-3$$

Wire diameter, W (mm) for 22 AWG wire $$W=7.366\times10-4$$

Gap between secondary windings, in gap=0.125

$$G=\text{gap}/25.4$$

In this embodiment, the amount of electrical power supplied to the forceps is controlled by varying the frequency of the switching signals used to switch the FETs 1803. This works because the resonant circuit 810 acts as a frequency dependent (loss less) attenuator. The closer the drive signal is to the resonant frequency of the resonant circuit 1810, the less the drive signal is attenuated. Similarly, as the frequency of the drive signal is moved away from the resonant frequency of the circuit 1810, the more the drive signal is attenuated and so the power supplied to the load reduces. In this embodiment, the frequency of the switching signals generated by the FET gate drive circuitry 1805 is controlled by a controller 1841 based on a desired power to be delivered to the load 1819 and measurements of the load voltage ($V_L$) and of the load current ($I_L$) obtained by conventional voltage sensing circuitry 1843 and current sensing circuitry 1845. The way that the controller 841 operates will be described in more detail below.

In one embodiment, the voltage sensing circuitry 1843 and the current sensing circuitry 1845 may be implemented with high bandwidth, high speed rail-to-rail amplifiers (e.g., LMH6643 by National Semiconductor). Such amplifiers, however, consume a relatively high current when they are operational. Accordingly, a power save circuit may be provided to reduce the supply voltage of the amplifiers when they are not being used in the voltage sensing circuitry 1843 and the current sensing circuitry 1845. In one-embodiment, a step-down regulator (e.g., LT3502 by Linear Technologies) may be employed by the power save circuit to reduce the supply voltage of the rail-to-rail amplifiers and thus extend the life of the battery 1300.

Figure 93:
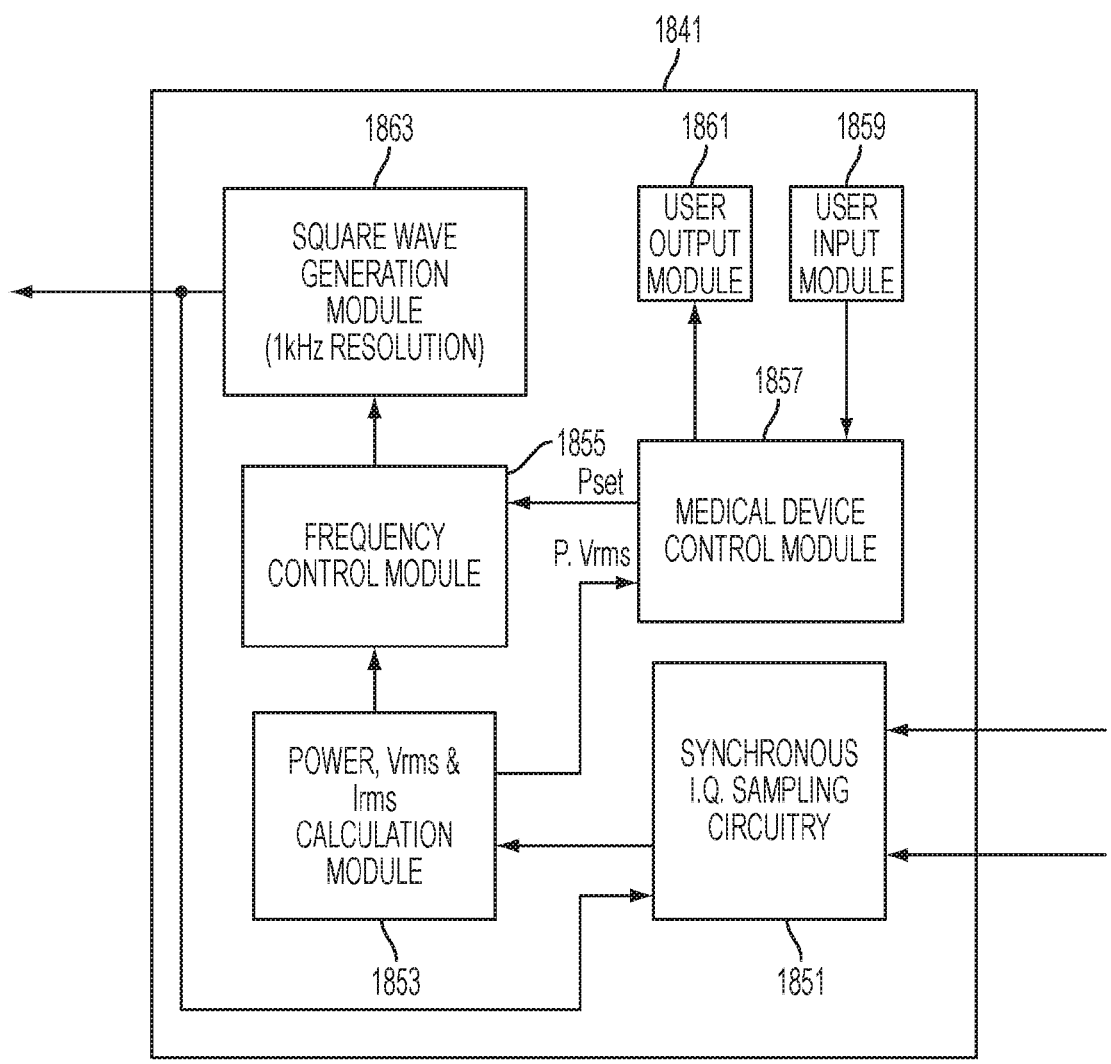
FIG. 93 illustrates main components of a controller, according to one embodiment.

FIG. 93 illustrates the main components of the controller 1841, according to one embodiment. In the embodiment illustrated in FIG. 93, the controller 1841 is a microprocessor based controller and so most of the components illustrated in FIG. 93 are software based components. Nevertheless, a hardware based controller 1841 may be used instead. As shown, the controller 1841 includes synchronous I,Q sampling circuitry 1851 that receives the sensed voltage and current signals from the sensing circuitry 1843 and 1845 and obtains corresponding samples which are passed to a power, $V_{rms}$ and $I_{rms}$ calculation module 1853. The calculation module 1853 uses the received samples to calculate the RMS voltage and RMS current applied to the load 1819 (FIG. 92; forceps and tissue/vessel gripped thereby) and from them the power that is presently being supplied to the load 1839. The determined values are then passed to a frequency control module 1855 and a medical device control module 1857. The medical device control module 1857 uses the values to determine the present impedance of the load 1819 and based on this determined impedance and a predefined algorithm, determines what set point power ($P_{set}$) should be applied to the frequency control module 1855. The medical device control module 1857 is in turn controlled by signals received from a user input module 1859 that receives inputs from the user (for example pressing buttons or activating the control levers on the handle) and also controls output devices (lights, a display, speaker or the like) on the handle via a user output module 1861.

The frequency control module 1855 uses the values obtained from the calculation module 1853 and the power set point ($P_{set}$) obtained from the medical device control module 1857 and predefined system limits (to be explained below), to determine whether or not to increase or decrease the applied frequency. The result of this decision is then passed to a square wave generation module 1863 which, in this embodiment, increments or decrements the frequency of a square wave signal that it generates by 1 kHz, depending on the received decision. As those skilled in the art will appreciate, in an alternative embodiment, the frequency control module 1855 may determine not only whether to increase or decrease the frequency, but also the amount of frequency change required. In this case, the square wave generation module 1863 would generate the corresponding square wave signal with the desired frequency shift. In this embodiment, the square wave signal generated by the square wave generation module 1863 is output to the FET gate drive circuitry 1805, which amplifies the signal and then applies it to the FET 1803-1. The FET gate drive circuitry 1805 also inverts the signal applied to the FET 1803-1 and applies the inverted signal to the FET 1803-2.

Figure 94:
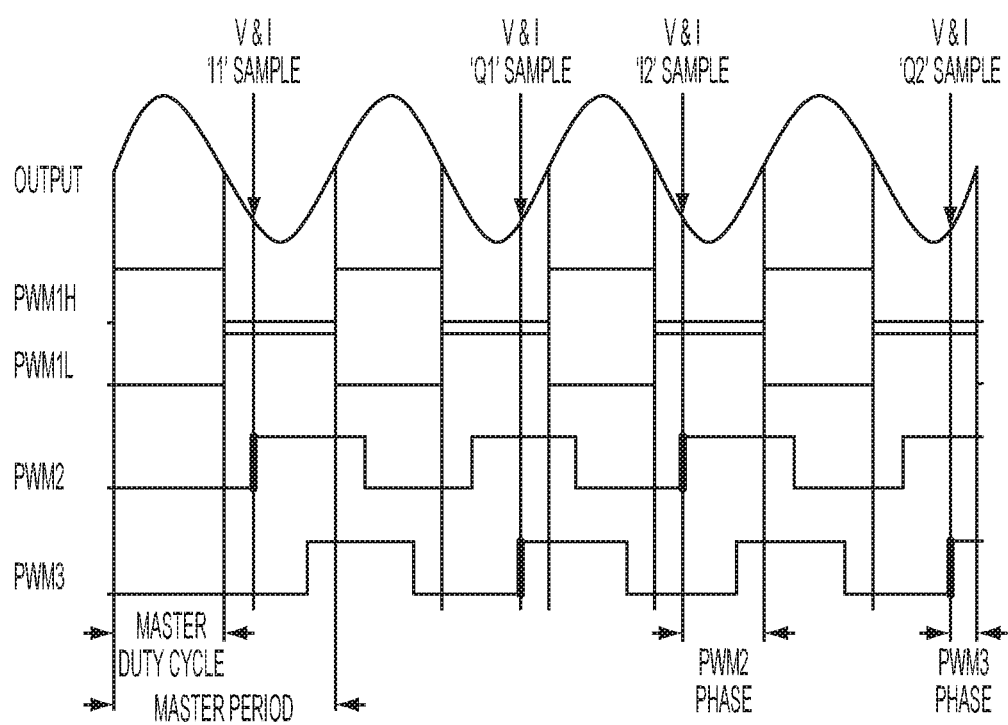
FIG. 94 is a signal plot illustrating a switching signals applied to field effect transistors (FETs), a sinusoidal signal representing the measured current or voltage applied to a load, and timings when a synchronous sampling circuit samples the sensed load voltage and load current, according to one embodiment.

FIG. 94 is a signal plot illustrating the switching signals applied to the FETs 1803, a sinusoidal signal representing the measured current or voltage applied to the load 1819, and the timings when the synchronous sampling circuitry 1851 samples the sensed load voltage and load current, according to one embodiment. In particular, FIG. 94 shows the switching signal (labeled PWM1 H) applied to upper FET 1803-1 and the switching signal (labeled PWM1 L) applied to lower FET 1803-2. Although not illustrated for simplicity, there is a dead time between PVVM1H and PVVM1L to ensure that that both FETs 1803 are not on at the same time. FIG. 94 also shows the measured load voltage/current (labeled OUTPUT). Both the load voltage and the load current will be a sinusoidal waveform, although they may be out of phase, depending on the impedance of the load 1819. As shown, the load current and load voltage are at the same drive frequency ($f_d$) as the switching Signals (PWM1 H and PWM1 L) used to switch the FETs 1803. Normally, when sampling a sinusoidal signal, it is necessary to sample the signal at a rate corresponding to at least twice the frequency of the signal being sampled—i.e. two samples per period. However, as the controller 1841 knows the frequency of the switching signals, the synchronous sampling circuit 1851 can sample the measured voltage/current signal at a lower rate. In this embodiment, the synchronous sampling circuit 1851 samples the measured signal once per period, but at different phases in adjacent periods. In FIG. 94, this is illustrated by the "I" sample and the "Q" sample. The timing that the synchronous sampling circuit 1851 makes these samples is controlled, in this embodiment, by the two control signals PWM2 and PWM3, which have a fixed phase relative to the switching signals (PWM1 H and PWM1 L) and are out of phase with each other (preferably by quarter of the period as this makes the subsequent calculations easier). As shown, the synchronous sampling circuit 1851 obtains an "I" sample on every other rising edge of the PWM2 signal and the synchronous sampling circuit 1851 obtains a "0" sample on every other rising edge of the PWM3 signal. The synchronous sampling circuit 1851 generates the PWM2 and PWM3 control signals from the square wave signal output by the square wave generator 1863 (which is at the same frequency as the switching signals PWM1 H and PWM1 L). Thus control signals PWM2 and PWM3 also changes (whilst their relative phases stay the same). In this way, the sampling circuitry 1851 continuously changes the timing at which it samples the sensed voltage and current signals as the frequency of the drive signal is changed so that the samples are always taken at the same time points within the period of the drive signal. Therefore, the sampling circuit 1851 is performing a "synchronous" sampling operation instead of a more conventional sampling operation that just samples the input signal at a fixed sampling rate defined by a fixed sampling clock.

The samples obtained by the synchronous sampling circuitry 1851 are then passed to the power, $V_{rms}$ and $I_{rms}$ calculation module 1853 which can determine the magnitude and phase of the measured signal from just one "I" sample and one "Q" sample of the load current and load voltage. However, in this embodiment, to achieve some averaging, the calculation module 1853 averages consecutive "I" samples to provide an average "I" value and consecutive "Q" samples to provide an average "0" value; and then uses the average I and Q values to determine the magnitude and phase of the measured signal (in a conventional manner). As those skilled in the art will appreciate, with a drive frequency of about 400 kHz and sampling once per period means that the synchronous sampling circuit 1851 will have a sampling rate of 400 kHz and the calculation module 1853 will produce a voltage measure and a current measure every 0.01 ms. The operation of the synchronous sampling circuit 1851 offers an improvement over existing products, where measurements can not be made at the same rate and where only magnitude information is available (the phase information being lost).

In one embodiment, the RF amplifier and drive circuitry for the electrosurgical surgical tool employs a resonant mode step-up switching regulator, running at the desired RF electrosurgical frequency to produce the required tissue effect. The waveform illustrated in FIG. 18 can be employed to boost system efficiency and to relax the tolerances required on several custom components in the electronics system 400. In one embodiment, a first generator control algorithm may be employed by a resonant mode switching topology to produce the high frequency, high voltage output signal necessary for the surgical tool. The first generator control algorithm shifts the operating frequency of the resonant mode converter to be nearer or farther from the resonance point in order to control the voltage on the output of the device, which in turn controls the current and power on the output of the device. The drive waveform to the resonant mode converter has heretofore been a constant, fixed duty cycle, with frequency (and not amplitude) of the drive waveform being the only means of control.

Figure 95:
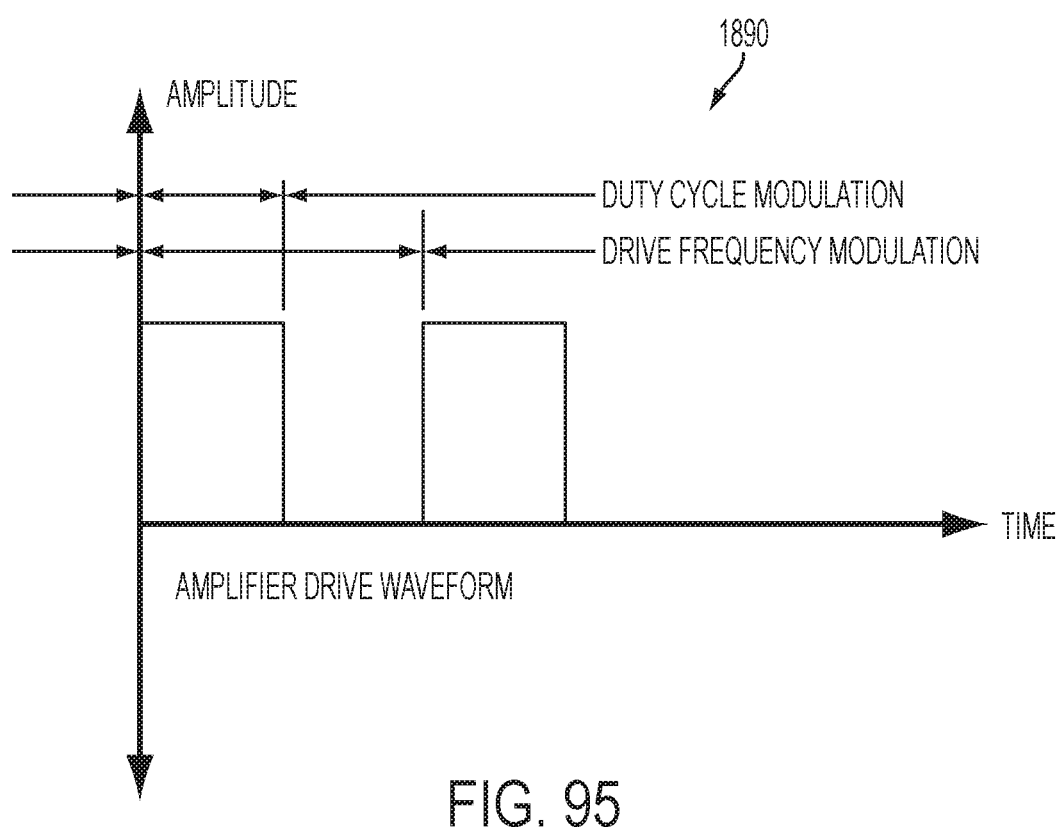
FIG. 95 illustrates a drive waveform for driving a field effect transistor (FET) gate drive circuitry, according to one embodiment.

FIG. 95 illustrates a drive waveform for driving the FET gate drive circuitry 1805, according to one embodiment. Accordingly, in another embodiment, a second generator control algorithm may be employed by a resonant mode switching topology to produce the high frequency, high voltage output signal necessary for the surgical tool. The second generator control algorithm provides an additional means of control over the amplifier in order to reduce power output in order for the control system to track gear the power curve while maintaining the operational efficiency of the converter. As shown in FIG. 95, according to one embodiment, the second generator control algorithm is configured to not only modulate the drive frequency that the converter is operating at, but to also control the duty cycle of the drive waveform by duty cycle modulation. Accordingly, the drive waveform 1890 illustrated in FIG. 95 exhibits two degrees of freedom. Advantages of utilizing the drive waveform 1890 modulation include flexibility, improved overall system efficiency, and reduced power dissipation and temperature rise in the amplifier's electronics and passive inductive components, as well as increased battery life due to increased system efficiency.

Figure 96:
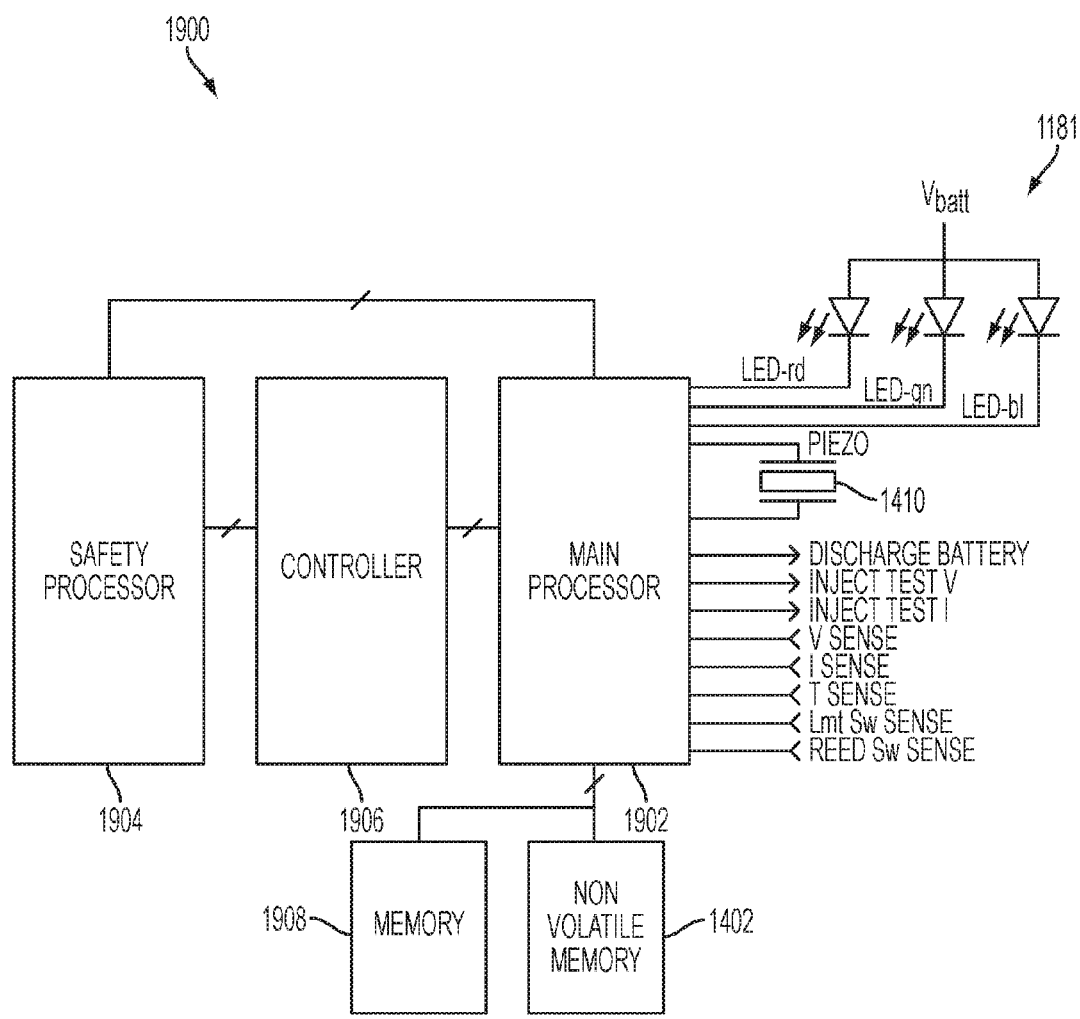
FIG. 96 illustrates a diagram of a digital processing system located on a first substrate, according to one embodiment.

FIG. 96 illustrates a diagram of the digital processing system 1900 located on the first substrate 1410, according to one embodiment. The digital processing system 1900 comprises a main processor 1902, a safety processor 1904, a controller 1906, a memory 1908, and a non-volatile memory 1402, among other components that are not shown for clarity of disclosure. The dual processor architecture comprises a first operation processor referred to as the main processor 1902, which is the primary processor for controlling the operation of the surgical tool. In one aspect, the main processor 1902 executes the software instructions to implement the controller 1841 shown in FIG. 93. In one embodiment, the main processor 1902 also may comprise an analog-to-digital (A/D) converter and pulse width modulators (PWM) for timing control.

The main processor 1902 controls various functions of the overall surgical tool. In one embodiment, the main processor receives voltage sense (V Sense) and current sense (I Sense) signals measured at the load (represented by the load resistance $R_{load}$ 1819 in FIG. 92) corresponding to the impedance of the forceps' jaws and any tissue or vessel gripped by the forceps. For example, the main processor 1902 receives the V Sense and I Sense signals for the voltage sensing circuitry 1843 and current sensing circuitry 1845, as shown in FIG.

92. The main processor 1902 also receives tissue temperature (T sense) measurement at the load. Using the V Sense, I Sense, and T Sense, the processor 1902 can execute a variety of algorithms to detect the state of the tissue based on impedance Z, where Z=V Sense/I Sense. In one embodiment, the surgical tool is frequency agile from about 350 kHz to about 650 kHz. As previously discussed, the controller 1841 changes the resonant operating frequency of the RF amplifier sections, controlling the pulse width modulation (PWM), reducing the output voltage (V) to the load, and enhancing the output current (I) to the load as described in connection with FIGS. 92-94, for example.

Examples of frequency agile algorithms that may be employed to operate the present surgical instrument 100 are described in the following commonly owned U.S. patent applications, each of which is incorporated herein by reference in its entirety: (1) U.S. Patent Application US2011/0082486 filed Oct. 1, 2012, published Apr. 7, 2011, entitled DEVICES AND TECHNIQUES FOR CUTTING AND COAGULATING TISSUE; (2) U.S. Patent Application US2011/0087216, filed Oct. 1, 2010, published Apr. 14, 2011, entitled SURGICAL GENERATOR FOR ULTRASONIC AND ELECTROSURGICAL DEVICES; (3) U.S. Patent Application US2011/0087212, filed Oct. 1, 2010, published Apr. 14, 2011, entitled SURGICAL GENERATOR FOR ULTRASONIC AND ELECTROSURGICAL DEVICES; (4) U.S. Patent Application US2011/0087213 filed Oct. 1, 2010, published Apr. 14, 2011, entitled SURGICAL GENERATOR FOR ULTRASONIC AND ELECTROSURGICAL DEVICES; (5) U.S. Patent Application US2011/0087215 filed Oct. 1, 2010, published Apr. 14, 2011, entitled SURGICAL GENERATOR FOR ULTRASONIC AND ELECTROSURGICAL DEVICES; (6) U.S. Patent Application US2011/0087214 filed Oct. 1, 2010, published Apr. 14, 2011, entitled SURGICAL GENERATOR FOR ULTRASONIC AND ELECTROSURGICAL DEVICES; (7) U.S. Patent Application US2011/0087217 filed Oct. 1, 2010, published Apr. 14, 2011, entitled SURGICAL GENERATOR FOR ULTRASONIC AND ELECTROSURGICAL DEVICES; and U.S. Pat. No. 8,058,771 Filed Jul. 15, 2009, issued Nov. 15, 2011, entitled ULTRASONIC DEVICE FOR CUTTING AND COAGULATING WITH STEPPED OUTPUT; the disclosure of each is herein incorporated by reference in its entirety.

In one embodiment, the main processor 1902 also detects the limit switch end of stroke position (Lmt Sw Sense). The limit switch is activated when the knife reaches the end of stroke limit. The signal generated by the limit switch Lmt Sw Sense is provided to the main processor 1902 to indicate the end-of-stroke condition of the knife.

In one embodiment, the main processor 1902 also senses an actuation signal (Reed Sw Sense) associated with a magnetically operated element located on the electronics system, limit switch, or other switch or input device. When initialization is detected by the main processor 1902, an algorithm is executed to control the operation of the surgical tool. One embodiment of such an algorithm is described in more detail hereinbelow. Further, on initial power up, when a magnetically operated element connects the battery 1300 supply to the electronics system, a low resistance load is applied to the terminals of the battery 1300 to check the internal resistance of the battery 1300. This enables the main processor 1902 to determine the charge state of the battery 1300 or in other words, determines the ability of the battery 1300 to deliver power to the electronics system. In one embodiment, the main processor 1902 may simply determine the absolute value of the difference between the unloaded and loaded battery 1300. If the main processor 1902 determines that the battery 1300 does not have enough capacity to deliver a suitable amount of power, the main processor 1902 disables the surgical tool and outputs a Discharge Battery signal, as discussed in more detail hereinbelow, to controllably discharge the battery 1300 such that it cannot be reused and is classified as an out-of-the box failure.

In one embodiment, as part of the algorithm, the main processor 1902 enables one or more visual feedback elements 1181. As shown in FIG. 96, the visual feedback elements 1181 comprise at least one red LED, at least one green LED, and at least one blue LED. Each of the LEDs are energized based on algorithms associated with the surgical tool. The main processor 1902 also actuates an audio feedback element based on algorithm associated with the surgical tool. In one embodiment, the audio feedback element includes a piezoelectric buzzer operating at 65 dBa at 1 meter at a frequency between about 2.605 kHz to 2.800 kHz, for example. As previously discussed, the visual and audio feedback elements 1181 are not limited to the devices disclosed herein and are intended to encompass other visual and audio feedback elements.

In one embodiment, the main processor 1902 provides certain output signals. For example, one output signal is provided to the circuitry to discharge the battery 1300 (Discharge Battery). This is explained in more detail with reference to FIG. 97. There may be a need to discharge the battery 1300 under several conditions according to algorithms associated with the surgical tool. Such conditions and algorithm are discussed in more detail hereinbelow. In one embodiment, the battery 1300 used to power the surgical tool has an initial out of the box capacity ranging from about 6 to about 8 hours up to about 10 hours under certain circumstances. After a medical procedure, some capacity will remain in the battery 1300. Since the battery 1300 is designed as a single use battery and is not rechargeable, the battery 1300 is controllably discharged after use to prevent reuse of the surgical tool when the battery 1300 has a partial capacity.

In one embodiment, the main processor 1902 can verify the output voltage (V) and current (I) sensing function by an artificial injection of voltage and current into the load. The main processor 1902 then reads back the voltage and current from the load and determines whether the surgical tool can operate or fail in safe mode. In one embodiment, the test voltage and current are applied to the dummy load via an electronically controlled switch. For example, the electronic switch may comprise a two-pole relay. The main processor 1902 verifies the output sensing function once per hour when it is inactive and once prior to every firing. It will be appreciated that these periods may vary based on the particular implementation. To verify the output sensing function, the main processor 1902 outputs inject test voltage (Inject Test V) and inject test current (Inject test I) signals to the output sensing test circuit described in connection with FIG. 98 hereinbelow. As previously described, the main processor 1902 reads the sensed voltage and current signals V Sense and I Sense to determine the operation of the voltage (V) and current (I) sensing function of the surgical tool.

The main processor 1902 is also coupled to a memory 1908 and the nonvolatile memory 1402. The computer program instructions executed by the main processor 1902 are stored in the nonvolatile memory 1402 (e.g., EEPROM, FLASH memory, and the like). The memory 1908, which may be random access memory (RAM) may be used for storing instructions during execution, measured data, variables, among others. The memory 1908 is volatile and its contents are erased when the battery 1300 is discharged below a predetermine voltage level. The nonvolatile memory 1402 is nonvolatile and its contents are not erased when the battery 1300 is discharged below a predetermined level. In one embodiment, it may be desirable to erase the contents of the nonvolatile memory 1402 to prevent its reuse, for example, when the surgical tool has already been utilized in a procedure, the surgical tool is determined to be an out-of-the box failure, or when the surgical tool otherwise fails. In each of these circumstances, the main processor 1902 initiates a battery 1300 discharge operation. In such circumstances, program instructions in the nonvolatile memory 1402 for erasing nonvolatile memory are transferred to the memory 1908 where program execution resumes. The instructions executed from the memory 1908 then erase the contents of the nonvolatile memory 1402.

The safety processor 1904 is coupled to the main processor 1902 and monitors the operation of the main processor 1902. If the safety processor 1904 determines a malfunction of the main processor 1902, the safety processor 1904 can disable the operation of the main processor 1902 and shuts down the surgical tool in a safe mode.

The controller 1906 is coupled to both the main processor 1902 and the safety processor 1904. In one embodiment, the controller 1906 also monitors the operation of the main processor 1902 and if the main processor 1902 loses control, the controller 1906 enables the safety processor to shut down the RF amplifier section in a safe manner. In one embodiment the controller 1906 may be implemented as complex programmable logic device (CPLD), without limitation.

To preserve or extend the life of the battery 1300, the main processor 1902, the safety processor 1904, and/or the controller 1906 may be powered down (e.g., place din sleep mode) when they are not in use. This enables the digital processing system 1900 to conserve energy to preserve or extend the life of the battery 1300.

In various embodiments, the main processor 1902, the safety processor 1904, or the controller 906 may comprise several separate functional elements, such as modules and/or blocks. Although certain modules and/or blocks may be described by way of example, it can be appreciated that a greater or lesser number of modules and/or blocks may be used and still fall within the scope of the embodiments. Further, although various embodiments may be described in terms of modules and/or blocks to facilitate description, such modules and/or blocks may be implemented by one or more than one hardware component, e.g., processor, Complex Programmable Logic Device (CPLD), Digital Signal Processor (DSP), Programmable Logic Devices (PLD), Application Specific Integrated Circuit (ASIC), circuits, registers and/or software components, e.g., programs, subroutines, logic and/or combinations of hardware and software components.

In one embodiment, the digital processing system 1900 may comprise one or more embedded applications implemented as firmware, software, hardware, or any combination thereof. The digital processing system 1900 may comprise various executable modules such as software, programs, data, drivers, application program interfaces (APIs), and so forth. The firmware may be stored in the nonvolatile memory 1402 (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory 1908 (RAM) such as dynamic RAM (DRAM), Double-Data-Rate DRAM (DDRAM), and/or synchronous DRAM (SDRAM).

Figure 97:
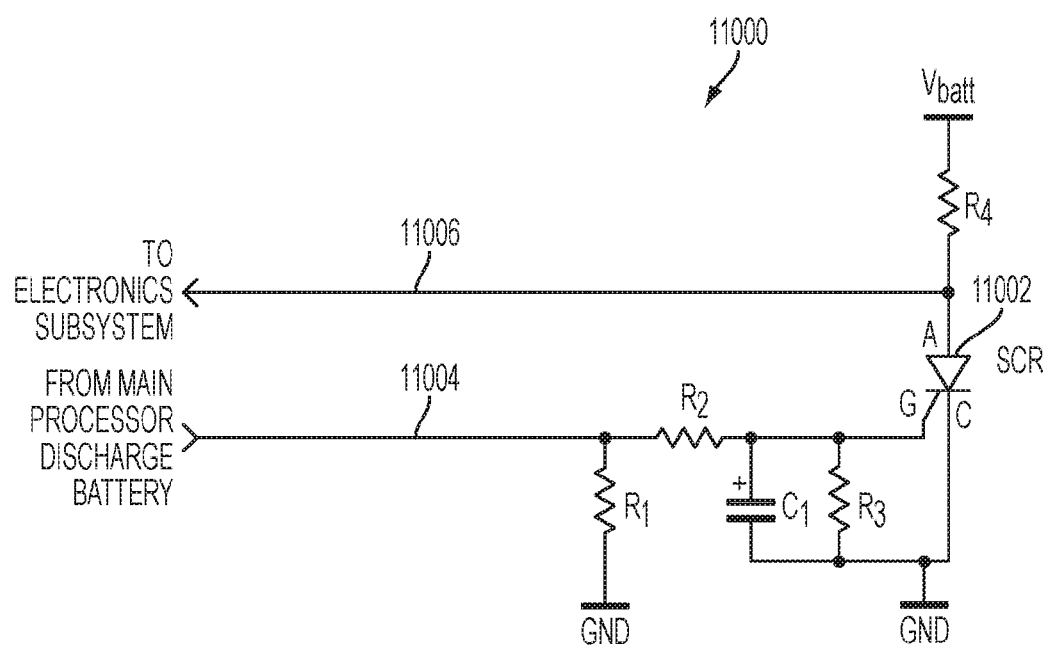
FIG. 97 illustrates an output signal provided to a circuit to discharge a battery.

FIG. 97 illustrates a battery discharge circuit 11000, according to one embodiment. Under normal operation line 11004 is held at a low potential and a current control device, such as a silicon controlled rectifier 11002, is in the OFF state and the battery voltage $V_{batt}$ is applied to the electronics system since no current flows from the anode "A" to the cathode "C" of the silicon controlled rectifier 11002. When, a high potential control signal "Discharge Battery" is applied by the main processor 1902 on line 11004, the gate "G" of the silicon controlled rectifier 11002 is held high by capacitor $C_1$ and the silicon controlled rectifier 11002 conducts current from the anode "A" to the "C." The discharge current is limited by resistor $R_4$. In alternate embodiments, rather then using the silicon controlled rectifier 11002, the current control device may be implemented using one or more diodes, transistors (e.g., FET, bipolar, unipolar), relays (solid state or electromechanical), optical isolators, optical couplers, among other electronic elements that can be configured to for an electronic switch to control the discharge of current from the battery 1300.

Figure 98:
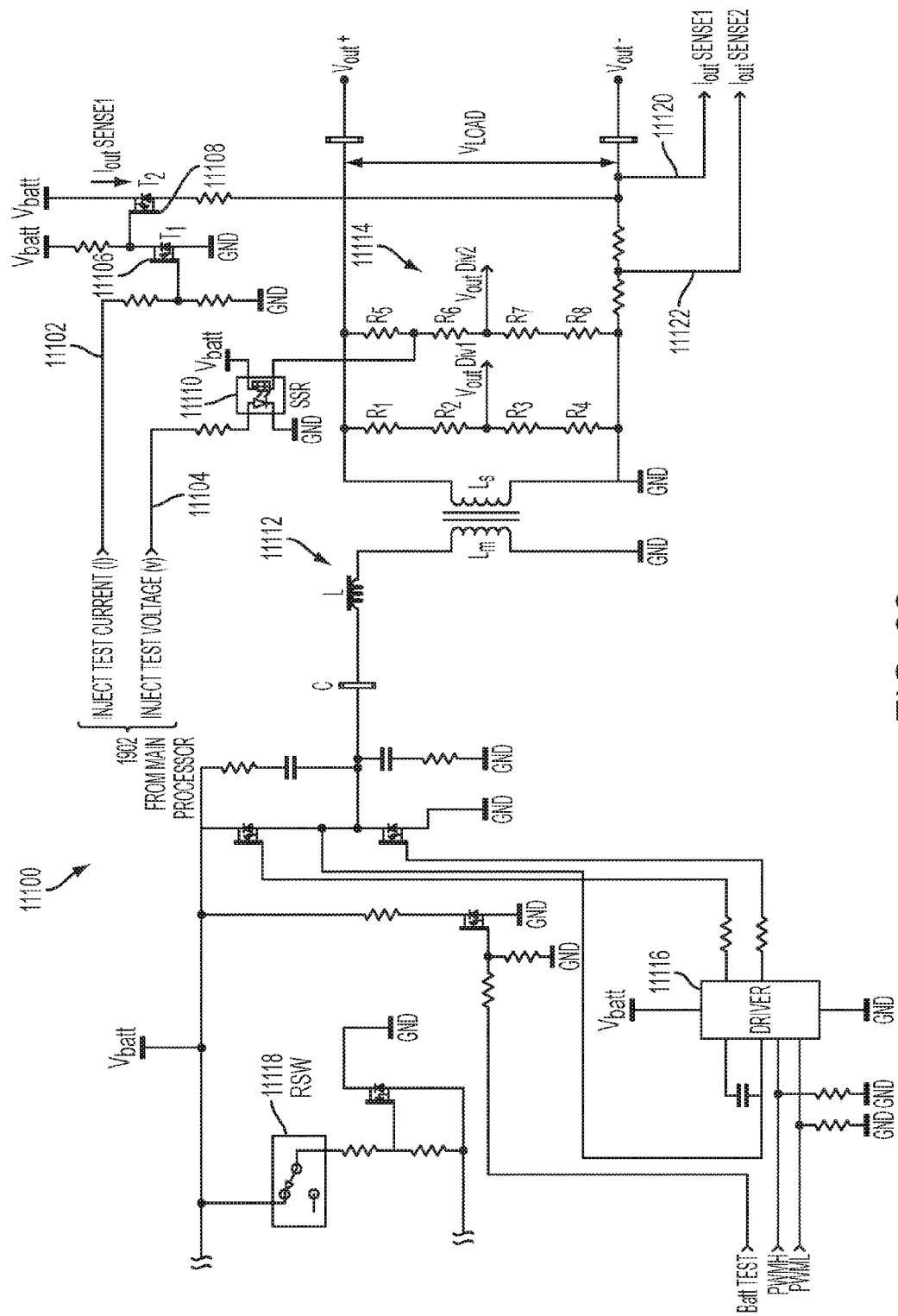
FIG. 98 illustrates a radio frequency (RF) amplifier section with an output sensing test circuit and magnetic switch element, according to one embodiment.

FIG. 98 illustrates a RF amplifier section with an output sensing test circuit and magnetic switch element, according to one embodiment. As previously discussed, in one embodiment, the main processor 1902 can verify the output current (I) and output voltage (V) sensing function by injecting a corresponding first test current 11102 and second test current 11104 into a dummy load 11114. The main processor 1902 then reads back the corresponding output sense current (I Out Sense 1) through current sense terminal 11120 and output sense current (I Out Sense 2) through voltage sense terminal 11122 from the dummy load 11114 and determines whether the surgical tool can operate or fail in safe mode. In one embodiment, the test current and voltage are applied to the dummy load via electronically controlled switches such as FET transistors, solid state relay, two-pole relay, and the like. The main processor 1902 verifies the output sensing functions once per hour when it is inactive and once prior to every firing. It will be appreciated that these periods may vary based on the particular implementation.

To verify the output sensing function, the main processor 1902 disables the operation of the RF amplifier section 11112 by disabling the driver circuit 11116. Once the RF amplifier section 11112 is disabled, the main processor 1902 outputs a first inject test current (Inject Test I) signal and a second inject test voltage (Inject Test V) signal to the output sensing test circuit 11100. As a result a first test current 11102 is injected into resistors that turn ON transistor T1 11106, which turns ON transistor T2 11108 to generate I Out Sense 1 current through the transistor T2 11108. The current I Out Sense 1 flows out of the current sense terminal 11120 and is detected by the main processor 1902 as the I Sense signal. A second test current 11104 is applied through the input section of a solid state relay 11110 (SSR). This causes a current I Out Sense 2 to flow through the dummy load 11114. The current I Out Sense 2 flows out of the current sense terminal 11122 and is detected by the main processor 1902 as the V Sense signal. The dummy load 11114 comprises a first voltage divider network comprised of resistors R1-R4 and a second voltage divider network comprised of R5-R8. As previously described, the main processor 1902 reads the sensed voltage and current signals V Sense and I Sense to determine the operation of the voltage (V) and current (I) sensing function of the surgical tool.

In one embodiment, the magnetically actuated element 1606, which works in conjunction with a magnet. As shown in FIG. 98, in one embodiment, a magnetically operated element may be implemented as a reed switch 11118. The reed switch 11118 electrically disconnects the battery power from the electronics system while it is held in a first state by the magnetic flux generated by the magnet. When the magnet is removed and the magnetic flux does not influence the reed switch 11118, battery power is connected to the electronics system and the system undergoes an initialization algorithm, as described hereinbelow.

Certain sections of the hardware circuits may be shut down or placed in sleep mode to conserve energy and thus extend the life of the battery 1300. In particular, amplifier circuits associated with the injection of the test current and test voltage and sensing the output sense currents may be placed in sleep mode or periodically shut down to conserve energy.

FIGS. 100-107 illustrate one embodiment of a shaft assembly 608 that may be employed with any of the various embodiments of the surgical tools 600, 700, 800, 900, 1000, 1100 described herein. It will be appreciated that a variety of articulation sections 612 may be employed for different configurations of the shaft assembly 608. Examples of a variety of articulation sections that may be employed with any of the surgical tools 600, 700, 800, 900, 1000, 1100 discussed herein can be found in the '247 application. Some examples of articulation joint configurations such as (A) articulation sections with parallel support rails, (B) articulation section formed by molded joint, (C) beaded articulation section, and (D) articulation control configurations are described in the '247 application, which is herein incorporated by reference.

FIGS. 108-111 illustrate one embodiment of a shaft assembly 1200 comprising an articulation section 1206 that may be employed in any of the surgical tools 600, 700, 800, 900, 1000, 1100 described herein. As shown, the shaft assembly 1200 comprises a distal slip ring 1204 that enables just the distal end effector 1202 (jaws) to rotate and the rest of the shaft assembly 1200 will remain stationary. The distal slip ring 1202 will enable the user to address tissue planes distal to the articulation section 1206 with improved access, improved visibility, and easier dissection sealing. The distal slip ring 1204 allows continuous rotation of the end effector 1202 distal to the articulation section 1206 without loss of electrical continuity. A bearing surface 1208 at the distal bead is provided for reduced surface are contact. Additional articulation configurations are described in the '247 application, which is herein incorporated by reference.

Figure 112:
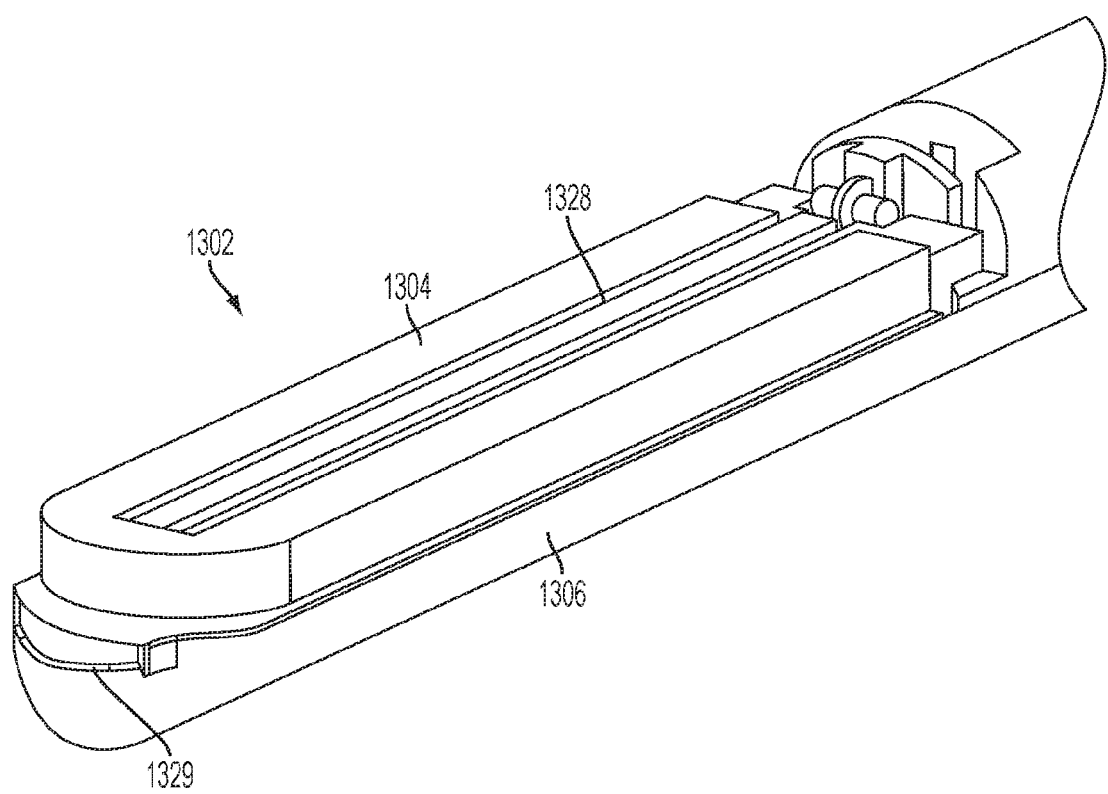
FIG. 112 illustrates one embodiment of an end effector that may be employed in a surgical tool.

FIG. 112 illustrates one embodiment of an end effector 1302 that may be employed in a surgical tool 600, 700, 800, 900, 1000, 1100 described herein. The end effector 1302 comprises a top jaw 1304, a bottom jaw 1306, and a slot 1328 for the cutter element. In the illustrated embodiment, the bottom jaw 1306 comprises a projected wire 1329 to enable the surgical tool 600, 700, 800, 900, 1000, 1100 to operate both in mono-polar and bipolar and modes. In one embodiment, a mode switching circuit and mechanism may be provided.

The various embodiments of the surgical tools 600, 700, 800, 900, 1000, 1100 discussed herein comprise motorized spools or rotatable bodies that are generally operated by power supplied by the robotic system 200 (FIG. 2). If additional power is required for tissue cutting and/or coagulation purposes, separate motors can be mounted inside the housing of the tool mounting portion 614, 714, 814, 914, 1014, 1114 in any suitable manner.

The various embodiments of the surgical tools 600, 700, 800, 900, 1000, 1100 discussed above may comprise shaft assemblies 608, 708, 808, 908, 1008, 1108 and tool mounting portions 614, 714, 814, 914, 1014, 1114 that are disposable. In other embodiments, however, it is contemplated that the surgical tools 600, 700, 800, 900, 1000, 1100 be designed such that the shaft assemblies 608, 708, 808, 908, 1008, 1108 can easily be disassembled and disposed whereas the tool mounting portions 614, 714, 814, 914, 1014, 1114 can be reused after cleaning and re-sterilization.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

While the examples herein are described mainly in the context of electrosurgical instruments, it should be understood that the teachings herein may be readily applied to a variety of other types of medical instruments. By way of example only, the teachings herein may be readily applied to tissue graspers, tissue retrieval pouch deploying instruments, surgical staplers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of devices and components thereof disclosed herein have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated herein by reference.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of devices and components thereof, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

While certain features of the aspects have been illustrated as described herein, many modifications, substitutions, changes and equivalents will now occur to those skilled in the art. It is therefore to be understood that the appended claims are intended to cover all such modifications and changes as fall within the true scope of the disclosed embodiments.

The invention claimed is:

1. A surgical tool, comprising:
   a tool mounting portion comprising a tool mounting housing, a tool mounting plate, and a coupler;
   a shaft assembly comprising an articulation section and an end effector, wherein the shaft assembly is operatively coupled to the tool mounting portion via the coupler;
   an articulation mechanism configured to receive a proximal end of the shaft assembly to articulate the articulation section of the shaft assembly, wherein the articulation mechanism comprises a cam mechanism configured to articulate the articulation section of the shaft assembly; and
   an interface adapted to mechanically and electrically couple the tool mounting portion to a manipulator;
   wherein the cam mechanism comprises:
   a multiple cam assembly comprising a first cam portion and a second cam portion, wherein the multiple cam assembly is rotatably coupled to a rotatable body, wherein the rotatable body is coupled to a driven element adapted to rotatably couple to the interface, and wherein the first cam portion is configured to act on the first follower arm and the second cam portion is configured to act on the second follower arm in response to a rotation of the rotatable body;
   a first follower arm operatively coupled to the first cam portion;
   a second follower arm operatively coupled to the second cam portion;
   a first articulation band attached to the first follower arm; and
   a second articulation band attached to the second follower arm, wherein the first articulation band and the second articulation band extend to a distal end of the shaft assembly.

2. The surgical tool of claim 1, further comprising a first bushing and a second bushing mounted beneath the respective first follower arm and second follower arm to allow rotation of the shaft assembly without affecting articulating positions of the first follower arm and the second follower arm.

3. The surgical tool of claim 2, wherein the first bushing and the second bushing reciprocate with the corresponding first follower arm and second follower arm without affecting a rotation position of the shaft assembly.

4. The surgical tool of claim 1, wherein the articulation section of the shaft assembly articulates in a first direction, via the first articulation band, as the first cam portion acts on the first follower arm, and wherein the articulation section of the shaft assembly articulates in a second direction, via the second articulation band, as the second cam portion acts on the second follower arm.

5. The surgical tool of claim 1, wherein the multiple cam assembly comprises a neutral position.

6. A surgical tool, comprising:
a tool mounting portion comprising a tool mounting housing, a tool mounting plate, and a coupler to couple a shaft assembly comprising an articulation section to the tool mounting portion;
an articulation mechanism configured to receive a proximal end of the shaft assembly to articulate the articulation section of the shaft assembly, wherein the articulation mechanism comprises a cam mechanism operative to articulate the articulation section of the shaft assembly; and
an interface adapted to mechanically and electrically couple the tool mounting portion to a manipulator;
wherein the cam mechanism comprises:
a dual cam assembly comprising a first cam portion and a second cam portion, wherein the dual cam assembly is rotatably coupled to a rotatable body, and wherein the rotatable body is coupled to a driven element adapted to rotatably couple to the interface;
a first follower arm having a first end operatively coupled to the first cam portion;
a second follower arm having a first end operatively coupled to the second cam portion, wherein the first cam portion is configured to act on the first follower arm and the second cam portion is configured to act on the second follower arm in response to a rotation of the rotatable body;
a first articulation band attached to the first follower arm; and
a second articulation band attached to the second follower arm wherein the first articulation band and the second articulation band extend to a distal end of the shaft assembly.

7. The surgical tool of claim 6, wherein the first follower arm has a second end rotatably coupled to a first pivot spool and the second follower arm has a second end rotatably coupled to a second pivot spool.

8. The surgical tool of claim 6, further comprising a first bushing and a second bushing mounted beneath the respective first follower arm and second follower arm to allow rotation of the shaft assembly without affecting articulating positions of the first follower arm and the second follower arm.

9. The surgical tool of claim 8, wherein the first bushing and the second bushing reciprocate with the corresponding first follower arm and second follower arm without affecting a rotation position of the shaft assembly.

10. A surgical tool, comprising:
a tool mounting portion;
a shaft assembly comprising an articulation section, wherein the shaft assembly is operatively coupled to the tool mounting portion;
an articulation mechanism, comprising:
a multiple cam assembly comprising a first cam and a second cam, wherein the multiple cam assembly is rotatably coupled to at least one rotatable body portion;
a first follower lever arrangement comprising:
a first lever comprising an aperture through which a proximal end of the shaft assembly extends, wherein a first end of the first lever is rotatably coupled to a first pivot spool and a second end of the first lever operably interfaces with the first cam;
a first bushing rotatably mounted on the proximal end of the shaft assembly, wherein an outer cylindrical surface of the first bushing operably interfaces with the first lever aperture; and
a first articulation wire operably attached to the first lever;
a second follower lever arrangement comprising:
a second lever comprising an aperture through which the proximal end of the shaft assembly extends, wherein a first end of the second lever is rotatably coupled to a second pivot spool and a second end of the second lever operably interfaces with the second cam;
a second bushing rotatably mounted on the proximal end of the shaft assembly, wherein an outer cylindrical surface of the second bushing operably interfaces with the second lever aperture; and
a second articulation wire operably attached to the second lever;
wherein as the at least one rotatable body portion coupled to the multiple cam assembly rotates:
the first cam is operative to pivot the first lever about the first pivot spool such that the attached first articulation wire articulates the articulation section of the shaft assembly in a first direction; and
the second cam is operative to pivot the second lever about the second pivot spool such that the attached second articulation wire articulates the articulation section of the shaft assembly in a second direction.

11. The surgical tool of claim 10, wherein the tool mounting portion comprises a tool mounting housing, a tool mounting plate, and a coupler, and wherein the tool mounting plate operably supports a plurality of rotatable body portions coupled to a plurality of driven elements.

12. The surgical tool of claim 11, wherein the shaft assembly further comprises an elongate tube portion, wherein the articulation section extends distally from the elongate tube portion, and wherein the elongate tube portion is rotatably coupled to the tool mounting housing via the coupler.

13. The surgical tool of claim 12, further comprising an interface adapted to mechanically and electrically couple the tool mounting portion to a manipulator.

14. The surgical tool of claim 10, wherein as the at least one rotatable body portion coupled to the multiple cam assembly rotates in a counter-clockwise direction the articulation section of the shaft assembly articulates in a right direction, and wherein as the at least one rotatable body portion coupled to the multiple cam assembly rotates in a clockwise direction the articulation section of the shaft assembly articulates in a left direction.

15. The surgical tool of claim 14, wherein the multiple cam assembly comprises a neutral position.

16. The surgical tool of claim 10, wherein the first bushing and the second bushing are each configured to:
reciprocate with the corresponding first lever and second lever without affecting a rotation position of the shaft assembly; and
allow rotation of the shaft assembly without affecting the pivoting of the corresponding first lever and second lever.

* * * * *